US011590197B2

(12) United States Patent
Pellecchia et al.

(10) Patent No.: US 11,590,197 B2
(45) Date of Patent: Feb. 28, 2023

(54) AGENTS TARGETING INHIBITOR OF APOPTOSIS PROTEINS

(71) Applicant: The Regents of the University of California, Oakland, CA (US)

(72) Inventors: Maurizio Pellecchia, San Diego, CA (US); Carlo Baggio, Moreno Valley, CA (US); Luca Gambini, Riverside, CA (US); Parima Udompholkul, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/760,646

(22) PCT Filed: Nov. 1, 2018

(86) PCT No.: PCT/US2018/058793
§ 371 (c)(1),
(2) Date: Apr. 30, 2020

(87) PCT Pub. No.: WO2019/089991
PCT Pub. Date: May 9, 2019

(65) Prior Publication Data
US 2020/0345804 A1    Nov. 5, 2020

Related U.S. Application Data

(60) Provisional application No. 62/580,328, filed on Nov. 1, 2017.

(51) Int. Cl.
| | | |
|---|---|---|
| *A61K 38/05* | (2006.01) | |
| *A61K 38/06* | (2006.01) | |
| *A61K 38/07* | (2006.01) | |
| *A61K 38/08* | (2019.01) | |
| *A61K 45/06* | (2006.01) | |
| *A61P 35/00* | (2006.01) | |
| *C07K 5/06* | (2006.01) | |
| *C07K 5/08* | (2006.01) | |
| *C07K 7/06* | (2006.01) | |
| *A61K 31/337* | (2006.01) | |
| *A61K 31/7068* | (2006.01) | |
| *C07K 5/072* | (2006.01) | |
| *C07K 5/093* | (2006.01) | |
| *C07K 5/113* | (2006.01) | |
| *A61N 5/10* | (2006.01) | |

(52) U.S. Cl.
CPC .......... *A61K 38/08* (2013.01); *A61K 31/337* (2013.01); *A61K 31/7068* (2013.01); *A61K 38/05* (2013.01); *A61K 38/06* (2013.01); *A61K 38/07* (2013.01); *A61P 35/00* (2018.01); *C07K 5/06104* (2013.01); *C07K 5/0819* (2013.01); *C07K 5/1021* (2013.01); *C07K 7/06* (2013.01); *A61N 5/10* (2013.01)

(58) Field of Classification Search
CPC .............. A61K 2300/00; A61K 31/337; A61K 31/635; A61K 31/7068; A61K 38/05; A61K 38/06; A61K 38/07; A61K 38/08; A61K 45/06; A61P 35/00; C07K 5/0202; C07K 5/0215; C07K 5/06; C07K 5/06026; C07K 5/06104; C07K 5/06191; C07K 5/08; C07K 5/0806; C07K 5/0819; C07K 5/0827; C07K 5/1021; C07K 5/1027; C07K 7/06; C07K 5/072; C07K 5/093; C07K 5/113
See application file for complete search history.

(56) References Cited

U.S. PATENT DOCUMENTS

| | | | |
|---|---|---|---|
| 8,986,993 B2 | 3/2015 | Condon et al. | |
| 2012/0015352 A1 | 1/2012 | Leverkus et al. | |
| 2012/0141496 A1* | 6/2012 | Laurent .............. | C07K 5/06034 530/323 |
| 2015/0105434 A1 | 4/2015 | Porter et al. | |

FOREIGN PATENT DOCUMENTS

WO     2011082285 A1    7/2011

OTHER PUBLICATIONS

Akcay, G. et al. (2016). Inhibition of Mcl-1 through covalent modification of a noncatalytic lysine side chain. Nat. Chem. Biol., 12, 931-936.
Anscombe, E. et al. (2015). Identification and characterization of an irreversible inhibitor of CDK2. Chem. Biol., 22, 1159-1164.
Ashley, S. L. et al. (2016). Targeting inhibitor of apoptosis proteins protects from bleomycin-induced lung fibrosis. Am. J. Respir. Cell Mol. Biol., 54, 482-492.
Baggio, C. et al. (2017). Enthalpy-based screening of focused combinatorial libraries for the identification of potent and selective ligands. ACS Chem. Biol., 12, 2981-2989.
Cai, Q. et al. (2011). A potent and orally active antagonist (SM-406/AT-406) of multiple inhibitor of apoptosis proteins (IAPs) in clinical development for cancer treatment. J. Med. Chem., 54, 2714-2726.
Chesi, M et al. (2016). IAP antagonists induce anti-tumor immunity in multiple myeloma. Nat. Med., 22, 1411-1420.
Clark, D. E. (1999). Rapid calculation of polar molecular surface area and its application to the prediction of transport phenomena. 1. Prediction of intestinal absorption. J. Pharm. Sci., 88, 807-814.
Cohen, F. et al. (2009). Orally bioavailable antagonists of inhibitor of apoptosis proteins based on an azabicyclooctane scaffold. J. Med. Chem., 52, 1723-1730.

(Continued)

*Primary Examiner* — Julie Ha
(74) *Attorney, Agent, or Firm* — Viksnins Harris Padys Malen LLP

(57) ABSTRACT

Disclosed herein, inter alia, are methods of use and composition of novel inhibitors that target the Smac binding site of a variety of inhibitor of apoptosis proteins that contain a Bir domain, including XIAP, cIAP1, cIAP2, or other IAP proteins.

17 Claims, 32 Drawing Sheets

Specification includes a Sequence Listing.

(56) References Cited

OTHER PUBLICATIONS

Deveraux, Q. L. et al. (1999). IAP family proteins—suppressors of apoptosis. Genes Dev., 13, 239-252.
Donnell, A. et al. (2013). Benzazepinones and benzoxazepinones as antagonists of inhibitor of apoptosis proteins (IAPs) selective for the second baculovirus IAP repeat (BIR2) domain. J. Med. Chem., 56, 7772-7787.
Du, C. et al. (2000). Smac, a mitochondrial protein that promotes cytochrome c-dependent caspase activation by eliminating IAP inhibition. Cell, 102, 33-42.
Flygare, J. A. et al. (2012). Discovery of a potent small-molecule antagonist of inhibitor of apoptosis (IAP) proteins and clinical candidate for the treatment of cancer (GDC-0152). J. Med. Chem., 55, 4101-4113.
Flygare, J. A. et al. (2010). Small-molecule pan-IAP antagonists: a patent review. Expert Opin. Ther. Pat., 20, 251-267.
Fox, J. M. et al. (2018). The molecular origin of enthalpy/entropy compensation in biomolecular recognition. Annu. Rev. Biophys., 47, 223-250.
Fulda, S. (2007). Inhibitor of apoptosis proteins as targets for anticancer therapy. Expert Rev. Anticancer Ther. 7, 1255-1264.
Fulda, S. et al. (2012). Targeting IAP proteins for therapeutic intervention in cancer. Nat. Rev. Drug Discov., 11, 109-124.
Gaither, A. et al. (2007). A Smac mimetic rescue screen reveals roles for inhibitor of apoptosis proteins in tumor necrosis factor-α signaling. Cancer Res., 67, 11493-11498.
Gyrd-Hansen, M. et al. (2010). IAPs: from caspase inhibitors to modulators of NF-kappaB, inflammation and cancer. Nat. Rev. Cancer, 10, 561-574.
Ha⊖, C. et al. (2016). Sensitization of acute lymphoblastic leukemia cells for LCL161-induced cell death by targeting redox homeostasis. Biochem. Pharmacol., 105, 14-22.
Hashimoto, K. et al. (2013). Design and synthesis of potent inhibitor of apoptosis (IAP) proteins antagonists bearing an octahydropyrrolo[1,2-a]pyrazine scaffold as a novel proline mimetic. J. Med. Chem., 56, 1228-1246.
Hennessy, E. J. (2012). Discovery of aminopiperidine-based Smac mimetics as IAP antagonists. Bioorg. Med. Chem. Lett., 22, 1690-1694.
Holcik, M. et al. (2001). XIAP: apoptotic brake and promising therapeutic target. Apoptosis, 6, 253-261.
Hoppmann, C. et al. (2016). Proximity-enabled bioreactivity to generate covalent peptide inhibitors of p53-Mdm4. Chem. Commun. (Camb.), 52, 5140-5143.
Houghton, P. J. et al. (2012). Initial testing (stage 1) of LCL161, a SMAC mimetic, by the pediatric preclinical testing program. Pediatr. Blood Cancer, 58, 636-639.
Huang, Y. et al. (2003). Requirement of both the second and third BIR domains for the relief of X-linked inhibitor of apoptosis protein (XIAP)-mediated caspase inhibition by Smac. J. Biol. Chem., 278, 49517-49522.
Huang, J. W. et al. (2008). Fragment-based design of small molecule X-linked inhibitor of apoptosis protein inhibitors. J. Med. Chem., 51, 7111-7118.
International Search Report dated Mar. 5, 2019, for PCT Application No. PCT/US2018/058793, filed Nov. 1, 2018, 6 pages.
LaCasse, E. C. et al. (2008). IAP-targeted therapies for cancer. Oncogene, 27, 6252-6275.
Li, L. et al. (2004). A small molecule Smac mimic potentiates TRAIL- and TNFalpha-mediated cell death. Science, 305, 1471-1474.
Liu, Z. et al. (2000). Structural basis for binding of Smac/DIABLO to the XIAP BIR3 domain. Nature, 408, 1004-1008.
Lopes, R. B. et al. (2007) Expression of the IAP protein family is dysregulated in pancreatic cancer cells and is important for resistance to chemotherapy. Int. J. Cancer, 120, 2344-2352.
Lu, J. et al. (2008). SM-164: a novel, bivalent Smac mimetic that induces apoptosis and tumor regression by concurrent removal of the blockade of cIAP-1/2 and XIAP. Cancer Res., 68, 9384-9393.
Mannhold, R. et al. (2010). IAP antagonists: promising candidates for cancer therapy. Drug Discov. Today, 15, 210-219.
Mizutani, Y. et al. (2007). Overexpression of XIAP expression in renal cell carcinoma predicts a worse prognosis. Int. J. Oncol., 30, 919-925.
Mohamed, M.S. et al. (2017). Inhibitors of apoptosis: clinical implications in cancer, Apoptosis 22, 1487-1509.
Nakagawa, Y. et al. (2006). "IAP family protein expression correlates with poor outcome of multiple myeloma patients in association with chemotherapy-induced overexpression of multidrug resistance genes," Am. J. Hematol., 81, 824-831.
Ndubaku, C. et al. (2009). Antagonism of c-IAP and XIAP proteins is required for efficient induction of cell death by small-molecule IAP antagonists. ACS Chem. Biol., 4, 557-566.
Oost, T. K. et al. (2004). Discovery of potent antagonists of the antiapoptotic protein XIAP for the treatment of cancer. J. Med. Chem., 47, 4417-4426.
Peng, Y. et al. (2008). Potent, orally bioavailable diazabicyclic small-molecule mimetics of second mitochondria-derived activator of caspases. J. Med. Chem., 51, 8158-8162.
Pettinger, J. et al. (2017). Lysine-targeting covalent inhibitors. Angew. Chem. Int. Ed. Engl. 15200-15209.
Ramakrishnan, V. et al. (2014). Inhibitor of apoptosis proteins as therapeutic targets in multiple myeloma. Leukemia, 28, 1519-1528.
Salvesen, G.S. et al. (2002). IAP proteins: blocking the road to death's door. Nat. Rev. Mol. Cell Biol., 3, 401-410.
Samuel, T. et al. (2006). Distinct BIR domains of cIAP1 mediate binding to and ubiquitination of tumor necrosis factor receptor-associated factor 2 and second mitochondrial activator of caspases. J. Biol. Chem., 281, 1080-1090.
Schon, A. et al. (2016). Enthalpy screen of drug candidates. Anal. Biochem., 513, 1-6.
Sheng, R. et al. (2013). A potent bivalent Smac mimetic (SM-1200) achieving rapid, complete, and durable tumor regression in mice. J. Med. Chem., 56, 3969-3979.
Shiozaki, E. N. et al. (2004). Caspases, IAPs and Smac/DIABLO: mechanisms from structural biology. Trends Biochem. Sci., 29, 486-494.
Sun H. et al. (2004). Structure-based design of potent, conformationally constrained Smac mimetics. J. Am. Chem. Soc., 126, 16686-16687.
Sun, H. et al. (2004). "Structure-based design, synthesis, and evaluation of conformationally constrained mimetics of the second mitochondria-derived activator of caspase that target the X-linked inhibitor of apoptosis protein/caspase-9 interaction site," J. Med. Chem., 47, 4147-4150.
Sun, H. et al. (2006). Design, synthesis, and evaluation of a potent, cell-permeable, conformationally constrained second mitochondria derived activator of caspase (Smac) mimetic. J. Med. Chem., 49, 7916-7920.
Sun, H. et al. (2007). Design, synthesis, and characterization of a potent, nonpeptide, cell-permeable, bivalent Smac mimetic that concurrently targets both the BIR2 and BIR3 domains in XIAP. J. Am. Chem. Soc., 129, 15279-15294.
Sun, H. et al. (2008). Design of small-molecule peptidic and nonpeptidic Smac mimetics. Acc. Chem. Res., 41, 1264-1277.
Sun, H. et al. (2008). "Structure-based design, synthesis, evaluation, and crystallographic studies of conformationally constrained Smac mimetics as inhibitors of the X-linked inhibitor of apoptosis protein (XIAP),"J. Med. Chem., 51, 7169-7180.
Sun, W. et al. (2009). Design, synthesis, and evaluation of potent, nonpeptidic mimetics of second mitochondria-derived activator of caspases. J. Med. Chem., 52, 593-596.
Sun, H. et al. (2010). Nonpeptidic and potent small-molecule inhibitors of cIAP-1/2 and XIAP proteins. J. Med. Chem., 53, 6361-6367.
Sun, H. et al. (2014). "Potent and selective small-molecule inhibitors of cIAP1/2 proteins reveal that the binding of Smac mimetics to XIAP BIR3 is not required for their effective induction of cell death in tumor cells," ACS Chem. Biol., 9, 994-1002.
Tamm, I. et al. (2000). Expression and prognostic significance of IAP-family genes in human cancers and myeloid leukemias. Clin. Cancer Res., 6, 1796-1803.

(56) References Cited

OTHER PUBLICATIONS

Varfolomeev, E. et al. (2007). IAP antagonists induce autoubiquitination of c-IAPs, NF-kappaB activation, and TNFalpha-dependent apoptosis. Cell, 131, 669-681.

Verhagen, A. M. et al. (2000). Identification of DIABLO, a mammalian protein that promotes apoptosis by binding to and antagonizing IAP proteins. Cell, 102, 43-53.

Vince, J. E. et al. (2007). IAP antagonists target cIAP1 to induce TNFalpha-dependent apoptosis. Cell, 131, 682-693.

Vucic, D. et al. (2007). The inhibitor of apoptosis proteins as therapeutic targets in cancer. Clin. Cancer Res., 13, 5995-6000.

Wang, S. (2011). Design of small-molecule Smac mimetics as IAP antagonists. Curr. Top. Microbiol. Immunol., 348, 89-113.

Written Opinion dated Mar. 5, 2019, for PCT Application No. PCT/US2018/058793, filed Nov. 1, 2018, 6 pages.

Wu, G. et al. (2000). Structural basis of IAP recognition by Smac/DIABLO. Nature, 408, 1008-1012.

Zhang, B. et al. (2008). Design, synthesis, and evaluation of tricyclic, conformationally constrained small-molecule mimetics of second mitochondria-derived activator of caspases. J. Med. Chem., 51, 7352-7355.

Zhao, Q. et al. (2017). Broad-spectrum kinase profiling in live cells with lysine-targeted sulfonyl fluoride probes. J. Am. Chem. Soc., 139, 680-685.

Zobel, K. et al. (2006). Design, synthesis, and biological activity of a potent Smac mimetic that sensitizes cancer cells to apoptosis by antagonizing IAPs. ACS Chem. Biol., 1, 525-533.

Hird, A, et al., "Small molecule inhibitor of apoptosis proteins antagonists: a patent review", Expert Opinion on Therapeutic Patents 25 (7), 755-774 (2015).

* cited by examiner

| | | |
|---|---|---|
| Conservation | | |
| Consensus | L r c W e s g d D | |
| XIAP-BIR3 | 307 L T D W K P S E D | 315 |
| cIAP1-BIR3 | 313 L R C W E S G D D | 321 |
| cIAP2-BIR3 | 299 L R C W E S G D D | 307 |

$$\Delta X_{pred.} = \Delta X_{Ref.} + \delta(\Delta X)_{P2} + \delta(\Delta X)_{P3/P4}$$

AGENTS TARGETING INHIBITOR OF APOPTOSIS PROTEINS

CROSS-REFERENCES TO RELATED APPLICATIONS

This application is a U.S. national phase application, pursuant to 35 U.S.C. 371, of PCT/US2018/058793, filed Nov. 1, 2018, designating the United States, which claims the priority to and benefit of U.S. Provisional Application No. 62/580,328, filed Nov. 1, 2017. The entire contents of the aforementioned patent applications are incorporated herein by this reference.

REFERENCE TO A "SEQUENCE LISTING," A TABLE, OR A COMPUTER PROGRAM LISTING APPENDIX SUBMITTED AS AN ASCII FILE

The instant application contains a Sequence Listing which has been submitted electronically in ASCII format and is hereby incorporated by reference in its entirety. Said ASCII copy, created on Jul. 1, 2022, is named 12111_054US1_SL.txt and is 19,672 bytes in size.

BACKGROUND

Inhibitors of apoptotic proteins (IAPs) are a class of important regulators of apoptosis, characterized by the presence of one to three baculovirus IAP repeat (BIR) domains. Cellular inhibitor of apoptosis protein 1 (cIAP1) and cellular inhibitor of apoptosis protein 2 (cIAP2) are involved in tumor necrosis factor receptor-mediated apoptosis. The X-linked inhibitor of apoptosis protein (XIAP) antagonizes three caspases, caspase-3 and -7, and caspase-9. The third BIR domain (BIR3) of XIAP binds to and inhibits caspase-9, whereas the second BIR domain (BIR2), binds to and inhibits both caspase-3 and caspase-7. These IAPs typically are overexpressed in many tumor cell lines and human tumor tissues and thus play important roles in the resistance of cancer cells to various anticancer treatments. Broad and selective inhibition of BIR3 or BIR2 domains of the protein XIAP, cIAP1, or cIAP2 remains an elusive challenge. Disclosed herein, inter alia, are solutions to these and other problems in the art.

BRIEF SUMMARY

In an aspect is provided a compound, or a pharmaceutical salt thereof, or a prodrug thereof, having the formula:

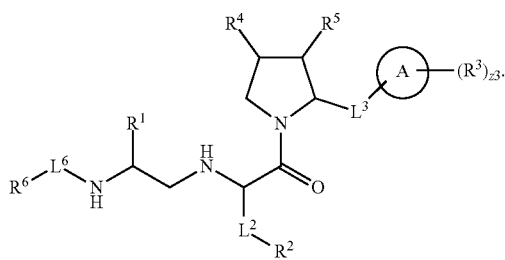

$R^1$ is $-CX^1_3$, $-CHX^1_2$, $-CH_2X^1$, substituted or unsubstituted $C_1$-$C_4$ alkyl. $L^2$ is a bond, $-NH-$, $-O-$, $-S-$, $-C(O)-$, $-C(O)NH-$, $-NHC(O)-$, $-NHC(O)NH-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^2$ is independently hydrogen, halogen, $-CX^2_3$, $-CHX^2_2$, $-CH_2X^2$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^2_3$, $-OCHX^2_2$, $-OCH_2X^2$, $-SO_2CH_3$, $-SO_2CX^2_3$, $-SO_2CH_3$, $-SO_2X^2$, $-SO_2CH=CH_2$, $-NHSO_2CH=CH_2$, $-OSO_2X^2$, $-NHSO_2X^2$, $-B(OH)_2$, $-CO$- oxiranyl, $-CO$-aziridinyl, epoxidinyl, oxaziridinyl, aziridinyl, $-OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^3$ is a bond, $-NH-$, $-O-$, $-S-$, $-C(O)-$, $-C(O)NH-$, $-NHC(O)-$, $-NHC(O)NH-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene. Ring A is a cycloalkyl, heterocycloalkyl, aryl, or heteroaryl. $R^3$ is independently halogen, $-CX^3_3$, $-CHX^3_2$, $-CH_2X^3$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^3_3$, $-OCHX^3_2$, $-OCH_2X^3$, $-SO_2X^3$, $-SO_2CH=CH_2$, $-NHSO_2CH=CH_2$, $-OSO_2X^3$, $-B(OH)_2$, $-NHSO_2X^3$, $-CO$-oxiranyl, $-CO$-aziridinyl, epoxidinyl, oxaziridinyl, aziridinyl, $-OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. $R^4$ is independently hydrogen, halogen, $-CX^4_3$, $-CHX^4_2$, $-CH_2X^4$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $-OCH_2X^4$, $-NHC(NH)NH_2$, $-SO_2X^4$, $-SO_2CH=CH_2$, $-NHSO_2CH=CH_2$, $-OSO_2X^4$, $-NHSO_2X^4$, $-B(OH)_2$, $-CO$-oxiranyl, $-CO$-aziridinyl, epoxidinyl, oxaziridinyl, aziridinyl, $-OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently hydrogen, halogen, $-CX^5_3$, $-CHX^5_2$, $-CH_2X^5$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^5_3$, $-OCHX^5_2$, $-OCH_2X^5$, $-NHC(NH)NH_2$, $-SO_2X^5$, $-SO_2CH=CH_2$, $-NHSO_2CH=CH_2$, $-OSO_2X^5$, $-NHSO_2X^5$, $-B(OH)_2$, $-CO-$ oxiranyl, $-CO$-aziridinyl, epoxidinyl, oxaziridinyl, aziridinyl, $-OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^6$ is a bond or unsubstituted methylene. $R^6$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $X^1$, $X^2$, $X^3$, $X^4$, and $X^5$ is independently —F, —Cl, —Br, or —I. The symbol z3 is independently an integer from 0 to 3.

In another aspect is a compound including a first moiety of a compound as described herein and a second moiety of a compound as described herein, wherein said first and second moieties are connected by a covalent linker.

In an aspect is provided a pharmaceutical composition including a compound, pharmaceutical salt thereof, or a prodrug thereof, as described herein and a pharmaceutically acceptable excipient.

In an aspect is provided a method of reducing the level of activity of XIAP, cIAP1, and/or cIAP2 relative to a control, the method including contacting the XIAP, cIAP1, and/or cIAP2 with a compound, pharmaceutical salt, or prodrug of a compound described herein, including embodiments.

In an aspect is provided a method for treating cancer, the method including administering to a subject in need thereof a therapeutically effective amount of a compound, pharmaceutical salt, or prodrug of a compound described herein, including embodiments.

In another aspect is provided a method for increasing apoptosis in a cancer cell in a subject in need thereof, said method comprising administering to a subject in need thereof a therapeutically effective amount of a compound, pharmaceutical salt, or prodrug of a compound described herein, including embodiments.

In an aspect is provided a method for inducing apoptosis in a cancer cell in a subject in need thereof, the method including administering to a subject in need thereof a therapeutically effective amount of a compound, pharmaceutical salt thereof, or prodrug thereof, as described herein, including embodiments.

BRIEF DESCRIPTION OF THE DRAWINGS

FIG. 3A: A positional scanning (POS) library of compounds needs to be assembled by first selecting an anchoring moiety (triangle). This can be any preferred scaffold that is essential for binding and recognition to the given target, such as for example, an optimized fragment hit, identified by screening methods and/or by defragmentation of known endogenous or synthetic inhibitors, etc. In the example, a four-position synthetic combinatorial library is then prepared with the first position fixed by an anchoring fragment (triangle). With a library of n elements, there will be 3×n mixtures, each containing n×n compounds. Hence, rather than synthesizing and testing n×n×n individual compounds, the approach would result in testing 3×n mixtures. For example, a library of 50 fragments assembled at three different positions could be sampled by synthetizing and screening 150 mixtures (50×3), rather than by synthesizing and testing 125,000 agents (503) individual compounds. FIG. 3B: Enthalpy (ΔH) screening of the 3×n mixtures can be performed by 1 or more injections of the target protein into the mixture solutions. FIG. 3C: The ΔH of each mixture is measured and plotted as a function of the fixed fragment at each position, thus potentially identifying elements that presents the highest enthalpy of binding for the given target at each position. FIG. 3D: Preferential fragments for each position are therefore selected and final individual test compounds are synthesized. The dissociation constant ($K_d$) and the relative thermodynamics of binding for the resulting compounds are determined by Isothermal Titration Calorimetry (ITC) analysis while selectivity can be accomplished by displacement biochemical assays with a series of related counter-targets.

FIG. 4A: Structure of the BIR3 domain of XIAP in complex with the N-terminal amino acid residues of SMAC of amino acid sequence AVPI (SEQ ID NO: 4). FIG. 4B: ΔH screening data for the AVPI peptide (SEQ ID NO: 4) and the known inhibitor GDC-0152. The measurements were performed by injecting four times 2.5 μL of a solution of 200 μM BIR3 domain of XIAP into the cell containing the test inhibitor at 50 μM concentration. The value of ΔH was calculated as the average of injections 2 to 4. FIG. 4C: HTS by ΔH data for three positive mixtures (one for each position), which identified the known BIR3 binding consensus motif of sequence AVPI (SEQ ID NO: 4) (or AVPF (SEQ ID NO: 5)). The ΔH was calculated using the first point obtained by injecting 2.5 μL of 200 μM BIR3 domain of XIAP into the cell containing 1 mM of each mixture consisting of 2,116 peptoids. FIG. 4D: HTS by ΔH data for three negative mixture for each position. The measurements were performed as indicated in panel FIG. 4C. Because of the focused nature of the library containing the anchoring element, a minimum ΔH value of approximately −2 kcal/mol is generally observed for most mixtures.

FIG. 5A: Summary of ΔH values for the highest ranking mixtures and selected low ranking mixtures for each position. In positions P2 and P4, the mixtures with the fixed residue phosphotyrosine (pY) and 4-fluoro-phenylalanine (4F-Phe), respectively, ranked higher than the mixtures containing Valine and Isoleucine at positions P2 and P4, respectively. While for position P3, the mixture with Proline as the fixed amino acid was confirmed as the highest ranking. FIG. 5B: HTS by ΔH data for the two mixtures Ala-pY-XX, and Ala-XX-4FPhe, respectively. The ΔH was calculated using the first point obtained by injecting 2.5 μL of 200 μM BIR3 domain of XIAP into the cell containing 1 mM of each mixture. FIG. 5C: Isothermal Titration Calorimetry (ITC) data for the binding of the BIR3 domain of XIAP to the tetrapeptide of sequence AVPI (SEQ ID NO: 4) and to the novel peptide of sequence A(pY)P(4F-Phe) (SEQ ID NO: 6). The measurements were performed as described in the methods section.

FIG. 6A: Isothermal Titration Calorimetry (ITC) data for the binding of BIR3 domain of XIAP to the known inhibitor GDC-0152 (structure reported). The measured thermodynamic parameters for GDC-0152 ($\Delta H$=−5.16 kcal/mol, −T$\Delta S$=−4.44 kcal/mol, $\Delta G$=−9.58 kcal/mol), AVPI (SEQ ID NO: 4) ($\Delta H$=−4.30 kcal/mol, −T$\Delta S$=−4.00 kcal/mol, $\Delta G$=−8.30 kcal/mol), and A(pY)P(4F-Phe) (SEQ ID NO: 6) ($\Delta H$=−12.17 kcal/mol, −T$\Delta S$=3.04 kcal/mol, $\Delta G$=−9.13 kcal/mol) are also reported. FIG. 6B: DELFIA displacement curves relative to the binding agents GDC-0152, AVPI (SEQ ID NO: 4), and A(pY)P(4F-Phe) (SEQ ID NO: 6) as tested against the BIR3 domains of XIAP, cIAP1, or cIAP2. FIG. 6B also discloses SEQ ID NO: 12. FIG. 6C: The docking pose of A(pY)P(4F-Phe) (SEQ ID NO: 6) into the binding site of XIAP-BIR3 domain is reported in the top panel; on the bottom panel, the structure of GDC-0152 bound to cIAP1-BIR3 domain (PDB 3UW4) (Flygare, J. A. et al., 2012, J. Med. Chem. 55, 4101-4113) is reported superimposed to the XIAP-BIR3 domain (PDB 1G73) (Wu, G. et al., 2000, Nature, 1008-1012). According to these models, the pY residue interacts directly with Lys311 on the binding surface of XIAP-BIR3. Such interaction is not present in GDC-0152. FIG. 6D: Sequence alignment of the BIR3 domains of XIAP, cIAP1, and cIAP2 showing that cIAP1, and cIAP2 contain a glutamic acid residue instead of the Lys311, hence, identifying this amino acid as potential residue for the design of selective binding agents. Likewise, Lys299 and/or Lys297 in XIAP-BIR3 (or equivalent Lys residues in XIAP-BIR2, or the BIR2 or BIR3 domains other IAPs) can be targeted by the same electrophiles introduced here. FIG. 6D discloses SEQ ID NOS 22, 14, 13, and 13, respectively, in order of appearance.

FIG. 7A: Docking pose of N-Me-AVPF-NH$_2$(SEQ ID NO: 7) into the binding pocket of the BIR3 domain of XIAP (PDB ID 2OPZ). FIG. 7B: Isothermal Titration Calorimetry (ITC) curve for the binding between the BIR3 domain of XIAP and N-Me-AVPF-NH$_2$ (SEQ ID NO: 7). FIG. 7C: DELFIA displacement curves relative to the compound N-Me-AVPF-NH$_2$ (SEQ ID NO: 7) tested against the BIR3 domains of XIAP, cIAP1, and cIAP2, respectively (IC$_{50}$ values 108.2 nM, 48.2 nM, and 209 nM, for XIAP, cIAP1, and cIAP2, respectively). FIG. 7D: Docking pose of the clinical compound LCL161 into the binding pocket of the BIR3 domain of XIAP (PDB ID 2OPZ). FIG. 7E: Isothermal Titration Calorimetry (ITC) curve for the interaction between the BIR3 domain of XIAP and LCL161. FIG. 7F: DELFIA displacement curves relative to the compound LCL161 tested against the BIR3 domains of XIAP, cIAP1, and cIAP2 (IC$_{50}$ values 52.7 nM, 10.4 nM, and 12.9 nM, for XIAP, cIAP1, and cIAP2, respectively). FIG. 7G: Docking pose of the compound 1 into the binding pocket of the BIR3 domain of XIAP (PDB ID 2OPZ). The XIAP BIR3 residue Lys311, interacting with the phosphonate group, is highlighted. FIG. 7H: Isothermal Titration Calorimetry (ITC) curve for the binding between the BIR3 domain of XIAP and compound 1. FIG. 7I: DELFIA displacement curves relative to the compound 1 tested against the BIR3 domain of XIAP, cIAP1, and cIAP2 (IC$_{50}$ values 35 nM, 197.6 nM, and 364.3 nM, for XIAP, cIAP1, and cIAP2, respectively).

FIG. 8A: Craig plot of $\delta(-T\Delta S)$ as function of $\delta(\Delta H)$, showing the difference in term of thermodynamics parameters in respect to the reference compound N-Me-AVPF-NH$_2$(SEQ ID NO: 7). Compounds on or near the diagonal (solid line) are expected to possess a similar affinity of the reference peptide; compounds falling below the diagonal will present an increase in activity, while agents falling above the diagonal will be less potent than N-Me-AVPF-NH$_2$ (SEQ ID NO: 7). Compounds that differ from N-Me-AVPF-NH$_2$ (SEQ ID NO: 7) in position P2 are depicted as circles, while those that differ at the P3/P4 position are depicted as triangles; the compounds resulted from the combination of different P2 and P3/P4 substituents are depicted as squares. FIG. 8B: Schematic representation of the combination of compounds with P2 and P3/P4 substituents selected based on the thermodynamic Craig plot analysis. On the left, the combination of the P2 element of compound 2 with the P3/P4 element of compound 19 resulted in compound 22 designed to be more selective for XIAP compared to cIAP1/2. On the right, the combination of the P2 element of compound 14 with the P3/P4 element of compound 17 resulted in compound 31 designed to be a pan agent for IAPs. FIG. 8C: Correlation plot between predicted (based on the thermodynamics Craig plot) and experimental thermodynamic values for the compounds synthesized. FIG. 8D: Isothermal Titration Calorimetry (ITC) curve for the binding between the BIR3 domain of XIAP and compound 22 (left panel) or compound 31 (right panel). FIG. 8E: DELFIA displacement curves relative to the compounds compound 22 (left panel) and compound 31 (right panel) tested against the BIR3 domain of XIAP, cIAP1, and cIAP2. The IC$_{50}$ values for compound 22 are 191 nM, >1000 nM, and >1000 nM, against the BIR3 domain of XIAP, cIAP1, and cIAP2, respectively. The IC$_{50}$ values for compound 31 are 37.1 nM, 4.5 nM, and 15 nM, against the BIR3 domain of XIAP, cIAP1, and cIAP2, respectively.

FIG. 9A: Covalent docking pose of compound 32 into the binding pocket of the BIR3 domain of XIAP (PDB ID 2OPZ). The Lysine 311 forming the covalent bond with compound 32 is highlighted. FIG. 9B: SDS-PAGE gel electrophoresis followed by Coomassie staining of the BIR3 domain of XIAP in the absence and presence of compound 32 after 10 minutes incubation at RT and at a protein-ligand ratio 1:2. FIG. 9C: LC-MS spectra of the BIR3 domain of XIAP in the absence (top) and presence (bottom) of compound 32 at a protein-ligand ratio 1:2. FIG. 9D: DELFIA displacement curves relative to the compound 32 tested against the BIR3 domain of XIAP, cIAP1, and cIAP2. The IC$_{50}$ values for compound 32 are 11.3 nM, 180.4 nM, and 306.7 nM, against the BIR3 domain of XIAP, cIAP1, and cIAP2, respectively. FIG. 9E: Covalent docking pose of compound 34 into the binding pocket of the BIR3 domain of XIAP (PDB ID 2OPZ). The Lysine 311 forming the covalent bond with compound 34 is highlighted. FIG. 9F: SDS-PAGE gel electrophoresis followed by Coomassie staining of the BIR3 domain of XIAP in the absence and presence of compound 34 and the diastereoisomer 34* after 10 minutes incubation at RT and at a protein-ligand ratio 1:2. FIG. 9G: LC-MS spectra of the BIR3 domain of XIAP in absence (top) and in presence (bottom) of compound 34 at a protein-ligand ratio 1:2. FIG. 9H: DELFIA displacement curves relative to the compound 34 tested against the BIR3 domain of XIAP, cIAP1, and cIAP2. The IC$_{50}$ values for compound 34 are 16.6 nM, >200 nM, and 353.3 nM, against the BIR3 domain of XIAP, cIAP1, and cIAP2, respectively. FIG. 9I: SDS-PAGE gel electrophoresis followed by Coomassie staining of the BIR3 domain of XIAP, XIAP-BIR3 K311E, and XIAP-BIR3 K322A in the absence and presence of compound 34 after 10 minutes incubation at RT and at a protein-ligand ratio 1:2. FIG. 9J: SDS-PAGE gel electrophoresis followed by Coomassie staining of the BIR3 domain of XIAP, cIAP1, and cIAP2 in the absence and presence of compound 34 after 10 minutes incubation at RT and at a protein-ligand ratio 1:2. FIG. 9K: Dose-response curves in DELFIA displacement assays for compound 34 against XIAP-BIR3, XIAP-BIR3 K311E, and XIAP-BIR3 K322A, respectively ($IC_{50}$ values 16.6 nM, 1039 nM, and 19.7 nM, for XIAP-BIR3, XIAP-BIR3 K311E, and XIAP-BIR3 K322A, respectively).

FIG. 10A: Cell viability of ALL cell line MOLT-4 cells was assessed after treating them with the indicated compounds for 48 hrs. Error bars are SD of triplicate readouts. FIG. 10B: IAP inhibitors induce degradation of IAP protein levels. MOLT-4 cells were treated for 3 hr with 1 µM and propped for XIAP, cIAP1 or cIAP2. The β-actin blot was detected to ensure equal sample loading. FIG. 10C: Multiple myeloma cell lines were treated for 48 hr with the indicated compounds at 20 µM concentration. Error bars are SD of triplicate readouts. FIG. 10D: Western blot analysis of the basal expression level of XIAP, cIAP1, and cIAP2 in pancreatic cancer cell lines BxPC3, PANC-1 and MIA PaCa-2. The β-actin blot was detected to ensure equal sample loading. FIG. 10E: Compound 34 and compound 31 significantly sensitize pancreatic cancer cell lines to gemcitabine (GEM). Cells were first treated with two doses of GEM or DMSO for 24 hrs. Next day, media was replenished with the co-treatment media containing GEM and 15 µM of the indicated IAP inhibitors for additional 24 hrs. Error bars are SD of quadruplicate readouts. *, $P<0.05$; , $P<0.005$, *, $P<0.0005$, and ****  $P<10^{-5}$.

DETAILED DESCRIPTION

Figure 1:
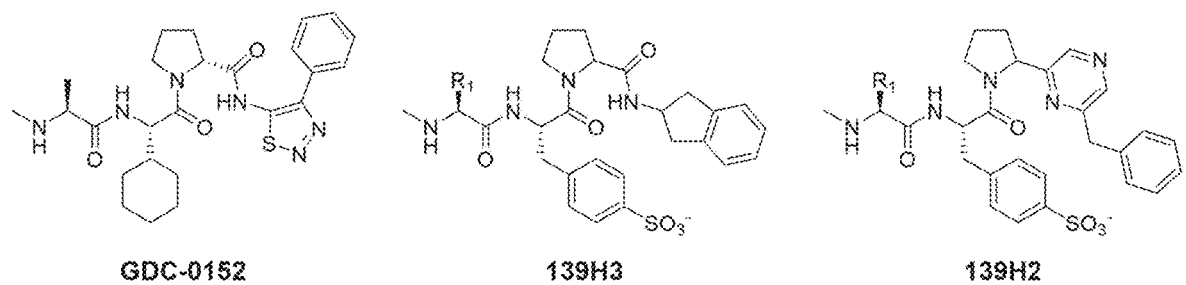
FIG. 1. Compounds 139H3 and 139H2 are XIAP Bir3 selective. Pan active compound GDG-0152 is showed as reference.

Disclosed herein, inter alia, are novel composition and methods of use of these compounds for anticancer therapies targeting broadly and/or selectively the Bir3 or Bir2 domains of the proteins XIAP, cIAP1, or cIAP2. The compounds described herein target the Smac binding site of a variety of inhibitor of apoptosis proteins that contain a Bir domain, including XIAP, cIAP1 and cIAP2. These agents inhibit these proteins with various selectivity and potencies, including the Bir2 and Bir3 domains of XIAP, and the Bir3 domains of cIAP1 and cIAP2, for example. These compounds differ from previously reported molecules both chemically and with respect to their selectivity against these targets.

I. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—

CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, benzocyclopentyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ⌇⌇⌇ " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

An alkylarylene moiety may be substituted (e.g. with a substituent group) on the alkylene moiety or the arylene linker (e.g., at carbons 2, 3, 4, or 6) with, for example, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$NHNH_2$, —$ONH_2$, —NHC(O)$NHNH_2$, —$SO_2F$, $SO_2Cl$, —$SO_2Br$, —$SO_2I$, substituted or unsubstituted $C_1$-$C_5$ alkyl or substituted or unsubstituted 2 to 5 membered heteroalkyl). In embodiments, the alkylarylene is unsubstituted.

The term "alkylheteroarylene" as a heteroarylene moiety covalently bonded to an alkylene moiety (also referred to herein as an alkylene linker). In embodiments, the alkylheteroarylene group has the formula:

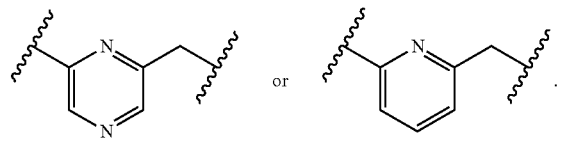 [SMILES: *Cc1cncc(*)n1 ; *Cc1cccc(*)n1]

A alkylheteroarylene moiety may be substituted (e.g., with a substituent group) on the alkylene moiety or the heteroarylene linker with, for example, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, —$SO_2F$, $SO_2Cl$, —$SO_2Br$, —$SO_2I$, substituted or unsubstituted $C_1$-$C_5$ alkyl or substituted or unsubstituted 2 to 5 membered heteroalkyl). In embodiments, the alkylheteroarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula-T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula-A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), boroin (B), and silicon (Si).

A "substituent group," as used herein, means a group selected from the following moieties:

(A) oxo, halogen, —SO$_2$F, SO$_2$Cl, —SO$_2$Br, —SO$_2$I, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O) H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
  (i) oxo, halogen, —SO$_2$F, SO$_2$Cl, —SO$_2$Br, —SO$_2$I, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
  (ii) alkyl, heteroalkyl, cycloalkyl, heterocycloalkyl, aryl, heteroaryl, substituted with at least one substituent selected from:
    (a) oxo, halogen, —SO$_2$F, SO$_2$Cl, —SO$_2$Br, —SO$_2$I, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —SO$_2$F, SO$_2$Cl, —SO$_2$Br, —SO$_2$I, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_5$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound is a chemical species set forth in the claims, Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)— or (S)— or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

The term "covalent modifier" is used in accordance with its common meaning in chemistry and refers to a chemical group capable of forming a covalent bond with a second chemical group. In embodiments, a covalent modifier is a chemical group capable of forming a covalent bond with an amino acid or protein (e.g., a side chain of an amino acid, for example, lysine or cysteine). A "covalent modifier moiety" is a monovalent covalent modifier. In embodiments, a covalent modifier is an electrophile and the covalent modifier is capable of contacting a nucleophile and forming a covalent bond with the nucleophile.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). A bioconjugate reactive group is a group capable of forming a bioconjugate in a bioconjugate reaction. A bioconjugate reactive moiety is a monovalent bioconjugate reactive group.

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds;

(n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "treating" or "treatment" refers to any indicia of success in the treatment or amelioration of an injury, disease (e.g., cancer), pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term "treating" and conjugations thereof, include prevention of an injury, pathology, condition, or disease. In embodiments, treating does not include preventing.

An "effective amount" is an amount sufficient for a compound to accomplish a stated purpose relative to the absence of the compound (e.g., achieve the effect for which it is administered, treat a disease, reduce enzyme activity, increase enzyme activity, reduce signaling pathway, reduce one or more symptoms of a disease or condition (e.g., reduce signaling pathway stimulated by XIAP, cIAP1, or cIAP2, or reduce the signaling pathway activity of XIAP, cIAP1, or cIAP2). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g., signaling pathway) of a protein in the absence of a compound as described herein (including embodiments, examples, figures, or Tables).

"Contacting" is used in accordance with its plain ordinary meaning and refers to the process of allowing at least two distinct species (e.g., chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g., XIAP, cIAP1, or cIAP2). In some embodiments contacting includes allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g., decreasing) the activity or function of the protein (e.g., decreasing the signaling pathway stimulated by XIAP, cIAP1, or cIAP2; or decreasing the inhibitory activity on a signaling pathway of XIAP, cIAP1, or cIAP2), relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway (e.g., reduction of a pathway involving XIAP, cIAP1, or cIAP2). Thus, inhibition includes, at least in part, partially or totally blocking stimulation, decreasing, preventing, or delaying activation, or inactivating, desensitizing, or down-regulating the signaling pathway or enzymatic activity or the amount of a protein (e.g., XIAP, cIAP1, or cIAP2).

The term "modulator" refers to a composition that increases or decreases the level of a target molecule or the function of a target molecule or the physical state of the target of the molecule (e.g., a target may be XIAP, cIAP1, or cIAP2) relative to a control (e.g., the absence of the composition).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g., caused by) a XIAP, cIAP1, or cIAP2. In some embodiments, the disease is a disease related to (e.g., caused by) a XIAP, cIAP1, or cIAP2 signaling pathway activity. In some embodiments, the disease is a disease related to (e.g., caused by) the overexpression of XIAP, cIAP1, or cIAP2 signaling pathway activity. Examples of diseases, disorders, or conditions include, but are not limited to cancer. In some instances, "disease" or "condition" refers to cancer. In some further instances, "cancer" refers to human cancers and carcinomas, sarcomas, adenocarcinomas, lymphomas, leukemias, etc., including solid and lymphoid cancers, kidney, breast, lung, bladder, colon, endometrial, esophageal, gastric, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the cancer is leukemia and lymphoma, including AML, ALL, CML, CLL, multiple myeloma, solid tumor breast cancer, triple negative breast cancer, HER-2 negative metastatic breast cancer, cervical cancer, colorectal cancer, endometrial cancer, esophageal cancer, gastric cancer, glioma, hepatocellular carcinoma, head and neck cancer, liver cancer, lung cancer, lymphoma, melanoma, myelodysplastic syndromes, ovarian cancer, pancreatic cancer, prostate cancer, renal cancer, skin cancer, stomach cancer, testis cancer, thyroid cancer, urothelial cancer, or all relapsing and/or chemoresistant and/or radiation resistant cancers that are driven by XIAP overexpression, including those with caspase 3 deletion.

As used herein, the term "cancer" refers to all types of cancer, neoplasm or malignant tumors found in mammals (e.g., humans), including leukemia, lymphomas, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is leukemia and lymphoma, including AML, ALL, CML, CLL, multiple myeloma, bladder cancer, brain gliomas, solid tumor breast cancer, triple negative breast cancer, HER-2 negative metastatic breast cancer, cervical cancer, colorectal cancer, endometrial cancer, esophageal cancer, gastric cancer, gastrointestinal stromal tumorglioma, head and neck cancer, hepatocellular carcinoma, liver cancer, lung cancer, lymphoma, melanoma, myelodysplastic syndromes, ovarian cancer, pancreatic cancer, prostate cancer, renal cancer, skin cancer, stomach cancer, testis cancer, thyroid cancer, urothelial cancer, or all relapsing and/or chemoresistant and/or radiation resistant cancers that are driven by XIAP overexpression, including those with caspase 3 deletion.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "lymphoma" refers to a neoplasm of the hematopoietic and lymphoid tissues (e.g., blood, bone marrow, lymph, or lymph tissues). Non-limiting examples of lymphoma include B-acute lymphoblastic lymphoma, non-Hodgkin's lymphomas (e.g., Burkitt's, Small Cell, and Large Cell lymphomas), or Hodgkin's lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

"XIAP associated cancer" (also referred to herein as "XIAP related cancer") refers to a cancer caused by aberrant XIAP activity or signaling or a cancer that may be treated by inhibiting XIAP activity (e.g., normal activity or aberrant). Other cancers that are associated with aberrant activity of XIAP are well known in the art (see, Mohamed et al., Apoptosis 2017, 22, 1487-1509) and determining such cancers are within the skill of a person of skill in the art.

"cIAP1 associated cancer" (also referred to herein as "cIAP1 related cancer") refers to a cancer caused by aberrant cIAP1 activity or signaling or a cancer that may be treated by inhibiting cIAP1 activity (e.g., normal activity or aberrant). Other cancers that are associated with aberrant activity of cIAP1 are well known in the art and determining such cancers are within the skill of a person of skill in the art.

"cIAP2 associated cancer" (also referred to herein as "cIAP2 related cancer") refers to a cancer caused by aberrant cIAP2 activity or signaling or a cancer that may be treated by inhibiting cIAP2 activity (e.g., normal activity or aberrant). Other cancers that are associated with aberrant activity of cIAP2 are well known in the art and determining such cancers are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

The compounds described herein can be used in combination with one another, with other active agents known to be useful in treating a disease associated with cells expressing XIAP, cIAP1, and/or cIAP2 (e.g., XIAP, cIAP1, and/or cIAP2 associated cancer) or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxalopatin, carboplatin, etc.), and the like. In embodiments, the compound described herein may be co-administered with a Bcl-2 family antagonist (e.g., venetoclax or navitoclax) which are described further in Lessene et al, Nat Rev Drug Discov. 2008 December; 7(12):989-1000, which is incorporated herein in its entirety for all purposes.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In therapeutic use for the treatment of cancer, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer or with adjunctive agents that may not be effective alone, but may contribute to the efficacy of the active agent.

The term "associated" or "associated with" in the context of a substance or substance activity or function associated with a disease (e.g., a protein associated disease, a cancer associated with aberrant XIAP activity, XIAP associated cancer, mutant XIAP associated cancer, activated XIAP associated cancer, aberrant cIAP1 activity, cIAP1 associated cancer, mutant cIAP1 associated cancer, activated cIAP1 associated cancer, aberrant cIAP2 activity, cIAP2 associated cancer, mutant cIAP2 associated cancer, activated cIAP2 associated cancer) means that the disease (e.g., cancer) is caused by (in whole or in part), or a symptom of the disease is caused by (in whole or inpart) the substance or substance activity or function. For example, a cancer associated with aberrant XIAP activity or function may be a cancer that results (entirely or partially) from aberrant XIAP activity or function (e.g., enzyme activity, protein-protein interaction, signaling pathway) or a cancer wherein a particular symptom of the disease is caused (entirely or partially) by aberrant XIAP activity or function. As used herein, what is described as being associated with a disease, if a causative agent, could be a target for treatment of the disease. For example, a cancer associated with aberrant XIAP activity or function or an XIAP associated cancer, may be treated with a XIAP modulator or XIAP inhibitor, in the instance where increased XIAP activity or function (e.g., signaling pathway activity) causes the cancer.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

"Anti-cancer agent" is used in accordance with its plain ordinary meaning and refers to a composition (e.g., compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "electrophilic" as used herein refers to a chemical group that is capable of accepting electron density. An "electrophilic substituent", "electrophilic chemical moiety", or "electrophic moiety" refers to an electron-poor chemical group, substituent, or moiety (monovalent chemical group), which may react with an electron-donating group, such as a nucleophile, by accepting an electron pair or electron density to form a bond. In some embodiments, the electrophilic substituent of the compound is capable of reacting with a cysteine residue. In some embodiments, the electrophilic substituent is capable of forming a covalent bond with a cysteine residue (e.g., XIAP cysteine residue, cIAP1 cysteine residue, cIAP2 cysteine residue) and may be referred to as a "covalent cysteine modifier moiety" or "covalent cysteine modifier substituent". The covalent bond formed between the electrophilic substituent and the sulfhydryl group of the cysteine may be a reversible or irreversible bond. In some embodiments, the electrophilic substituent is capable of forming a covalent bond with a lysine residue (e.g., XIAP lysine residue) and may be referred to as a "covalent lysine modifier moiety" or "covalent lysine modifier substituent".

"Nucleophilic" as used herein refers to a chemical group that is capable of donating electron density.

The term "signaling pathway" as used herein refers to a series of interactions between cellular and optionally extracellular components (e.g., proteins, nucleic acids, small molecules, ions, lipids) that conveys a change in one component to one or more other components, which in turn may convey a change to additional components, which is optionally propagated to other signaling pathway components. For example, binding of a XIAP, cIAP1, or cIAP2 protein (e.g., to a BIR domain such as BIR3 or BIR2) with a compound as described herein may result in a change in one or more protein-protein interactions of XIAP, cIAP1, or cIAP2 (e.g., with caspase-3, caspase-7, and/or caspase-9) or interactions between the XIAP, cIAP1, or cIAP2 and a membrane, resulting in changes in cell growth, proliferation, or survival.

The term "apoptosis inducing agent" is used in accordance with its common meaning in biology and refers to an agent capable of increasing apoptosis (e.g., relative to the absence of the agent, in a cell, when contacting a protein, when contacting a cell).

The term "Bcl-2 (B-cell lymphoma 2) family antagonist" is used in accordance with its common meaning in biology and refers to an agent capable of decreasing (e.g., inhibiting) the activity or function of a Bcl-2 family protein relative to the absence of a Bcl-2 family antagonist, wherein a Bcl-2 family protein is a protein including a Bcl-2 homology domain. In embodiments, a Bcl-2 family protein regulates apoptosis. In embodiments a Bcl-2 family protein modulates mitochondrial outer membrane permeabilization. In embodiments, a Bcl-2 family antagonist is capable of contacting a Bcl-2 family protein and reducing the activity or function of the Bcl-2 family protein (e.g., relative to absence of the Bcl-2 family antagonist).

The terms "XIAP" and "X-linked inhibitor of apoptosis protein" refer to a protein (including homologs, isoforms, and functional fragments thereof) also known as inhibitor of apoptosis protein 3 (IAP3) and baculoviral IAP repeat-containing protein 4 (BIRC4), is a protein involved in cellular apoptotic death, which includes one or more BIR domains (e.g., BIR2 domain or BIR3 domain). In embodiments, the XIAP protein encoded by the XIAP gene has the amino acid sequence set forth in or corresponding to Entrez 331, UniProt P98170, RefSeq (protein) NP_001191330, or RefSeq (protein) NP_001158 (SEQ ID NO:1). In embodiments, the XIAP gene has the nucleic acid sequence set forth in RefSeq (mRNA) NM_001167.3. In embodiments, the XIAP gene has the nucleic acid sequence set forth in RefSeq (mRNA) NM_001204401.1. In embodiments, the XIAP protein refers to amino acid sequence NP_001158.2. In embodiments, the XIAP protein refers to amino acid sequence NP_001191330.1. In embodiments, the XIAP protein has the following amino acid sequence:

(SEQ ID NO: 1)
MTFNSFEGSKTCVPADINKEEEFVEEFNRLKTFANFPSGSPVSASTLARA

GFLYTGEGDTVRCFSCHAAVDRWQYGDSAVGRHRKVSPNCRFINGFYLEN

SATQSTNSGIQNGQYKVENYLGSRDHFALDRPSETHADYLLRTGQVVDIS

DTIYPRNPAMYSEEARLKSFQNWPDYAHLTPRELASAGLYYTGIGDQVQC

FCCGGKLKNWEPCDRAWSEHRRHFPNCFFVLGRNLNIRSESDAVSSDRNF

PNSTNLPRNPSMADYEARIFTFGTWIYSVNKEQLARAGFYALGEGDKVKC

-continued
FHCGGGLTDWKPSEDPWEQHAKWYPGCKYLLEQKGQEYINNIHLTHSLEE

CLVRTTEKTPSLTRRIDDTIFQNPMVQEAIRMGFSFKDIKKIMEEKIQIS

GSNYKSLEVLVADLVNAQKDSMQDESSQTSLQKEISTEEQLRRLQEEKLC

KICMDRNIAIVFVPCGHLVTCKQCAEAVDKCPMCYTVITFKQKIFMS

The terms "cIAP1" and "cellular inhibitor of apoptosis protein 1" refer to a protein (including homologs, isoforms, and functional fragments thereof) also known as baculoviral IAP repeat-containing protein 2 (BIRC2), is a protein involved in cellular apoptotic death, which includes one or more BIR domains (e.g., BIR2 domain or BIR3 domain). In embodiments, the cIAP1 protein has the amino acid sequence set forth in or corresponding to Entrez 329, Uni-Prot Q13490, RefSeq (mRNA) NM 001256163, RefSeq (mRNA) NM_001166, RefSeq (protein) NP_001157, or RefSeq (protein) NP_001243092 (SEQ ID NO:2). In embodiments, the cIAP1 the nucleic acid sequence set forth in RefSeq (mRNA) NM_001256163.1. In embodiments, the cIAP1 the nucleic acid sequence set forth in RefSeq (mRNA) NM_001166.4. In embodiments, the cIAP1 protein refers to amino acid sequence NP_001157.1. In embodiments, the cIAP1 protein refers to amino acid sequence NP_001243092.1. In embodiments, the cIAP1 protein has the following amino acid sequence:

(SEQ ID NO: 2)
MHKTASQRLFPGPSYQNIKSIMEDSTILSDWTNSNKQKMKYDFSCELYRM

STYSTFPAGVPVSERSLARAGFYYTGVNDKVKCFCCGLMLDNWKLGDSPI

QKHKQLYPSCSFIQNLVSASLGSTSKNTSPMRNSFAHSLSPTLEHSSLFS

GSYSSLSPNPLNSRAVEDISSSRTNPYSYAMSTEEARFLTYHMWPLTFLS

PSELARAGFYYIGPGDRVACFACGGKLSNWEPKDDAMSEHRRHFPNCPFL

ENSLETLRFSISNLSMQTHAARMRTFMYWPSSVPVQPEQLASAGFYYVGR

NDDVKCFCCDGGLRCWESGDDPWVEHAKWFPRCEFLIRMKGQEFVDEIQG

RYPHLLEQLLSTSDTTGEENADPPIIHFGPGESSSEDAVMMNTPVVKSAL

EMGFNRDLVKQTVQSKILTTGENYKTVNDIVSALLNAEDEKREEEKEKQA

EEMASDDLSLIRKNRMALFQQLTCVLPILDNLLKANVINKQEHDIIKQKT

QIPLQARELIDTILVKGNAAANIFKNCLKEIDSTLYKNLFVDKNMKYIPT

EDVSGLSLEEQLRRLQEERTCKVCMDKEVSVVFIPCGHLVVCQECAPSLR

KCPICRGIIKGTVRTFLS

The terms "cIAP2" and "cellular inhibitor of apoptosis protein 2" refer to a protein (including homologs, isoforms, and functional fragments thereof) also known as baculoviral IAP repeat-containing protein 3 (BIRC3), is a protein involved in cellular apoptotic death, which includes one or more BIR domains (e.g., BIR2 domain or BIR3 domain). In embodiments, the cIAP2 protein has the amino acid sequence set forth in or corresponding to Entrez 330, Uni-Prot Q13489, RefSeq (mRNA) NM 001165, RefSeq (mRNA) NM 182962, RefSeq (protein) NP_001156, or RefSeq (protein) NP_892007 (SEQ ID NO:3). In embodiments, the cIAP2 the nucleic acid sequence set forth in RefSeq (mRNA) NM_001165.4. In embodiments, the cIAP2 the nucleic acid sequence set forth in RefSeq (mRNA) NM_182962.2. In embodiments, the cIAP2 protein refers to amino acid sequence NP_001156.1. In embodiments, the cIAP2 protein refers to amino acid sequence NP_892007.1. In embodiments, inhibiting the activity of cIAP2 is modulates the apoptotic pathway (e.g., modulating the activity or function of CASP9, RIPK1, TRAF1, TRAF2, or UBE2D2). In embodiments, the cIAP2 protein has the following amino acid sequence:

(SEQ ID NO: 3)
MNIVENSIFLSNLMKSANTFELKYDLSCELYRMSTYSTFPAGVPVSERSL

ARAGFYYTGVNDKVKCFCCGLMLDNWKRGDSPTEKHKKLYPSCRFVQSLN

SVNNLEATSQPTFPSSVTNSTHSLLPGTENSGYFRGSYSNSPSNPVNSRA

NQDFSALMRSSYHCAMNNENARLLTFQTWPLTFLSPTDLAKAGFYYIGPG

DRVACFACGGKLSNWEPKDNAMSEHLRHFPKCPFIENQLQDTSRYTVSNL

SMQTHAARFKTFFNWPSSVLVNPEQLASAGFYYVGNSDDVKCFCCDGGLR

CWESGDDPWVQHAKWFPRCEYLIRIKGQEFIRQVQASYPHLLEQLLSTSD

SPGDENAESSIIHFEPGEDHSEDAIMMNTPVINAAVEMGFSRSLVKQTVQ

RKILATGENYRLVNDLVLDLLNAEDEIREEERERATEEKESNDLLLIRKN

RMALFQHLTCVIPILDSLLTAGIINEQEHDVIKQKTQTSLQARELIDTIL

VKGNIAATVFRNSLQEAEAVLYEHLFVQQDIKYIPTEDVSDLPVEEQLRR

LQEERTCKVCMDKEVSIVFIPCGHLVVCKDCAPSLRKCPICRSTIKGTVR

TFLS

The term "BIR domain" is used in accordance with its plain ordinary meaning and refers to baculoviral IAP repeat (BIR) domain, a domain a structural motif found in proteins (e.g., proteins involved in the apoptotic pathway) typically including 3 conserved cysteines and one conserved histidine, which coordinate a zinc ion. Non-limiting examples of proteins containing BIR are known as inhibitor of apoptosis proteins (IAPs), BIRC1 (NAIP), BIRC2 (cIAP1), BIRC3 (cIAP2), BIRC4 (XIAP), BIRC5 or BIRC6.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e., a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g., triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^6$ and a substituent on the divalent linker) are allowed to contact such that the leaving groups are sufficiently proximal to react, interact or physically touch. In embodiments, the leaving groups is designed to facilitate the reaction.

II. COMPOUNDS AND COMPOSITIONS

In an aspect is provided a compound, or a pharmaceutical salt thereof, or a prodrug thereof, having the formula:

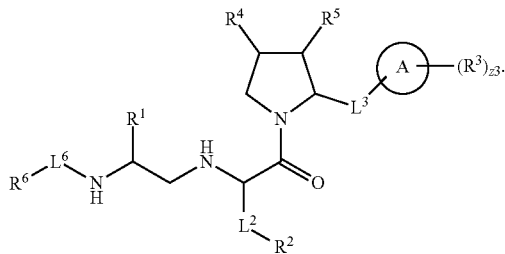

$R^1$ is —$CX^1_3$, —$CHX^1_2$, —$CH_2X^1$, substituted or unsubstituted $C_1$-$C_4$ alkyl. $L^2$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^2$ is independently hydrogen, halogen, —$CX^2_3$, —$CHX^2_2$, —$CH_2X^2$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^2_3$, —$OCHX^2_2$, —$OCH_2X^2$, —$SO_2CH_3$, —$SO_2CX^2_3$, —$SO_2CH_3$, —$SO_2X^2$, —$SO_2CH$=$CH_2$, —$NHSO_2CH$=$CH_2$, —$OSO_2X^2$, —$NHSO_2X^2$, —$B(OH)_2$, —CO-oxiranyl, —CO-aziridinyl, epoxidinyl, oxaziridinyl, aziridinyl, —$OCH_2C$≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^3$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, or substituted or unsubstituted alkylheteroarylene. Ring A is a cycloalkyl, heterocycloalkyl, aryl, or heteroaryl. $R^3$ is independently halogen, —$CX^3_3$, —$CHX^3_2$, —$CH_2X^3$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^3_3$, —$OCHX^3_2$, —$OCH_2X^3$, —$SO_2X^3$, —$SO_2CH$=$CH_2$, —$NHSO_2CH$=$CH_2$, —$OSO_2X^3$, —$NHSO_2X^3$, —$B(OH)_2$, —CO-oxiranyl, —CO-aziridinyl, epoxidinyl, oxaziridinyl, aziridinyl, —$OCH_2C$≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. $R^4$ is independently hydrogen, halogen, —$CX^4_3$, —$CHX^4_2$, —$CH_2X^4$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^4_3$, —$OCHX^4_2$, —$OCH_2X^4$, —NHC(NH)$NH_2$, —$SO_2X^4$, —$SO_2CH$=$CH_2$, —$NHSO_2CH$=$CH_2$, —$OSO_2X^4$, —$NHSO_2X^4$, —$B(OH)_2$, —CO-oxiranyl, —CO-aziridinyl, epoxidinyl, oxaziridinyl, aziridinyl, —$OCH_2C$≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently hydrogen, halogen, —$CX^5_3$, —$CHX^5_2$, —$CH_2X^5$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^5_3$, —$OCHX^5_2$, —$OCH_2X^5$, —NHC(NH)$NH_2$, —$SO_2X^5$, —$SO_2CH$=$CH_2$, —$NHSO_2CH$=$CH_2$, —$OSO_2X^5$, —$NHSO_2X^5$, —$B(OH)_2$, —CO— oxiranyl, —CO-aziridinyl, epoxidinyl, oxaziridinyl, aziridinyl, —$OCH_2C$≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^6$ is a bond or unsubstituted methylene. $R^6$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $X^1$, $X^2$, $X^3$, $X^4$, and $X^5$ is independently —F, —Cl, —Br, or —I. The symbol z3 is independently an integer from 0 to 3.

In embodiments, the compound, or a pharmaceutical salt thereof, or a prodrug thereof, has the formula:

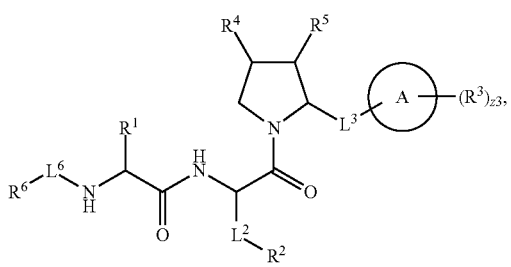

wherein $R^1$ is —$CX^1_3$, —$CHX^1_2$, —$CH_2X^1$, substituted or unsubstituted $C_1$-$C_4$ alkyl; $L^2$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, or unsubstituted heterocycloalkylene, substituted or unsubstituted arylene, or substituted or unsubstituted heteroarylene; $R^2$ is independently substituted or unsubstituted aryl, or substituted or unsubstituted heteroaryl; $L^3$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene; Ring A is a cycloalkyl, heterocycloalkyl, aryl, or heteroaryl; $R^3$ is independently halogen, $-CX^3{}_3$, $-CHX^3{}_2$, $-CH_2X^3$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^3{}_3$, $-OCHX^3{}_2$, $-OCH_2X^3$, $-SO_2X^3$, $-SO_2CH=CH_2$, $-NHSO_2CH=CH_2$, $-OSO_2X^3$, $-NHSO_2X^3$, $-B(OH)_2$, $-CO$-oxiranyl, $-CO$-aziridinyl, epoxidinyl, oxaziridinyl, aziridinyl, $-OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^4$ is independently hydrogen, halogen, $-CX^4{}_3$, $-CHX^4{}_2$, $-CH_2X^4$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4{}_3$, $-OCHX^4{}_2$, $-OCH_2X^4$, $-NHC(NH)NH_2$, $-SO_2X^4$, $-SO_2CH=CH_2$, $-NHSO_2CH=CH_2$, $-OSO_2X^4$, $-NHSO_2X^4$, $-B(OH)_2$, $-CO$-oxiranyl, $-CO$-aziridinyl, epoxidinyl, oxaziridinyl, aziridinyl, $-OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently hydrogen, halogen, $-CX^5{}_3$, $-CHX^5{}_2$, $-CH_2X^5$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^5{}_3$, $-OCHX^5{}_2$, $-OCH_2X^5$, $-NHC(NH)NH_2$, $-SO_2X^5$, $-SO_2CH=CH_2$, $-NHSO_2CH=CH_2$, $-OSO_2X^5$, $-NHSO_2X^5$, $-B(OH)_2$, $-CO$- oxiranyl, $-CO$-aziridinyl, epoxidinyl, oxaziridinyl, aziridinyl, $-OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^6$ is a bond or unsubstituted methylene; $R^6$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $X^1$, $X^2$, $X^3$, $X^4$, and $X^5$ is independently $-F$, $-Cl$, $-Br$, or $-I$. The symbol z3 is independently an integer from 0 to 3.

In embodiments, the compound, or a pharmaceutical salt thereof, or a prodrug thereof, has the formula:

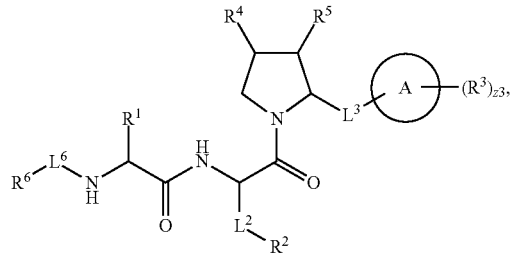

wherein at least one of $R^2$, $R^3$, $R^4$, or $R^5$ includes a covalent modifier moiety selected from $-SO_2CH=CH_2$, $-SO_2X$, $-NHSO_2CH=CH_2$, $-OSO_2X$, $-B(OH)_2$, $-NHSO_2X$, or $-CH_2X$; wherein X is independently $-F$, $-Cl$, $-Br$, or $-I$; and wherein Ring A, $L^3$, $L^6$, $R^6$, $R^1$, $L^2$, $R^2$, $R^4$, $R^5$, $R^3$, and z3 are as described herein, including embodiments. In embodiments, only one of $R^2$, $R^3$, $R^4$, or $R^5$ includes a covalent modifier moiety. In embodiments, more than one (e.g., 2, 3, or 4) of $R^2$, $R^3$, $R^4$, or $R^5$ includes a covalent modifier moiety. In embodiments, at least one of $R^2$, $R^3$, $R^4$, or $R^5$ includes $-SO_2CH=CH_2$, $-SO_2X$, $-NHSO_2CH=CH_2$, $-OSO_2X$, $-B(OH)_2$, $-NHSO_2X$, or $-CH_2X$. In embodiments, $R^2$ includes $-SO_2CH=CH_2$, $-SO_2X$, $-NHSO_2CH=CH_2$, $-OSO_2X$, $-B(OH)_2$, $-NHSO_2X$, or $-CH_2X$. In embodiments, $R^3$ includes $-SO_2CH=CH_2$, $-SO_2X$, $-NHSO_2CH=CH_2$, $-OSO_2X$, $-B(OH)_2$, $-NHSO_2X$, or $-CH_2X$. In embodiments, $R^4$ includes $-SO_2CH=CH_2$, $-SO_2X$, $-NHSO_2CH=CH_2$, $-OSO_2X$, $-B(OH)_2$, $-NHSO_2X$, or $-CH_2X$. In embodiments, $R^5$ includes $-SO_2CH=CH_2$, $-SO_2X$, $-NHSO_2CH=CH_2$, $-OSO_2X$, $-B(OH)_2$, $-NHSO_2X$, or $-CH_2X$. In embodiments, at least one of $R^2$, $R^3$, $R^4$, or $R^5$ is $-SO_2CH=CH_2$, $-SO_2X$, $-NHSO_2CH=CH_2$, $-OSO_2X$, $-B(OH)_2$, $-NHSO_2X$, $-CH_2X$, $-CO$-oxiranyl, $-CO$- aziridinyl, epoxidinyl, oxaziridinyl, aziridinyl, or $-OCH_2C\equiv CH$. In embodiments, $R^2$ is $-SO_2CH=CH_2$, $-SO_2X$, $-NHSO_2CH=CH_2$, $-OSO_2X$, $-B(OH)_2$, $-NHSO_2X$, or $-CH_2X$. In embodiments, $R^3$ is $-SO_2CH=CH_2$, $-SO_2X$, $-NHSO_2CH=CH_2$, $-OSO_2X$, $-B(OH)_2$, $-NHSO_2X$, or $-CH_2X$. In embodiments, $R^4$ is $-SO_2CH=CH_2$, $-SO_2X$, $-NHSO_2CH=CH_2$, $-OSO_2X$, $-B(OH)_2$, $-NHSO_2X$, or $-CH_2X$. In embodiments, $R^5$ is $-SO_2CH=CH_2$, $-SO_2X$, $-NHSO_2CH=CH_2$, $-OSO_2X$, $-B(OH)_2$, $-NHSO_2X$, or $-CH_2X$.

In embodiments, at least one of $R^2$, $R^3$, $R^4$, $R^5$, $R^7$, $R^8$, $R^9$, $R^{31}$, $R^{32}$, $R^{40}$, $R^{50}$, $R^{101}$, $R^{102}$ or $R^{103}$ includes a covalent modifier moiety selected from $-SO_2CH=CH_2$, $-SO_2X$, $-NHSO_2CH=CH_2$, $-OSO_2X$, $-B(OH)_2$, $-NHSO_2X$, or $-CH_2X$; wherein X is independently $-F$, $-Cl$, $-Br$, or $-I$. In embodiments, at least one of $R^2$, $R^3$, $R^4$, $R^5$, $R^7$, $R^8$, $R^9$, $R^{31}$, $R^{32}$, $R^{40}$, $R^{50}$, $R^{101}$, $R^{102}$ or $R^{103}$ includes a covalent modifier moiety. In embodiments, at least one of $R^2$, $R^3$, $R^4$, $R^5$, $R^7$, $R^8$, $R^9$, $R^{31}$, $R^3$, $R^{40}$, $R^{50}$, $R^{101}$, $R^{102}$ or $R^{103}$ is a covalent modifier moiety. In embodiments, only one of $R^2$, $R^3$, $R^4$, $R^5$, $R^7$, $R^8$, $R^9$, $R^{31}$, $R^{32}$, $R^{40}$, $R^{50}$, $R^{101}$, $R^{102}$ or $R^{103}$ includes a covalent modifier moiety. In embodiments, more than one (e.g., 2, 3, or 4) of $R^2$, $R^3$, $R^4$, $R^5$, $R^7$, $R^8$, $R^9$, $R^{31}$, $R^{32}$, $R^{40}$, $R^{50}$, $R^{101}$, $R^{102}$ or $R^{103}$ includes a covalent modifier moiety. In embodiments, at least one of $R^2$, $R^3$, $R^4$, $R^5$, $R^7$, $R^8$, $R^9$, $R^{31}$, $R^{32}$, $R^{40}$, $R^{50}$, $R^{101}$, $R^{102}$ or $R^{103}$ includes $-SO_2CH=CH_2$, $-SO_2X$, $-NHSO_2CH=CH_2$, —OSO$_2$X, —B(OH)$_2$, —NHSO$_2$X, or —CH$_2$X. In embodiments, R$^7$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^8$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^9$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{31}$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{32}$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{40}$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{50}$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{101}$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{102}$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{103}$ includes —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^7$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^8$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^9$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{31}$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{32}$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{40}$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{50}$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{101}$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{102}$ is —SO$_2$CH=CH$_2$, —SO$_2$X, —NHSO$_2$CH=CH$_2$, —OSO$_2$X, —B(OH)$_2$, —NHSO$_2$X, or —CH$_2$X. In embodiments, R$^{103}$ is —SO$_2$CH=CH$_2$, —SO$_2$X, —NHSO$_2$CH=CH$_2$, —OSO$_2$X, —B(OH)$_2$, —NHSO$_2$X, or —CH$_2$X.

In embodiments, z3 is 0. In embodiments, z3 is 1. In embodiments, z3 is 2. In embodiments, z3 is 3.

In embodiments, the compound, or a pharmaceutical salt thereof, or a prodrug thereof, has the formula:

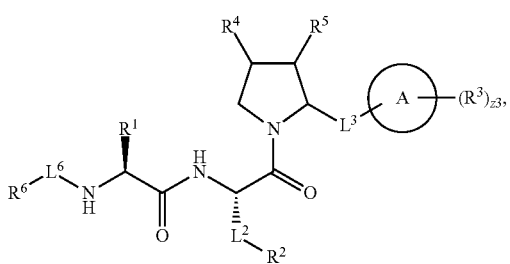

wherein Ring A, L$^3$, R$^6$, L$^6$, R$^1$, L$^2$, R$^2$, R$^4$, R$^5$, R$^3$, and z3 are as described herein, including embodiments.

In embodiments, the compound, or a pharmaceutical salt thereof, or a prodrug thereof, has the formula:

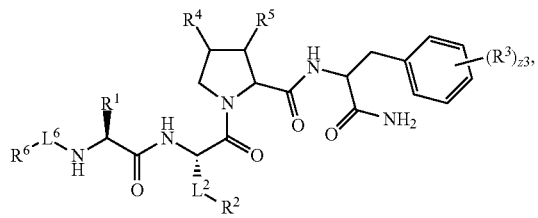

wherein R$^6$, L$^6$, R$^1$, L$^2$, R$^2$, R$^4$, R$^5$, R$^3$, and z3 are as described herein, including embodiments.

In embodiments, the compound, or a pharmaceutical salt thereof, or a prodrug thereof, has the formula:

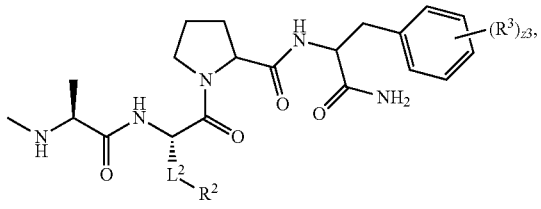

wherein L$^2$, R$^2$, R$^3$, and z3 are as described herein, including embodiments.

In embodiments, the compound, or a pharmaceutical salt thereof, or a prodrug thereof, has the formula:

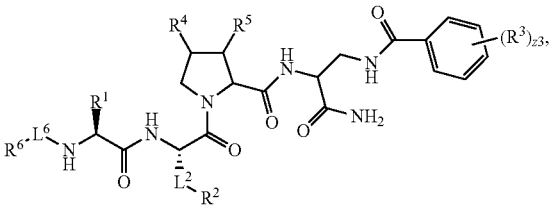

wherein R$^6$, L$^6$, R$^1$, L$^2$, R$^2$, R$^4$, R$^5$, R$^3$, and z3 are as described herein, including embodiments.

In embodiments, the compound, or a pharmaceutical salt thereof, or a prodrug thereof, has the formula:

wherein L$^2$, R$^2$, R$^3$, and z3 are as described herein, including embodiments.

In embodiments, the compound, pharmaceutical salt thereof or a prodrug thereof, has formula:

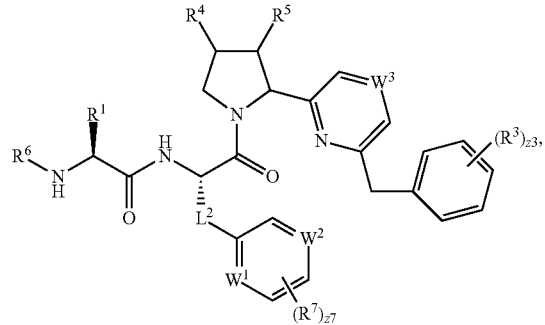

wherein $R^6$, $R^1$, $L^2$, $R^7$, z7, $R^4$, $R^5$, $R^3$, and z3 are as described herein, including embodiments. $W^1$, $W^2$, and $W^3$ are independently —CH= or —N=.

In embodiments, the compound, pharmaceutical salt thereof or a prodrug thereof, has formula:

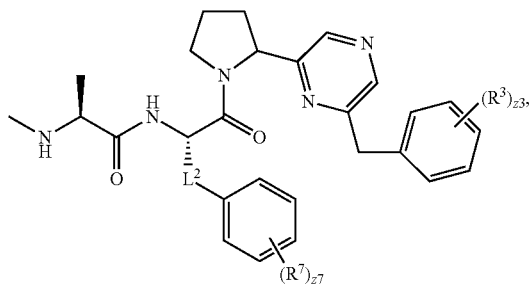

wherein $L^2$, $R^7$, z7, $R^3$, and z3 are as described herein, including embodiments.

In embodiments, the compound, or a pharmaceutical salt thereof, or a prodrug thereof has the formula:

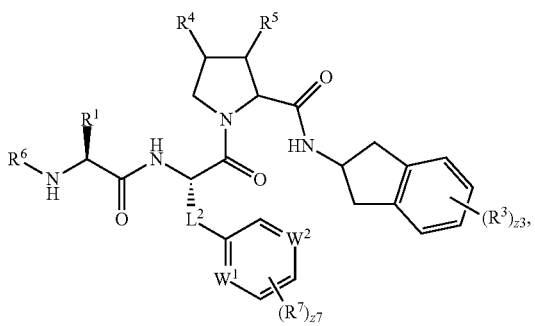

wherein $R^6$, $R^1$, $L^2$, $R^7$, z7, $R^4$, $R^5$, $R^3$, and z3 are as described herein, including embodiments. $W^1$ and $W^2$ are independently —CH= or —N=.

In embodiments, the compound, or a pharmaceutical salt thereof or a prodrug thereof has the formula:

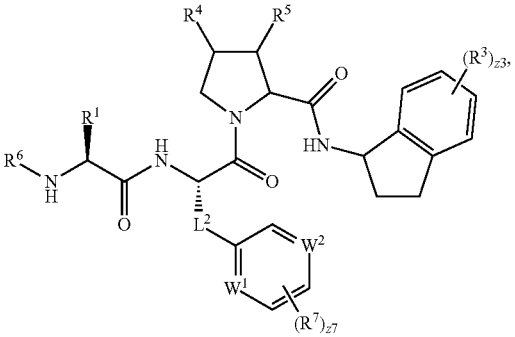

wherein $R^6$, $R^1$, $L^2$, $R^7$, z7, $R^4$, $R^5$, $R^3$, and z3 are as described herein, including embodiments. $W^1$ and $W^2$ are independently —CH= or —N=.

In embodiments, the compound, or a pharmaceutical salt thereof or a prodrug thereof has the formula:

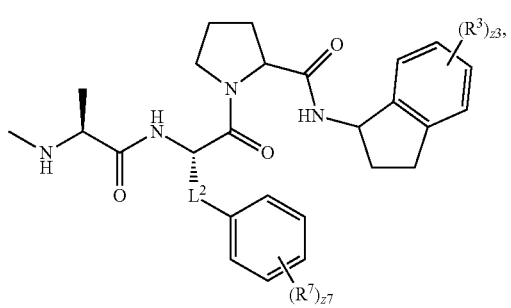

wherein $L^2$, $R^7$, z7, $R^3$, and z3 are as described herein, including embodiments.

In embodiments, the compound, or a pharmaceutical salt thereof or a prodrug thereof has the formula:

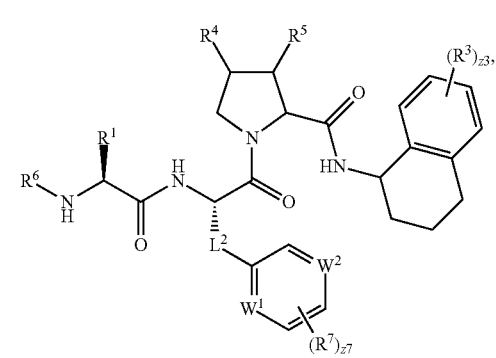

wherein $R^6$, $R^1$, $L^2$, $R^7$, z7, $R^4$, $R^5$, $R^3$, and z3 are as described herein, including embodiments. $W^1$ and $W^2$ are independently —CH= or —N=.

In embodiments, the compound, or pharmaceutical salt thereof, or a prodrug thereof has the formula:

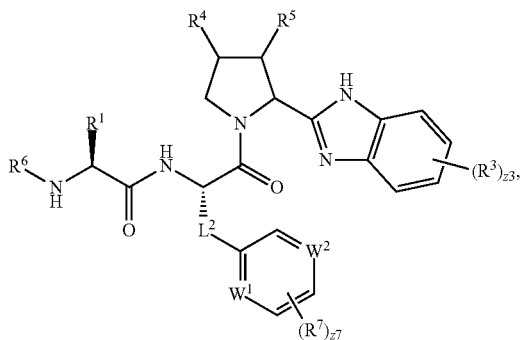

wherein $R^6$, $R^1$, $L^2$, $R^7$, z7, $R^4$, $R^5$, $R^3$, and z3 are as described herein, including embodiments. $W^1$ and $W^2$ are independently —CH= or —N=.

In embodiments, the compound or a pharmaceutical salt thereof or a prodrug thereof has the formula:

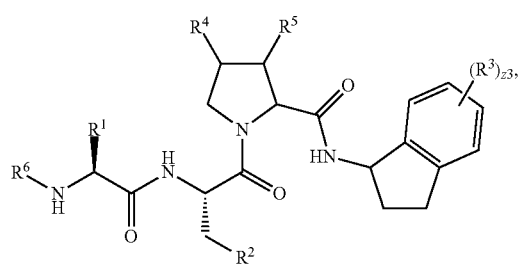

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

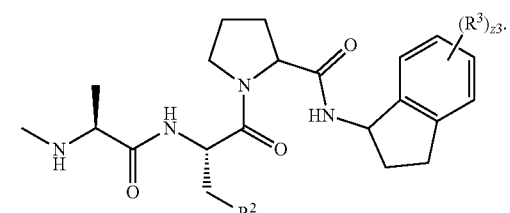

wherein $R^2$, $R^3$, and z3 are as described herein, including embodiments.

In embodiments, the compound or a pharmaceutical salt thereof or a prodrug thereof has the formula:

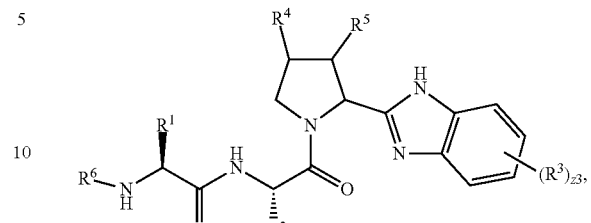

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

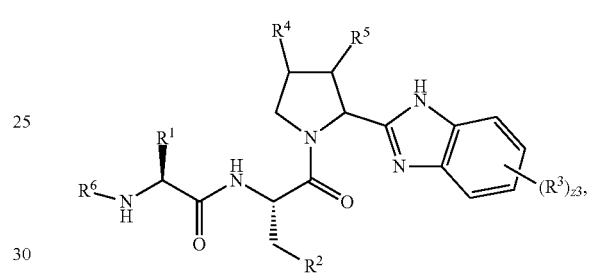

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

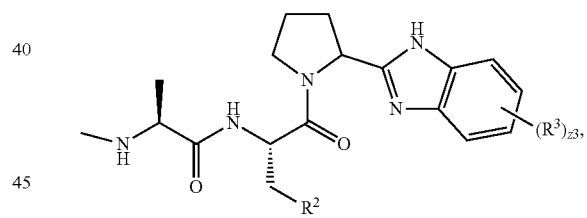

wherein $R^2$, $R^3$, and z3 are as described herein, including embodiments.

In embodiments, the compound or a pharmaceutical salt thereof or a prodrug thereof has the formula:

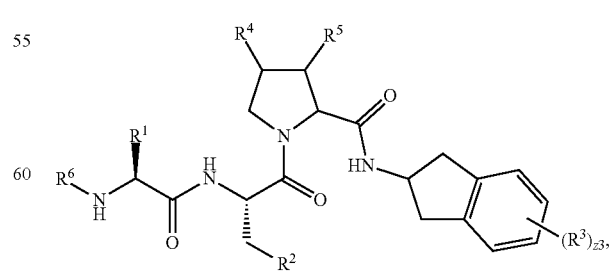

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

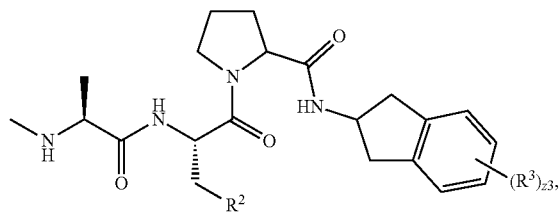

wherein $R^2$, $R^3$, and z3 are as described herein, including embodiments.

In embodiments, the compound or a pharmaceutical salt thereof or a prodrug thereof has the formula:

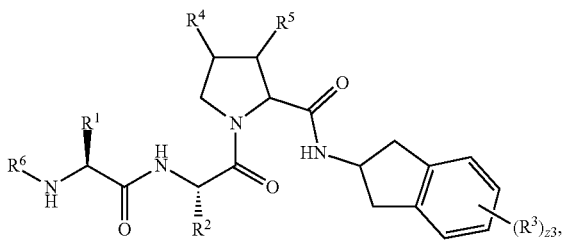

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

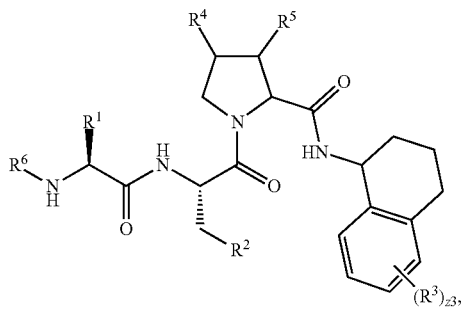

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

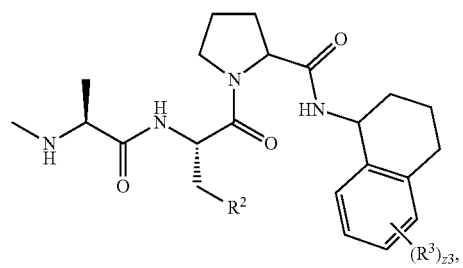

wherein $R^2$, $R^3$, and z3 are as described herein, including embodiments.

In embodiments, the compound or a pharmaceutical salt thereof or a prodrug thereof has the formula:

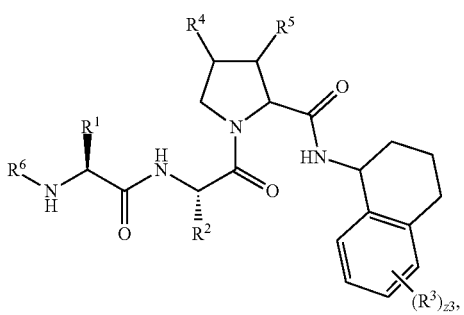

wherein $R^6$, $R^1$, $R^2$, $R^4$, $R^5$, $R^3$, and z3 are as described herein, including embodiments.

In embodiments, the compound or a pharmaceutical salt thereof, or a prodrug thereof has the formula:

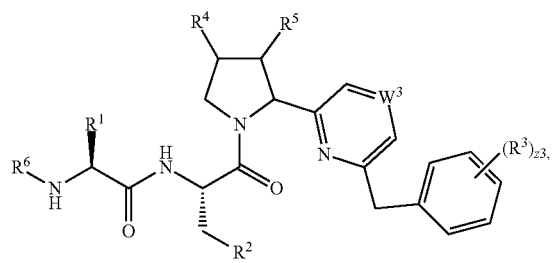

wherein $R^6$, $R^1$, $R^2$, $R^4$, $R^5$, $R^3$, and z3 are as described herein, including embodiments. $W^3$ is independently —CH= or —N=.

In embodiments, the compound or a pharmaceutical salt thereof, or a prodrug thereof has the formula:

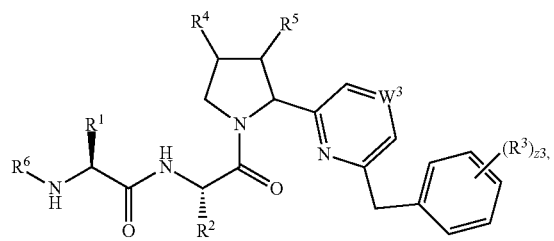

wherein $R^6$, $R^1$, $R^2$, $R^4$, $R^5$, $R^3$, and z3 are as described herein, including embodiments. $W^3$ is independently —CH= or —N=.

In embodiments, the compound, or a pharmaceutical salt thereof, or a prodrug thereof, has the formula:

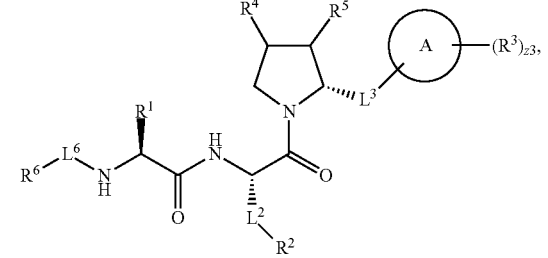

wherein Ring A, $L^3$, $R^6$, $R^1$, $L^2$, $R^7$, z7, $R^4$, $R^5$, $R^3$, and z3 are as described herein, including embodiments.

In embodiments, the compound, pharmaceutical salt thereof or a prodrug thereof, has formula:

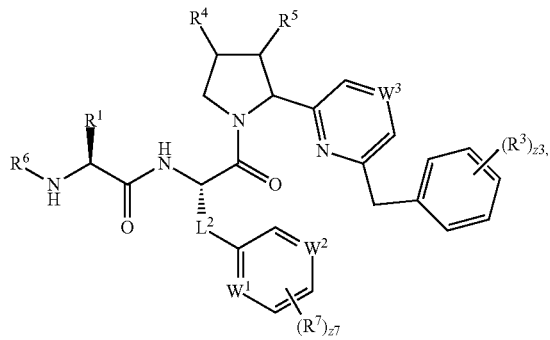

wherein $R^6$, $R^1$, $L^2$, $R^7$, z7, $R^4$, $R^5$, $R^3$, and z3 are as described herein, including embodiments. $W^1$, $W^2$, and $W^3$ are independently —CH= or —N=.

In embodiments, the compound, or a pharmaceutical salt thereof, or a prodrug thereof has the formula:

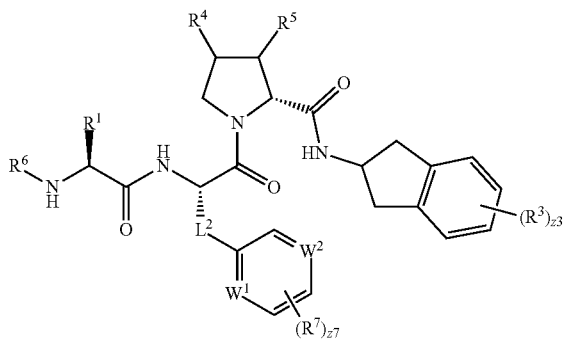

wherein $R^6$, $R^1$, $L^2$, $R^7$, z7, $R^4$, $R^5$, $R^3$, and z3 are as described herein, including embodiments. $W^1$ and $W^2$ are independently —CH= or —N=.

In embodiments, the compound, or a pharmaceutical salt thereof or a prodrug thereof has the formula:

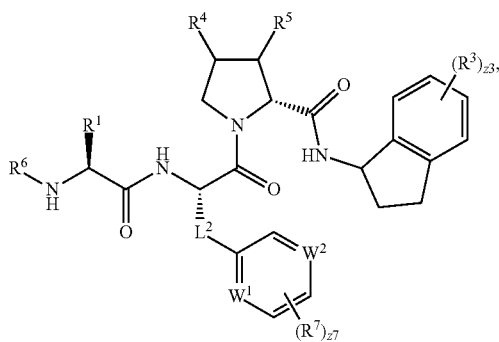

wherein $R^6$, $R^1$, $L^2$, $R^7$, z7, $R^4$, $R^5$, $R^3$, and z3 are as described herein, including embodiments. $W^1$ and $W^2$ are independently —CH= or —N=.

In embodiments, the compound, or a pharmaceutical salt thereof or a prodrug thereof has the formula:

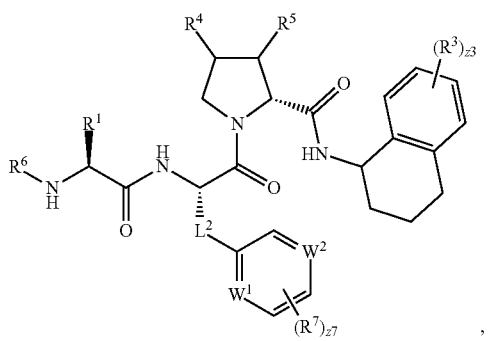

wherein $R^6$, $R^1$, $L^2$, $R^7$, z7, $R^4$, $R^5$, $R^3$, and z3 are as described herein, including embodiments. $W^1$ and $W^2$ are independently —CH= or —N=.

In embodiments, the compound, or pharmaceutical salt thereof, or a prodrug thereof has the formula:

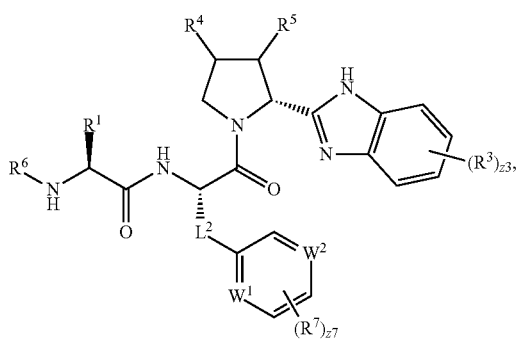

wherein $R^6$, $R^1$, $L^2$, $R^7$, z7, $R^4$, $R^5$, $R^3$, and z3 are as described herein, including embodiments. $W^1$ and $W^2$ are independently —CH= or —N=.

In embodiments, the compound or a pharmaceutical salt thereof or a prodrug thereof has the formula:

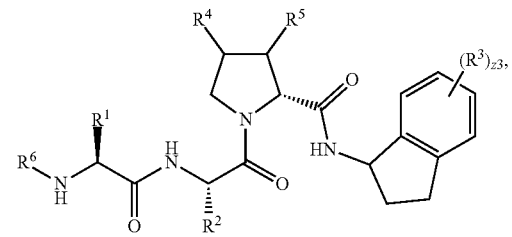

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

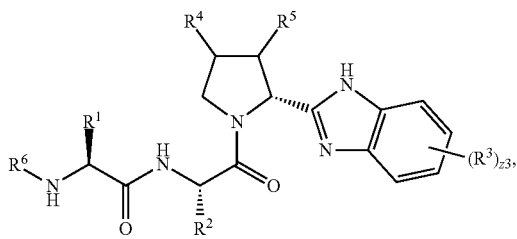

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

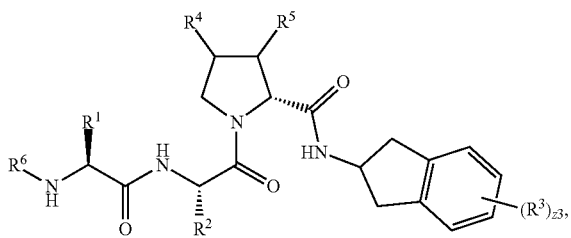

wherein $R^6$, $R^1$, $R^2$, $R^4$, $R^5$, $R^3$, and z3 are as described herein, including embodiments.

In embodiments, the compound or a pharmaceutical salt thereof or a prodrug thereof has the formula:

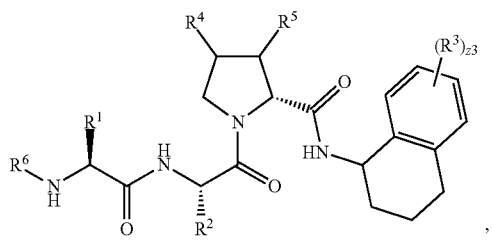

wherein $R^6$, $R^1$, $R^2$, $R^4$, $R^5$, $R^3$, and z3 are as described herein, including embodiments.

In embodiments, the compound or a pharmaceutical salt thereof, or a prodrug thereof has the formula:

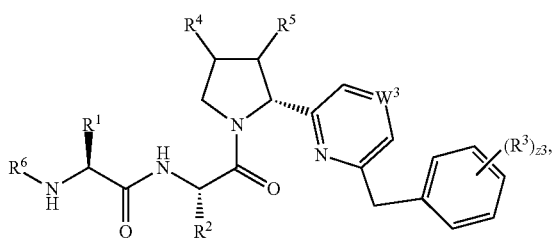

wherein $R^6$, $R^1$, $R^2$, $R^4$, $R^5$, $R^3$, and z3 are as described herein, including embodiments. $W^3$ is independently —CH= or —N=.

In embodiments, the compound, or a pharmaceutical salt thereof, or a prodrug thereof, has the formula:

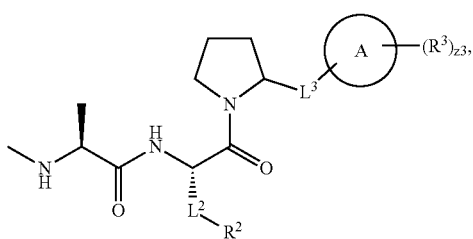

wherein Ring A, $L^3$, $L^2$, $R^7$, z7, $R^3$, and z3 are as described herein, including embodiments.

In embodiments, the compound, pharmaceutical salt thereof or a prodrug thereof, has formula:

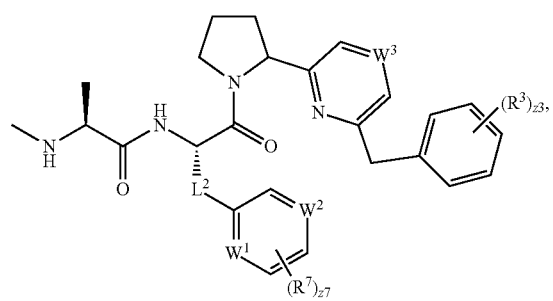

wherein $L^2$, $R^7$, z7, $R^3$, and z3 are as described herein, including embodiments. $W^1$, $W^2$, and $W^3$ are independently —CH= or —N=.

In embodiments, the compound, or a pharmaceutical salt thereof, or a prodrug thereof has the formula:

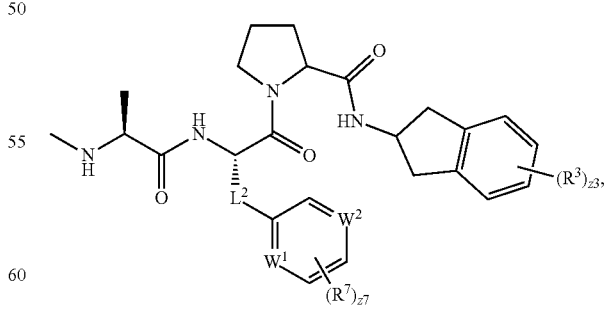

wherein $L^2$, $R^7$, z7, $R^3$, and z3 are as described herein, including embodiments. $W^1$ and $W^2$ are independently —CH= or —N=.

In embodiments, the compound, or a pharmaceutical salt thereof or a prodrug thereof has the formula:

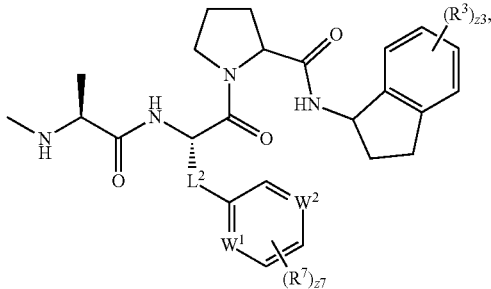

wherein $L^2$, $R^7$, $z7$, $R^3$, and $z3$ are as described herein, including embodiments. $W^1$ and $W^2$ are independently —CH= or —N=.

In embodiments, the compound, or a pharmaceutical salt thereof or a prodrug thereof has the formula:

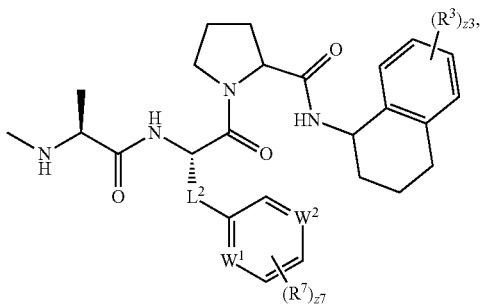

wherein $L^2$, $R^7$, $z7$, $R^3$, and $z3$ are as described herein, including embodiments. $W^1$ and $W^2$ are independently —CH= or —N=.

In embodiments, the compound, or pharmaceutical salt thereof, or a prodrug thereof has the formula:

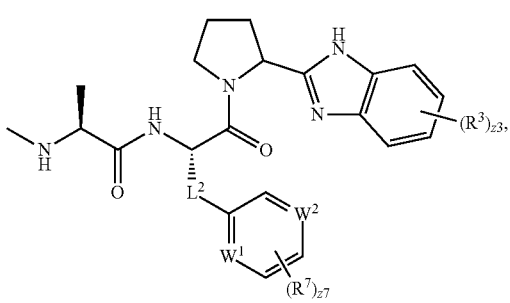

wherein $L^2$, $R^7$, $z7$, $R^3$, and $z3$ are as described herein, including embodiments. $W^1$ and $W^2$ are independently —CH= or —N=.

In embodiments, the compound or a pharmaceutical salt thereof or a prodrug thereof has the formula:

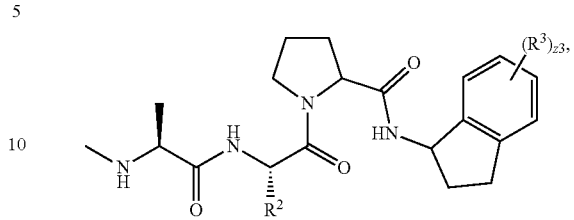

wherein $R^2$, $R^3$, and $z3$ are as described herein, including embodiments.

In embodiments, the compound or a pharmaceutical salt thereof or a prodrug thereof has the formula:

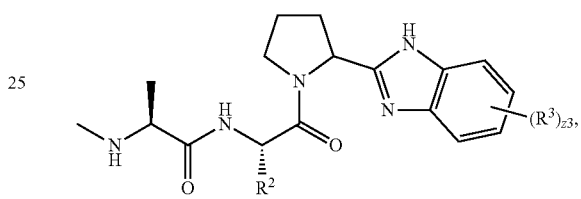

wherein $R^2$, $R^3$, and $z3$ are as described herein, including embodiments.

In embodiments, the compound or a pharmaceutical salt thereof or a prodrug thereof has the formula:

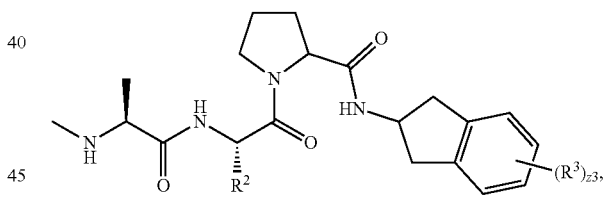

wherein $R^2$, $R^3$, and $z3$ are as described herein, including embodiments.

In embodiments, the compound or a pharmaceutical salt thereof or a prodrug thereof has the formula:

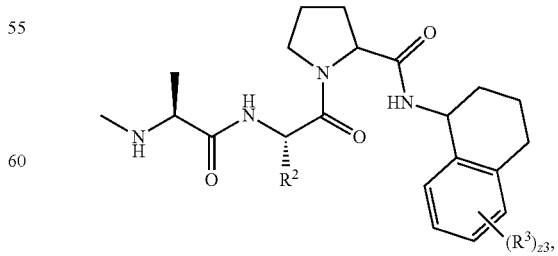

wherein $R^2$, $R^3$, and $z3$ are as described herein, including embodiments.

In embodiments, the compound or a pharmaceutical salt thereof, or a prodrug thereof has the formula:

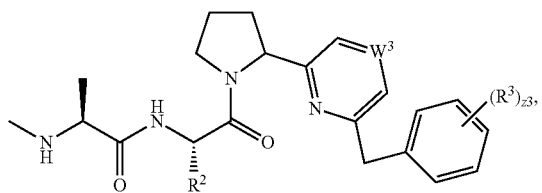

wherein $R^2$, $R^3$, and z3 are as described herein, including embodiments. $W^3$ is independently —CH= or —N=.

In embodiments, the compound, or a pharmaceutical salt thereof, or a prodrug thereof, has the formula:

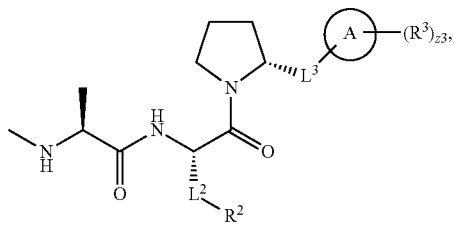

wherein Ring A, $L^3$, $L^2$, $R^2$, $R^3$, and z3 are as described herein, including embodiments.

In embodiments, the compound, or a pharmaceutical salt thereof, or a prodrug thereof, has the formula:

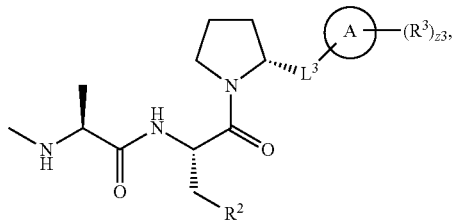

wherein Ring A, $L^3$, $R^2$, $R^3$, and z3 are as described herein, including embodiments.

In embodiments, the compound, or a pharmaceutical salt thereof, or a prodrug thereof, has the formula:

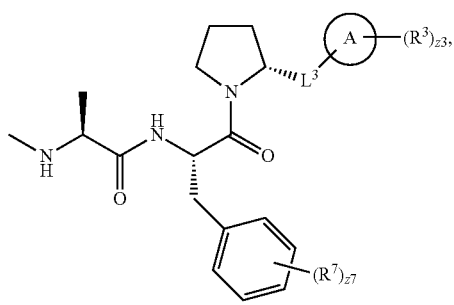

wherein Ring A, $L^3$, $L^2$, $R^7$, z7, $R^3$, and z3 are as described herein, including embodiments.

In embodiments, the compound, pharmaceutical salt thereof or a prodrug thereof, has formula:

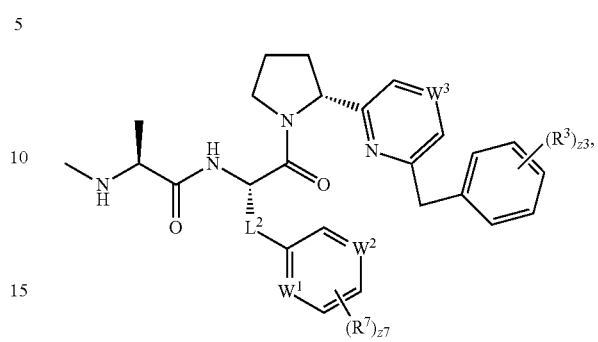

wherein $L^2$, $R^7$, z7, $R^3$, and z3 are as described herein, including embodiments. $W^1$, $W^2$, and $W^3$ are independently —CH= or —N=.

In embodiments, the compound, or a pharmaceutical salt thereof, or a prodrug thereof has the formula:

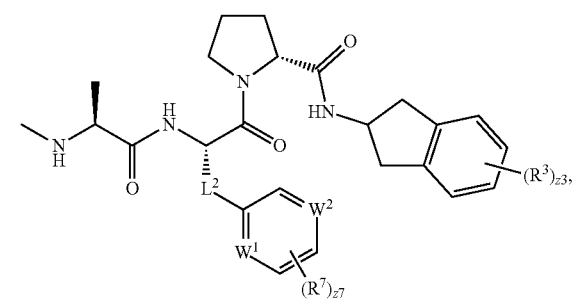

wherein $L^2$, $R^7$, z7, $R^3$, and z3 are as described herein, including embodiments. $W^1$ and $W^2$ are independently —CH= or —N=.

In embodiments, the compound, or a pharmaceutical salt thereof or a prodrug thereof has the formula:

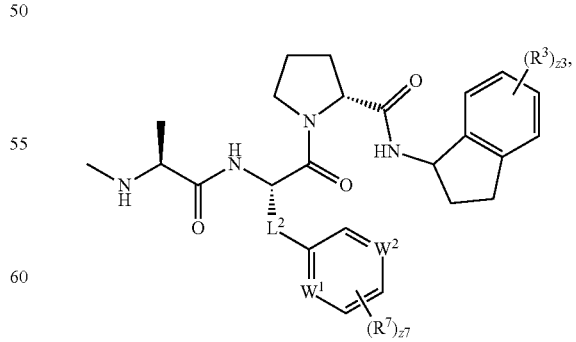

wherein $L^2$, $R^7$, z7, $R^3$, and z3 are as described herein, including embodiments. $W^1$ and $W^2$ are independently —CH= or —N=.

In embodiments, the compound, or a pharmaceutical salt thereof or a prodrug thereof has the formula:

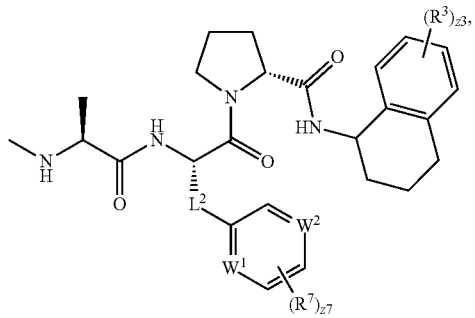

wherein $L^2$, $R^7$, z7, $R^3$, and z3 are as described herein, including embodiments. $W^1$ and $W^2$ are independently —CH= or —N=.

In embodiments, the compound, or pharmaceutical salt thereof, or a prodrug thereof has the formula:

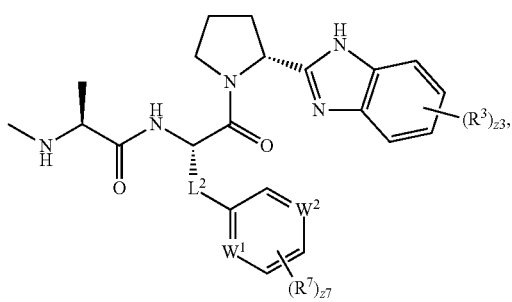

wherein $L^2$, $R^7$, z7, $R^3$, and z3 are as described herein, including embodiments. $W^1$ and $W^2$ are independently —CH= or —N=.

In embodiments, the compound or a pharmaceutical salt thereof or a prodrug thereof has the formula:

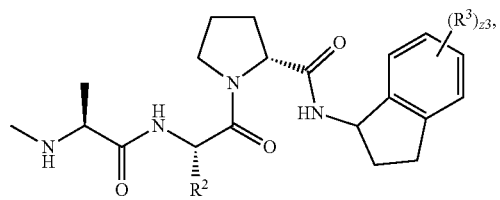

wherein $R^2$, $R^3$, and z3 are as described herein, including embodiments.

In embodiments, the compound or a pharmaceutical salt thereof or a prodrug thereof has the formula:

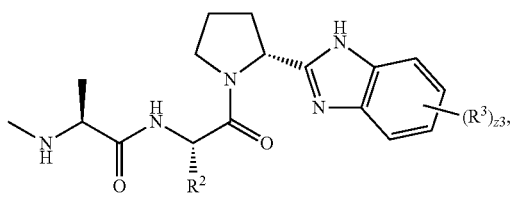

wherein $R^2$, $R^3$, and z3 are as described herein, including embodiments.

In embodiments, the compound or a pharmaceutical salt thereof or a prodrug thereof has the formula:

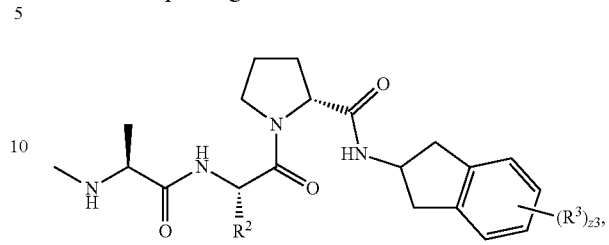

wherein $R^2$, $R^3$, and z3 are as described herein, including embodiments.

In embodiments, the compound or a pharmaceutical salt thereof or a prodrug thereof has the formula:

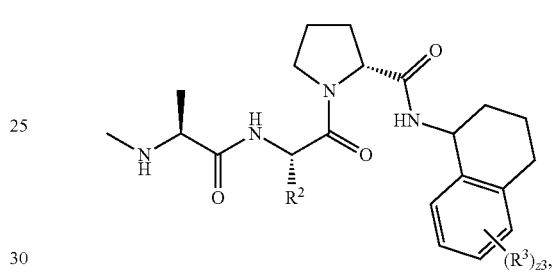

wherein $R^2$, $R^3$, and z3 are as described herein, including embodiments.

In embodiments, the compound or a pharmaceutical salt thereof, or a prodrug thereof has the formula:

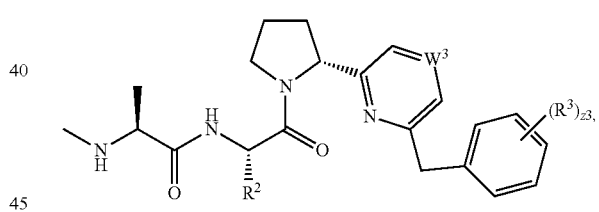

wherein $R^2$, $R^3$, and z3 are as described herein, including embodiments. $W^3$ is independently —CH= or —N=.

In embodiments, $R^1$ is —$CX^1_3$, —$CHX^1_2$, —$CH_2X^1$, $R^{10}$-substituted or unsubstituted $C_1$-$C_4$ alkyl. In embodiments, $R^1$ is —$CX^1_3$. In embodiments, $R^1$ is —$CHX^1_2$. In embodiments, $R^1$ is —$CH_2X^1$. In embodiments, $R^1$ is $R^{10}$-substituted or unsubstituted $C_1$-$C_4$ alkyl. In embodiments, $R^1$ is unsubstituted $C_1$-$C_4$ alkyl. In embodiments, $R^1$ is unsubstituted $C_4$ alkyl. In embodiments, $R^1$ is unsubstituted $C_3$ alkyl. In embodiments, $R^1$ is unsubstituted $C_2$ alkyl. In embodiments, $R^1$ is unsubstituted methyl.

$R^{10}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^1$ is —$CH_3$, —$C_2H_5$, —$CF_3$, —$CH_2F$, —$CHF_2$, —$CH_2CF_3$, —$CF_2CH_3$, —$CH_2OH$, —$CF_2OH$, or —$CHFOH$. In embodiments, $R^1$ is —$CH_3$. In embodiments, $R^1$ is —$C_2H5$. In embodiments, $R^1$ is —$CF_3$. In embodiments, $R^1$ is —$CH_2F$. In embodiments, $R^1$ is —$CHF_2$. In embodiments, $R^1$ is —$CH_2CF_3$. In embodiments, $R^1$ is —$CF_2CH_3$. In embodiments, $R^1$ is —$CH_2OH$. In embodiments, $R^1$ is —$CF_2OH$. In embodiments, $R^1$ or —$CHFOH$.

In embodiments, $L^2$ is a bond, —NH—, —O—, —S—, —C(O)—, —C(O)NH—, —NHC(O)—, —NH(CH$_2$)$_{1-5}$—, —NHC(O)NH—, —C(O)O—, —OC(O)—, —(CH$_2$)$_{1-5}$—, —(CH$_2$)$_{1-5}$O—, —(CH$_2$)$_{1-5}$NHC(O)—, —(CH$_2$)$_{1-5}$S—, —(CH$_2$)$_{1-5}$C(O)NH—, —O(CH$_2$)$_{1-5}$—, —(CH$_2$)$_{1-5}$NH—, —(CH$_2$)$_{1-5}$NH(CH$_2$)$_{1-5}$—, or —(CH$_2$)$_{1-5}$C(O)—.

In embodiments, $L^2$ is a bond, —NH—, —O—, —S—, —C(O)—, —C(O)NH—, —NHC(O)—, —NH(CH$_2$)$_{1-3}$—, —NHC(O)NH—, —C(O)O—, —OC(O)—, —(CH$_2$)$_{1-3}$—, —(CH$_2$)$_{1-3}$O—, —(CH$_2$)$_{1-3}$NHC(O)—, —(CH$_2$)$_{1-3}$S—, —(CH$_2$)$_{1-3}$C(O)NH—, —O(CH$_2$)$_{1-3}$—, —(CH$_2$)$_{1-3}$NH—, —(CH$_2$)$_{1-3}$NH(CH$_2$)$_{1-3}$—, or —(CH$_2$)$_{1-3}$C(O)—. In embodiments, $L^2$ is a bond. In embodiments, $L^2$ is not a bond. In embodiments, $L^2$ is —NH—. In embodiments, $L^2$ is —O—. In embodiments, $L^2$ is —S—. In embodiments, $L^2$ is —C(O)—. In embodiments, $L^2$ is —C(O)NH—. In embodiments, $L^2$ is —NHC(O)—. In embodiments, $L^2$ is —NH(CH$_2$)$_{1-3}$—. In embodiments, $L^2$ is —NH(CH$_2$)$_3$—. In embodiments, $L^2$ is —NH(CH$_2$)$_2$—. In embodiments, $L^2$ is —NH(CH$_2$)—. In embodiments, $L^2$ is —NHC(O)NH—. In embodiments, $L^2$ is —C(O)O—. In embodiments, $L^2$ is —OC(O)—. In embodiments, $L^2$ is —(CH$_2$)$_{1-3}$—. In embodiments, $L^2$ is —(CH$_2$)$_3$—. In embodiments, $L^2$ is —(CH$_2$)$_2$—. In embodiments, $L^2$ is —(CH$_2$)—. In embodiments, $L^2$ is —(CH$_2$)$_{1-3}$O—. In embodiments, $L^2$ is —(CH$_2$)$_3$O—. In embodiments, $L^2$ is —(CH$_2$)$_2$O—. In embodiments, $L^2$ is —(CH$_2$)O—. In embodiments, $L^2$ is —(CH$_2$)$_{1-3}$NHC(O)—. In embodiments, $L^2$ is —(CH$_2$)$_3$NHC(O)—. In embodiments, $L^2$ is —(CH$_2$)$_2$NHC(O)—. In embodiments, $L^2$ is —(CH$_2$)NHC(O)—. In embodiments, $L^2$ is —(CH$_2$)$_{1-3}$S—. In embodiments, $L^2$ is —(CH$_2$)$_3$S—. In embodiments, $L^2$ is —(CH$_2$)$_2$S—. In embodiments, $L^2$ is —(CH$_2$)S—. In embodiments, $L^2$ is —(CH$_2$)$_{1-3}$C(O)NH—. In embodiments, $L^2$ is —(CH$_2$)$_3$C(O)NH—. In embodiments, $L^2$ is —(CH$_2$)$_2$C(O)NH—. In embodiments, $L^2$ is —(CH$_2$)C(O)NH—. In embodiments, $L^2$ is —O(CH$_2$)$_{1-3}$—. In embodiments, $L^2$ is —O(CH$_2$)$_3$—. In embodiments, $L^2$ is —O(CH$_2$)$_2$—. In embodiments, $L^2$ is —O(CH$_2$)—. In embodiments, $L^2$ is —(CH$_2$)$_{1-3}$NH—. In embodiments, $L^2$ is —(CH$_2$)$_3$NH—. In embodiments, $L^2$ is —(CH$_2$)$_2$NH—. In embodiments, $L^2$ is —(CH$_2$)NH—. In embodiments, $L^2$ is —(CH$_2$)$_{1-3}$NH(CH$_2$)$_{1-3}$—. In embodiments, $L^2$ is —(CH$_2$)$_3$NH(CH$_2$)$_3$—. In embodiments, $L^2$ is —(CH$_2$)$_2$NH(CH$_2$)$_3$—. In embodiments, $L^2$ is —(CH$_2$)NH(CH$_2$)$_3$—. In embodiments, $L^2$ is —(CH$_2$)$_3$NH(CH$_2$)$_2$—. In embodiments, $L^2$ is —(CH$_2$)$_2$NH(CH$_2$)$_2$—. In embodiments, $L^2$ is —(CH$_2$)NH(CH$_2$)$_2$—. In embodiments, $L^2$ is —(CH$_2$)$_3$NH(CH$_2$)—. In embodiments, $L^2$ is —(CH$_2$)$_2$NH(CH$_2$)—. In embodiments, $L^2$ is —(CH$_2$)NH(CH$_2$)—. In embodiments, $L^2$ is —(CH$_2$)$_{1-3}$C(O)—. In embodiments, $L^2$ is —(CH$_2$)$_3$C(O)—. In embodiments, $L^2$ is —(CH$_2$)$_2$C(O)—. In embodiments, $L^2$ is —(CH$_2$)C(O)—.

In embodiments, $L^2$ is a bond. In embodiments, $L^2$ is not a bond. In embodiments, $L^2$ is —NH—. In embodiments, $L^2$ is —O—. In embodiments, $L^2$ is —S—. In embodiments, $L^2$ is —C(O)—. In embodiments, $L^2$ is —C(O)NH—. In embodiments, $L^2$ is —NHC(O)—. In embodiments, $L^2$ is —NHC(O)NH—. In embodiments, $L^2$ is —C(O)O—. In embodiments, $L^2$ is —OC(O)—. In embodiments, $L^2$ is $R^{20}$-substituted or unsubstituted alkylene (e.g., $C_1$-$C_8$ alkylene, $C_1$-$C_6$ alkylene, or $C_1$-$C_4$ alkylene). In embodiments, $L^2$ is $R^{20}$-substituted or unsubstituted heteroalkylene (e.g., 2 to 8 membered heteroalkylene, 2 to 6 membered heteroalkylene, or 2 to 4 membered heteroalkylene). In embodiments, $L^2$ is $R^{20}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is $R^{20}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is $R^{20}$-substituted or unsubstituted arylene (e.g., $C_6$-$C_{10}$ arylene, $C_{10}$ arylene, or phenylene). In embodiments, $L^2$ is $R^{20}$-substituted or unsubstituted heteroarylene (e.g., 5 to 10 membered heteroarylene, 5 to 9 membered heteroarylene, or 5 to 6 membered heteroarylene).

In embodiments, $L^2$ is $R^{20}$-substituted or unsubstituted alkylene (e.g., $C_1$-$C_8$ alkylene, $C_1$-$C_6$ alkylene, or $C_1$-$C_4$ alkylene). In embodiments, $L^2$ is $R^{20}$-substituted alkylene (e.g., $C_1$-$C_8$ alkylene, $C_1$-$C_6$ alkylene, or $C_1$-$C_4$ alkylene). In embodiments, $L^2$ is an unsubstituted alkylene (e.g., $C_1$-$C_8$ alkylene, $C_1$-$C_6$ alkylene, or $C_1$-$C_4$ alkylene).

In embodiments, $L^2$ is $R^{20}$-substituted or unsubstituted heteroalkylene (e.g., 2 to 8 membered heteroalkylene, 2 to 6 membered heteroalkylene, or 2 to 4 membered heteroalkylene). In embodiments, $L^2$ is $R^{20}$-substituted heteroalkylene (e.g., 2 to 8 membered heteroalkylene, 2 to 6 membered heteroalkylene, or 2 to 4 membered heteroalkylene). In embodiments, $L^2$ is an unsubstituted heteroalkylene (e.g., 2 to 8 membered heteroalkylene, 2 to 6 membered heteroalkylene, or 2 to 4 membered heteroalkylene).

$R^{20}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $L^2$ is $L^{20}$-substituted or unsubstituted methylene. In embodiments, $L^2$ is $L^{20}$-substituted or unsubstituted $C_2$ alkylene. In embodiments, $L^2$ is $L^{20}$-substituted or unsubstituted $C_3$ alkylene. In embodiments, $L^2$ is $L^{20}$-substituted or unsubstituted $C_4$ alkylene. In embodiments, $L^2$ is $L^{20}$-substituted or unsubstituted $C_5$ alkylene. In embodiments, $L^2$ is $L^{20}$-substituted or unsubstituted $C_6$ alkylene. In embodiments, $L^2$ is $L^{20}$-substituted or unsubstituted $C_7$ alkylene. In embodiments, $L^2$ is $L^{20}$-substituted or unsubstituted $C_8$ alkylene. In embodiments, $L^2$ is $L^{20}$-substituted methylene. In embodiments, $L^2$ is $L^{20}$-substituted $C_2$ alkylene. In embodiments, $L^2$ is $L^{20}$-substituted $C_3$ alkylene. In embodiments, $L^2$ is $L^{20}$-substituted $C_4$ alkylene. In embodiments, $L^2$ is $L^{20}$-substituted $C_5$ alkylene. In embodiments, $L^2$ is $L^{20}$-substituted $C_6$ alkylene. In embodiments, $L^2$ is $L^{20}$-substituted $C_7$ alkylene. In embodiments, $L^2$ is $L^{20}$-substituted $C_8$ alkylene. In embodiments, $L^2$ is an unsubstituted methylene. In embodiments, $L^2$ is an unsubstituted $C_2$ alkylene. In embodiments, $L^2$ is an unsubstituted $C_3$ alkylene. In embodiments, $L^2$ is an unsubstituted $C_4$ alkylene. In embodiments, $L^2$ is an unsubstituted $C_5$ alkylene. In embodiments, $L^2$ is an unsubstituted $C_6$ alkylene. In embodiments, $L^2$ is an unsubstituted $C_7$ alkylene. In embodiments, $L^2$ is an unsubstituted $C_8$ alkylene.

In embodiments, $L^2$ is $R^{20}$-substituted or unsubstituted $C_1$-$C_6$ alkylene. In embodiments, $L^2$ is $R^{20}$-substituted $C_1$-$C_6$ alkylene. In embodiments, $L^2$ is unsubstituted $C_1$-$C_6$ alkylene. In embodiments, $L^2$ is $R^{20}$-substituted or unsubstituted $C_2$-$C_6$ alkylene. In embodiments, $L^2$ is $R^{20}$-substituted $C_2$-$C_6$ alkylene. In embodiments, $L^2$ is unsubstituted $C_2$-$C_6$ alkylene. In embodiments, $L^2$ is $R^{20}$-substituted or unsubstituted $C_1$ alkylene. In embodiments, $L^2$ is $R^{20}$-substituted $C_1$ alkylene. In embodiments, $L^2$ is unsubstituted $C_1$ alkylene. In embodiments, $L^2$ is $R^{20}$-substituted or unsubstituted $C_2$ alkylene. In embodiments, $L^2$ is $R^{20}$-substituted $C_2$ alkylene. In embodiments, $L^2$ is unsubstituted $C_2$ alkylene. In embodiments, $L^2$ is $R^{20}$-substituted or unsubstituted $C_3$ alkylene. In embodiments, $L^2$ is $R^{20}$-substituted $C_3$ alkylene. In embodiments, $L^2$ is unsubstituted $C_3$ alkylene. In embodiments, $L^2$ is $R^{20}$-substituted or unsubstituted $C_4$ alkylene. In embodiments, $L^2$ is $R^{20}$-substituted $C_4$ alkylene. In embodiments, $L^2$ is unsubstituted $C_4$ alkylene. In embodiments, $L^2$ is $R^{20}$-substituted or unsubstituted $C_5$ alkylene. In embodiments, $L^2$ is $R^{20}$-substituted $C_5$ alkylene. In embodiments, $L^2$ is unsubstituted $C_5$ alkylene. In embodiments, $L^2$ is $R^{20}$-substituted or unsubstituted $C_6$ alkylene. In embodiments, $L^2$ is $R^{20}$-substituted $C_6$ alkylene. In embodiments, $L^2$ is unsubstituted $C_6$ alkylene.

In embodiments, $L^2$ is $R^{20}$-substituted or unsubstituted 2 to 6 membered heteroalkylene. In embodiments, $L^2$ is $R^{20}$-substituted 2 to 6 membered heteroalkylene. In embodiments, $L^2$ is unsubstituted 2 to 6 membered heteroalkylene. In embodiments, $L^2$ is $R^{20}$-substituted or unsubstituted 2 membered heteroalkylene. In embodiments, $L^2$ is $R^{20}$-substituted 2 membered heteroalkylene. In embodiments, $L^2$ is unsubstituted 2 membered heteroalkylene. In embodiments, $L^2$ is $R^{20}$-substituted or unsubstituted 3 membered heteroalkylene. In embodiments, $L^2$ is $R^{20}$-substituted 3 membered heteroalkylene. In embodiments, $L^2$ is unsubstituted 3 membered heteroalkylene. In embodiments, $L^2$ is $R^{20}$-substituted or unsubstituted 4 membered heteroalkylene. In embodiments, $L^2$ is $R^{20}$-substituted 4 membered heteroalkylene. In embodiments, $L^2$ is unsubstituted 4 membered heteroalkylene. In embodiments, $L^2$ is $R^{20}$-substituted or unsubstituted 5 membered heteroalkylene. In embodiments, $L^2$ is $R^{20}$-substituted 5 membered heteroalkylene. In embodiments, $L^2$ is unsubstituted 5 membered heteroalkylene. In embodiments, $L^2$ is $R^{20}$-substituted or unsubstituted 6 membered heteroalkylene. In embodiments, $L^2$ is $R^{20}$-substituted 6 membered heteroalkylene. In embodiments, $L^2$ is unsubstituted 6 membered heteroalkylene.

In embodiments, -$L^2$-$R^2$ is

[chemical structures]

In embodiments, -$L^2$-$R^2$ is

[chemical structure]

In embodiments, -L²-R² is
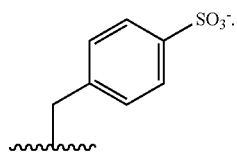
In embodiments, -L²-R² is
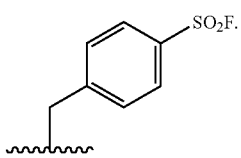 [SMILES: *Cc1ccc(S(=O)(=O)F)cc1]
In embodiments, -L²-R² is
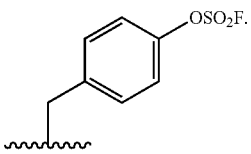
In embodiments, -L²-R² is
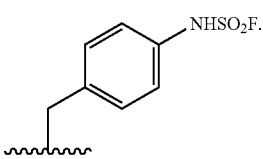
In embodiments, -L²-R² is
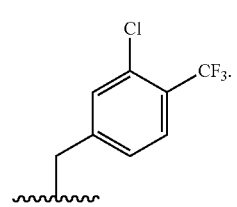 [SMILES: *Cc1ccc(C(F)(F)F)c(Cl)c1]
In embodiments, -L²-R² is
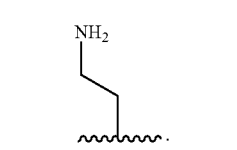
In embodiments, -L²-R² is
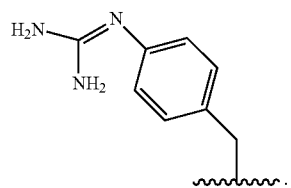 [SMILES: *Cc1ccc(N=C(N)N)cc1]
In embodiments, -L²-R² is
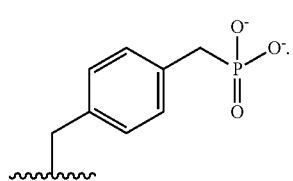
In embodiments, -L²-R² is
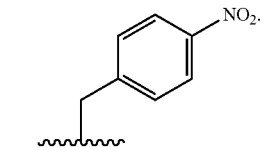
In embodiments, -L²-R² is
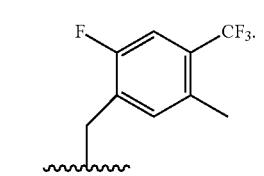 [SMILES: *Cc1cc(C)c(C(F)(F)F)cc1F]
In embodiments, -L²-R² is
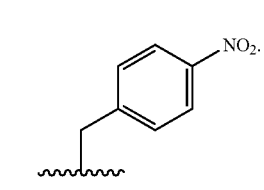
In embodiments, -L²-R² is
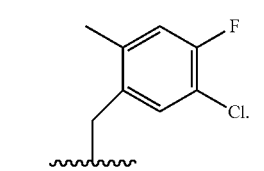

In embodiments, -L²-R² is

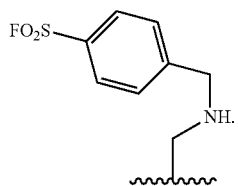

In embodiments, -L²-R² is

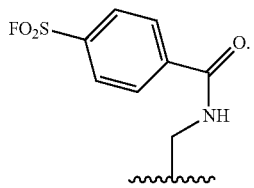

In embodiments, R² is independently halogen, —CX²₃, —CHX²₂, —CH₂X², —CN, —OH, —NH₂, —COH, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCX²₃, —OCHX²₂, —OCH₂X², —SO₂CH₃, —SO₂CX²₃, —SO₂CH₃, —SO₂X², —SO₂CH=CH₂, —NHSO₂CH=CH₂, —OSO₂X², —NHSO₂X², —B(OH)₂, —CO-oxiranyl, —CO-aziridinyl, epoxidinyl, oxaziridinyl, aziridinyl, —OCH₂C≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R² is independently substituted or unsubstituted aryl, or substituted or unsubstituted heteroaryl. In embodiments, R² is independently substituted or unsubstituted aryl. In embodiments, R² is independently substituted aryl. In embodiments, R² is independently unsubstituted aryl. In embodiments, R² is independently substituted or unsubstituted heteroaryl. In embodiments, R² is independently substituted heteroaryl. In embodiments, R² is independently unsubstituted heteroaryl.

In embodiments, R² is R⁷-substituted aryl or R⁷-substituted heteroaryl, wherein R⁷ is a covalent modifier moiety selected from: —SO₂CH=CH₂, —SO₂X⁷, —NHSO₂CH=CH₂, —OSO₂X⁷, —B(OH)₂, —NHSO₂X⁷, or —CH₂X⁷, wherein X⁷ is independently —F, —Cl, —Br, or —I. In embodiments, R² is R⁷-substituted aryl, wherein R⁷ is a covalent modifier moiety selected from: —SO₂CH=CH₂, —SO₂X⁷, —NHSO₂CH=CH₂, —OSO₂X⁷, —B(OH)₂, —NHSO₂X⁷, or —CH₂X⁷. In embodiments, R² is R⁷-substituted heteroaryl, wherein R⁷ is a covalent modifier moiety selected from: —SO₂CH=CH₂, —SO₂X⁷, —NHSO₂CH=CH₂, —OSO₂X⁷, —B(OH)₂, —NHSO₂X⁷, or —CH₂X⁷.

In embodiments, R² is independently —Cl, —NH₂, —COH, —COOH, —CONH₂, —SO₂NH₂, —SO₂CH₃, —SO₂CF₃, —SO₂F, —SO₂CH=CH₂, —NHSO₂CH=CH₂, —OSO₂F, —NHSO₂F, —B(OH)₂, —CHCH₂, —CO-oxiranyl, —CO-aziridinyl, epoxidinyl, oxaziridinyl, aziridinyl, —OCH₂C≡CH, unsubstituted tetrazolyl, unsubstituted aziridinyl, unsubstituted oxiranyl, R⁷-substituted or unsubstituted 2-pyridyl, R⁷-substituted or unsubstituted 3-pyridyl, R⁷-substituted or unsubstituted 4-pyridyl,

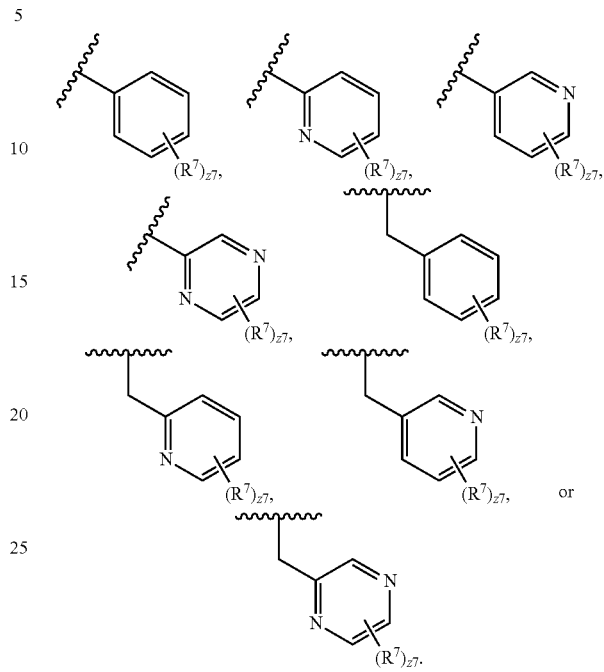

In embodiments, R² is independently —Cl. In embodiments, R² is independently —NH₂. In embodiments, R² is independently —COOH. In embodiments, R² is independently —CONH₂. In embodiments, R² is independently —SO₂NH₂. In embodiments, R² is independently —SO₂CH₃. In embodiments, R² is independently —SO₂CF₃. In embodiments, R² is independently —SO₂F. In embodiments, R² is independently —SO₂CH=CH₂. In embodiments, R² is independently —NHSO₂CH=CH₂. In embodiments, R² is independently —OSO₂F. In embodiments, R² is independently —NHSO₂F. In embodiments, R² is independently —B(OH)₂. In embodiments, R² is independently —CHCH₂. In embodiments, R² is independently —CO-oxiranyl. In embodiments, R² is independently —CO-aziridinyl. In embodiments, R² is independently —OCH₂C≡CH. In embodiments, R² is independently unsubstituted tetrazolyl. In embodiments, R² is independently unsubstituted aziridinyl. In embodiments, R² is independently unsubstituted oxiranyl. In embodiments, R² is independently epoxidinyl. In embodiments, R² is independently R⁷-substituted or unsubstituted 2-pyridyl. In embodiments, R² is independently R⁷-substituted or unsubstituted 3-pyridyl. In embodiments, R² is independently R⁷-substituted or unsubstituted 4-pyridyl. In embodiments, R² is independently

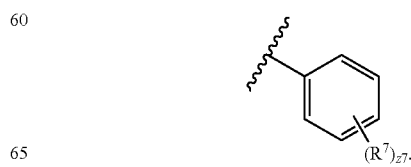

In embodiments, $R^2$ is independently

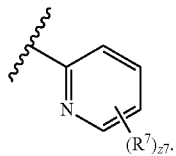

In embodiments, $R^2$ is independently

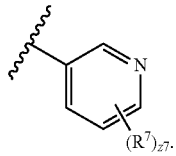

In embodiments, $R^2$ is independently

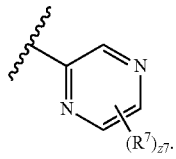

In embodiments, $R^2$ is independently

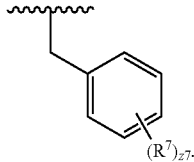

In embodiments, $R^2$ is independently

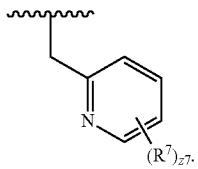

In embodiments, $R^2$ is independently

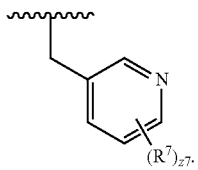

In embodiments, $R^2$ is independently

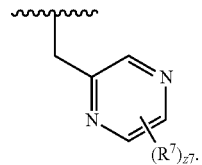

In embodiments, $R^7$ is independently halogen, $-CX^7{}_3$, $-CHX^7{}_2$, $-CH_2X^7$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^7{}_3$, $-OCHX^7{}_2$, $-OCH_2X^7$, $-NHC(NH)NH_2$, $-N=C(NH_2)_2$, $-CH_2SO_3{}^-$, $-PO_3{}^{-2}$, $-SO_3{}^-$, $-SO_2NH_2$, $-CH_2PO_3{}^{-2}-CH_2SO_2NH_2$, $-NHC(O)CHCH_2$, $-NHC(O)CH_2Cl$, $-B(OH)_2$, $-SO_2X^7$, $-OSO_2X^7$, $-NHSO_2X^7$, $-SO_2CH=CH_2$, $-NHSO_2CH=CH_2$, $-CO$-oxiranyl, $-CO$-aziridinyl, epoxidinyl, oxaziridinyl, aziridinyl, $-OCH_2C\equiv CH$, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl. $X^7$ is independently $-F$, $-Cl$, $-Br$, or $-I$; and z7 is an integer from 0 to 3.

In embodiments, $R^7$ is independently halogen. In embodiments, $R^7$ independently is $-CX^7{}_3$. In embodiments, $R^7$ is independently $-CHX^7{}_2$. In embodiments, $R^7$ is independently $-CH_2X^7$. In embodiments, $R^7$ is independently $-CN$. In embodiments, $R^7$ is independently $-OH$. In embodiments, $R^7$ is independently $-NH_2$. In embodiments, $R^7$ is independently $-COH$. In embodiments, $R^7$ is independently $-COOH$. In embodiments, $R^7$ is independently $-CONH_2$. In embodiments, $R^7$ is independently $-NO_2$. In embodiments, $R^7$ is independently $-SH$. In embodiments, $R^7$ is independently $-SO_3H$. In embodiments, $R^7$ is independently $-SO_4H$. In embodiments, $R^7$ is independently $-SO_2NH_2$. In embodiments, $R^7$ is independently $-NHNH_2$. In embodiments, $R^7$ is independently $-ONH_2$. In embodiments, $R^7$ is independently $-NHC(O)NHNH_2$. In embodiments, $R^7$ is independently $-NHC(O)NH_2$. In embodiments, $R^7$ is independently $-NHSO_2H$. In embodiments, $R^7$ is independently $-NHC(O)H$. In embodiments, $R^7$ is independently $-NHC(O)OH$. In embodiments, $R^7$ is independently $-NHOH$. In embodiments, $R^7$ is independently $-OCX^7{}_3$. In embodiments, $R^7$ is independently $-OCHX^7{}_2$. In embodiments, $R^7$ is independently $-OCH_2X^7$. In embodiments, $R^7$ is independently $-NHC(NH)NH_2$. In embodiments, $R^7$ is independently $-N=C(NH_2)_2$. In embodiments, $R^7$ is independently $-CH_2SO_3$. In embodiments, $R^7$ is independently $-PO_3{}^{-2}$. In embodiments, $R^7$ is independently $-SO_3$. In embodiments, $R^7$ is independently $-SO_2NH_2$. In embodiments, $R^7$ is independently $-CH_2PO_3{}^{-2}$. In embodiments, $R^7$ is independently $-CH_2SO_2NH_2$. In embodiments, $R^7$ is independently $-NHC(O)CHCH_2$. In embodiments, $R^7$ is independently $-NHC(O)CH_2Cl$. In embodiments, $R^7$ is independently $-B(OH)_2$. In embodiments, $R^7$ is independently $-SO_2X^7$. In embodiments, $R^7$ is independently $-OSO_2X^7$. In embodiments, $R^7$ is independently $-NHSO_2X^7$. In embodiments, $R^7$ is independently $-SO_2CH=CH_2$. In embodiments, $R^7$ is independently $-NHSO_2CH=CH_2$. In embodiments, $R^7$ is independently $-CO-$ oxiranyl. In embodiments, $R^7$ is independently $-CO$-aziridinyl. In embodiments, $R^7$ is independently epoxidinyl. In embodiments, $R^7$ is independently oxaziridinyl. In embodiments, $R^7$ is independently aziridinyl. In embodiments, $R^7$ is independently —OCH$_2$C≡CH. In embodiments, $R^7$ is independently $R^8$-substituted or unsubstituted alkyl. In embodiments, $R^7$ is independently $R^8$-substituted or unsubstituted heteroalkyl. In embodiments, $R^7$ is independently $R^8$-substituted or unsubstituted cycloalkyl. In embodiments, $R^7$ is independently $R^8$-substituted or unsubstituted heterocycloalkyl. In embodiments, $R^7$ is independently $R^8$-substituted or unsubstituted aryl. In embodiments, $R^7$ is independently $R^8$-substituted or unsubstituted heteroaryl.

In embodiments, $R^7$ is independently halogen, —CX$^7_3$, —CHX$^7_2$, —CH$_2$X$^7$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^7_3$, —OCHX$^7_2$, —OCH$_2$X$^7$, —NHC(NH)NH$_2$, —N=C(NH$_2$)$_2$, —CH$_2$SO$_3^-$, —PO$_3^{-2}$, —SO$_3^-$, —SO$_2$NH$_2$, —CH$_2$PO$_3^{-2}$, —CH$_2$SO$_2$NH$_2$, —NHC(O)CHCH$_2$, —NHC(O)CH$_2$Cl, —B(OH)$_2$, —SO$_2$F, —OSO$_2$F, —NHSO$_2$F, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl.

In embodiments, $R^7$ is independently —CH$_2$F. In embodiments, $R^7$ is independently —B(OH)$_2$. In embodiments, $R^7$ is independently —SO$_2$F. In embodiments, $R^7$ is independently —OSO$_2$F. In embodiments, $R^7$ is independently —NHSO$_2$F. In embodiments, $R^7$ is independently —SO$_2$CH=CH$_2$. In embodiments, $R^7$ is independently —NHSO$_2$CH=CH$_2$. In embodiments, $R^7$ is independently —CO— oxiranyl. In embodiments, $R^7$ is independently —CO-aziridinyl. In embodiments, $R^7$ is independently epoxidinyl. In embodiments, $R^7$ is independently oxaziridinyl. In embodiments, $R^7$ is independently aziridinyl. In embodiments, $R^7$ is independently —OCH$_2$C≡CH.

In embodiments, $R^8$ is independently halogen, —CX$^8_3$, —CHX$^8_2$, —CH$_2$X$^8$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^8_3$, —OCHX$^8_2$, —OCH$_2$X$^8$, —NHC(NH)NH$_2$, —N=C(NH$_2$)$_2$, —CH$_2$SO$_3^-$, —PO$_3^{-2}$, —SO$_3$, —SO$_2$NH$_2$, —CH$_2$PO$_3^{-2}$, —CH$_2$SO$_2$NH$_2$, —NHC(O)CHCH$_2$, —NHC(O)CH$_2$Cl, —B(OH)$_2$, —SO$_2$X$^8$, —OSO$_2$X$^8$, —NHSO$_2$X$^8$, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^8$ is independently —F, —Cl, —Br, or —I.

In embodiments, $R^8$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —NHC(NH)NH$_2$, —N=C(NH$_2$)$_2$, CH$_2$SO$_3^-$, —PO$_3^{-2}$, —SO$_3^-$, —SO$_2$NH$_2$, —CH$_2$PO$_3^{-2}$, —CH$_2$SO$_2$NH$_2$, —NHC(O)CHCH$_2$, —NHC(O)CH$_2$Cl, —B(OH)$_2$, —SO$_2$F, —OSO$_2$F, —SO$_2$CH=CH$_2$, —NHSO$_2$CH=CH$_2$, —CO-oxiranyl, —CO-aziridinyl, —OCH$_2$C≡CH, $R^9$-substituted or unsubstituted alkyl (e.g., C$_1$-C$_8$ alkyl, C$_1$-C$_6$ alkyl, or C$_1$-C$_4$ alkyl), $R^9$-substituted or unsubstituted heteroalkyl (e.g., 2 to 8 membered heteroalkyl, 2 to 6 membered heteroalkyl, or 2 to 4 membered heteroalkyl), $R^9$-substituted or unsubstituted cycloalkyl (e.g., C$_3$-C$_8$ cycloalkyl, C$_3$-C$_6$ cycloalkyl, or C$_5$-C$_6$ cycloalkyl), $R^9$-substituted or unsubstituted heterocycloalkyl (e.g., 3 to 8 membered heterocycloalkyl, 3 to 6 membered heterocycloalkyl, or 5 to 6 membered heterocycloalkyl), $R^9$-substituted or unsubstituted aryl (e.g., C$_6$-C$_{10}$ aryl, C$_{10}$ aryl, or phenyl), or $R^9$-substituted or unsubstituted heteroaryl (e.g., 5 to 10 membered heteroaryl, 5 to 9 membered heteroaryl, or 5 to 6 membered heteroaryl).

In embodiments, $R^8$ is independently oxo. In embodiments, $R^8$ is independently halogen. In embodiments, $R^8$ is independently —CCl$_3$. In embodiments, $R^8$ is independently —CBr$_3$. In embodiments, $R^8$ is independently —CF$_3$. In embodiments, $R^8$ is independently —CI$_3$. In embodiments, $R^8$ is independently —CHCl$_2$. In embodiments, $R^8$ is independently —CHBr$_2$. In embodiments, $R^8$ is independently —CHF$_2$. In embodiments, $R^8$ is independently —CHI$_2$. In embodiments, $R^8$ is independently —CH$_2$Cl. In embodiments, $R^8$ is independently —CH$_2$Br. In embodiments, $R^8$ is independently —CH$_2$F. In embodiments, $R^8$ is independently —CH$_2$I. In embodiments, $R^8$ is independently —CN. In embodiments, $R^8$ is independently —OH. In embodiments, $R^8$ is independently —NH$_2$. In embodiments, $R^8$ is independently —COH. In embodiments, $R^8$ is independently —COOH. In embodiments, $R^8$ is independently —CONH$_2$. In embodiments, $R^8$ is independently —NO$_2$. In embodiments, $R^8$ is independently —SH. In embodiments, $R^8$ is independently —SO$_3$H. In embodiments, $R^8$ is independently —SO$_4$H. In embodiments, $R^8$ is independently —SO$_2$NH$_2$. In embodiments, $R^8$ is independently —NHNH$_2$. In embodiments, $R^8$ is independently —ONH$_2$. In embodiments, $R^8$ is independently —NHC(O)NHNH$_2$. In embodiments, $R^8$ is independently —NHC(O)NH$_2$. In embodiments, $R^8$ is independently —NHSO$_2$H. In embodiments, $R^8$ is independently —NHC(O)H. In embodiments, $R^8$ is independently —NHC(O)OH. In embodiments, $R^8$ is independently —NHOH. In embodiments, $R^8$ is independently —OCCl$_3$. In embodiments, $R^8$ is independently —OCF$_3$. In embodiments, $R^8$ is independently —OCBr$_3$. In embodiments, $R^8$ is independently —OCI$_3$. In embodiments, $R^8$ is independently —OCHCl$_2$. In embodiments, $R^8$ is independently —OCHBr$_2$. In embodiments, $R^8$ is independently —OCHI$_2$. In embodiments, $R^8$ is independently —OCHF$_2$. In embodiments, $R^8$ is independently —OCH$_2$Cl. In embodiments, $R^8$ is independently —OCH$_2$Br. In embodiments, $R^8$ is independently —OCH$_2$I. In embodiments, $R^8$ is independently —OCH$_2$F. In embodiments, $R^8$ is independently —N$_3$. In embodiments, $R^8$ is independently —NHC(NH)NH$_2$. In embodiments, $R^8$ is independently —N=C(NH$_2$)$_2$. In embodiments, $R^8$ is independently —CH$_2$SO$_3^-$. In embodiments, $R^8$ is independently —PO$_3^{-2}$. In embodiments, $R^8$ is independently —SO$_3$. In embodiments, $R^8$ is independently —SO$_2$NH$_2$. In embodiments, $R^8$ is independently —CH$_2$PO$_3^{-2}$. In embodiments, $R^8$ is independently —CH$_2$SO$_2$NH$_2$. In embodiments, $R^8$ is independently —NHC(O)CHCH$_2$. In embodiments, $R^8$ is independently —NHC(O)CH$_2$Cl. In embodiments, $R^8$ is independently —B(OH)$_2$. In embodiments, $R^8$ is independently —SO$_2$X$^8$. In embodiments, $R^8$ is independently —OSO$_2$X$^8$. In embodiments, $R^8$ is independently —NHSO$_2$X$^8$. In embodiments, R$^8$ is independently —SO$_2$CH=CH$_2$. In embodiments, R$^8$ is independently —NHSO$_2$CH=CH$_2$. In embodiments, R$^8$ is independently —CO— oxiranyl. In embodiments, R$^8$ is independently —CO-aziridinyl. In embodiments, R$^8$ is independently epoxidinyl. In embodiments, R$^8$ is independently oxaziridinyl. In embodiments, R$^8$ is independently aziridinyl. In embodiments, R$^8$ is independently —OCH$_2$C≡CH.

In embodiments, R$^8$ is independently —CH$_2$F. In embodiments, R$^8$ is independently —B(OH)$_2$. In embodiments, R$^8$ is independently —SO$_2$F. In embodiments, R$^8$ is independently —OSO$_2$F. In embodiments, R$^8$ is independently —NHSO$_2$F. In embodiments, R$^8$ is independently —SO$_2$CH=CH$_2$. In embodiments, R$^8$ is independently —NHSO$_2$CH=CH$_2$.

In embodiments, R$^9$ is independently halogen, —CX$^9_3$, —CHX$^9_2$, —CH$_2$X$^9$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^9_3$, —OCHX$^9_2$, —OCH$_2$X$^9$, —NHC(NH)NH$_2$, —N=C(NH$_2$)$_2$, —CH$_2$SO$_3^-$, —PO$_3^{-2}$, —SO$_3^-$, —SO$_2$NH$_2$, —CH$_2$PO$_3^{-2}$, —CH$_2$SO$_2$NH$_2$, —NHC(O)CHCH$_2$, —NHC(O)CH$_2$Cl, —B(OH)$_2$, —SO$_2$X$^9$, —OSO$_2$X$^9$, —NHSO$_2$X$^9$, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, unsubstituted alkyl, unsubstituted heteroalkyl, unsubstituted cycloalkyl, unsubstituted heterocycloalkyl, unsubstituted aryl, or unsubstituted heteroaryl. X$^9$ is independently —F, —Cl, —Br, or —I.

In embodiments, R$^9$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —CO H, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —NHC(NH)NH$_2$, —N=C(NH$_2$)$_2$, —CH$_2$SO$_3^-$, —PO$_3^{-2}$, —SO$_3^-$, —SO$_2$NH$_2$, —CH$_2$PO$_3^{-2}$, —CH$_2$SO$_2$NH$_2$, —NHC(O)CHCH$_2$, —NHC(O)CH$_2$Cl, —B(OH)$_2$, —SO$_2$F, —OSO$_2$F, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^9$ is independently oxo. In embodiments, R$^9$ is independently halogen. In embodiments, R$^9$ is independently —CCl$_3$. In embodiments, R$^9$ is independently —CBr$_3$. In embodiments, R$^9$ is independently —CF$_3$. In embodiments, R$^9$ is independently —CI$_3$. In embodiments, R$^9$ is independently —CHCl$_2$. In embodiments, R$^9$ is independently —CHBr$_2$. In embodiments, R$^9$ is independently —CHF$_2$. In embodiments, R$^9$ is independently —CHI$_2$. In embodiments, R$^9$ is independently —CH$_2$Cl. In embodiments, R$^9$ is independently —CH$_2$Br. In embodiments, R$^9$ is independently —CH$_2$F. In embodiments, R$^9$ is independently —CH$_2$I. In embodiments, R$^9$ is independently —CN. In embodiments, R$^9$ is independently —OH. In embodiments, R$^9$ is independently —NH$_2$. In embodiments, R$^9$ is independently —COH. In embodiments, R$^9$ is independently —COOH. In embodiments, R$^9$ is independently —CONH$_2$. In embodiments, R$^9$ is independently —NO$_2$. In embodiments, R$^9$ is independently —SH. In embodiments, R$^9$ is independently —SO$_3$H. In embodiments, R$^9$ is independently —SO$_4$H. In embodiments, R$^9$ is independently —SO$_2$NH$_2$. In embodiments, R$^9$ is independently —NHNH$_2$. In embodiments, R$^9$ is independently —ONH$_2$. In embodiments, R$^9$ is independently —NHC(O)NHNH$_2$. In embodiments, R$^9$ is independently —NHC(O)NH$_2$. In embodiments, R$^9$ is independently —NHSO$_2$H. In embodiments, R$^9$ is independently —NHC(O)H. In embodiments, R$^9$ is independently —NHC(O)OH. In embodiments, R$^9$ is independently —NHOH. In embodiments, R$^9$ is independently —OCCl$_3$. In embodiments, R$^9$ is independently —OCF$_3$. In embodiments, R$^9$ is independently —OCBr$_3$. In embodiments, R$^9$ is independently —OCI$_3$. In embodiments, R$^9$ is independently —OCHCl$_2$. In embodiments, R$^9$ is independently —OCHBr$_2$. In embodiments, R$^9$ is independently —OCHI$_2$. In embodiments, R$^9$ is independently —OCHF$_2$. In embodiments, R$^9$ is independently —OCH$_2$Cl. In embodiments, R$^9$ is independently —OCH$_2$Br. In embodiments, R$^9$ is independently —OCH$_2$I. In embodiments, R$^9$ is independently —OCH$_2$F. In embodiments, R$^9$ is independently —N$_3$. In embodiments, R$^9$ is independently —NHC(NH)NH$_2$. In embodiments, R$^9$ is independently —N=C(NH$_2$)$_2$. In embodiments, R$^9$ is independently —CH$_2$SO$_3$. In embodiments, R$^9$ is independently —PO$_3^{-2}$. In embodiments, R$^9$ is independently —SO$_3$. In embodiments, R$^9$ is independently —SO$_2$NH$_2$. In embodiments, R$^9$ is independently —CH$_2$PO$_3^{-2}$. In embodiments, R$^9$ is independently —CH$_2$SO$_2$NH$_2$. In embodiments, R$^9$ is independently —NHC(O)CHCH$_2$. In embodiments, R$^9$ is independently —NHC(O)CH$_2$Cl. In embodiments, R$^9$ is independently —B(OH)$_2$. In embodiments, R$^9$ is independently —SO$_2$X$^9$. In embodiments, R$^9$ is independently —OSO$_2$X$^9$. In embodiments, R$^9$ is independently —NHSO$_2$X$^9$. In embodiments, R$^9$ is independently —SO$_2$CH=CH$_2$. In embodiments, R$^9$ is independently —NHSO$_2$CH=CH$_2$. In embodiments, R$^9$ is independently —CO— oxiranyl. In embodiments, R$^9$ is independently —CO-aziridinyl. In embodiments, R$^9$ is independently epoxidinyl. In embodiments, R$^9$ is independently oxaziridinyl. In embodiments, R$^9$ is independently aziridinyl. In embodiments, R$^9$ is independently —OCH$_2$C≡CH.

In embodiments, R$^9$ is independently —CH$_2$F. In embodiments, R$^9$ is independently —B(OH)$_2$. In embodiments, R$^9$ is independently —SO$_2$F. In embodiments, R$^9$ is independently —OSO$_2$F. In embodiments, R$^9$ is independently —NHSO$_2$F. In embodiments, R$^9$ is independently —SO$_2$CH=CH$_2$. In embodiments, R$^9$ is independently —NHSO$_2$CH=CH$_2$.

In embodiments, R$^2$ is independently —(CH$_2$)$_{1-5}$NH$_2$, —(CH$_2$)$_{1-5}$COOH, —(CH$_2$)$_{1-5}$CONH$_2$, —(CH$_2$)$_{1-5}$-tetrazolium, —(CH$_2$)$_{1-5}$SO$_2$NH$_2$, —(CH$_2$)$_{1-5}$CONHSO$_2$CH$_3$, —(CH$_2$)$_{1-5}$CONHSO$_2$CF$_3$, —(CH$_2$)$_{1-5}$NHSO$_2$CH$_3$, —(CH$_2$)$_{1-5}$SO$_2$NH$_2$, —(CH$_2$)$_{1-5}$NHCOCl, —(CH$_2$)$_{1-5}$CONH-aziridine, —(CH$_2$)$_{1-5}$NHCOCH=CH$_2$, —(CH$_2$)$_{1-5}$CO-epoxide, —(CH$_2$)$_{1-5}$SO$_2$F, substituted or unsubstituted 2-pyridyl, substituted or unsubstituted 3-pyridyl, substituted or unsubstituted 4-pyridyl, or —(CH$_2$)$_{1-5}$B(OH)$_2$.

In embodiments, R$^2$ is independently —(CH$_2$)$_{1-5}$NH$_2$. In embodiments, R$^2$ is independently —(CH$_2$)$_5$NH$_2$. In embodiments, $R^2$ is independently —$(CH_2)_4NH_2$. In embodiments, $R^2$ is independently —$(CH_2)_3NH_2$. In embodiments, $R^2$ is independently —$(CH_2)_2NH_2$. In embodiments, $R^2$ is independently —$(CH_2)NH_2$. In embodiments, $R^2$ is independently —$(CH_2)_{1-5}COOH$. In embodiments, $R^2$ is independently —$(CH_2)_5COOH$. In embodiments, $R^2$ is independently —$(CH_2)_4COOH$. In embodiments, $R^2$ is independently —$(CH_2)_3COOH$. In embodiments, $R^2$ is independently —$(CH_2)_2COOH$. In embodiments, $R^2$ is independently —$(CH_2)COOH$. In embodiments, $R^2$ is independently —$(CH_2)_{1-5}CONH_2$. In embodiments, $R^2$ is independently —$(CH_2)_5CONH_2$. In embodiments, $R^2$ is independently —$(CH_2)_4CONH_2$. In embodiments, $R^2$ is independently —$(CH_2)_3CONH_2$. In embodiments, $R^2$ is independently —$(CH_2)_2CONH_2$. In embodiments, $R^2$ is independently —$(CH_2)CONH_2$. In embodiments, $R^2$ is independently —$(CH_2)_{1-5}$-tetrazolyl. In embodiments, $R^2$ is independently —$(CH_2)_5$-tetrazolyl. In embodiments, $R^2$ is independently —$(CH_2)_4$-tetrazolyl. In embodiments, $R^2$ is independently —$(CH_2)_3$-tetrazolyl. In embodiments, $R^2$ is independently —$(CH_2)_2$-tetrazolyl. In embodiments, $R^2$ is independently —$(CH_2)$-tetrazolyl. In embodiments, $R^2$ is independently —$(CH_2)_{1-5}SO_2NH_2$. In embodiments, $R^2$ is independently —$(CH_2)_5SO_2NH_2$. In embodiments, $R^2$ is independently —$(CH_2)_4SO_2NH_2$. In embodiments, $R^2$ is independently —$(CH_2)_3SO_2NH_2$. In embodiments, $R^2$ is independently —$(CH_2)_2SO_2NH_2$. In embodiments, $R^2$ is independently —$(CH_2)SO_2NH_2$. In embodiments, $R^2$ is independently —$(CH_2)_{1-5}CONHSO_2CH_3$. In embodiments, $R^2$ is independently —$(CH_2)_5CONHSO_2CH_3$. In embodiments, $R^2$ is independently —$(CH_2)_4CONHSO_2CH_3$. In embodiments, $R^2$ is independently —$(CH_2)_3CONHSO_2CH_3$. In embodiments, $R^2$ is independently —$(CH_2)_2CONHSO_2CH_3$. In embodiments, $R^2$ is independently —$(CH_2)CONHSO_2CH_3$. In embodiments, $R^2$ is independently —$(CH_2)_{1-5}CONHSO_2CF_3$. In embodiments, $R^2$ is independently —$(CH_2)_5CONHSO_2CF_3$. In embodiments, $R^2$ is independently —$(CH_2)_4CONHSO_2CF_3$. In embodiments, $R^2$ is independently —$(CH_2)_3CONHSO_2CF_3$. In embodiments, $R^2$ is independently —$(CH_2)_2CONHSO_2CF_3$. In embodiments, $R^2$ is independently —$(CH_2)CONHSO_2CF_3$. In embodiments, $R^2$ is independently —$(CH_2)_{1-5}NHSO_2CH_3$. In embodiments, $R^2$ is independently —$(CH_2)_5NHSO_2CH_3$. In embodiments, $R^2$ is independently —$(CH_2)_4NHSO_2CH_3$. In embodiments, $R^2$ is independently —$(CH_2)_3NHSO_2CH_3$. In embodiments, $R^2$ is independently —$(CH_2)_2NHSO_2CH_3$. In embodiments, $R^2$ is independently —$(CH_2)NHSO_2CH_3$. In embodiments, $R^2$ is independently —$(CH_2)_{1-5}SO_2NH_2$. In embodiments, $R^2$ is independently —$(CH_2)_5SO_2NH_2$. In embodiments, $R^2$ is independently —$(CH_2)_4SO_2NH_2$. In embodiments, $R^2$ is independently —$(CH_2)_3SO_2NH_2$. In embodiments, $R^2$ is independently —$(CH_2)_2SO_2NH_2$. In embodiments, $R^2$ is independently —$(CH_2)SO_2NH_2$. In embodiments, $R^2$ is independently —$(CH_2)_{1-5}NHCOCl$. In embodiments, $R^2$ is independently —$(CH_2)_5NHCOCl$. In embodiments, $R^2$ is independently —$(CH_2)_4NHCOCl$. In embodiments, $R^2$ is independently —$(CH_2)_3NHCOCl$. In embodiments, $R^2$ is independently —$(CH_2)_2NHCOCl$. In embodiments, $R^2$ is independently —$(CH_2)NHCOCl$. In embodiments, $R^2$ is independently —$(CH_2)_{1-5}CONH$-aziridinyl. In embodiments, $R^2$ is independently —$(CH_2)_5CONH$-aziridinyl. In embodiments, $R^2$ is independently —$(CH_2)_4CONH$-aziridinyl. In embodiments, $R^2$ is independently —$(CH_2)_3CONH$-aziridinyl. In embodiments, $R^2$ is independently —$(CH_2)_2CONH$-aziridinyl. In embodiments, $R^2$ is independently —$(CH_2)CONH$-aziridinyl. In embodiments, $R^2$ is independently —$(CH_2)_{1-5}NHCOCH=CH_2$. In embodiments, $R^2$ is independently —$(CH_2)_5NHCOCH=CH_2$. In embodiments, $R^2$ is independently —$(CH_2)_4NHCOCH=CH_2$. In embodiments, $R^2$ is independently —$(CH_2)_3NHCOCH=CH_2$. In embodiments, $R^2$ is independently —$(CH_2)_2NHCOCH=CH_2$. In embodiments, $R^2$ is independently —$(CH_2)NHCOCH=CH_2$. In embodiments, $R^z$ is independently —$(CH_2)_{1-5}CO$-epoxide. In embodiments, $R^2$ is independently —$(CH_2)_5CO$-epoxide. In embodiments, $R^2$ is independently —$(CH_2)_4CO$-epoxide. In embodiments, $R^2$ is independently —$(CH_2)_3CO$-epoxide. In embodiments, $R^2$ is independently —$(CH_2)_2CO$-epoxide. In embodiments, $R^2$ is independently —$(CH_2)_1CO$-epoxide. In embodiments, $R^2$ is independently —$(CH_2)_{1-5}SO_2F$. In embodiments, $R^2$ is independently —$(CH_2)_5SO_2F$. In embodiments, $R^2$ is independently —$(CH_2)_4SO_2F$. In embodiments, $R^2$ is independently —$(CH_2)_3SO_2F$. In embodiments, $R^2$ is independently —$(CH_2)_2SO_2F$. In embodiments, $R^2$ is independently —$(CH_2)SO_2F$. In embodiments, $R^2$ is independently substituted or unsubstituted 2-pyridyl. In embodiments, $R^2$ is independently substituted or unsubstituted 3-pyridyl. In embodiments, $R^2$ is independently substituted or unsubstituted 4-pyridyl. In embodiments, $R^2$ is independently —$(CH_2)_{1-5}B(OH)_2$. In embodiments, $R^2$ is independently —$(CH_2)_5B(OH)_2$. In embodiments, $R^2$ is independently —$(CH_2)_4B(OH)_2$. In embodiments, $R^2$ is independently —$(CH_2)_3B(OH)_2$. In embodiments, $R^2$ is independently —$(CH_2)_2B(OH)_2$. In embodiments, $R^2$ is independently —$(CH_2)B(OH)_2$.

In embodiments, $R^2$ is independently

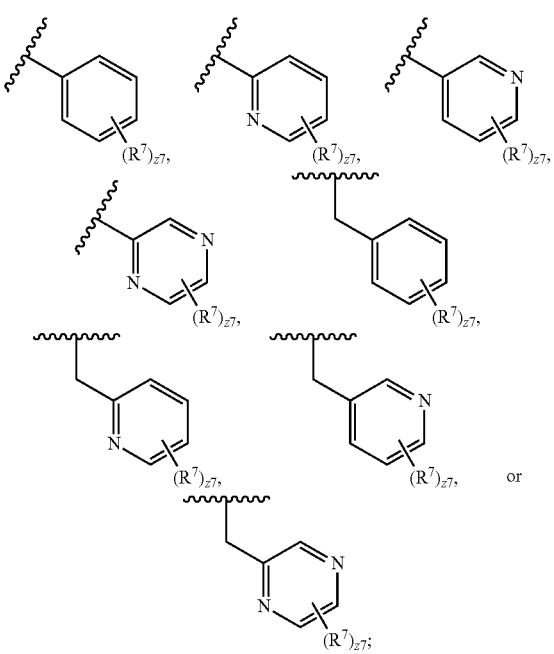

wherein $R^7$ is independently —$CH_2SO_3^-$, —$PO_3^{-2}$, —$OPO_3^{-2}$, —$SO_3^-$, —$SO_2NH_2$, —$CH_2PO_3^{-2}$, —$CO_2$—, —$CH_2SO_2NH_2$, —$CF_3$, —Cl, —F, —$CH_3$, —$NO_2$, —$C_2H_5$, —$OCH_3$, —$OCF_3$, guanidino, acrylamide, -2-chloroacetamide, —$B(OH)_2$, —$SO_2F$, —$OSO_2F$, —$NHSO_2F$, —$SO_2CH=CH_2$, —$NHSO_2CH=CH_2$, —COH, —$OCH_2C\equiv CH$, —CO-epoxide, —CO-aziridine, epoxide, aziridine, or oxaziridine; and z7 is an integer from 0 to 3. In embodiments, z7 is 0. In embodiments, z7 is 1. In embodiments, z7 is 2. In embodiments, z7 is 3.

In embodiments, $R^2$ is an electronegative moiety. In embodiments, $R^2$ is an electronegative moiety, independently having the formula: —F, —Cl, —Br, —I, —CH$_3$, —C$_2$H$_5$, —OH, —OCH$_3$, —OCH$_2$F, —OCF$_3$, —CF$_3$, —CN, —C(O)H, —C(O)NH$_2$, —CO$_2$CH$_3$. —NO$_2$, —NH$_2$, —NHCH$_3$, —N(CH$_3$)$_2$, —SH, —SCH$_3$, or —SO$_2$NH$_2$.

In embodiments, $R^2$ is an electronegative moiety, independently having the formula:

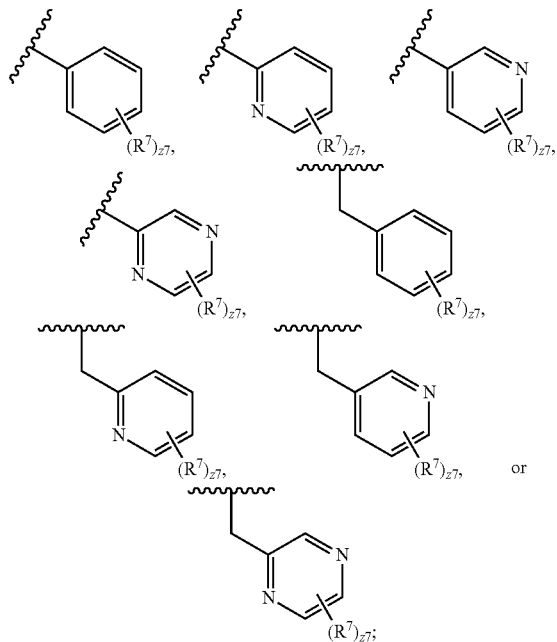

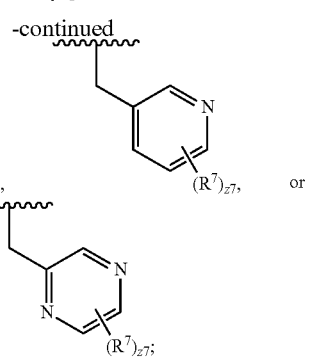

wherein $R^7$ is independently —F, —Cl, —Br, —I, —CH$_3$, —C$_2$H$_5$, —OH, —OCH$_3$, —OCH$_2$F, —OCF$_3$, —CF$_3$, —CN, —C(O)H, —C(O)NH$_2$, —CO$_2$CH$_3$. —NO$_2$, —NH$_2$, —NHCH$_3$, —N(CH$_3$)$_2$, —SH, —SCH$_3$, or —SO$_2$NH$_2$.

In embodiments, $R^2$ is capable of forming a salt bridge (e.g., with an amino acid residue such as a lysine). In embodiments, $R^2$ is capable of forming a salt bridge, independently having the formula: —CH$_2$SO$_3^-$, —PO$_3^{-2}$, —OPO$_3^{-2}$, —SO$_3^-$, —CH$_2$PO$_3^{-2}$, or —CO$_2^-$. In embodiments, $R^2$ forms a salt bridge with a lysine residue.

In embodiments, $R^2$ is capable of forming a salt bridge, independently having the formula:

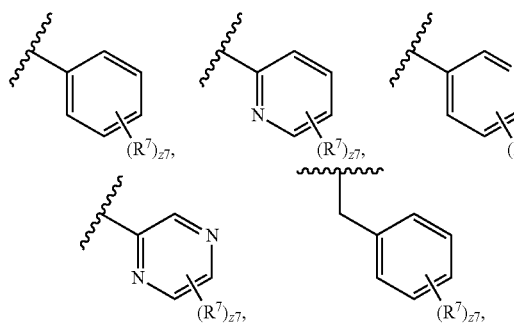

wherein $R^7$ is independently —CH$_2$SO$_3^-$, —PO$_3^{-2}$, —OPO$_3^{-2}$, —SO$_3^-$, —CH$_2$PO$_3^{-2}$, or —CO$_2^-$.

In embodiments, $R^2$ is a covalent lysine modifier moiety. In embodiments, $R^2$ is capable of forming a covalent bond with an amino acid residue (e.g., a lysine residue). In embodiments, $R^2$ is a covalent lysine modifier moiety, independently having the formula: —SO$_2$X$^2$, —SO$_2$CH=CH$_2$, —NHSO$_2$CH=CH$_2$, —OSO$_2$X$^2$, —B(OH)$_2$, —NHSO$_2$X$^2$, or CH$_2$X$^2$. X$^2$ is independently —F, —Cl, —Br, or —I.

In embodiments, $R^2$ is a covalent lysine modifier moiety, independently having the formula:

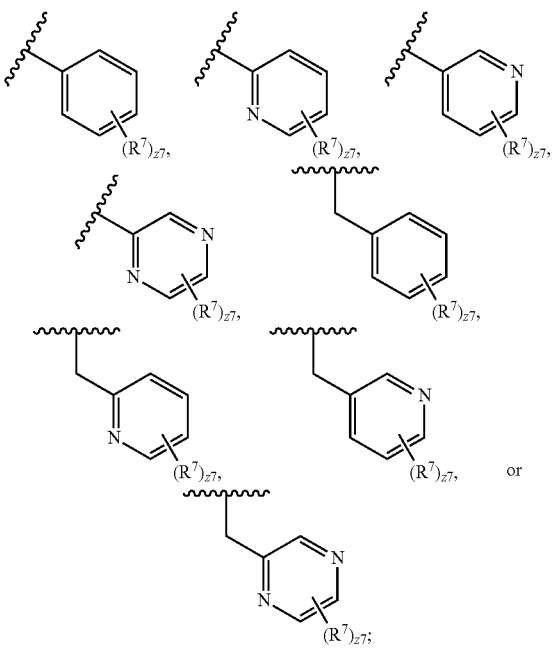

wherein $R^7$ is independently —SO$_2$X$^7$, —SO$_2$CH=CH$_2$, —NHSO$_2$CH=CH$_2$, —OSO$_2$X$^7$, —B(OH)$_2$, —NHSO$_2$X$^7$, or CH$_2$X$^7$. X$^7$ is independently —F, —Cl, —Br, or —I.

In embodiments, $R^2$ is a covalent lysine modifier moiety, independently having the formula:

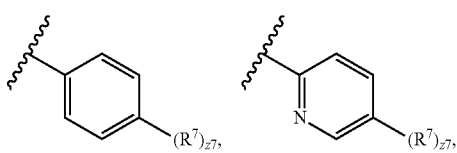

-continued

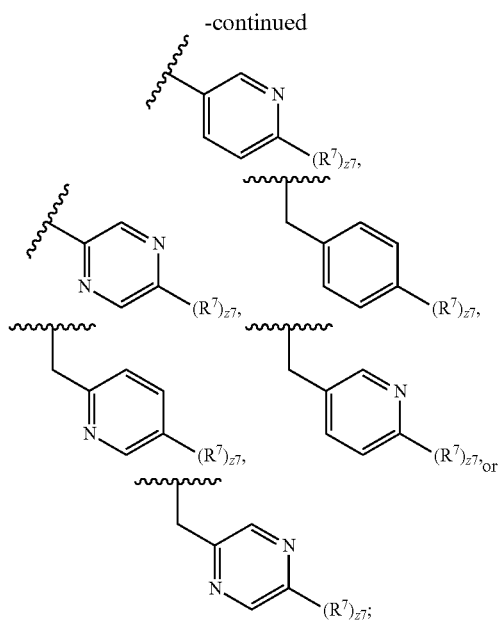

wherein R⁷ is independently —SO$_2$X$^7$, —SO$_2$CH═CH$_2$, —NHSO$_2$CH═CH$_2$, —OSO$_2$X$^7$, —B(OH)$_2$, —NHSO$_2$X$^7$, or CH$_2$X$^7$. X$^7$ is independently —F, —Cl, —Br, or —I.

In embodiments, R² is independently halogen, —CX²$_3$, —CHX²$_2$, —CH$_2$X², —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX²$_3$, —OCHX²$_2$, —OCH$_2$X², —SO$_2$CH$_3$, —SO$_2$CX²$_3$, —SO$_2$CH$_3$, —SO$_2$X², —SO$_2$CH═CH$_2$, —NHSO$_2$CH═CH$_2$, —OSO$_2$X², —NHSO$_2$X², —B(OH)$_2$, —CO-oxiranyl, —CO-aziridinyl, epoxidinyl, oxaziridinyl, aziridinyl, —OCH$_2$C≡CH, R$^7$-substituted or unsubstituted alkyl, R$^7$-substituted or unsubstituted heteroalkyl, R$^7$-substituted or unsubstituted cycloalkyl, R$^7$-substituted or unsubstituted heterocycloalkyl, R$^7$-substituted or unsubstituted aryl, or R$^7$-substituted or unsubstituted heteroaryl. In embodiments, R² is independently halogen, —CX²$_3$, —CHX²$_2$, —CH$_2$X², —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX²$_3$, —OCHX²$_2$, —OCH$_2$X², —SO$_2$CH$_3$, —SO$_2$CX²$_3$, —SO$_2$CH$_3$, —SO$_2$X², —SO$_2$CH═CH$_2$, —NHSO$_2$CH═CH$_2$, —OSO$_2$X², —B(OH)$_2$, —CO-oxiranyl, —CO-aziridinyl, epoxidinyl, oxaziridinyl, aziridinyl, —OCH$_2$C≡CH, unsubstituted alkyl, unsubstituted heteroalkyl, unsubstituted cycloalkyl, unsubstituted heterocycloalkyl, unsubstituted aryl, or unsubstituted heteroaryl.

In embodiments, R² is:

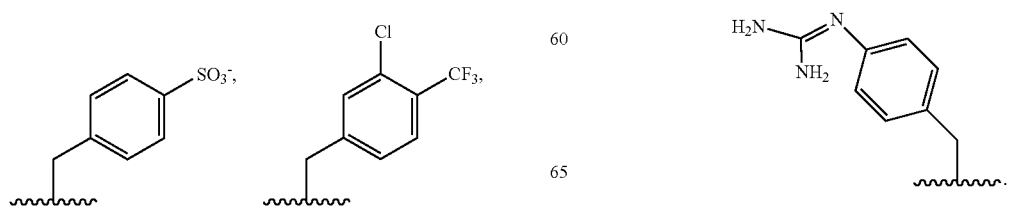

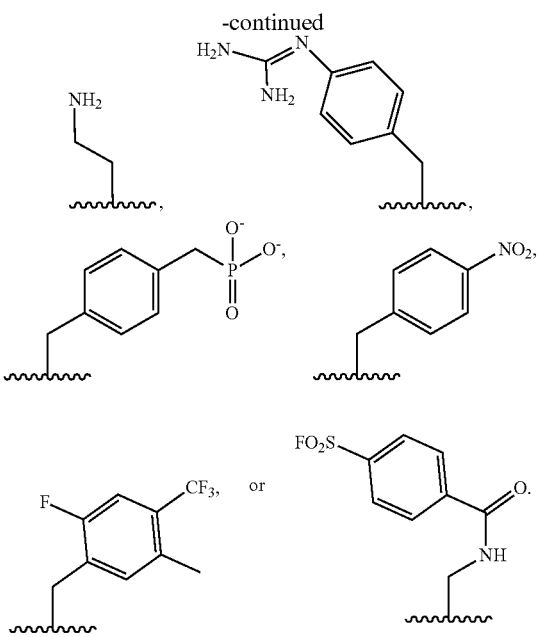

In embodiments, R² is

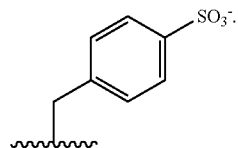

In embodiments, R² is

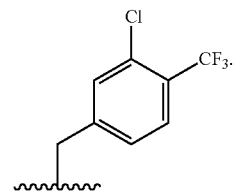 [SMILES: *Cc1ccc(C(F)(F)F)c(Cl)c1]

In embodiments, R² is

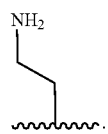

In embodiments, R² is

In embodiments, R² is

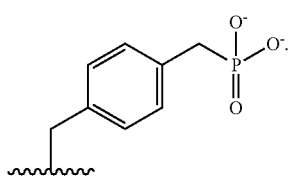

In embodiments, R² is

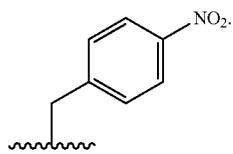 [SMILES: *Cc1ccc([N+](=O)[O-])cc1]

In embodiments, R² is

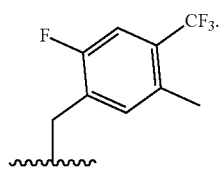 [SMILES: *Cc1cc(C)c(C(F)(F)F)cc1F]

In embodiments, R² is

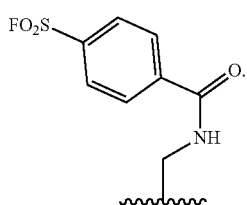

In embodiments, R⁷ is capable of forming a salt bridge (e.g., with an amino acid residue such as a lysine). In embodiments, R⁷ is capable of forming a salt bridge, independently having the formula: —CH₂SO₃, —PO₃⁻², —OPO₃⁻², —SO₃, —CH₂PO₃⁻², or —CO₂. In embodiments, R⁷ forms a salt bridge with a lysine residue.

In embodiments, R⁷ is a covalent lysine modifier moiety. In embodiments, R⁷ is capable of forming a covalent bond with an amino acid residue (e.g., a lysine residue). In embodiments, R⁷ is a covalent lysine modifier moiety, independently having the formula: —SO₂F, —SO₂CH=CH₂, —NHSO₂CH=CH₂, —OSO₂F, —NHSO₂F, or —B(OH)₂.

In embodiments, L³ is a bond, —C(O)NH—, unsubstituted alkylene, substituted heteroalkylene, unsubstituted alkylheteroarylene, or unsubstituted heteroarylene. In embodiments, L³ is a bond, —C(O)NH—, —CH₂—

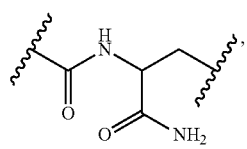 [SMILES: *CC(NC(*)=O)C(N)=O]

-continued

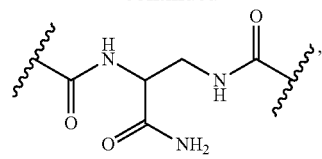 [SMILES: *C(=O)NCC(NC(*)=O)C(N)=O]

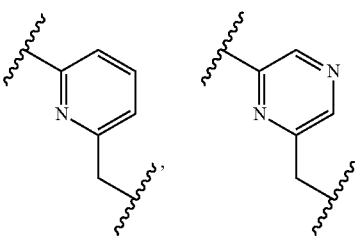, or

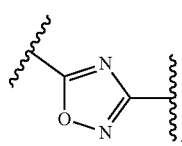

In embodiments, L³ is a bond. In embodiments, L³ is —C(O)NH—. In embodiments, L³ is unsubstituted alkylene. In embodiments, L³ is substituted heteroalkylene. In embodiments, L³ is unsubstituted alkylheteroarylene. In embodiments, L³ is unsubstituted heteroarylene. In embodiments, L³ is —C(O)NH—. In embodiments, L³ is —CH₂—. In embodiments, L³ is

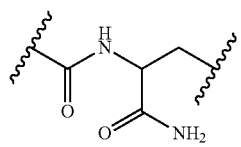

In embodiments, L³ is

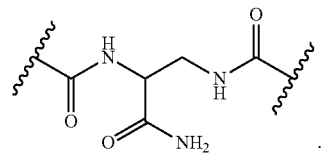

In embodiments, L³ is

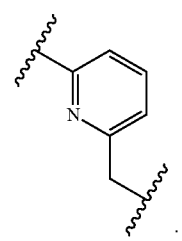 [SMILES: *Cc1cccc(*)n1]

In embodiments, L³ is

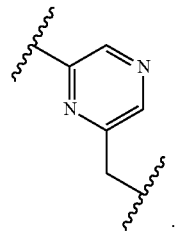 [SMILES: *Cc1cncc(*)n1]

In embodiments, L³ is

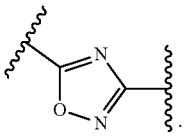 [SMILES: *c1noc(*)n1]

In embodiments, L³ is R³⁰-substituted or unsubstituted arylene. In embodiments, L³ is unsubstituted arylene. In embodiments, L³ is R³⁰-substituted or unsubstituted heteroarylene. In embodiments, L³ is an unsubstituted heteroarylene. In embodiments, L³ is an unsubstituted 6 membered heteroarylene.

In embodiments, L³ is a bond, —NH—, —O—, —S—, —C(O)—, —C(O)NH—, —NHC(O)—, —NHC(O)NH—, —C(O)O—, —OC(O)—, R³⁰-substituted or unsubstituted alkylene, R³⁰-substituted or unsubstituted heteroalkylene, R³⁰-substituted or unsubstituted cycloalkylene, R³⁰-substituted or unsubstituted heterocycloalkylene, R³⁰-substituted or unsubstituted arylene, R³⁰-substituted or unsubstituted heteroarylene, R³⁰-substituted or unsubstituted alkylarylene, R³⁰-substituted or unsubstituted alkylheteroarylene.

In embodiments, -L³-(Ring A)-(R³)$_{z3}$ is

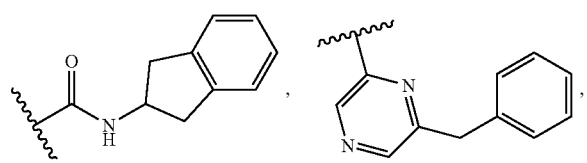

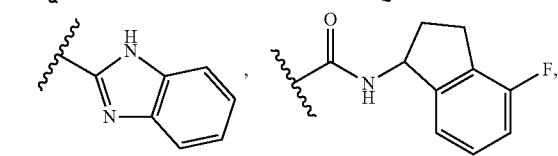

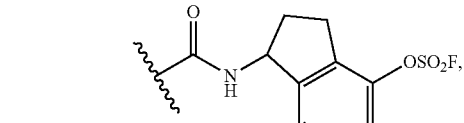

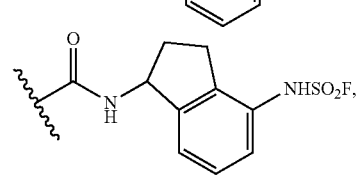

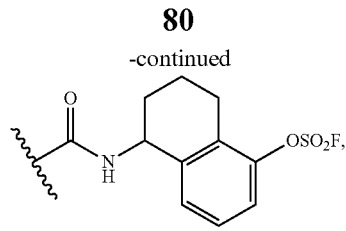

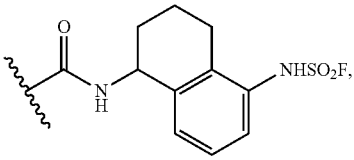

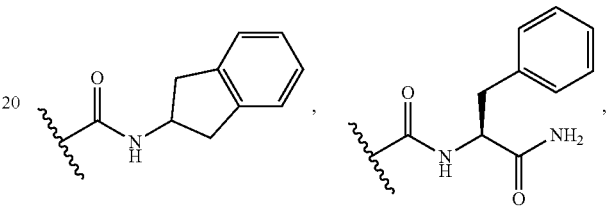

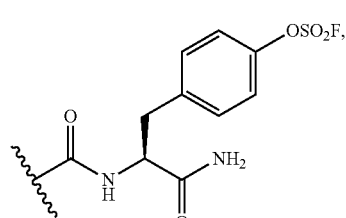

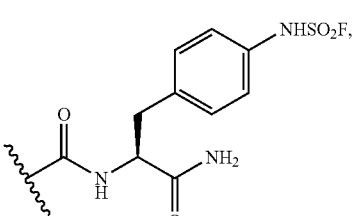

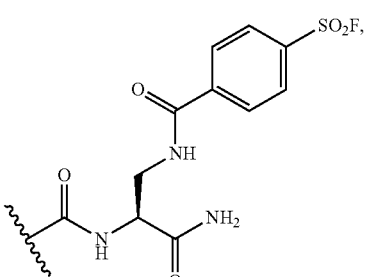

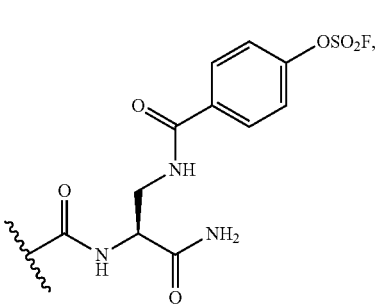

-continued
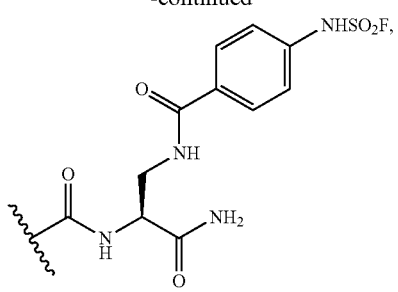
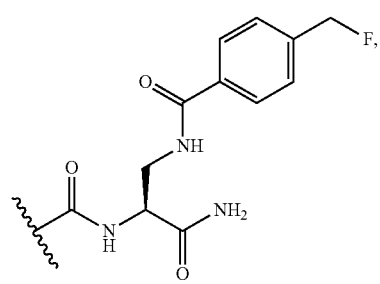
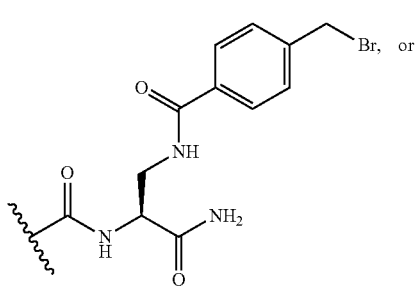
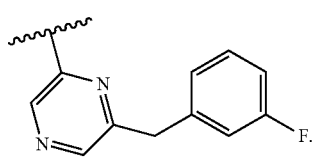
In embodiments, -L³-(Ring A)-(R³)$_{z3}$ is
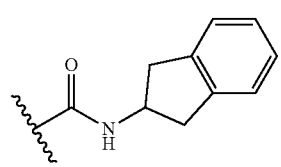
In embodiments, -L³-(Ring A)-(R³)$_{z3}$ is
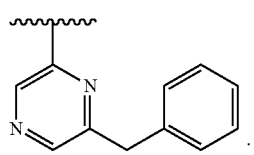 [SMILES: *c1cncc(Cc2ccccc2)n1]
In embodiments, -L³-(Ring A)-(R³)$_{z3}$ is
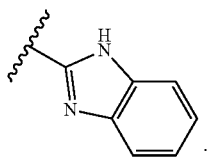 [SMILES: *c1nc2ccccc2[nH]1]
In embodiments, -L³-(Ring A)-(R³)$_{z3}$ is
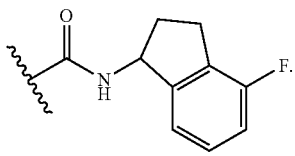 [SMILES: *C(=O)NC1CCc2c(F)cccc21]
In embodiments, -L³-(Ring A)-(R³)$_{z3}$ is
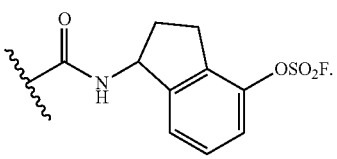
In embodiments, -L³-(Ring A)-(R³)$_{z3}$ is
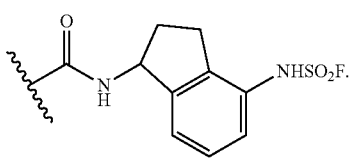
In embodiments, -L³-(Ring A)-(R³)$_{z3}$ is
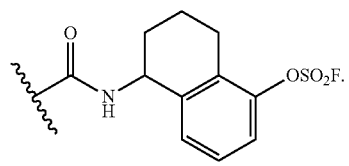
In embodiments, -L³-(Ring A)-(R³)$_{z3}$ is
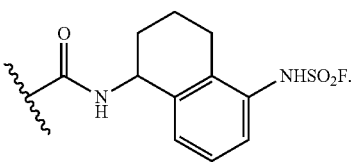

In embodiments, -L³-(Ring A)-(R³)_{z3} is
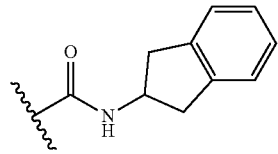
In embodiments, -L³-(Ring A)-(R³)_{z3} is
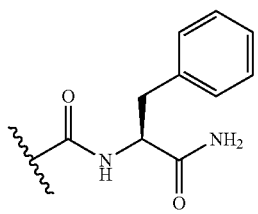
In embodiments, -L³-(Ring A)-(R³)_{z3} is
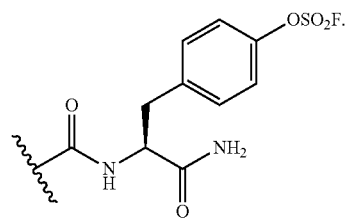
In embodiments, -L³-(Ring A)-(R³)_{z3} is
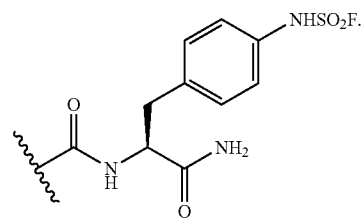
In embodiments, -L³-(Ring A)-(R³)_{z3} is
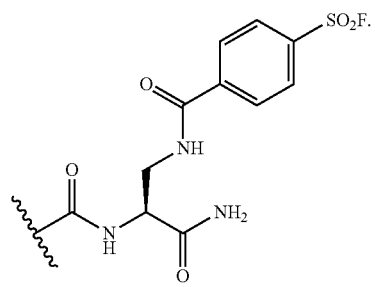 [SMILES: *C(=O)N[C@@H](CNC(=O)c1ccc(S(=O)(=O)F)cc1)C(N)=O]
In embodiments, -L³-(Ring A)-(R³)_{z3} is
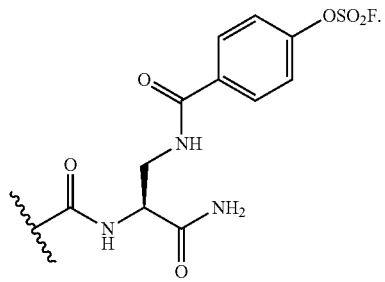
In embodiments, -L³-(Ring A)-(R³)_{z3} is
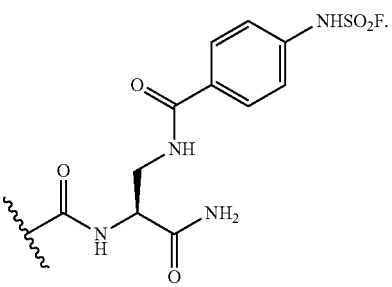
In embodiments, -L³-(Ring A)-(R³)_{z3} is
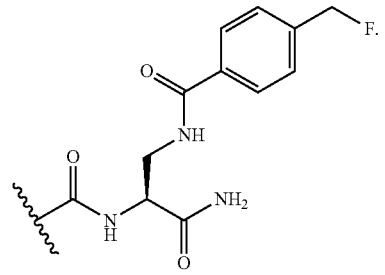 [SMILES: *C(=O)N[C@@H](CNC(=O)c1ccc(CF)cc1)C(N)=O]
In embodiments, -L³-(Ring A)-(R³)_{z3} is
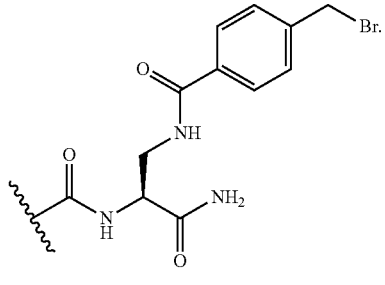 [SMILES: *C(=O)N[C@@H](CNC(=O)c1ccc(CBr)cc1)C(N)=O]
In embodiments, -L³-(Ring A)-(R³)_{z3} is
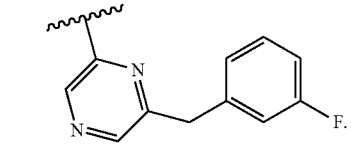 [SMILES: *c1cncc(Cc2cccc(F)c2)n1]

R³⁰ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O) NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, unsubstituted alkyl (e.g., C₁-C₈ alkyl, C₁-C₆ alkyl, or C₁-C₄ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C₃-C₈ cycloalkyl, C₃-C₆ cycloalkyl, or C₅-C₆ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C₆-C₁₀ aryl, C₁₀ aryl, or phenyl), or unsubstituted heteroaryl (e.g., 5 to 10 membered heteroaryl, 5 to 9 membered heteroaryl, or 5 to 6 membered heteroaryl).

In embodiments, Ring A is substituted (e.g., R³ substituted) or unsubstituted cycloalkyl (e.g., C₃-C₈ cycloalkyl, C₃-C₆ cycloalkyl, or C₅-C₆ cycloalkyl). In embodiments, Ring A is substituted (e.g., R³ substituted) or unsubstituted C₃-C₈ cycloalkyl. In embodiments, Ring A is substituted (e.g., R³ substituted) or unsubstituted C₃-C₆ cycloalkyl. In embodiments, Ring A is substituted (e.g., R³ substituted) or unsubstituted C₅-C₆ cycloalkyl. In embodiments, Ring A is substituted (e.g., R³ substituted) or unsubstituted C₆ cycloalkyl. In embodiments, Ring A is substituted (e.g., R³ substituted) or unsubstituted C₅ cycloalkyl.

In embodiments, Ring A is substituted (e.g., R³ substituted) or unsubstituted heterocycloalkyl (e.g., 3 to 8 membered heterocycloalkyl, 3 to 6 membered heterocycloalkyl, or 5 to 6 membered heterocycloalkyl). In embodiments, Ring A is substituted (e.g., R³ substituted) or unsubstituted 3 to 8 membered heterocycloalkyl. In embodiments, Ring A is substituted (e.g., R³ substituted) or unsubstituted 3 to 6 membered heterocycloalkyl. In embodiments, Ring A is substituted (e.g., R³ substituted) or unsubstituted 5 to 6 membered heterocycloalkyl. In embodiments, Ring A is substituted (e.g., R³ substituted) or unsubstituted 6 membered heterocycloalkyl. In embodiments, Ring A is substituted (e.g., R³ substituted) or unsubstituted 5 membered heterocycloalkyl. It will be understood by a person having ordinary skill in the art that Ring A is unsubstituted when Ring A is bonded to L3 and z3 is 0, and Ring A is substituted when Ring A is bonded to L3 and z3 is non-zero.

In embodiments, Ring A is aziridinyl, oziranyl, thiiranyl, azetidinyl, 1,2-dihydroazotyl, oxetanyl, 2H-oxetyl, thietanyl, 2H-thietyl, pyrrolidinyl, 2,5-dihydro-1H-pyrrolyl, 4,5-dihydro-1H-imidazolyl, imidazolinyl, pyrazolinyl, tetrahydrofuranyl, thiolanyl, piperidinyl, piperazinyl, 2H-pyranyl, morpholinyl, 1,4-dioxanyl, tetrahydro-2H-pyranyl, thianyl, or dithianyl.

In embodiments, Ring A is substituted (e.g., R³ substituted) or unsubstituted (C₆-C₁₀) aryl. In embodiments, Ring A is substituted (e.g., R³ substituted) (C₆-C₁₀) aryl. In embodiments, Ring A is unsubstituted (C₆-C₁₀) aryl. In embodiments, Ring A is phenyl. In embodiments, Ring A is naphthyl.

In embodiments, Ring A is imidazolyl, pyrrolyl, pyrazolyl, triazolyl, tetrazolyl, furanyl, oxazolyl, isooxazolyl, oxadiazolyl, oxatriazolyl, thienyl, thiazolyl, isothiazolyl, pyridinyl, pyrazinyl, pyrimidinyl, pyridazinyl, or triazinyl (e.g., 1,3,5-triazinyl, 1,2,3-triazinyl, or 1,2,4-triazinyl).

In embodiments, Ring A is substituted (e.g., R³ substituted) or unsubstituted 5 to 10 membered heteroaryl. In embodiments, Ring A is substituted (e.g., R³ substituted) 5 to 10 membered heteroaryl. In embodiments, Ring A is unsubstituted 5 to 10 membered heteroaryl. In embodiments, Ring A is substituted (e.g., R³ substituted) or unsubstituted 5 to 9 membered heteroaryl. In embodiments, Ring A is substituted (e.g., R³ substituted) 5 to 9 membered heteroaryl. In embodiments, Ring A is unsubstituted 5 to 9 membered heteroaryl. In embodiments, Ring A is substituted (e.g., R³ substituted) or unsubstituted 5 to 6 membered heteroaryl. In embodiments, Ring A is substituted (e.g., R³ substituted) 5 to 6 membered heteroaryl. In embodiments, Ring A is unsubstituted 5 to 6 membered heteroaryl.

In embodiments, Ring A is indolyl, benzimidazolyl, indazolyl, benzotriazolyl, pyrrolopyrimidinyl, purinyl, indolizinyl, pyrrolopyriazinyl, pyrrolopyriminyl, imidazopyridazinyl, imidazopyridinyl, imidazopyrimidinyl, cinnolinyl, quinazolinyl, quinoxalinyl, phthalazinyl, pyridopyrazinyl, pteridinyl, pyrazolopyridinyl, quinolinyl, isoquinolinyl, naphthyridinyl, or carbazolyl.

In embodiments, Ring A is a fused ring aryl. In embodiments, Ring A is benzocyclopentyl.

In embodiments, -(Ring A)-(R³)^z³ is

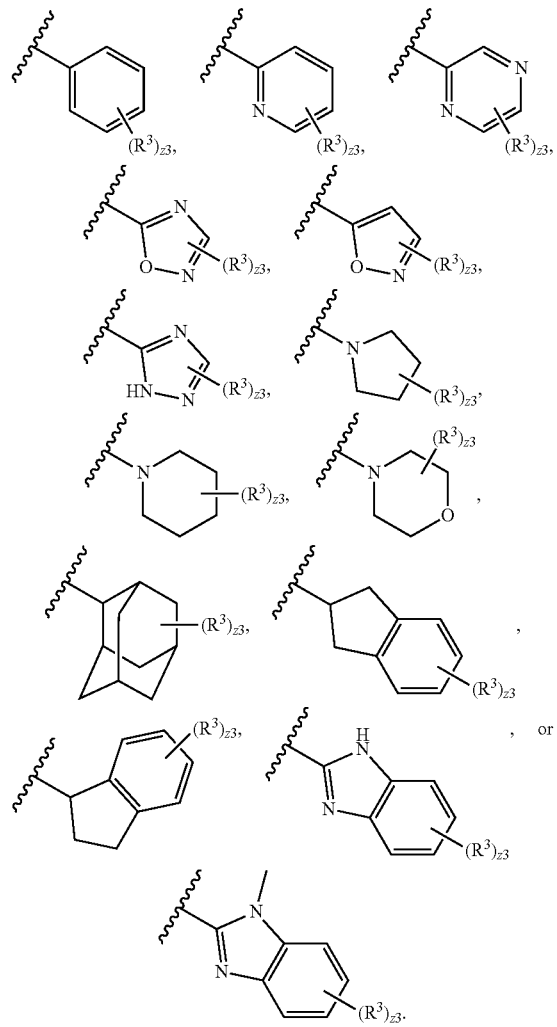

In embodiments, -(Ring A)-$(R^3)_{z3}$ is

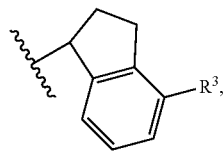

wherein $R^3$ is as described herein. In embodiments, $R^3$ is halogen. In embodiments, $R^3$ is —F. In embodiments, $R^3$ is an electronegative moiety. In embodiments, $R^3$ is an electronegative moiety, independently having the formula: —F, —Cl, —Br, —I, —$CH_3$, —$C_2H5$, —OH, —$OCH_3$, —$OCH_2F$, —$OCF_3$, —$CF_3$, —CN, —C(O)H, —C(O)$NH_2$, —$CO_2CH_3$, —$NO_2$, —$NH_2$, —$NHCH_3$, —$N(CH_3)_2$, —SH, —$SCH_3$, or —$SO_2NH_2$.

In embodiments, $R^3$ is independently halogen, —$CX^3{}_3$, —$CHX^3{}_2$, —$CH_2X^3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^3{}_3$, —$OCHX^3{}_2$, —$OCH_2X^3$, —$SO_2X^3$, —$SO_2CH=CH_2$, —$NHSO_2CH=CH_2$, —$OSO_2X^3$, —B(OH)$_2$, —$NHSO_2X^3$, $CH_2X^3$, —CO-oxiranyl, —CO-aziridinyl, epoxidinyl, oxaziridinyl, aziridinyl, —$OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl.

In embodiments, $R^3$ is independently halogen, —$CX^3{}_3$, —$CHX^3{}_2$, —$CH_2X^3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^3{}_3$, —$OCHX^3{}_2$, —$OCH_2X^3$, —CO-oxiranyl, —CO-aziridinyl, epoxidinyl, oxaziridinyl, aziridinyl, —$OCH_2C\equiv CH$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl.

In embodiments, $R^3$ is independently halogen, —$CX^3{}_3$, —$CHX^3{}_2$, —$CH_2X^3$, —OH, —$OCX^3{}_3$, —$OCHX^3{}_2$, —$OCH_2X^3$, unsubstituted $C_1$-$C_4$ alkyl, or unsubstituted 2 to 3 membered heteroalkyl. In embodiments, $R^3$ is independently —F, —Cl, —Br, —I, —$CH_3$, —$C_2H5$, —OH, —$OCH_3$, —$OCH_2F$, —$OCF_3$, —$CF_3$, —CN, —C(O)H, —C(O)$NH_2$, —$CO_2CH_3$, —$NO_2$, —$NH_2$, —$NHCH_3$, —$N(CH_3)_2$, —SH, —$SCH_3$, or —$SO_2NH_2$.

In embodiments, $R^3$ is an electronegative moiety. In embodiments, $R^3$ is an electronegative moiety, independently having the formula: —F, —Cl, —Br, —I, —$CH_3$, —$C_2H5$, —OH, —$OCH_3$, —$OCH_2F$, —$OCF_3$, —$CF_3$, —CN, —C(O)H, —C(O)$NH_2$, —$CO_2CH_3$, —$NO_2$, —$NH_2$, —$NHCH_3$, —$N(CH_3)_2$, —SH, —$SCH_3$, or —$SO_2NH_2$.

In embodiments, $R^3$ is independently halogen, —$CX^3{}_3$, —$CHX^3{}_2$, —$CH_2X^3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^3{}_3$, —$OCHX^3{}_2$, —$OCH_2X^3$, —$SO_2X^3$, —$SO_2CH=CH_2$, —$NHSO_2CH=CH_2$, —$OSO_2X^3$, —$NHSO_2X^3$, —B(OH)$_2$, —CO-oxiranyl, —CO-aziridinyl, epoxidinyl, oxaziridinyl, aziridinyl, —$OCH_2C\equiv CH$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl. Two adjacent $R^3$ substituents may optionally be joined to form an $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^{31}$ is independently oxo, halogen, —$CX^{313}$, —$CHX^{312}$, —$CH_2X^{31}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{31}{}_3$, —$OCHX^{31}{}_2$, —$OCH_2X^{31}$, —$N_3$, —$SO_2X^{31}$, —$SO_2CH=CH_2$, —$NHSO_2CH=CH_2$, —$OSO_2X^{31}$, —B(OH)$_2$, —$NHSO_2X^{31}$, —CO-oxiranyl, —CO-aziridinyl, epoxidinyl, oxaziridinyl, aziridinyl, —$OCH_2C\equiv CH$, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl). $X^{31}$ is independently —F, —Cl, —Br, or —I.

In embodiments, $R^{31}$ is independently —$CH_2F$, —$SO_2F$, —$SO_2CH=CH_2$, —$NHSO_2CH=CH_2$, —$OSO_2F$, —B(OH)$_2$, or —$NHSO_2F$.

In embodiments, $R^{31}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl).

$R^{32}$ is independently oxo, halogen, —$CX^{323}$, —$CHX^3{}_{22}$, —$CH_2X^{32}$, —CN, —OH, —$NH_2$, —COH, —COOH, —$CONH_2$, —$NO_2$, —SH, —$SO_3H$, —$SO_4H$, —$SO_2NH_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{32}$$_3$, —OCHX$^3$$_{22}$, —OCH$_2$X$^{32}$, —N$_3$, —SO$_2$X$^{32}$, —SO$_2$CH═CH$_2$, —NHSO$_2$CH═CH$_2$, —OSO$_2$X$^{32}$, —B(OH)$_2$, —NHSO$_2$X$^{32}$, —CO-oxiranyl, —CO-aziridinyl, epoxidinyl, oxaziridinyl, aziridinyl, —OCH$_2$C≡CH, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl). X$^{32}$ is independently —F, —Cl, —Br, or —I.

In embodiments, R$^{32}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{32}$ is independently —CH$_2$F, —SO$_2$F, —SO$_2$CH═CH$_2$, —NHSO$_2$CH═CH$_2$, —OSO$_2$F, —B(OH)$_2$, or —NHSO$_2$F.

In embodiments, R$^4$ is independently hydrogen, halogen, —CX$^4$$_3$, —CHX$^4$$_2$, —CH$_2$X$^4$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^4$$_3$, —OCHX$^4$$_2$, —OCH$_2$X$^4$, —NHC(NH)NH$_2$, —SO$_2$X$^4$, —SO$_2$CH═CH$_2$, —NHSO$_2$CH═CH$_2$, —OSO$_2$X$^4$, —B(OH)$_2$, —NHSO$_2$X$^4$, —CH$_2$X$^4$, —CO-oxiranyl, —CO-aziridinyl, epoxidinyl, oxaziridinyl, aziridinyl, —OCH$_2$C≡CH, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl). X$^4$ is independently —F, —Cl, —Br, or —I.

In embodiments, R$^4$ is independently hydrogen, halogen, —CX$^4$$_3$, —CHX$^4$$_2$, —CH$_2$X$^4$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^4$$_3$, —OCHX$^4$$_2$, —OCH$_2$X$^4$, —NHC(NH)NH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^4$ is independently hydrogen, —F, —OH, —OCF$_3$, —OCH$_3$, —OCH$_2$CH$_3$, or —NHC(NH)NH$_2$.

In embodiments, R$^4$ is independently hydrogen, halogen, —CX$^4$$_3$, —CHX$^4$$_2$, —CH$_2$X$^4$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^4$$_3$, —OCHX$^4$$_2$, —OCH$_2$X$^4$, —NHC(NH)NH$_2$, —SO$_2$X$^4$, —SO$_2$CH═CH$_2$, —NHSO$_2$CH═CH$_2$, —OSO$_2$X$^4$, —NHSO$_2$X$^4$, —B(OH)$_2$, —CO-oxiranyl, —CO-aziridinyl, epoxidinyl, oxaziridinyl, aziridinyl, —OCH$_2$C≡CH, R$^{40}$-substituted or unsubstituted alkyl (e.g., C$_1$-C$_8$ alkyl, C$_1$-C$_6$ alkyl, or C$_1$-C$_4$ alkyl), R$^{40}$-substituted or unsubstituted heteroalkyl (e.g., 2 to 8 membered heteroalkyl, 2 to 6 membered heteroalkyl, or 2 to 4 membered heteroalkyl), R$^{40}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{40}$-substituted or unsubstituted heterocycloalkyl (e.g., 3 to 8 membered heterocycloalkyl, 3 to 6 membered heterocycloalkyl, or 5 to 6 membered heterocycloalkyl), R$^{40}$-substituted or unsubstituted aryl (e.g., C$_6$-C$_{10}$ aryl, C$_{10}$ aryl, or phenyl), or R$^{40}$-substituted or unsubstituted heteroaryl (e.g., 5 to 10 membered heteroaryl, 5 to 9 membered heteroaryl, or 5 to 6 membered heteroaryl).

In embodiments, R$^4$ is independently —CH$_2$F, —SO$_2$F, —SO$_2$CH═CH$_2$, —NHSO$_2$CH═CH$_2$, —OSO$_2$F, —B(OH)$_2$, or —NHSO$_2$F.

In embodiments, R$^5$ is independently hydrogen, halogen, —CX$^5$$_3$, —CHX$^5$$_2$, —CH$_2$X$^5$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^5$$_3$, —OCHX$^5$$_2$, —OCH$_2$X$^5$, —NHC(NH)NH$_2$, —SO$_2$X$^5$, —SO$_2$CH═CH$_2$, —NHSO$_2$CH═CH$_2$, —OSO$_2$X$^5$, —B(OH)$_2$, —NHSO$_2$X$^5$, —CH$_2$X$^5$, —CO-oxiranyl, —CO-aziridinyl, epoxidinyl, oxaziridinyl, aziridinyl, —OCH$_2$C≡CH, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl). L$^6$ is a bond or unsubstituted methylene. X$^5$ is independently —F, —Cl, —Br, or —I.

In embodiments, $R^5$ is independently hydrogen, halogen, $-CX^5_3$, $-CHX^5_2$, $-CH_2X^5$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^5_3$, $-OCHX^5_2$, $-OCH_2X^5$, $-NHC(NH)NH_2$, $-CO$-oxiranyl, $-CO$-aziridinyl, epoxidinyl, oxaziridinyl, aziridinyl, $-OCH_2C\equiv CH$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). $L^6$ is a bond or unsubstituted methylene.

In embodiments, $R^5$ is independently hydrogen, $-F$, $-OH$, $-OCF_3$, $-OCH_3$, $-OCH_2CH_3$, or $-NHC(NH)NH_2$.

In embodiments, $R^5$ is independently $-CH_2F$, $-SO_2F$, $-SO_2CH=CH_2$, $-NHSO_2CH=CH_2$, $-OSO_2F$, $-B(OH)_2$, or $-NHSO_2F$.

In embodiments, $R^5$ is independently hydrogen, halogen, $-CX^5_3$, $-CHX^5_2$, $-CH_2X^5$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^5_3$, $-OCHX^5_2$, $-OCH_2X^5$, $-NHC(NH)NH_2$, $-SO_2X^5$, $-SO_2CH=CH_2$, $-NHSO_2CH=CH_2$, $-OSO_2X^5$, $-NHSO_2X^5$, $-B(OH)_2$, $-CO$-oxiranyl, $-CO$-aziridinyl, epoxidinyl, oxaziridinyl, aziridinyl, $-OCH_2C\equiv CH$, $R^{50}$-substituted or unsubstituted alkyl (e.g., $C_1$-$C_8$ alkyl, $C_1$-$C_6$ alkyl, or $C_1$-$C_4$ alkyl), $R^{50}$-substituted or unsubstituted heteroalkyl (e.g., 2 to 8 membered heteroalkyl, 2 to 6 membered heteroalkyl, or 2 to 4 membered heteroalkyl), $R^{50}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{50}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50}$-substituted or unsubstituted aryl (e.g., $C_6$-$C_{10}$ aryl, $C_{10}$ aryl, or phenyl), or $R^{50}$-substituted or unsubstituted heteroaryl (e.g., 5 to 10 membered heteroaryl, 5 to 9 membered heteroaryl, or 5 to 6 membered heteroaryl).

$R^{40}$ is independently oxo, halogen, $-CX^{40}_3$, $-CHX^{40}_2$, $-CH_2X^{40}$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{40}_3$, $-OCHX^{40}_2$, $-OCH_2X^{40}$, $-NHC(NH)NH_2$, $-N=C(NH_2)_2$, $-CH_2SO_3^-$, $-PO_3^{-2}$, $-SO_3$, $-SO_2NH_2$, $-CH_2PO_3^{-2}$, $-CH_2SO_2NH_2$, $-NHC(O)CHCH_2$, $-NHC(O)CH_2Cl$, $-B(OH)_2$, $-SO_2X^{40}$, $-OSO_2X^{40}$, $-NHSO_2X^{40}$, $-SO_2CH=CH_2$, $-NHSO_2CH=CH_2$, $-CO$-oxiranyl, $-CO$-aziridinyl, epoxidinyl, oxaziridinyl, aziridinyl, $-OCH_2C\equiv CH$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^{40}$ is independently $-F$, $-Cl$, $-Br$, or $-I$.

$R^{50}$ is independently oxo, halogen, $-CX^{50}_3$, $-CHX^{50}_2$, $-CH_2X^{50}$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{50}_3$, $-OCHX^{50}_2$, $-OCH_2X^{50}$, $-NHC(NH)NH_2$, $-N=C(NH_2)_2$, $-CH_2SO_3^-$, $-PO_3^{-2}$, $-SO_3$, $-SO_2NH_2$, $-CH_2PO_3^{-2}$, $-CH_2SO_2NH_2$, $-NHC(O)CHCH_2$, $-NHC(O)CH_2Cl$, $-B(OH)_2$, $-SO_2X^{50}$, $-OSO_2X^{50}$, $-NHSO_2X^{50}$, $-SO_2CH=CH_2$, $-NHSO_2CH=CH_2$, $-CO$-oxiranyl, $-CO$-aziridinyl, epoxidinyl, oxaziridinyl, aziridinyl, $-OCH_2C\equiv CH$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^{50}$ is independently $-F$, $-Cl$, $-Br$, or $-I$.

In embodiments, $R^{40}$ and $R^{50}$ are independently oxo, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COH$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-CO$-oxiranyl, $-CO$-aziridinyl, epoxidinyl, oxaziridinyl, aziridinyl, $-OCH_2C\equiv CH$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $L^6$ is a bond. In embodiments, $L^6$ is unsubstituted methylene.

In embodiments, $R^6$ is independently hydrogen, substituted or unsubstituted methyl, substituted or unsubstituted ethyl, substituted or unsubstituted isopropyl, substituted or unsubstituted cyclopropyl, substituted or unsubstituted cyclobutyl, substituted or unsubstituted cyclopentyl, substituted or unsubstituted cyclohexyl, substituted or unsubstituted n-butyl, substituted or unsubstituted isobutyl, substituted or unsubstituted sec-butyl, substituted or unsubstituted pentyl, substituted or unsubstituted hexyl, or substituted or unsubstituted phenyl.

In embodiments, $R^6$ is independently hydrogen, unsubstituted methyl, unsubstituted ethyl, unsubstituted isopropyl, unsubstituted cyclopropyl, unsubstituted cyclobutyl, unsubstituted cyclopentyl, unsubstituted cyclohexyl, unsubstituted n-butyl, unsubstituted isobutyl, unsubstituted sec-butyl, unsubstituted pentyl, unsubstituted hexyl, or unsubstituted phenyl.

In embodiments, $R^6$ is independently hydrogen, —$CH_3$, —$C_2H_5$, —$CH(CH_3)_2$, cyclopropyl, cyclopropyl-$CH_2$—, cyclobutyl, cyclobutyl-$CH_2$—, cyclopentyl, cyclopentyl-$CH_2$—, cyclohexyl, cyclohexyl-$CH_2$—, n-butyl, isobutyl, sec-butyl, pentyl, hexyl, phenyl, or substituted or unsubstituted benzyl.

In embodiments, $R^6$ is independently hydrogen, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^{60}$ is oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^1$, $R^2$, $R^3$, $R^4$, $R^5$, $R^6$, and $R^7$ are each independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^1$, $R^2$, $R^3$, $R^4$, $R^5$, $R^6$, and $R^7$ are each independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^1$, $R^2$, $R^3$, $R^4$, $R^5$, $R^6$, and $R^7$ are each independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$, $R^2$, $R^3$, $R^4$, $R^5$, $R^6$, and $R^7$ are each independently substituted (e.g., substituted with a substituent group, a size-limited substituent group, or lower substituent group) or unsubstituted alkyl. In embodiments, $R^1$, $R^2$, $R^3$, $R^4$, $R^5$, $R^6$, and $R^7$ are each independently substituted (e.g., substituted with a substituent group, a size-limited substituent group, or lower substituent group) alkyl. In embodiments, $R^1$, $R^2$, $R^3$, $R^4$, $R^5$, $R^6$, and $R^7$ are each independently unsubstituted alkyl. In embodiments, $R^1$, $R^2$, $R^3$, $R^4$, $R^5$, $R^6$, and $R^7$ are each independently substituted or unsubstituted alkyl (e.g., $C_1$-$C_8$, $C_1$-$C_6$, $C_1$-$C_4$, or $C_1$-$C_2$). In embodiments, $R^1$, $R^2$, $R^3$, $R^4$, $R^5$, $R^6$, and $R^7$ are each independently substituted alkyl (e.g., $C_1$-$C_8$, $C_1$-$C_6$, $C_1$-$C_4$, or $C_1$-$C_2$). In embodiments, $R^1$, $R^2$, $R^3$, $R^4$, $R^5$, $R^6$, and $R^7$ are each independently unsubstituted alkyl (e.g., $C_1$-$C_8$, $C_1$-$C_6$, $C_1$-$C_4$, or $C_1$-$C_2$).

In embodiments, $R^1$, $R^2$, $R^3$, $R^4$, $R^5$, $R^6$, and $R^7$ are each independently substituted (e.g., substituted with a substituent group, a size-limited substituent group, or lower substituent group) or unsubstituted heteroalkyl. In embodiments, $R^1$, $R^2$, $R^3$, $R^4$, $R^5$, $R^6$, and $R^7$ are each independently substituted (e.g., substituted with a substituent group, a size-limited substituent group, or lower substituent group) heteroalkyl. In embodiments, $R^1$, $R^2$, $R^3$, $R^4$, $R^5$, $R^6$, and $R^7$ are each independently unsubstituted heteroalkyl. In embodiments, $R^1$, $R^2$, $R^3$, $R^4$, $R^5$, $R^6$, and $R^7$ are each independently substituted or unsubstituted heteroalkyl (e.g., 2 to 8 membered, 2 to 6 membered, 4 to 6 membered, 2 to 3 membered, or 4 to 5 membered). In embodiments, $R^1$, $R^2$, $R^3$, $R^4$, $R^5$, $R^6$, and $R^7$ are each independently substituted heteroalkyl (e.g., 2 to 8 membered, 2 to 6 membered, 4 to 6 membered, 2 to 3 membered, or 4 to 5 membered). In embodiments, $R^1$, $R^2$, $R^3$, $R^4$, $R^5$, $R^6$, and $R^7$ are each independently an unsubstituted heteroalkyl (e.g., 2 to 8 membered, 2 to 6 membered, 4 to 6 membered, 2 to 3 membered, or 4 to 5 membered).

In embodiments, $R^1$, $R^2$, $R^3$, $R^4$, $R^5$, $R^6$, and $R^7$ are each independently substituted (e.g., substituted with a substituent group, a size-limited substituent group, or lower substituent group) or unsubstituted cycloalkyl. In embodiments, $R^1$, $R^2$, $R^3$, $R^4$, $R^5$, $R^6$, and $R^7$ are each independently substituted (e.g., substituted with a substituent group, a size-limited substituent group, or lower substituent group) cycloalkyl. In embodiments, $R^1$, $R^2$, $R^3$, $R^4$, $R^5$, $R^6$, and $R^7$ are each independently an unsubstituted cycloalkyl. In embodiments, $R^1$, $R^2$, $R^3$, $R^4$, $R^5$, $R^6$, and $R^7$ are each independently substituted or unsubstituted cycloalkyl (e.g., $C_3$-$C_8$, $C_3$-$C_6$, $C_4$-$C_6$, or $C_5$-$C_6$). In embodiments, $R^1$, $R^2$, $R^3$, $R^4$, $R^5$, $R^6$, and $R^7$ are each independently substituted cycloalkyl (e.g., $C_3$-$C_8$, $C_3$-$C_6$, $C_4$-$C_6$, or $C_5$-$C_6$). In embodiments, $R^1$, $R^2$, $R^3$, $R^4$, $R^5$, $R^6$, and $R^7$ are each independently unsubstituted cycloalkyl (e.g., $C_3$-$C_8$, $C_3$-$C_6$, $C_4$-$C_6$, or $C_5$-$C_6$).

In embodiments, $R^1$, $R^2$, $R^3$, $R^4$, $R^5$, $R^6$, and $R^7$ are each independently substituted (e.g., substituted with a substituent group, a size-limited substituent group, or lower substituent group) or unsubstituted heterocycloalkyl. In embodiments, $R^1$, $R^2$, $R^3$, $R^4$, $R^5$, $R^6$, and $R^7$ are each independently substituted (e.g., substituted with a substituent group, a size-limited substituent group, or lower substituent group) heterocycloalkyl. In embodiments, $R^1$, $R^2$, $R^3$, $R^4$, $R^5$, $R^6$, and $R^7$ are each independently an unsubstituted heterocycloalkyl. In embodiments, $R^1$, $R^2$, $R^3$, $R^4$, $R^5$, $R^6$, and $R^7$ are each independently substituted or unsubstituted heterocycloalkyl (e.g., 3 to 8 membered, 3 to 6 membered, 4 to 6 membered, 4 to 5 membered, or 5 to 6 membered). In embodiments, $R^1$, $R^2$, $R^3$, $R^4$, $R^5$, $R^6$, and $R^7$ are each independently substituted heterocycloalkyl (e.g., 3 to 8 membered, 3 to 6 membered, 4 to 6 membered, 4 to 5 membered, or 5 to 6 membered). In embodiments, $R^1$, $R^2$, $R^3$, $R^4$, $R^5$, $R^6$, and $R^7$ are each independently an unsubstituted heterocycloalkyl (e.g., 3 to 8 membered, 3 to 6 membered, 4 to 6 membered, 4 to 5 membered, or 5 to 6 membered).

In embodiments, $R^1$, $R^2$, $R^3$, $R^4$, $R^5$, $R^6$, and $R^7$ are each independently substituted (e.g., substituted with a substituent group, a size-limited substituent group, or lower substituent group) or unsubstituted aryl. In embodiments, $R^1$, $R^2$, $R^3$, $R^4$, $R^5$, $R^6$, and $R^7$ are each independently substituted (e.g., substituted with a substituent group, a size-limited substituent group, or lower substituent group) aryl. In embodiments, $R^1$, $R^2$, $R^3$, $R^4$, $R^5$, $R^6$, and $R^7$ are each independently an unsubstituted aryl. In embodiments, $R^1$, $R^2$, $R^3$, $R^4$, $R^5$, $R^6$, and $R^8$ are each independently substituted or unsubstituted aryl (e.g., $C_6$-$C_{10}$ or phenyl). In embodiments, $R^1$, $R^2$, $R^3$, $R^4$, $R^5$, $R^6$, and $R^7$ are each independently substituted aryl (e.g., $C_6$-$C_{10}$ or phenyl). In embodiments, $R^1$, $R^2$, $R^3$, $R^4$, $R^5$, $R^6$, and $R^7$ are each independently an unsubstituted aryl (e.g., $C_6$-$C_{10}$ or phenyl).

In embodiments, $R^1$, $R^2$, $R^3$, $R^4$, $R^5$, $R^6$, and $R^7$ are each independently substituted (e.g., substituted with a substituent group, a size-limited substituent group, or lower substituent group) or unsubstituted heteroaryl. In embodiments, $R^1$, $R^2$, $R^3$, $R^4$, $R^5$, $R^6$, and $R^7$ are each independently substituted (e.g., substituted with a substituent group, a size-limited substituent group, or lower substituent group) heteroaryl. In embodiments, $R^1$, $R^2$, $R^3$, $R^4$, $R^5$, $R^6$, and $R^7$ are each independently an unsubstituted heteroaryl. In embodiments, $R^1$, $R^2$, $R^3$, $R^4$, $R^5$, $R^6$, and $R^7$ are each independently substituted or unsubstituted heteroaryl (e.g., 5 to 10 membered, 5 to 9 membered, or 5 to 6 membered). In embodiments, $R^1$, $R^2$, $R^3$, $R^4$, $R^5$, $R^6$, and $R^7$ are each independently substituted heteroaryl (e.g., 5 to 10 membered, 5 to 9 membered, or 5 to 6 membered). In embodiments, $R^1$, $R^2$, $R^3$, $R^4$, $R^5$, $R^6$, and $R^7$ are each independently an unsubstituted heteroaryl (e.g., 5 to 10 membered, 5 to 9 membered, or 5 to 6 membered).

In embodiments, $L^2$, $L^3$, and $L^6$ are each independently substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^2$, $L^3$, and $L^6$ are each independently substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene.

In embodiments, $L^2$, $L^3$, and $L^6$ are each independently unsubstituted alkylene, unsubstituted heteroalkylene, unsubstituted cycloalkylene, unsubstituted heterocycloalkylene, unsubstituted arylene, or unsubstituted heteroarylene.

In embodiments, the compound is:

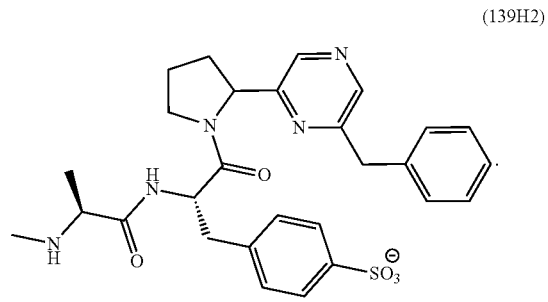

(139H2)

In embodiments, the compound is:

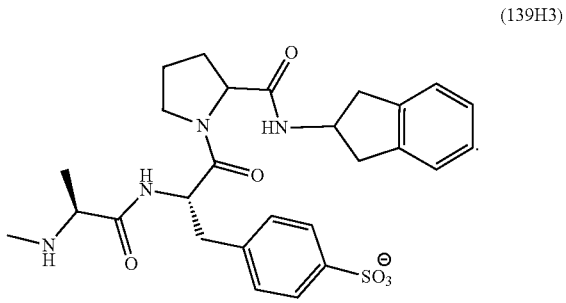

(139H3)

In embodiments, the compound is:

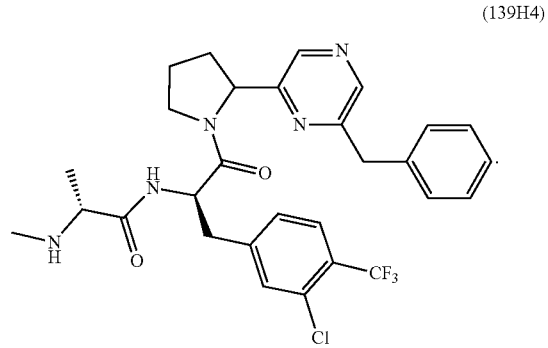 [SMILES: CN[C@H](C)C(=O)N[C@H](Cc1ccc(C(F)(F)F)c(Cl)c1)C(=O)N1CCCC1c1cncc(Cc2ccccc2)n1]

(139H4)

In embodiments, the compound is:
(139H7)
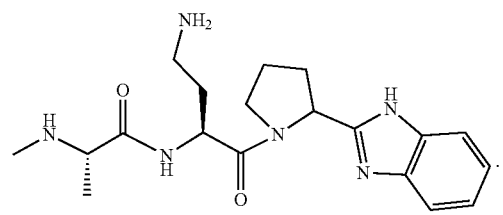
In embodiments, the compound is:
(139H8)
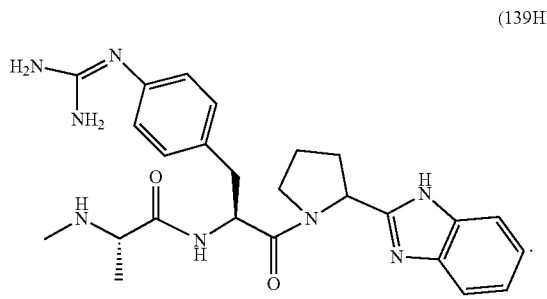
In embodiments, the compound is:
(139H9)
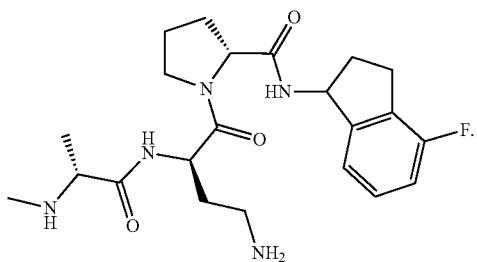
In embodiments, the compound is:
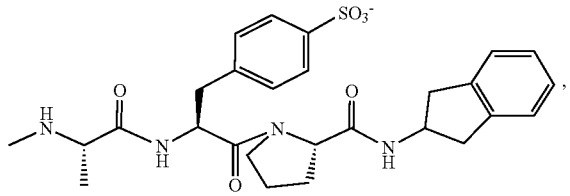
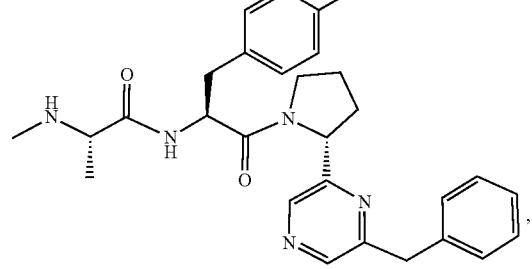
-continued
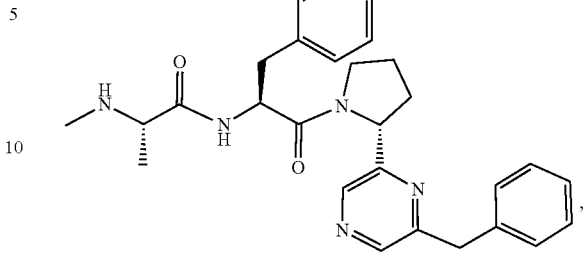
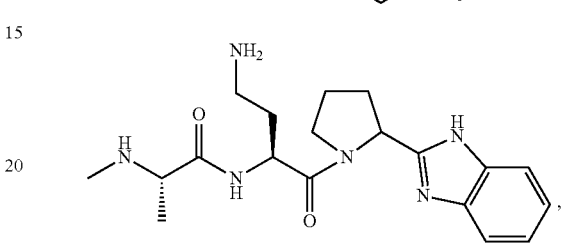
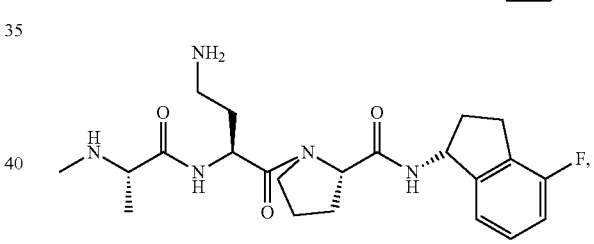
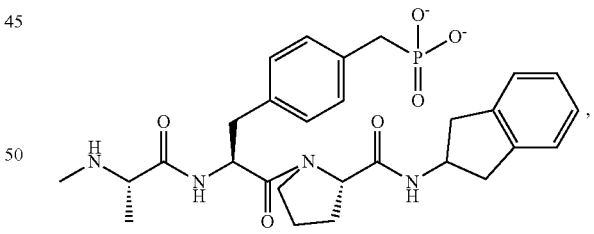
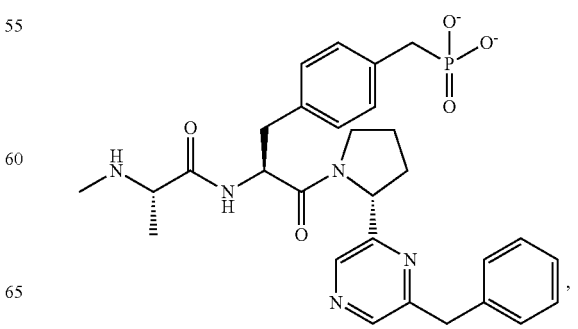

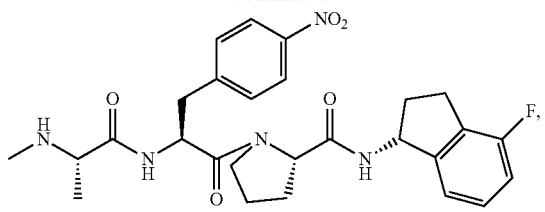
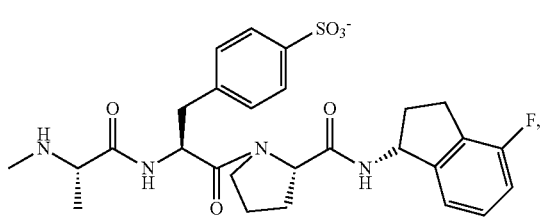
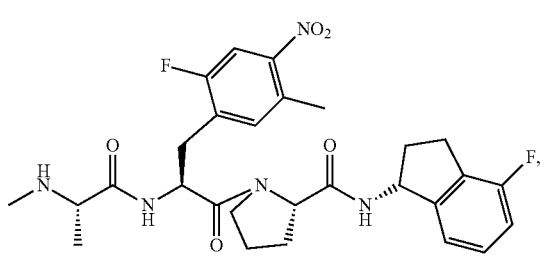
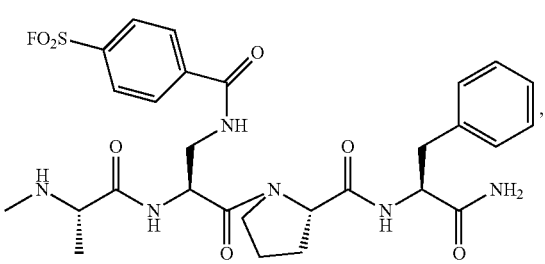
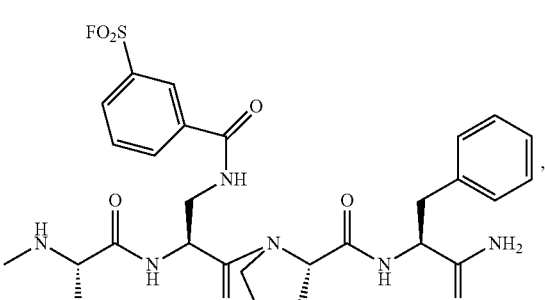
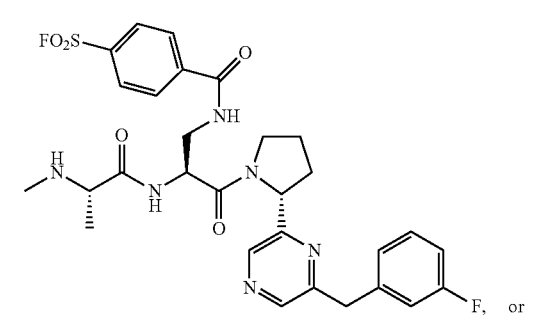
, or
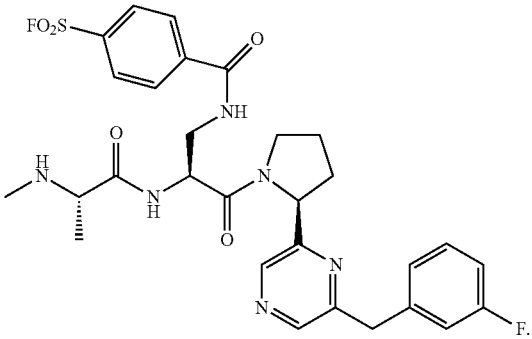
In embodiments, the compound is:
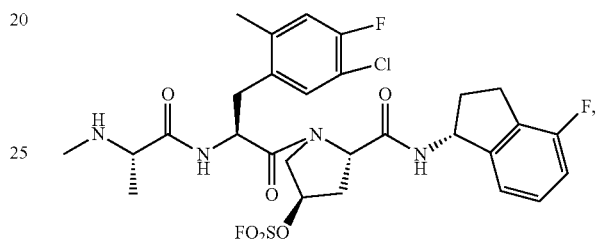
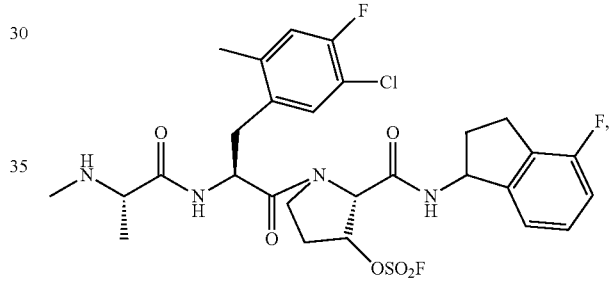
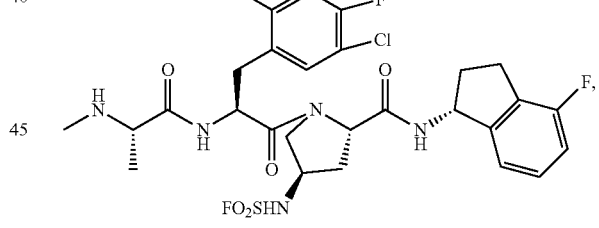
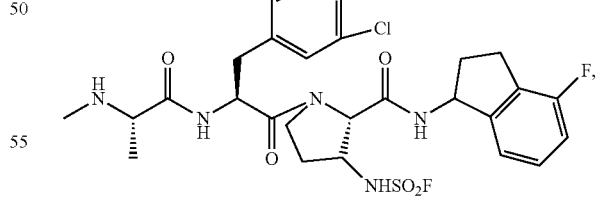
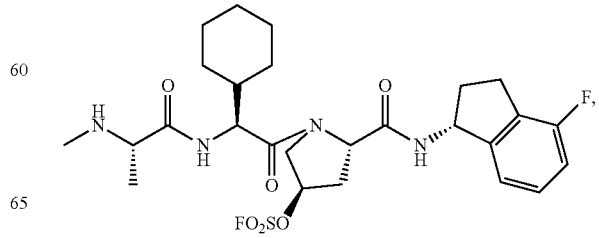

101
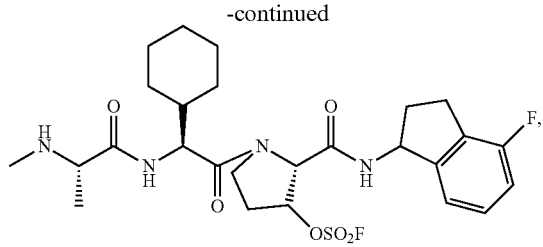
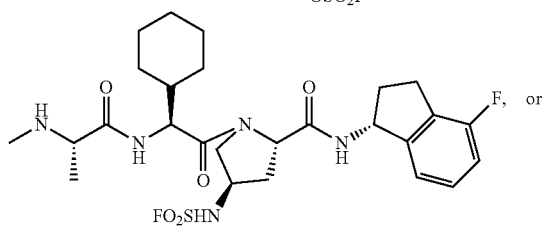
In embodiments, the compound is:
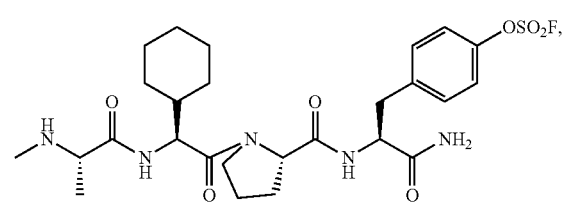
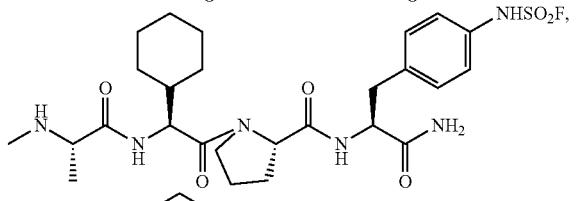
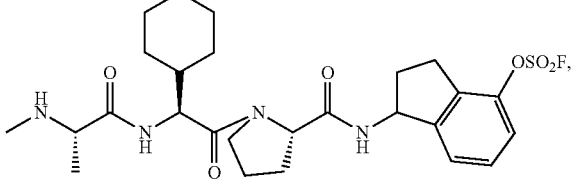
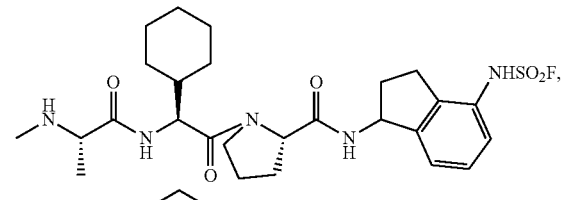
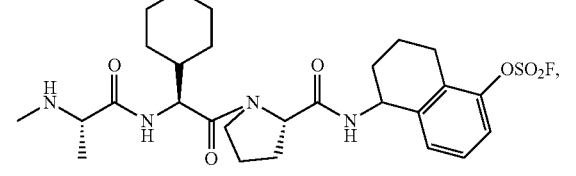
102
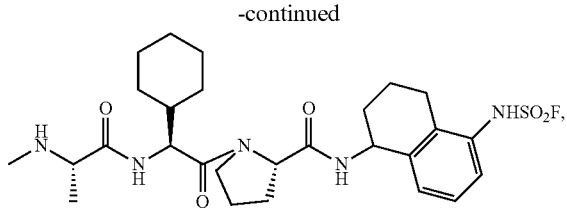
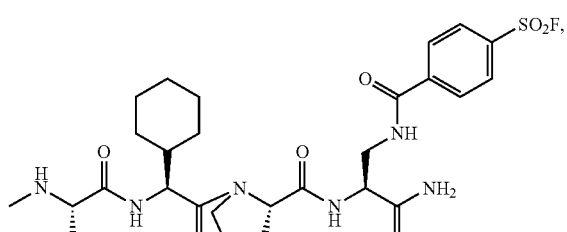
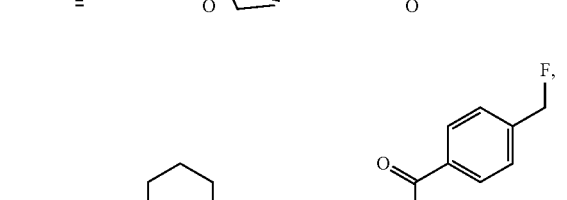
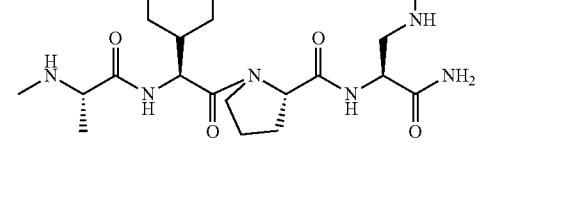
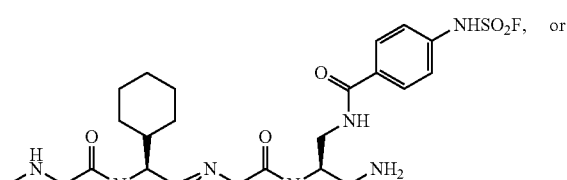
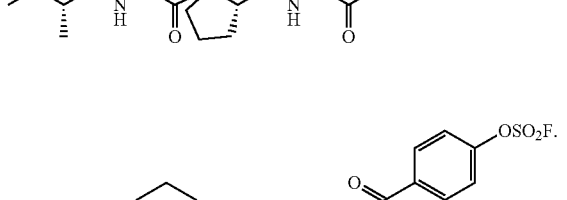
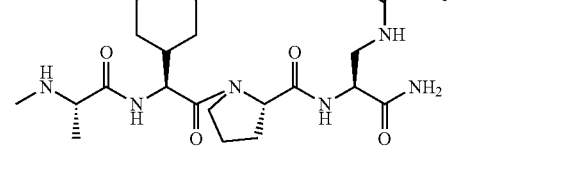

In embodiments, the compounds is:

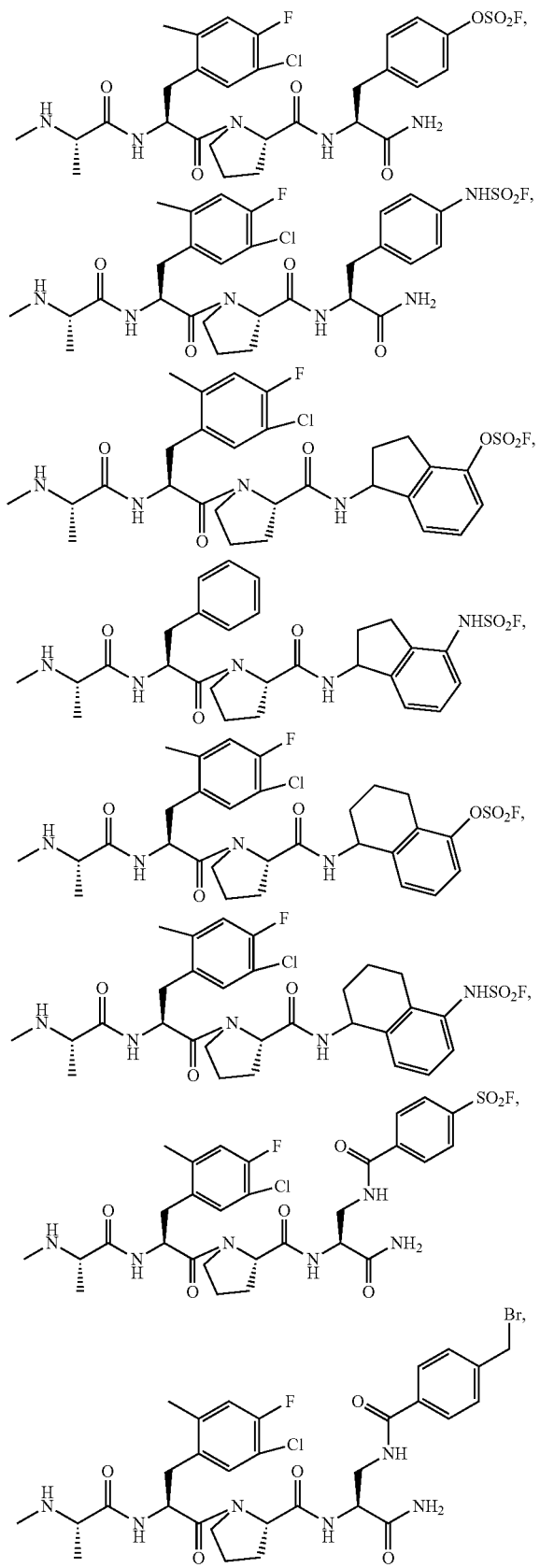

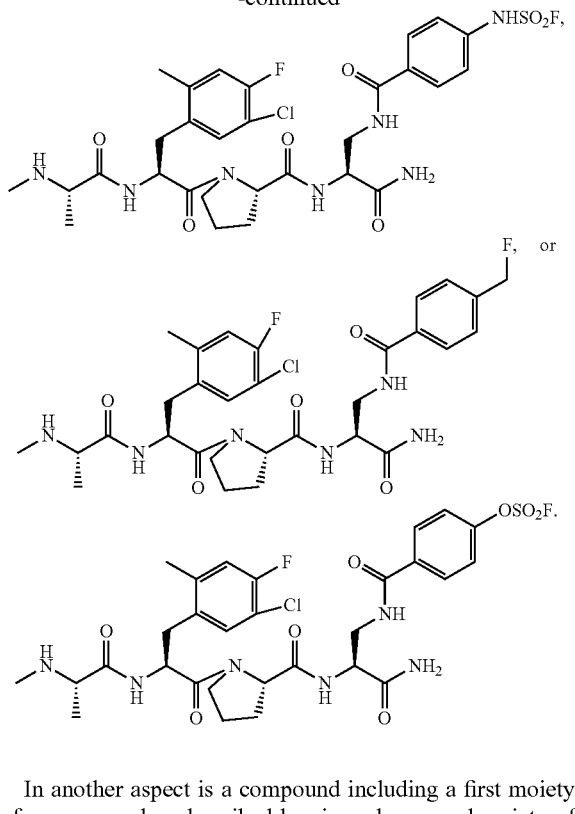

In another aspect is a compound including a first moiety of a compound as described herein and a second moiety of a compound as described herein, wherein said first and second moieties are connected by a divalent linker (e.g., a covalent linker, $L^{100}$). It is understood that one of ordinary skill in the art would recognize the first moiety is monovalent, e.g.,

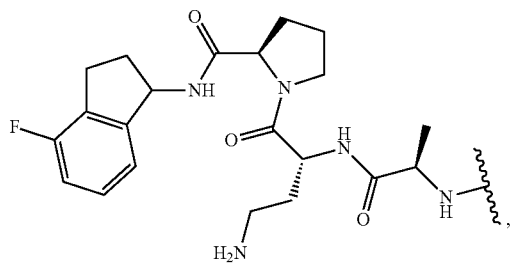 [SMILES: *N[C@H](C)C(=O)N[C@H](CCN)C(=O)N1CCC[C@@H]1C(=O)NC1CCc2c(F)cccc21]

and the second moiety is monovalent, e.g.,

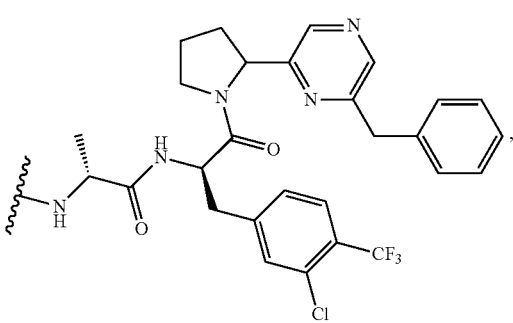 [SMILES: *N[C@H](C)C(=O)N[C@H](Cc1ccc(C(F)(F)F)c(Cl)c1)C(=O)N1CCCC1c1cncc(Cc2ccccc2)n1]

when connected to a divalent linker. In embodiments, the compound described herein (e.g., the first moiety) is conjugated to the divalent linker following a reaction (e.g., a cross coupling reaction). In embodiments, any substituent (e.g., $R^6$) may participate in a cross coupling reaction. In embodiments, any substituent (e.g., $R^6$) or hydrogen, may be considered a leaving group when conjugating the first moiety to the divalent linker or the second moiety to the divalent linker.

In embodiments, the compound conjugated to the divalent linker has the formula:

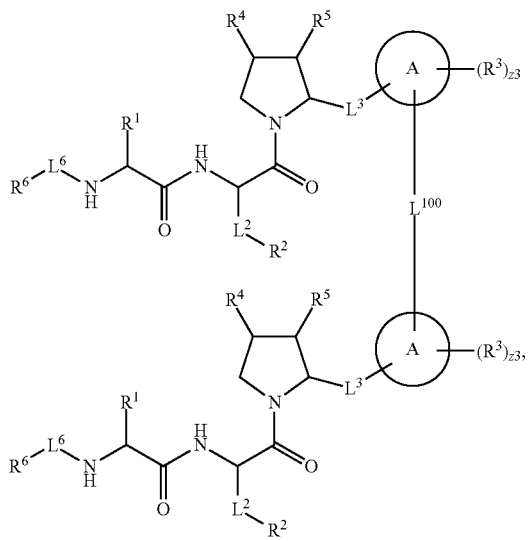

wherein, $R^1$, $R^2$, $R^3$, $R^4$, $R^5$, $R^6$, $L^2$, $L^3$, $L^6$, and z3 are as described herein. $L^{100}$ is a covalent linker.

In embodiments, the compound conjugated to the divalent linker has the formula:

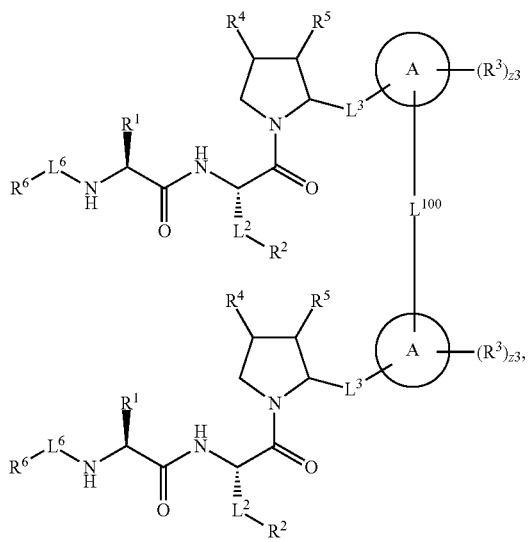

wherein, $R^1$, $R^2$, $R^3$, $R^4$, $R^5$, $R^6$, $L^2$, $L^3$, $L^6$, and z3 are as described herein. $L^{100}$ is a covalent linker.

In embodiments, the compound conjugated to the divalent linker has the formula:

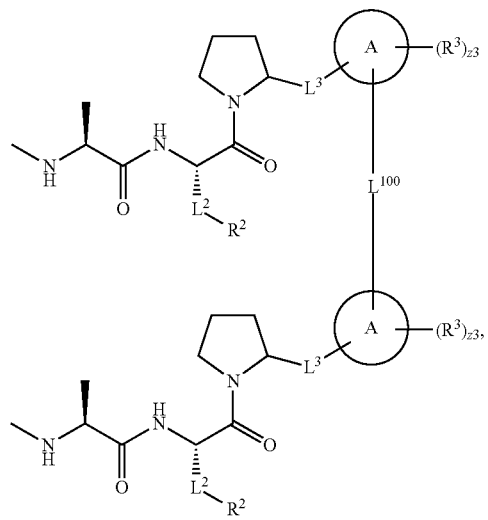

wherein $R^2$, $R^3$, $L^2$, $L^3$, and z3 are as described herein. $L^{100}$ is a covalent linker.

In embodiments, the compound conjugated to the divalent linker has the formula:

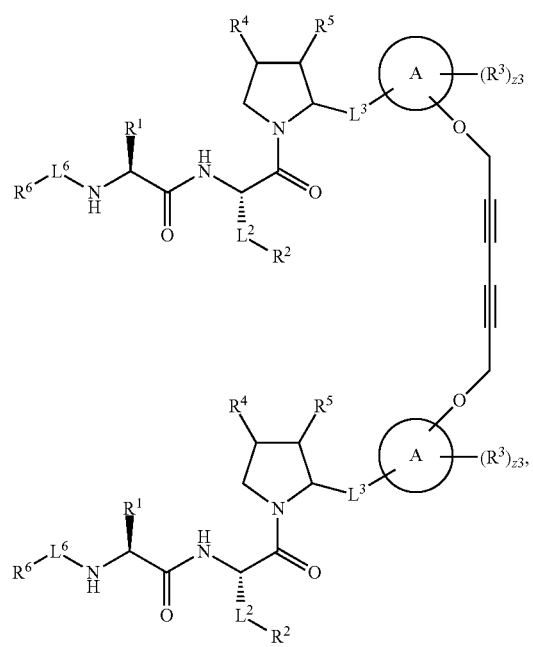

wherein, $R^1$, $R^2$, $R^3$, $R^4$, $R^5$, $R^6$, $L^2$, $L^3$, $L^6$, and z3 are as described herein.

In embodiments, the compound conjugated to the divalent linker has the formula:

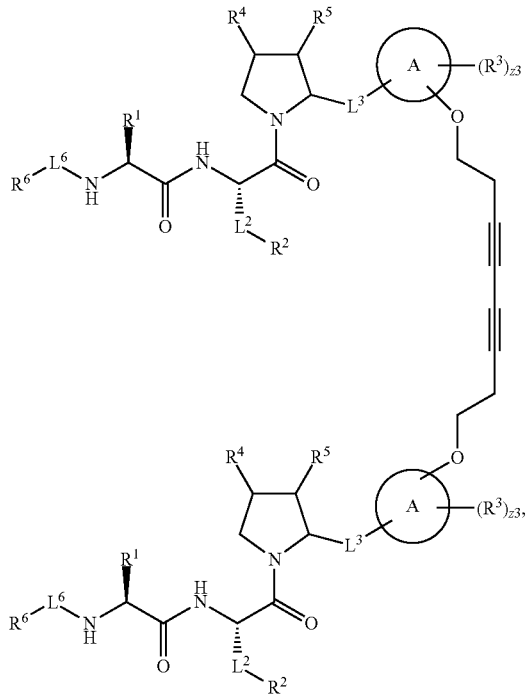

wherein, $R^1$, $R^2$, $R^3$, $R^4$, $R^5$, $R^6$, $L^2$, $L^3$, $L^6$, and z3 are as described herein.

In embodiments, the compound conjugated to the divalent linker has the formula:

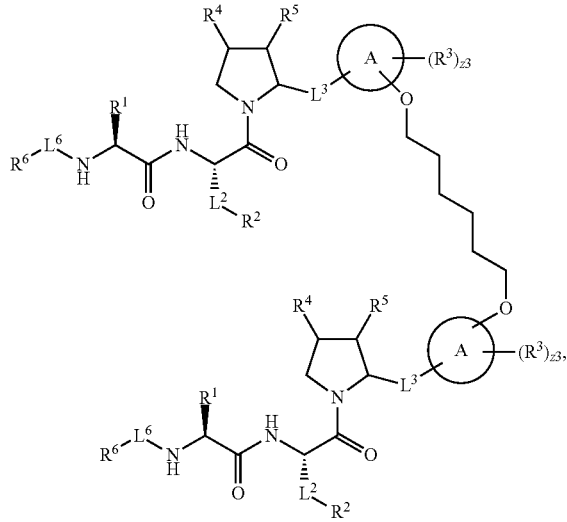

wherein, $R^1$, $R^2$, $R^3$, $R^4$, $R^5$, $R^6$, $L^2$, $L^3$, $L^6$, and z3 are as described herein.

In embodiments, the compound conjugated to the divalent linker has the formula:

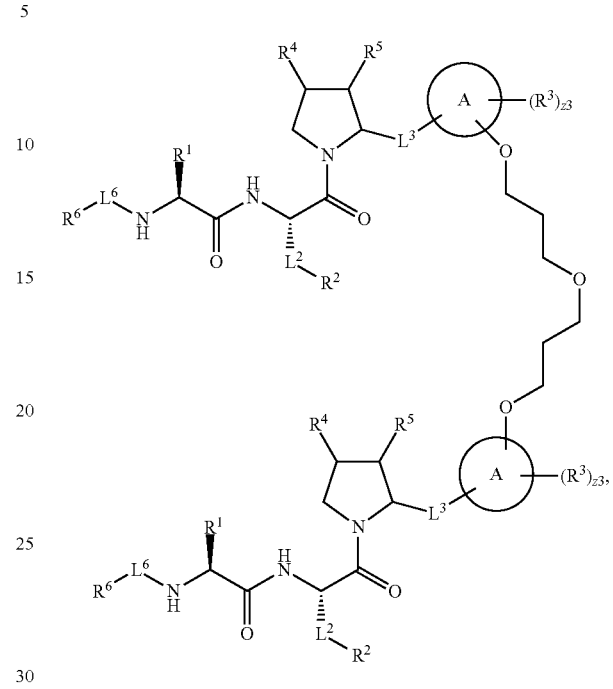

wherein, $R^1$, $R^2$, $R^3$, $R^4$, $R^5$, $R^6$, $L^2$, $L^3$, $L^6$, and z3 are as described herein.

In embodiments, the compound conjugated to the divalent linker has the formula.

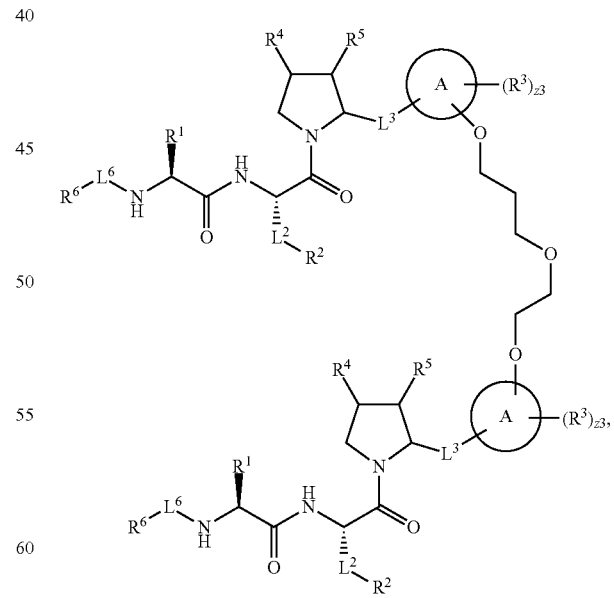

wherein, $R^1$, $R^2$, $R^3$, $R^4$, $R^5$, $R^6$, $L^2$, $L^3$, $L^6$, and z3 are as described herein.

In embodiments, the compound conjugated to the divalent linker has the formula:

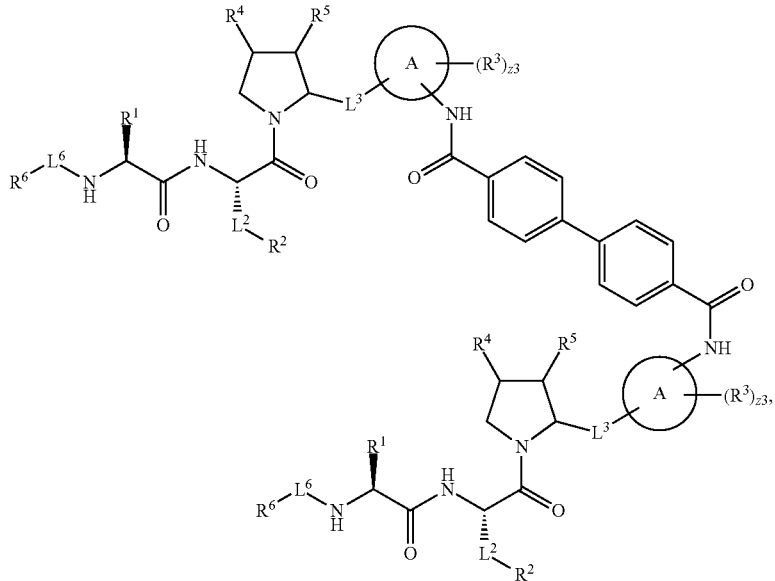

wherein, R¹, R², R³, R⁴, R⁵, R⁶, L², L³, L⁶, and z3 are as described herein.

In embodiments, the compound conjugated to the divalent linker has the formula:

In embodiments, the compound conjugated to the divalent linker has the formula:

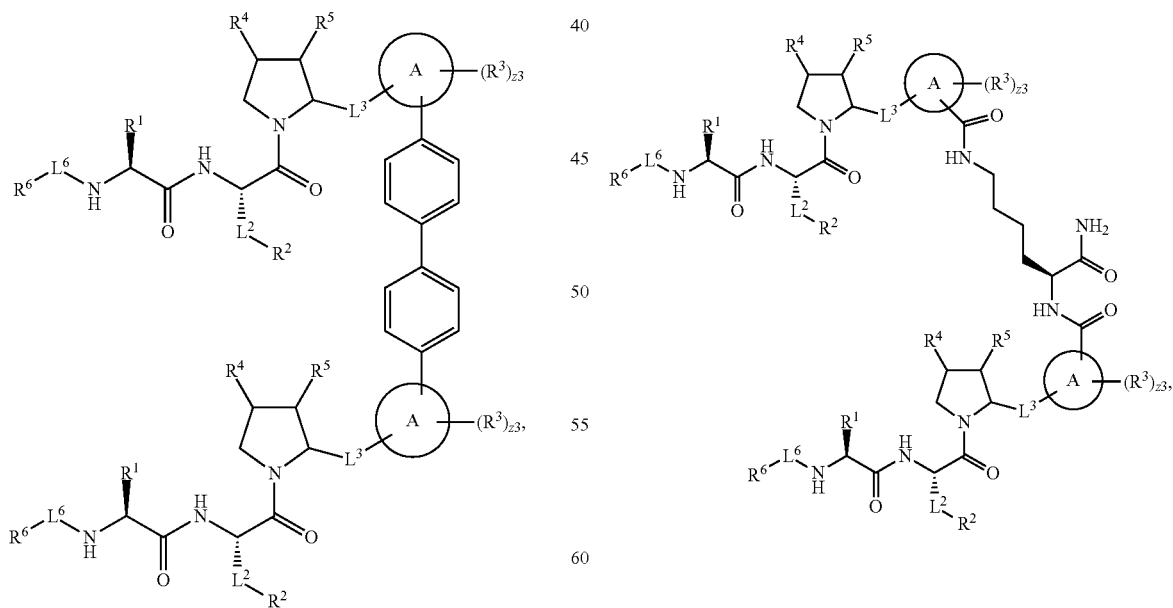

wherein, R¹, R², R³, R⁴, R⁵, R⁶, L², L³, L⁶, and z3 are as described herein.

wherein, R¹, R², R³, R⁴, R⁵, R⁶, L², L³, L⁶, and z3 are as described herein.

In embodiments, the compound conjugated to the divalent linker has the formula:
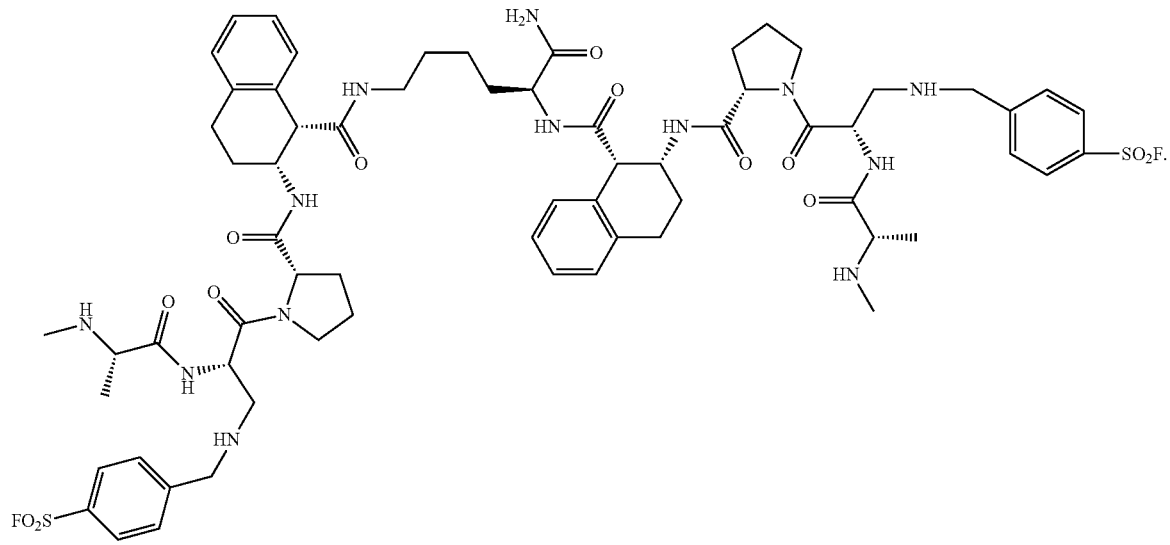
In embodiments, the compound conjugated to the divalent linker has the formula:
In embodiments, the compound conjugated to the divalent linker has the formula:
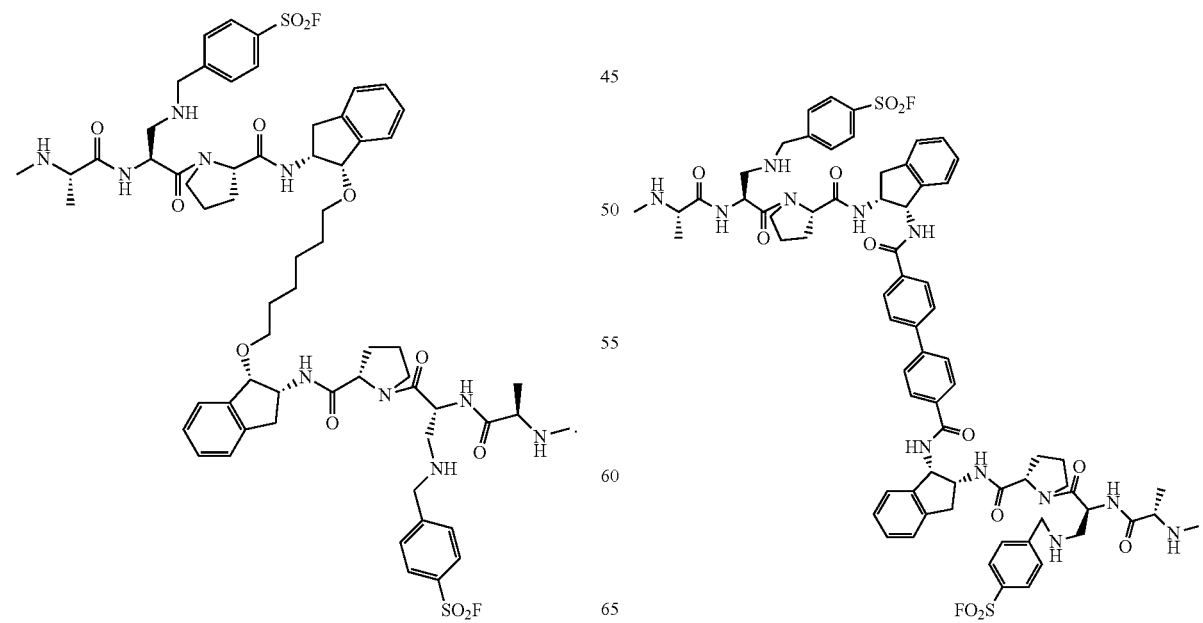

In embodiments, the compound conjugated to the divalent linker has the formula:
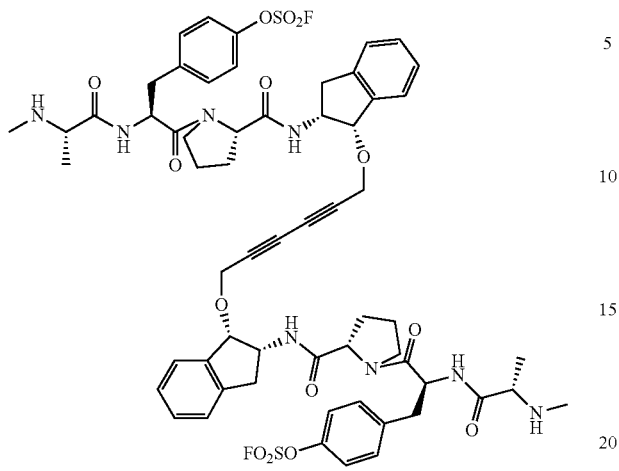
In embodiments, the compound conjugated to the divalent linker has the formula:
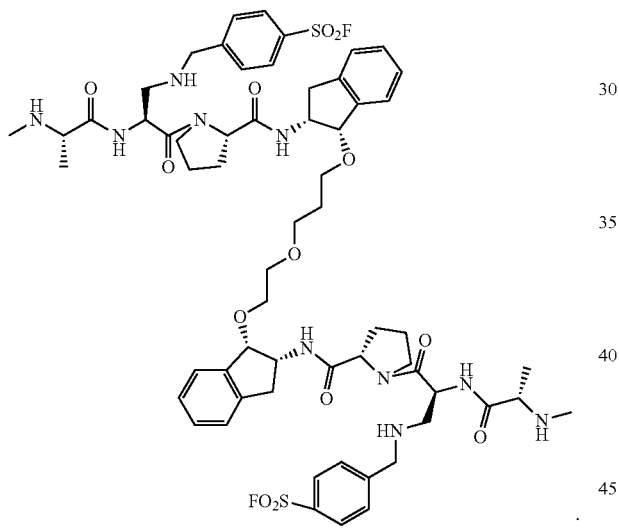
In embodiments, the compound conjugated to the divalent linker has the formula:
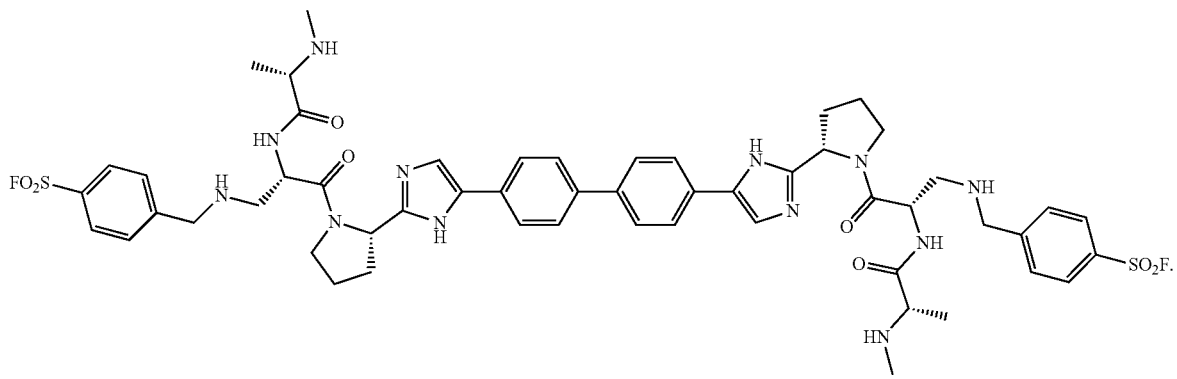

In embodiments, the compound conjugated to the divalent linker has the formula:
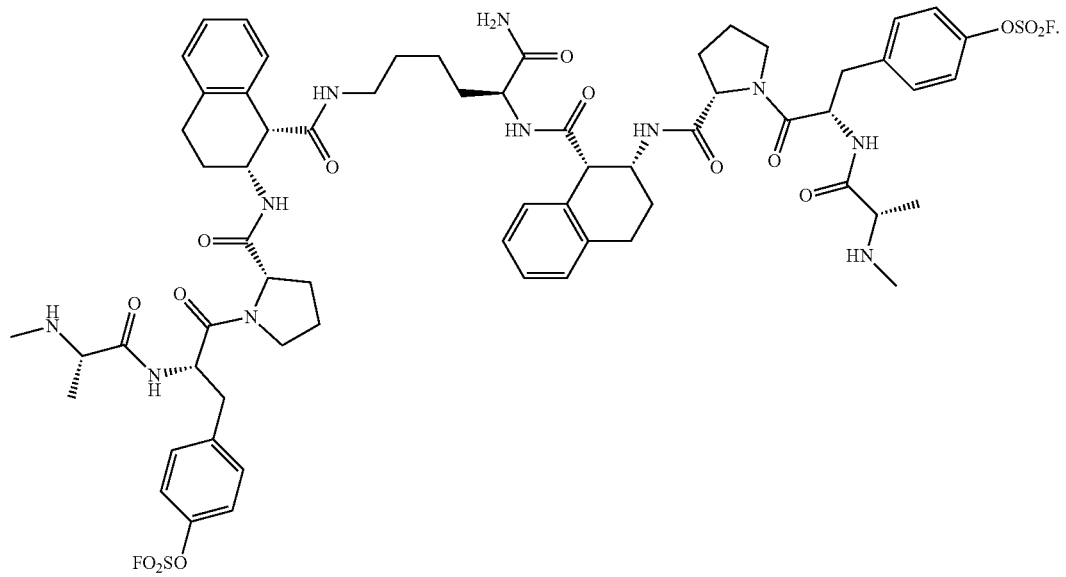
In embodiments, the compound conjugated to the divalent linker has the formula:
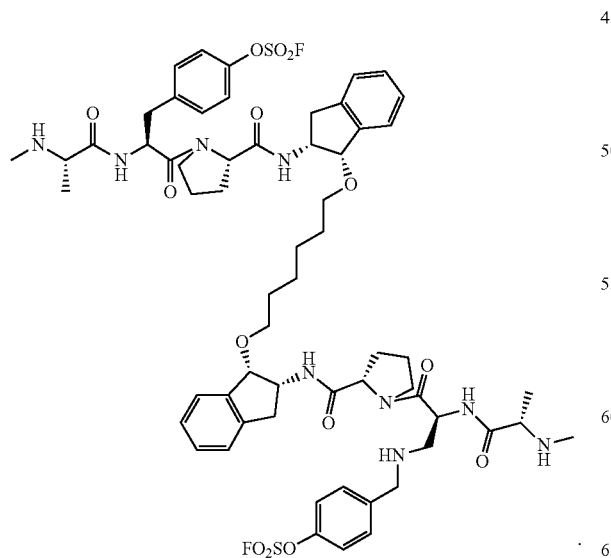
In embodiments, the compound conjugated to the divalent linker has the formula:
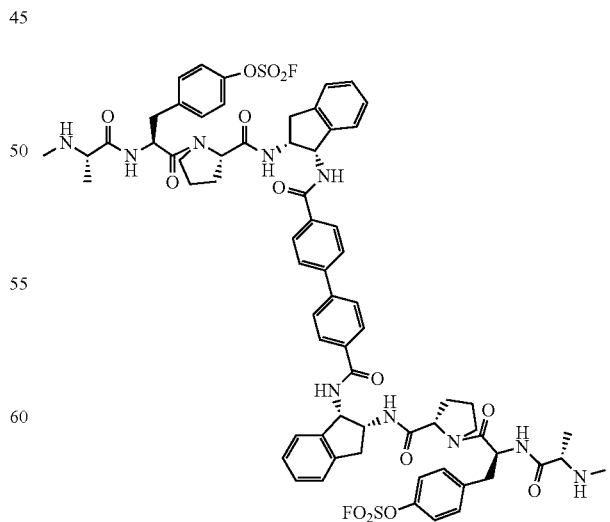

In embodiments, the compound conjugated to the divalent linker has the formula:
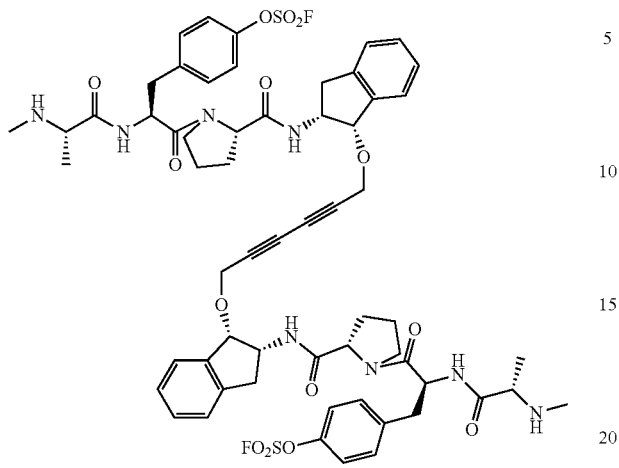
In embodiments, the compound conjugated to the divalent linker has the formula:
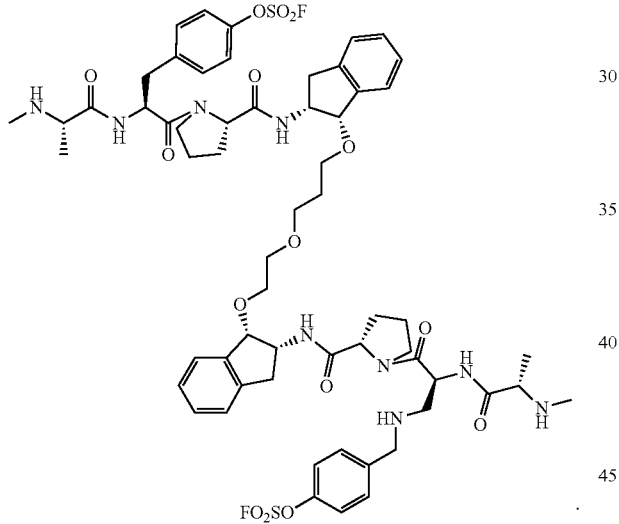
In embodiments, the compound conjugated to the divalent linker has the formula:
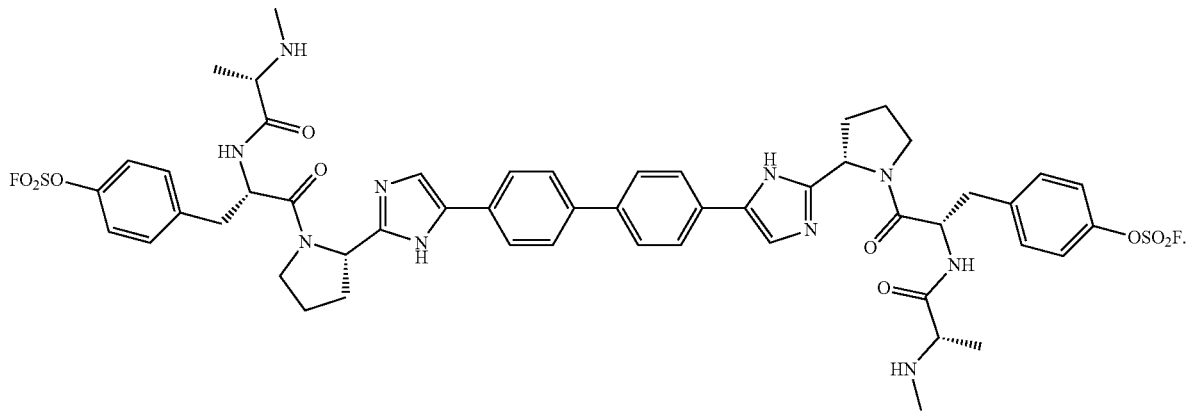

In embodiments, the linker (e.g., $L^{100}$) is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene. In embodiments, the linker is a bioconjugate linker.

In embodiments, the linker (e.g., $L^{100}$) is a bond, —NH—, —O—, —S—, —C(O)—, —C(O)NH—, —NHC(O)—, —NHC(O)NH—, —C(O)O—, —OC(O)—, $R^{101}$-substituted or unsubstituted alkylene, $R^{101}$-substituted or unsubstituted heteroalkylene, $R^{101}$-substituted or unsubstituted cycloalkylene, $R^{101}$-substituted or unsubstituted heterocycloalkylene, $R^{101}$-substituted or unsubstituted arylene, $R^{101}$-substituted or unsubstituted heteroarylene, $R^{101}$-substituted or unsubstituted alkylarylene, $R^{101}$-substituted or unsubstituted alkylheteroarylene.

$R^{101}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $L^{100}$ is $R^{101}$-substituted or unsubstituted methylene. In embodiments, $L^{100}$ is $R^{101}$-substituted or unsubstituted C$_2$ alkylene. In embodiments, $L^{100}$ is $R^{101}$-substituted or unsubstituted C$_3$ alkylene. In embodiments, $L^{100}$ is $R^{101}$-substituted or unsubstituted C$_4$ alkylene. In embodiments, $L^{100}$ is $R^{101}$-substituted or unsubstituted C$_5$ alkylene. In embodiments, $L^{100}$ is $R^{101}$-substituted or unsubstituted C$_6$ alkylene. In embodiments, $L^{100}$ is $R^{101}$-substituted or unsubstituted C$_7$ alkylene. In embodiments, $L^{100}$ is $R^{101}$-substituted or unsubstituted C$_8$ alkylene. In embodiments, $L^{100}$ is $R^{101}$-substituted methylene. In embodiments, $L^{100}$ is $R^{101}$-substituted C$_2$ alkylene. In embodiments, $L^{100}$ is $R^{101}$-substituted C$_3$ alkylene. In embodiments, $L^{100}$ is $R^{101}$-substituted C$_4$ alkylene. In embodiments, $L^{100}$ is $R^{101}$-substituted C$_5$ alkylene. In embodiments, $L^{100}$ is $R^{101}$-substituted C$_6$ alkylene. In embodiments, $L^{100}$ is $R^{101}$-substituted C$_7$ alkylene. In embodiments, $L^{100}$ is $R^{101}$-substituted C$_8$ alkylene. In embodiments, $L^{100}$ is an unsubstituted methylene. In embodiments, $L^{100}$ is an unsubstituted C$_2$ alkylene. In embodiments, $L^{100}$ is an unsubstituted C$_3$ alkylene. In embodiments, $L^{100}$ is an unsubstituted C$_4$ alkylene. In embodiments, $L^{100}$ is an unsubstituted C$_5$ alkylene. In embodiments, $L^{100}$ is an unsubstituted C$_6$ alkylene. In embodiments, $L^{100}$ is an unsubstituted C$_7$ alkylene. In embodiments, $L^{100}$ is an unsubstituted C$_8$ alkylene.

In embodiments, $L^{100}$ is $R^{101}$-substituted or unsubstituted C$_1$-C$_6$ alkylene. In embodiments, $L^{100}$ is $R^{101}$-substituted C$_1$-C$_6$ alkylene. In embodiments, $L^{100}$ is unsubstituted C$_1$-C$_6$ alkylene. In embodiments, $L^{100}$ is $R^{101}$-substituted or unsubstituted C$_2$-C$_6$ alkylene. In embodiments, $L^{100}$ is $R^{101}$-substituted C$_2$-C$_6$ alkylene. In embodiments, $L^{100}$ is unsubstituted C$_2$-C$_6$ alkylene. In embodiments, $L^{100}$ is $R^{101}$-substituted or unsubstituted C$_1$ alkylene. In embodiments, $L^{100}$ is $R^{101}$-substituted C$_1$ alkylene. In embodiments, $L^{100}$ is unsubstituted C$_1$ alkylene. In embodiments, $L^{100}$ is $R^{101}$-substituted or unsubstituted C$_2$ alkylene. In embodiments, $L^{100}$ is $R^{101}$-substituted C$_2$ alkylene. In embodiments, $L^{100}$ is unsubstituted C$_2$ alkylene. In embodiments, $L^{100}$ is $R^{101}$-substituted or unsubstituted C$_3$ alkylene. In embodiments, $L^{100}$ is $R^{101}$-substituted C$_3$ alkylene. In embodiments, $L^{100}$ is unsubstituted C$_3$ alkylene. In embodiments, $L^{100}$ is $R^{101}$-substituted or unsubstituted C$_4$ alkylene. In embodiments, $L^{100}$ is $R^{101}$-substituted C$_4$ alkylene. In embodiments, $L^{100}$ is unsubstituted C$_4$ alkylene. In embodiments, $L^{100}$ is $R^{101}$-substituted or unsubstituted C$_5$ alkylene. In embodiments, $L^{100}$ is $R^{101}$-substituted C$_5$ alkylene. In embodiments, $L^{100}$ is unsubstituted C$_5$ alkylene. In embodiments, $L^{100}$ is $R^{101}$-substituted or unsubstituted C$_6$ alkylene. In embodiments, $L^{100}$ is $R^{101}$-substituted C$_6$ alkylene. In embodiments, $L^{100}$ is unsubstituted C$_6$ alkylene.

In embodiments, $L^{100}$ is $R^{101}$-substituted or unsubstituted 2 to 8 membered heteroalkylene. In embodiments, $L^{100}$ is $R^{101}$-substituted 2 to 8 membered heteroalkylene. In embodiments, $L^{100}$ is unsubstituted 2 to 8 membered heteroalkylene. In embodiments, $L^{100}$ is $R^{101}$-substituted or unsubstituted 2 membered heteroalkylene. In embodiments, $L^{100}$ is $R^{101}$-substituted 2 membered heteroalkylene. In embodiments, $L^{100}$ is unsubstituted 2 membered heteroalkylene. In embodiments, $L^{100}$ is $R^{101}$-substituted or unsubstituted 3 membered heteroalkylene. In embodiments, $L^{100}$ is $R^{101}$-substituted 3 membered heteroalkylene. In embodiments, $L^{100}$ is unsubstituted 3 membered heteroalkylene. In embodiments, $L^{100}$ is $R^{101}$-substituted or unsubstituted 4 membered heteroalkylene. In embodiments, $L^{100}$ is $R^{101}$-substituted 4 membered heteroalkylene. In embodiments, $L^{100}$ is unsubstituted 4 membered heteroalkylene. In embodiments, $L^{100}$ is $R^{101}$-substituted or unsubstituted 5 membered heteroalkylene. In embodiments, $L^{100}$ is $R^{101}$-substituted 5 membered heteroalkylene. In embodiments, $L^{100}$ is unsubstituted 5 membered heteroalkylene. In embodiments, $L^{100}$ is $R^{101}$-substituted or unsubstituted 6 membered heteroalkylene. In embodiments, $L^{100}$ is $R^{101}$-substituted 6 membered heteroalkylene. In embodiments, $L^{100}$ is unsubstituted 6 membered heteroalkylene. In embodiments, $L^{100}$ is $R^{101}$-substituted or unsubstituted 7 membered heteroalkylene. In embodiments, $L^{100}$ is $R^{101}$-substituted 7 membered heteroalkylene. In embodiments, $L^{100}$ is unsubstituted 7 membered heteroalkylene.

In embodiments, the linker (e.g., $L^{100}$) is a divalent saturated or unsaturated aliphatic, aromatic, hetero-aromatic, saturated or unsaturated aliphatic and aromatic, saturated or unsaturated aliphatic and hetero-aromatic, ether, thioether, amide, amine, ester, carbamate, urea, sulfonamide, or acyl-sulfonamide.

In embodiments, the linker (e.g., $L^{100}$) is a substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, the linker (e.g., $L^{100}$) is a substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene.

In embodiments, the linker (e.g., $L^{100}$) is unsubstituted alkylene, unsubstituted heteroalkylene, unsubstituted cycloalkylene, unsubstituted heterocycloalkylene, unsubstituted arylene, or unsubstituted heteroarylene.

In embodiments, $L^{100}$ has the formula: -$L^{100A}$-$L^{100B}$-$L^{100C}$-$L^{100D}$-$L^{100E}$-. $L^{100A}$, $L^{100B}$, $L^{100C}$, $L^{100D}$ and $L^{100E}$ are each independently a bond, —N($R^{101}$)—, —C(O)—, —C(O)N($R^{101}$)—, —N($R^{101}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconugate linker.

In embodiments, $L^{100}$ has the formula: -$L^{100A}$-$L^{100B}$-$L^{100C}$-$L^{100D}$-$L^{100E}$-. $L^{100A}$, $L^{100B}$, $L^{100C}$, $L^{100D}$ and $L^{100E}$ are each independently a bond, —N($R^{101}$)—, —C(O)—, —C(O)N($R^{101}$)—, —N($R^{101}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{101}$-substituted or unsubstituted alkylene, $R^{101}$-substituted or unsubstituted heteroalkylene, $R^{101}$-substituted or unsubstituted cycloalkylene, $R^{101}$-substituted or unsubstituted heterocycloalkylene, $R^{101}$-substituted or unsubstituted arylene, or $R^{101}$-substituted or unsubstituted heteroarylene, or a bioconugate linker.

$R^{101}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —B(OH)$_2$, —SO$_2$F, —OSO$_2$F, —NHSO$_2$F, —SO$_2$CH=CH$_2$, —NHSO$_2$CH=CH$_2$, —COH, —CO-oxiranyl, —CO-aziridinyl, epoxidinyl, oxaziridinyl, aziridinyl, —OCH$_2$C≡CH, a bioconjugate reactive moiety, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{101}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —B(OH)$_2$, —SO$_2$F, —OSO$_2$F, —NHSO$_2$F, —SO$_2$CH=CH$_2$, —NHSO$_2$CH=CH$_2$, —COH, —CO-oxiranyl, —CO-aziridinyl, epoxidinyl, oxaziridinyl, aziridinyl, —OCH$_2$C≡CH, a bioconjugate reactive moiety, $R^{102}$-substituted or unsubstituted alkyl (e.g., $C_1$-$C_8$ alkyl, $C_1$-$C_6$ alkyl, or $C_1$-$C_4$ alkyl), $R^{102}$-substituted or unsubstituted heteroalkyl (e.g., 2 to 8 membered heteroalkyl, 2 to 6 membered heteroalkyl, or 2 to 4 membered heteroalkyl), $R^{102}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{102}$-substituted or unsubstituted heterocycloalkyl (e.g., 3 to 8 membered heterocycloalkyl, 3 to 6 membered heterocycloalkyl, or 5 to 6 membered heterocycloalkyl), $R^{102}$-substituted or unsubstituted aryl (e.g., $C_6$-$C_{10}$ aryl, $C_{10}$ aryl, or phenyl), or $R^{102}$-substituted or unsubstituted heteroaryl (e.g., 5 to 10 membered heteroaryl, 5 to 9 membered heteroaryl, or 5 to 6 membered heteroaryl).

In embodiments, $R^{101}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —B(OH)$_2$, —SO$_2$F, —OSO$_2$F, —NHSO$_2$F, —SO$_2$CH=CH$_2$, —NHSO$_2$CH=CH$_2$, —COH, —CO-oxiranyl, —CO-aziridinyl, epoxidinyl, oxaziridinyl, aziridinyl, —OCH$_2$C≡CH, a bioconjugate reactive moiety, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

$R^{102}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —B(OH)$_2$, —SO$_2$F, —OSO$_2$F, —NHSO$_2$F, —SO$_2$CH=CH$_2$, —NHSO$_2$CH=CH$_2$, —COH, —CO-oxiranyl, —CO-aziridinyl, epoxidinyl, oxaziridinyl, aziridinyl, —OCH₂C≡CH, a bioconjugate reactive moiety, $R^{103}$-substituted or unsubstituted alkyl (e.g., $C_1$-$C_8$ alkyl, $C_1$-$C_6$ alkyl, or $C_1$-$C_4$ alkyl), $R^{103}$-substituted or unsubstituted heteroalkyl (e.g., 2 to 8 membered heteroalkyl, 2 to 6 membered heteroalkyl, or 2 to 4 membered heteroalkyl), $R^{103}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{103}$-substituted or unsubstituted heterocycloalkyl (e.g., 3 to 8 membered heterocycloalkyl, 3 to 6 membered heterocycloalkyl, or 5 to 6 membered heterocycloalkyl), $R^{103}$-substituted or unsubstituted aryl (e.g., $C_6$-$C_{10}$ aryl, $C_{10}$ aryl, or phenyl), or $R^{103}$-substituted or unsubstituted heteroaryl (e.g., 5 to 10 membered heteroaryl, 5 to 9 membered heteroaryl, or 5 to 6 membered heteroaryl).

In embodiments, $R^{102}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OC HCl₂, —OCHBr₂, —OCHI₂, —OCHF₂, —OCH₂Cl, —OCH₂Br, —OCH₂I, —OCH₂F, —N₃, —SF₅, —B(OH)₂, —SO₂F⁷, —OSO₂F, —NHSO₂F, —SO₂CH=CH₂, —NHSO₂CH=CH₂, —COH, —CO-oxiranyl, —CO-aziridinyl, epoxidinyl, oxaziridinyl, aziridinyl, —OCH₂C≡CH, a bioconjugate reactive moiety, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

$R^{103}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, —B(OH)₂, —SO₂F, —OSO₂F, —NHSO₂F, —SO₂CH=CH₂, —NHSO₂CH=CH₂, —COH, —CO-oxiranyl, —CO-aziridinyl, epoxidinyl, oxaziridinyl, aziridinyl, —OCH₂C≡CH, a bioconjugate reactive moiety, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments the compound, or a pharmaceutical salt thereof, or a prodrug thereof, is a compound described herein, including embodiments. In embodiments the compound, or a pharmaceutical salt thereof, or a prodrug thereof, is a pharmaceutical salt of a compound described herein, including embodiments. In embodiments the compound, or a pharmaceutical salt thereof, or a prodrug thereof, is a prodrug of a compound described herein, including embodiments.

In embodiments, the compound is not

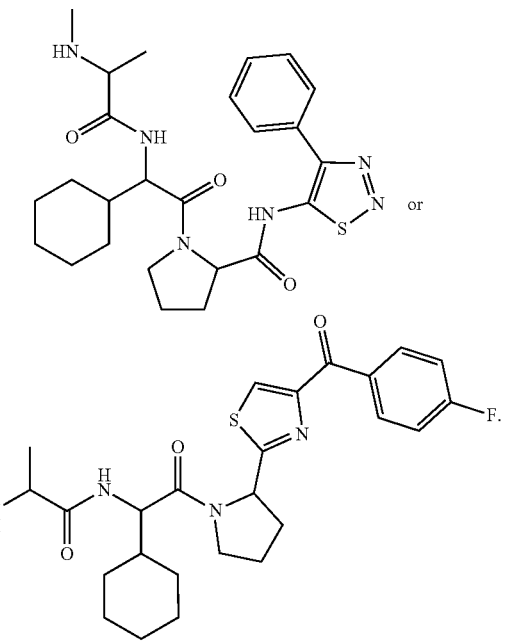

In embodiments, the compound is not

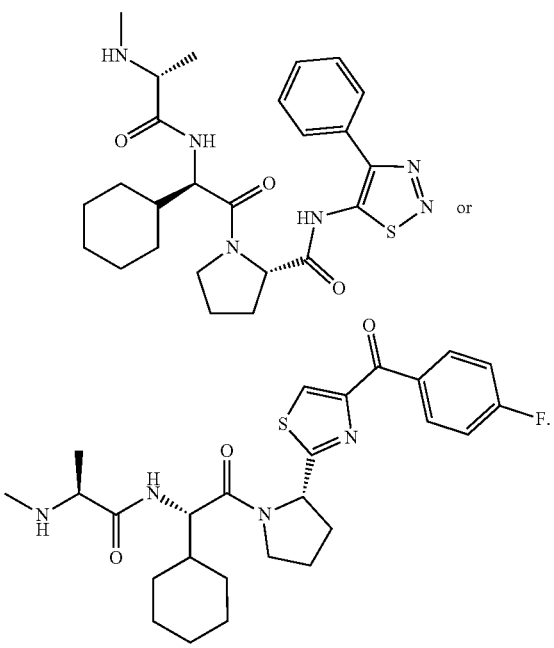

In embodiments, $L^3$ is not a 5 to 6 membered heteroaryl. In embodiments, $L^3$ is not a heteroaryl. In embodiments, $L^2$ is not a bond. In embodiments, -$L^2$-$R^2$ is not a substituted or unsubstituted cyclohexyl. In embodiments, -$L^2$-$R^2$ is not a substituted or unsubstituted $C_6$ cycloalkyl. In embodiments, -$L^2$-$R^2$ is not a substituted or unsubstituted cycloalkyl.

III. PHARMACEUTICAL COMPOSITIONS

In an aspect is provided a pharmaceutical composition including a compound, pharmaceutical salt thereof, or a prodrug thereof, as described herein and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent (e.g., an anti-cancer agent).

In embodiments, the second agent is an apoptosis increasing agent. In embodiments, the second agent is a Bcl-2 family antagonist. In embodiments, the Bcl-2 family antagonist is venetoclax or navitoclax. In embodiments, the second agent is abraxane or gemcitabine. In embodiments, the second agent is gemcitabine. In embodiments of the pharmaceutical compositions, the pharmaceutical composition includes a second agent in a therapeutically effective amount.

The pharmaceutical compositions may include optical isomers, diastereomers, or pharmaceutically acceptable salts of the modulators disclosed herein. The compound included in the pharmaceutical composition may be covalently attached to a carrier moiety. Alternatively, the compound included in the pharmaceutical composition is not covalently linked to a carrier moiety.

IV. METHODS OF USE

In an aspect is provided a method of reducing the level of activity of XIAP, cIAP1, and/or cIAP2 (e.g., reducing relative to a control), the method including contacting the XIAP, cIAP1, and/or cIAP2 with a compound, pharmaceutical salt, or prodrug of a compound described herein, including embodiments. In embodiments, the method is a method of reducing the level of activity of XIAP (e.g., reducing relative to a control). In embodiments, the method is a method of reducing the level of activity of cIAP1 (e.g., reducing relative to a control). In embodiments, the method is a method of reducing the level of activity of cIAP2 (e.g., reducing relative to a control). In embodiments, the method of reducing refers to a decrease in the level of activity of the protein (e.g., XIAP, cIAP1, or cIAP2) relative to the absence of the compound. In embodiments, the method includes contacting the XIAP (e.g., Lys311 of Bir3 of XIAP) with a compound, pharmaceutical salt, or prodrug of a compound described herein, including embodiments.

In an aspect is provided a method for treating cancer, the method including administering to a subject in need thereof a therapeutically effective amount of a compound, pharmaceutical salt, or prodrug of a compound described herein, including embodiments. In embodiments, the cancer is leukemia and lymphoma, including AML, ALL, CML, CLL, multiple myeloma, advanced solid tumors, bladder cancer, brain gliomas, solid tumor breast cancer, triple negative breast cancer, HER-2 negative metastatic breast cancer, cervical cancer, colorectal cancer, endometrial cancer, esophageal cancer, gastric cancer, gastrointestinal stromal tumor, glioma, head and neck cancer, head and neck squamous cell carcinoma, hepatocellular carcinoma, Hodgkin lymphoma, non Hodgkin lymphoma, liver cancer, lung cancer, lymphoma, medulloblastoma, melanoma, myelodysplastic syndomes, neuroblastoma, non-small cell lung cancer, squamous non-small cell lung cancer, osteosarcoma, ovarian cancer, platinum-refractory ovarian cancer, pancreatic cancer, metastatic pancreatic cancer, prostate cancer, renal cancer, rhabdomyosarcoma, skin cancer, stomach cancer, testis cancer, thyroid cancer, urothelial cancer, or all relapsing and/or chemoresistant and/or radiation resistant cancers that are driven by XIAP overexpression, including those with caspase 3 deletion. In embodiments, the cancer is an XIAP associated cancer (e.g., the level of XIAP or activity of XIAP is increased relative to a control). In embodiments, the cancer is pancreatic cancer, Acute lymphoblastic leukemia (ALL), or multiple myeloma.

In embodiments, the cancer is leukemia. In embodiments, the cancer is lymphoma. In embodiments, the cancer is AML. In embodiments, the cancer is ALL. In embodiments, the cancer is CML. In embodiments, the cancer is CLL. In embodiments, the cancer is multiple myeloma. In embodiments, the cancer is advanced solid tumors. In embodiments, the cancer is bladder cancer. In embodiments, the cancer is brain gliomas. In embodiments, the cancer is breast cancer. In embodiments, the cancer is triple negative breast cancer. In embodiments, the cancer is HER-2 negative metastatic breast cancer. In embodiments, the cancer is cervical cancer. In embodiments, the cancer is colorectal cancer. In embodiments, the cancer is endometrial cancer. In embodiments, the cancer is esophageal cancer. In embodiments, the cancer is gastric cancer. In embodiments, the cancer is a gastrointestinal stromal tumor. In embodiments, the cancer is glioma. In embodiments, the cancer is head and neck cancer. In embodiments, the cancer is head and neck squamous cell carcinoma. In embodiments, the cancer is hepatocellular carcinoma. In embodiments, the cancer is Hodgkin lymphoma. In embodiments, the cancer is non Hodgkin lymphoma. In embodiments, the cancer is liver cancer. In embodiments, the cancer is lung cancer. In embodiments, the cancer is lymphoma. In embodiments, the cancer is medulloblastoma. In embodiments, the cancer is melanoma. In embodiments, the cancer is myelodysplastic syndromes. In embodiments, the cancer is neuroblastoma. In embodiments, the cancer is non-small cell lung cancer. In embodiments, the cancer is squamous non-small cell lung cancer. In embodiments, the cancer is osteosarcoma. In embodiments, the cancer is ovarian cancer. In embodiments, the cancer is platinum-refractory ovarian cancer. In embodiments, the cancer is pancreatic cancer. In embodiments, the cancer is metastatic pancreatic cancer. In embodiments, the cancer is prostate cancer. In embodiments, the cancer is renal cancer. In embodiments, the cancer is rhabdomyosarcoma. In embodiments, the cancer is skin cancer. In embodiments, the cancer is stomach cancer. In embodiments, the cancer is testis cancer. In embodiments, the cancer is thyroid cancer. In embodiments, the cancer is urothelial cancer. In embodiments, the cancer is a relapsing and/or chemoresistant and/or radiation resistant cancers that are driven by XIAP overexpression.

In another aspect is provided a method for increasing apoptosis in a cancer cell in a subject in need thereof (e.g., increasing relative to a control), the method including administering to the subject in need thereof a therapeutically effective amount of a compound, pharmaceutical salt, or prodrug of a compound described herein, including embodiments. In embodiments, the method further includes administering to the subject a therapeutically effective amount of a second agent. In embodiments, the second agent is an apoptosis increasing agent. In embodiments, the second agent is a Bcl-2 family antagonist (e.g., oblimersen, ABT-737, ABT-263 (i.e. navitoclax), ABT-199 (i.e. venetoclax). In embodiments, the Bcl-2 family antagonist is venetoclax or navitoclax. In embodiments, the Bcl-2 family antagonist is venetoclax. In embodiments, the Bcl-2 family antagonist is navitoclax. In embodiments, the method further includes administering to the subject a therapeutically effective amount of radiation.

In another aspect is provided a method for increasing apoptosis in a cancer cell (e.g., increasing relative to a control), the method including contacting the cell with a compound, pharmaceutical salt, or prodrug of a compound described herein, including embodiments.

In an aspect is provided a method for inducing apoptosis in a cancer cell in a subject in need thereof, the method including administering to the subject in need thereof a therapeutically effective amount of a compound, pharmaceutical salt thereof, or prodrug thereof, as described herein, including embodiments. In embodiments, the method further includes administering to the subject a therapeutically effective amount of a second agent. In embodiments, the second agent is an apoptosis increasing agent. In embodiments, the second agent is a Bcl-2 family antagonist (e.g., oblimersen, ABT-737, ABT-263 (i.e., navitoclax), ABT-199 (i.e., venetoclax). In embodiments, the Bcl-2 family antagonist is venetoclax or navitoclax. In embodiments, the Bcl-2 family antagonist is venetoclax. In embodiments, the Bcl-2 family antagonist is navitoclax. In embodiments, the method further includes administering to the subject a therapeutically effective amount of radiation.

In an aspect is provided a method for inducing apoptosis in a cancer cell, the method including contacting the cancer cell with a compound, pharmaceutical salt thereof, or prodrug thereof, as described herein, including embodiments. In embodiments the cell is a mesenchymal cell.

In another aspect is provided a method for increasing apoptosis in a cancer cell (e.g., increasing relative to a control), the method including contacting the XIAP, cIAP1, and/or cIAP2 with a compound, pharmaceutical salt, or prodrug of a compound described herein, including embodiments. In embodiments, the method is a method for increasing apoptosis in a cancer cell (e.g., increasing relative to a control), the method including contacting the XIAP. In embodiments, the method is a method for increasing apoptosis in a cancer cell (e.g., increasing relative to a control), the method including contacting the cIAP1. In embodiments, the method is a method for increasing apoptosis in a cancer cell (e.g., increasing relative to a control), the method including contacting the cIAP2.

In another aspect is provided a method for inducing apoptosis in a cancer cell (e.g., increasing relative to a control), the method including contacting the XIAP, cIAP1, and/or cIAP2 with a compound, pharmaceutical salt, or prodrug of a compound described herein, including embodiments. In embodiments, the method is a method for inducing apoptosis in a cancer cell (e.g., increasing relative to a control), the method including contacting the XIAP. In embodiments, the method is a method for inducing apoptosis in a cancer cell (e.g., increasing relative to a control), the method including contacting the cIAP1. In embodiments, the method is a method for inducing apoptosis in a cancer cell (e.g., increasing relative to a control), the method including contacting the cIAP2.

In an aspect is provided a method for treating respiratory disease, the method including administering to a subject in need thereof a therapeutically effective amount of a compound, pharmaceutical salt, or prodrug of a compound described herein, including embodiments. In embodiments, the respiratory disease is pulmonary fibrosis. In an aspect is provided a method for inducing apoptosis in a mesenchymal cell.

In embodiments, the method includes preferentially binding BIR3 relative to BIR2 (e.g., a BIR3 domain of XIAP, cIAP1, or cIAP2). In embodiments, the method includes preferentially binding BIR2 relative to BIR3 (e.g., a BIR2 domain of XIAP, cIAP1, or cIAP2). In embodiments, the compound (e.g., compound described herein) preferentially binds XIAP compared to cIAP1 (e.g., preferentially binds at least 1.1, 1.5, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 100000, or 1000000-fold stronger). In embodiments, the compound (e.g., compound described herein) preferentially binds XIAP compared to cIAP2 (e.g., preferentially binds at least 1.1, 1.5, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 100000, or 1000000-fold stronger). In embodiments, the compound (e.g., compound described herein) preferentially binds cIAP1 compared to cIAP2 (e.g., preferentially binds at least 1.1, 1.5, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 100000, or 1000000-fold stronger). In embodiments, the compound (e.g., compound described herein) preferentially binds cIAP1 compared to XIAP (e.g., preferentially binds at least 1.1, 1.5, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 100000, or 1000000-fold stronger). In embodiments, the compound (e.g., compound described herein) preferentially binds cIAP2 compared to cIAP1 (e.g., preferentially binds at least 1.1, 1.5, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 100000, or 1000000-fold stronger). In embodiments, the compound (e.g., compound described herein) preferentially binds cIAP2 compared to XIAP (e.g., preferentially binds at least 1.1, 1.5, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 100000, or 1000000-fold stronger).

In embodiments, the method includes a compound (e.g., a compound described herein) covalently binding the amino acid corresponding to Lys311 of Bir3 of XIAP. In embodiments, the method includes a compound (e.g., a compound described herein) covalently binding Lys311 of Bir3 of XIAP.

In embodiments, the cell is a MOLT-4 cell (e.g., an ALL model cell). In embodiments, the cell is a H929 or L363 (e.g., a multiple myeloma model cell). In embodiments, cell is a MM1S, RPMI 8226, LP1, or U266 (e.g., a multiple myeloma model cell). In embodiments, the cell is a BxPC3 or PANC-1 cell. In embodiments, the cell is a LCL161-resistant cell. In embodiments, the cell is a chemoresistant cell.

V. EMBODIMENTS

Embodiment 1: according to embodiments of the present invention, compounds are provided having the general structure I listed below, or pharmaceutically acceptable salts thereof, including pro-drug versions:

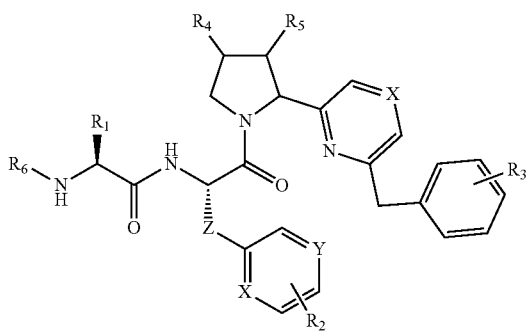

I wherein R₁ is any of the following: —CH₃, —C₂H₅, —CF₃, —CH₂F, —CHF₂, —CH₂CF₃, —CF₂CH₃, —CH₂OH, —CF₂OH, —CHFOH; R₂ is mono, di- or tri-substituted with: —CH₂SO₃⁻, —PO₃⁻², —SO₃⁻, —SO₂NH₂, —CH₂PO₃⁻², —CH₂SO₂NH₂, —CF₃, —Cl, —F, —CH₃, —NO₂, —C₂H₅, —OCH₃, —OCF₃, guanidino, acrylamide, -2-chloroacetamide, —B(OH)₂, —SO₂F, —SO₂CH=CH₂, —COH, —CO-epoxide, —CO-aziridine; R₃ represents mono, di- or tri-substitutions with —F, —Cl, —CH₃, —C₂H₅, —OH, —OCH₃, —OCF₃; X, Y=C or N; R₄ and R₅ can independently be —H, —F, —OH, —OCH₃, —OCF₃, guanidine, —OC₂H₅. Z=—(CH₂)ₙ—, —(CH₂)ₙO—, —(CH₂)ₙNHCO—, —(CH₂)ₙS—, —(CH₂)ₙCONH—, —O(CH₂)ₙ—, —(CH₂)ₙNH—, —(CH₂)ₙCO—; R₆=—H, —CH₃, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=0, 1, 2, 3.

Embodiment 1-i: according to embodiments of the present invention, compounds are provided having the general structure I-i listed below, or pharmaceutically acceptable salts thereof, including pro-drug versions:

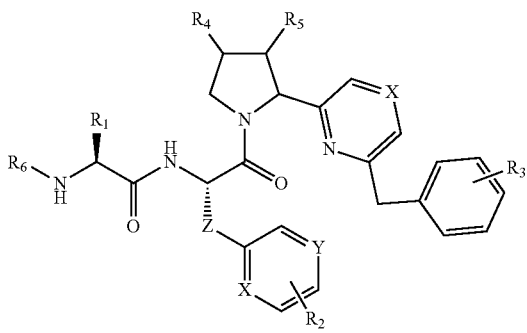

I-i wherein R₁ is any of the following: —CH₃, —C₂H₅, —CF₃, —CH₂F, —CHF₂, —CH₂CF₃, —CF₂CH₃, —CH₂OH, —CF₂OH, —CHFOH; R₂ is mono, di- or tri-substituted with: —CH₂SO₃⁻, —PO₃⁻², —SO₃⁻, —SO₂NH₂, —CH₂PO₃⁻², —CH₂SO₂NH₂, —CF₃, —Cl, —F, —CH₃, —NO₂, —C₂H₅, —OCH₃, —OCF₃, guanidino, acrylamide, -2-chloroacetamide, —B(OH)₂, —SO₂F, —OSO₂F, —NHSO₂F, —SO₂CH=CH₂, —NHSO₂CH=CH₂, —COH, —CO-epoxide, —CO-aziridine, epoxide, aziridine, oxaziridine; R₃ represents mono, di- or tri-substitutions with —F, —Cl, —CH₃, —C₂H₅, —OH, —OCH₃, —OCF₃, —SO₂F, —SO₂CH=CH₂, —NHSO₂CH=CH₂, —OSO₂F, —B(OH)₂, —NHSO₂F; X, Y=C or N; R₄ and R₅ can independently be —H, —F, —OH, —OCH₃, —OCF₃, guanidine, —OC₂H₅, —SO₂F, —SO₂CH=CH₂, —NHSO₂CH=CH₂, —OSO₂F, —B(OH)₂, —NHSO₂F. Z=—(CH₂)ₙ—, —(CH₂)ₙO—, —(CH₂)ₙNHCO—, —(CH₂)ₙS—, —(CH₂)ₙCONH—, —O(CH₂)ₙ—, —(CH₂)ₙNH—, —(CH₂)ₙNHCH₂—, —(CH₂)ₙCO—; R₆=—H, —CH₃, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=0, 1, 2, 3.

Embodiment 2: according to embodiments of the present invention, compounds are provided having the general structure II listed below, or pharmaceutically acceptable salts thereof, including pro-drug versions:

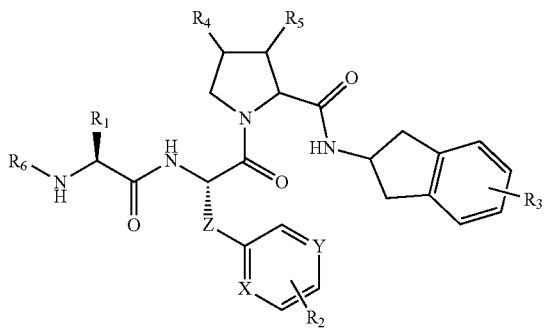

II wherein R₁ is any of the following: —CH₃, —C₂H₅, —CF₃, —CH₂F, —CHF₂, —CH₂CF₃, —CF₂CH₃, —CH₂OH, —CF₂OH, —CHFOH; R₂ is mono, di- or tri-substituted with: —CH₂SO₃⁻, —PO₃⁻², —SO—, —SO₂NH₂, —CH₂PO₃⁻², —CH₂SO₂NH₂, —CF₃, —Cl, —F, —CH₃, —NO₂, —C₂H₅, —OCH₃, —OCF₃, guanidino, acrylamide, -2-chloroacetamide, —B(OH)₂, —SO₂F, —SO₂CH=CH₂, —COH, —CO-epoxide, —CO-aziridine; R₃ represents mono, di- or tri-substitutions with —F, —Cl, —CH₃, —C₂H₅, —OH, —OCH₃, —OCF₃; X, Y=C or N; R₄ and R₅ can independently be —H, —F, —OH, —OCH₃, —OCF₃, guanidine, —OC₂H₅. Z=—(CH₂)ₙ—, —(CH₂)ₙO—, —(CH₂)ₙNHCO—, —(CH₂)ₙS—, —(CH₂)ₙCONH—, —O(CH₂)ₙ—, —(CH₂)ₙNH—, —(CH₂)ₙCO—; R⁶=—H, —CH₃, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=0, 1, 2, 3.

Embodiment 2-i: according to embodiments of the present invention, compounds are provided having the general structure II-i listed below, or pharmaceutically acceptable salts thereof, including pro-drug versions:

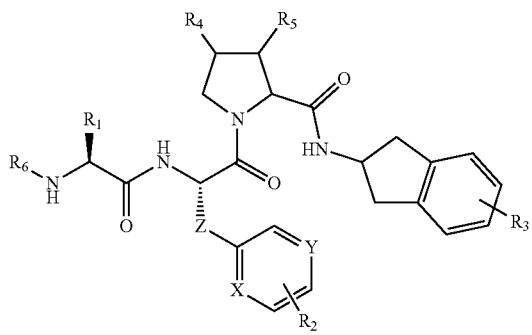

II-i wherein $R_1$ is any of the following: —$CH_3$, —$C_2H_5$, —$CF_3$, —$CH_2F$, —$CHF_2$, —$CH_2CF_3$, —$CF_2CH_3$, —$CH_2OH$, —$CF_2OH$, —CHFOH; $R_2$ is mono, di- or tri-substituted with: —$CH_2SO_3^-$, —$PO_3^{-2}$, —SO—, —$SO_2NH_2$, —$CH_2PO_3^{-2}$, —$CH_2SO_2NH_2$, —$CF_3$, —Cl, —F, —$CH_3$, —$NO_2$, —$C_2H_5$, —$OCH_3$, —$OCF_3$, guanidino, acrylamide, -2-chloroacetamide, —$B(OH)_2$, —$SO_2F$, —$OSO_2F$, —$NHSO_2F$, —$SO_2CH=CH_2$, —$NHSO_2CH=CH_2$, —COH, —CO-epoxide, —CO-aziridine, epoxide, aziridine, oxaziridine; $R_3$ represents mono, di- or tri-substitutions with —F, —Cl, —$CH_3$, —$C_2H_5$, —OH, —$OCH_3$, —$OCF_3$, —$SO_2F$, —$SO_2CH=CH_2$, —$NHSO_2CH=CH_2$, —$OSO_2F$, —$B(OH)_2$, —$NHSO_2F$; X, Y=C or N; $R_4$ and $R_5$ can independently be —H, —F, —OH, —$OCH_3$, —$OCF_3$, guanidine, —$OC_2H_5$, —$SO_2F$, —$SO_2CH=CH_2$, —$NHSO_2CH=CH_2$, —$OSO_2F$, —$B(OH)_2$, —$NHSO_2F$. Z=—$(CH_2)_n$—, —$(CH_2)_nO$—, —$(CH_2)_nNHCO$—, —$(CH_2)_nS$—, —$(CH_2)_nCONH$—, —$O(CH_2)_n$—, —$(CH_2)_n$NH—, —$(CH_2)_nNHCH_2$—, —$(CH_2)_nCO$—; R6=—H, —CH3, —$C_2H_5$, —$CH(CH_3)_2$, cyclopropyl-, cyclopropyl-$CH_2$—, cyclobutyl-, cyclobutyl-$CH_2$—, cyclopentyl-, cyclopentyl-$CH_2$—, cyclohexyl-, cyclohexyl-$CH_2$, n-butyl, isobutyl, sec-butyl, pentyl, hexyl, phenyl, benzyl (substituted or unsubstituted); n=0, 1, 2, 3.

Embodiment 3: according to embodiments of the present invention, compounds are provided having the general structure III listed below, or pharmaceutically acceptable salts thereof, including pro-drug versions:

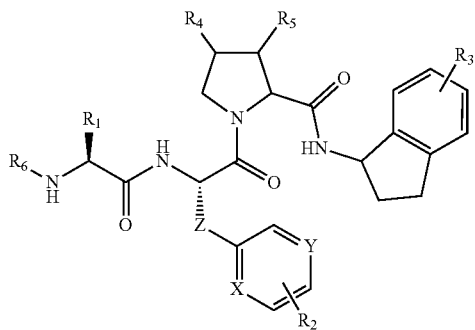

III wherein $R_1$ is any of the following: —$CH_3$, —$C_2H_5$, —$CF_3$, —$CH_2F$, —$CHF_2$, —$CH_2CF_3$, —$CF_2CH_3$, —$CH_2OH$, —$CF_2OH$, —CHFOH; $R_2$ is mono, di- or tri-substituted with: —$CH_2SO_3^-$, —$PO_3^{-2}$, —SO—, —$SO_2NH_2$, —$CH_2PO_3^{-2}$, —$CH_2SO_2NH_2$, —$CF_3$, —Cl, —F, —$CH_3$, —$NO_2$, —$C_2H_5$, —$OCH_3$, —$OCF_3$, guanidino, acrylamide, -2-chloroacetamide, —$B(OH)_2$, —$SO_2F$, —$SO_2CH=CH_2$, —COH, —CO-epoxide, —CO-aziridine; $R_3$ represents mono, di- or tri-substitutions with —F, —Cl, —$CH_3$, —$C_2H_5$, —OH, —$OCH_3$, —$OCF_3$; X, Y=C or N; $R_4$ and $R_5$ can independently be —H, —F, —OH, —$OCH_3$, —$OCF_3$, guanidine, —$OC_2H_5$. Z=—$(CH_2)_n$—, —$(CH_2)_nO$—, —$(CH_2)_nNHCO$—, —$(CH_2)_nS$—, —$(CH_2)_nCONH$—, —$O(CH_2)_n$—, —$(CH_2)_nNH$—, —$(CH_2)_nCO$—; $R_6$=—H, —CH3, —$C_2H_5$, —$CH(CH_3)_2$, cyclopropyl-, cyclopropyl-$CH_2$—, cyclobutyl-, cyclobutyl-$CH_2$—, cyclopentyl-, cyclopentyl-$CH_2$—, cyclohexyl-, cyclohexyl-$CH_2$, n-butyl, isobutyl, sec-butyl, pentyl, hexyl, phenyl, benzyl (substituted or unsubstituted); n=0, 1, 2, 3.

Embodiment 3-i: according to embodiments of the present invention, compounds are provided having the general structure III-i listed below, or pharmaceutically acceptable salts thereof, including pro-drug versions:

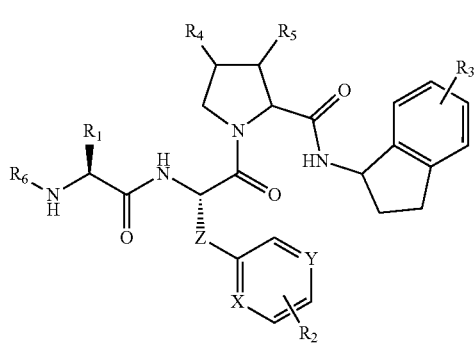

III-i wherein $R_1$ is any of the following: —$CH_3$, —$C_2H_5$, —$CF_3$, —$CH_2F$, —$CHF_2$, —$CH_2CF_3$, —$CF_2CH_3$, —$CH_2OH$, —$CF_2OH$, —CHFOH; $R_2$ is mono, di- or tri-substituted with: —$CH_2SO_3^-$, —$PO_3^{-2}$, —$SO_3^-$, —$SO_2NH_2$, —$CH_2PO_3^{-2}$, —$CH_2SO_2NH_2$, —$CF_3$, —Cl, —F, —$CH_3$, —$NO_2$, —$C_2H_5$, —$OCH_3$, —$OCF_3$, guanidino, acrylamide, -2-chloroacetamide, —$B(OH)_2$, —$SO_2F$, —$OSO_2F$, —$NHSO_2F$, —$SO_2CH=CH_2$, —$NHSO_2CH=CH_2$, —COH, —CO-epoxide, —CO-aziridine, epoxide, aziridine, oxaziridine; $R_3$ represents mono, di- or tri-substitutions with —F, —Cl, —$CH_3$, —$C_2H_5$, —OH, —$OCH_3$, —$OCF_3$, —$SO_2F$, —$SO_2CH=CH_2$, —$NHSO_2CH=CH_2$, —$OSO_2F$, —$B(OH)_2$, —$NHSO_2F$; X, Y=C or N; $R_4$ and $R_5$ can independently be —H, —F, —OH, —$OCH_3$, —$OCF_3$, guanidine, —$OC_2H_5$, —$SO_2F$, —$SO_2CH=CH_2$, —$NHSO_2CH=CH_2$, —$OSO_2F$, —$B(OH)_2$, —$NHSO_2F$. Z=—$(CH_2)_n$—, —$(CH_2)_nO$—, —$(CH_2)_nNHCO$—, —$(CH_2)_nS$—, —$(CH_2)_nCONH$—, —$O(CH_2)_n$—, —$(CH_2)_n$NH—, —$(CH_2)_nNHCH_2$—, —$(CH_2)$, CO—; $R_6$=—H, —CH3, —$C_2H_5$, —$CH(CH_3)_2$, cyclopropyl-, cyclopropyl-$CH_2$—, cyclobutyl-, cyclobutyl-$CH_2$—, cyclopentyl-, cyclopentyl-$CH_2$—, cyclohexyl-, cyclohexyl-$CH_2$, n-butyl, isobutyl, sec-butyl, pentyl, hexyl, phenyl, benzyl (substituted or unsubstituted); n=0, 1, 2, 3.

Embodiment 4: according to embodiments of the present invention, compounds are provided having the general structure IV listed below, or pharmaceutically acceptable salts thereof, including pro-drug versions:

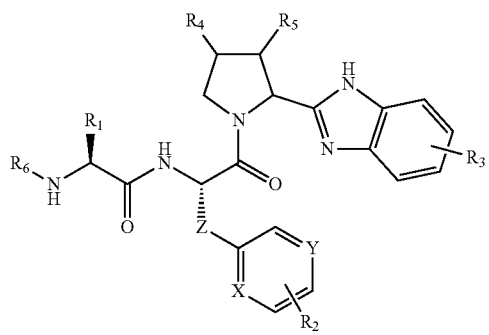

IV wherein R₁ is any of the following: —CH₃, —C₂H₅, —CF₃, —CH₂F, —CHF₂, —CH₂CF₃, —CF₂CH₃, —CH₂OH, —CF₂OH, —CHFOH; R₂ is mono, di- or tri-substituted with: —CH₂SO₃⁻, —PO₃⁻², —SO₃⁻, —SO₂NH₂, —CH₂PO₃⁻², —CH₂SO₂NH₂, —CF₃, —Cl, —F, —CH₃, —NO₂, —C₂H₅, —OCH₃, —OCF₃, guanidino, acrylamide, -2-chloroacetamide, —B(OH)₂, —SO₂F, —SO₂CH=CH₂, —COH, —CO-epoxide, —CO-aziridine; R₃ represents mono, di- or tri-substitutions with —F, —Cl, —CH₃, —C₂H₅, —OH, —OCH₃, —OCF₃; X, Y=C or N; R₄ and R₅ can independently be —H, —F, —OH, —OCH₃, —OCF₃, guanidine, —OC₂H₅. Z=—(CH₂)ₙ—, —(CH₂)ₙO—, —(CH₂)ₙNHCO—, —(CH₂)ₙS—, —(CH₂)ₙCONH—, —O(CH₂)ₙ—, —(CH₂)ₙNH—, —(CH₂)ₙCO—; R⁶=—H, —CH₃, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=0, 1, 2, 3.

Embodiment 4-i: according to embodiments of the present invention, compounds are provided having the general structure IV-i listed below, or pharmaceutically acceptable salts thereof, including pro-drug versions:

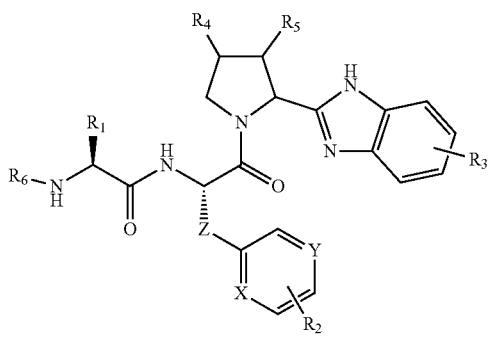

IV-i wherein R₁ is any of the following: —CH₃, —C₂H₅, —CF₃, —CH₂F, —CHF₂, —CH₂CF₃, —CF₂CH₃, —CH₂OH, —CF₂OH, —CHFOH; R₂ is mono, di- or tri-substituted with: —CH₂SO₃⁻, —PO₃⁻², —SO—, —SO₂NH₂, —CH₂PO₃⁻², —CH₂SO₂NH₂, —CF₃, —Cl, —F, —CH₃, —NO₂, —C₂H₅, —OCH₃, —OCF₃, guanidino, acrylamide, -2-chloroacetamide, —B(OH)₂, —SO₂F, —OSO₂F, —NHSO₂F, —SO₂CH=CH₂, —NHSO₂CH=CH₂, —COH, —CO-epoxide, —CO-aziridine, epoxide, aziridine, oxaziridine; R₃ represents mono, di- or tri-substitutions with —F, —Cl, —CH₃, —C₂H₅, —OH, —OCH₃, —OCF₃, —SO₂F, —SO₂CH=CH₂, —NHSO₂CH=CH₂, —OSO₂F, —B(OH)₂, —NHSO₂F; X, Y=C or N; R₄ and R₅ can independently be —H, —F, —OH, —OCH₃, —OCF₃, guanidine, —OC₂H₅, —SO₂F, —SO₂CH=CH₂, —NHSO₂CH=CH₂, —OSO₂F, —B(OH)₂, —NHSO₂F. Z=—(CH₂)ₙ—, —(CH₂)ₙO—, —(CH₂)ₙNHCO—, —(CH₂)ₙS—, —(CH₂)ₙCONH—, —O(CH₂)ₙ—, —(CH₂)ₙNH—, —(CH₂)ₙNHCH₂—, —(CH₂)ₙCO—; R₆=—H, —CH3, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=0, 1, 2, 3.

Embodiment 5: according to embodiments of present invention, there are provided compounds having the general structures V, or pharmaceutically acceptable salts thereof, including pro-drug versions:

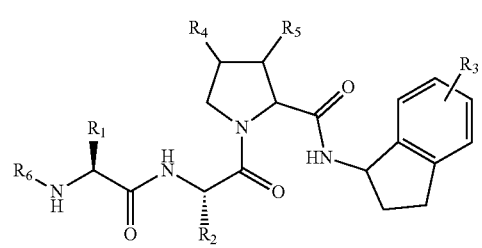

V wherein R₁ is any of the following: —CH₃, —C₂H₅, —CF₃, —CH₂F, —CHF₂, —CH₂CF₃, —CF₂CH₃, —CH₂OH, —CF₂OH, —CHFOH; R₂=—(CH₂)ₙNH₂, —(CH₂)ₙCOOH, —(CH₂)ₙCONH₂, —(CH₂)ₙ-tetrazolium, —(CH₂)ₙSO₂NH₂, —(CH₂)ₙCONHSO₂CH₃, —(CH₂)ₙCONHSO₂CF₃, —(CH₂)ₙNHSO₂CH₃, —(CH₂)ₙSO₂NH₂, —(CH₂)ₙNHCOCl, —(CH₂)ₙCONH-aziridine, —(CH₂), NHCOCH=CH₂, —(CH₂), CO— epoxide, —(CH₂)ₙSO₂F, substituted or unsubstituted 2-pyridyl or 3-pyridyl or 4-pyridyl, —(CH₂)ₙB(OH)₂; R₃ represents mono, di- or tri-substitutions with —F, —Cl, —CH₃, —C₂H₅, —OH, —OCH₃, —OCF₃; X=C or N; R₄ and R₅ can independently be —H, —F, —OH, —OCH₃, —OCF₃, guanidine, —OC₂H₅; R₆=—H, —CH3, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=1, 2, 3, 4, 5.

Embodiment 5-i: according to embodiments of present invention, there are provided compounds having the general structures V-i, or pharmaceutically acceptable salts thereof, including pro-drug versions:

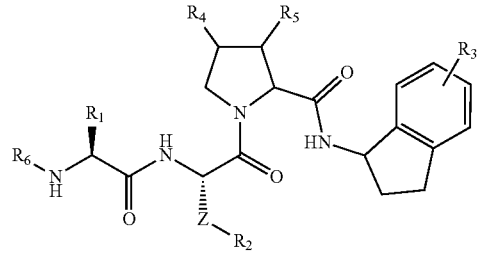

V-i wherein R₁ is any of the following: —CH₃, —C₂H₅, —CF₃, —CH₂F, —CHF₂, —CH₂CF₃, CF₂CH₃, —CH₂OH, —CF₂OH, —CHFOH; R₂=—(CH₂)$_n$NH₂, —(CH₂)$_n$COOH, —(CH₂)$_n$CONH₂, —(CH₂)$_n$-tetrazolium, —(CH₂)$_n$SO₂NH₂, —(CH₂)$_n$CONHSO₂CH₃, —(CH₂)$_n$CONHSO₂CF₃, —(CH₂)$_n$NHSO₂CH₃, —(CH₂)$_n$NHCOCl, —(CH₂)$_n$CONH-aziridine, —(CH₂)$_n$NHCOCH=CH₂, —(CH₂)$_n$CO-epoxide, —(CH₂)$_n$CO-aziridine, —(CH₂)$_n$SO₂F, —(CH₂)$_n$OSO₂F, —(CH₂)$_n$NHSO₂F, substituted or unsubstituted 2-pyridyl or 3-pyridyl or 4-pyridyl, —(CH₂)$_n$B(OH)₂, epoxide, aziridine, oxaziridine; R₃ represents mono, di- or tri-substitutions with —F, —Cl, —CH₃, —C₂H₅, —OH, —OCH₃, —OCF₃, —SO₂F, —SO₂CH=CH₂, —NHSO₂CH=CH₂, —OSO₂F, —B(OH)₂, —NHSO₂F; X=C or N; R₄ and R₅ can independently be —H, —F, —OH, —OCH₃, —OCF₃, guanidine, —OC₂H₅, —SO₂F, —SO₂CH=CH₂, —NHSO₂CH=CH₂, —OSO₂F, —B(OH)₂, —NHSO₂F; Z=—(CH₂)$_n$—, —(CH₂)$_n$O—, —(CH₂)$_n$NHCO—, —(CH₂)$_n$S—, —(CH₂)$_n$CONH—, —O(CH₂)$_n$—, —(CH₂)$_n$NH—, —(CH₂)$_n$NHCH₂—, —(CH₂)$_n$CO—; R₆=—H, —CH3, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=1, 2, 3, 4, 5.

Embodiment 6: according to embodiments of present invention, there are provided compounds having the general structures VI, or pharmaceutically acceptable salts thereof, including pro-drug versions:

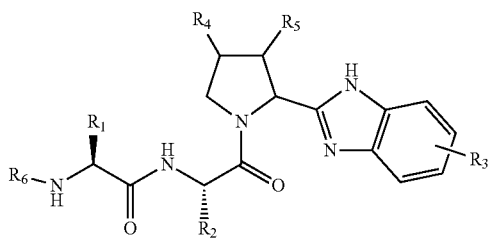

VI wherein R₁ is any of the following: —CH₃, —C₂H₅, —CF₃, —CH₂F, —CHF₂, —CH₂CF₃, CF₂CH₃, —CH₂OH, —CF₂OH, —CHFOH; R₂=—(CH₂)$_n$NH₂, —(CH₂)$_n$COOH, —(CH₂)$_n$CONH₂, —(CH₂)$_n$-tetrazolium, —(CH₂)$_n$SO₂NH₂, —(CH₂)$_n$CONHSO₂CH₃, —(CH₂)$_n$CONHSO₂CF₃, —(CH₂)$_n$NHSO₂CH₃, —(CH₂)$_n$SO₂NH₂, —(CH₂)$_n$NHCOCl; —(CH₂)$_n$CONH-aziridine, —(CH₂)$_n$NHCOCH=CH₂, —(CH₂)$_n$CO-epoxide, —(CH₂)$_n$SO₂F, substituted or unsubstituted 2-pyridyl or 3-pyridyl or 4-pyridyl, —(CH₂)$_n$B(OH)₂; R₃ represents mono, di- or tri-substitutions with —F, —Cl, —CH₃, —C₂H₅, —OH, —OCH₃, —OCF₃; X=C or N; R₄ and R₅ can independently be —H, —F, —OH, —OCH₃, —OCF₃, guanidine, —OC₂H₅; R₆=—H, —CH3, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=1, 2, 3, 4, 5.

Embodiment 6-i: according to embodiments of present invention, there are provided compounds having the general structures VI-i, or pharmaceutically acceptable salts thereof, including pro-drug versions:

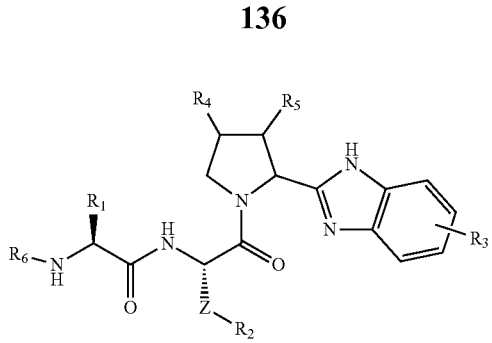

Vi-i wherein R₁ is any of the following: —CH₃, —C₂H₅, —CF₃, —CH₂F, —CHF₂, —CH₂CF₃, CF₂CH₃, —CH₂OH, —CF₂OH, —CHFOH; R₂=—(CH₂)$_n$NH₂, —(CH₂)$_n$COOH, —(CH₂)$_n$CONH₂, —(CH₂)$_n$-tetrazolium, —(CH₂)$_n$SO₂NH₂, —(CH₂)$_n$CONHSO₂CH₃, —(CH₂)$_n$CONHSO₂CF₃, —(CH₂)$_n$NHSO₂CH₃, —(CH₂)$_n$NHCOCl, —(CH₂)$_n$CONH-aziridine, —(CH₂)$_n$NHCOCH=CH₂, —(CH₂)$_n$CO-epoxide, —(CH₂)$_n$CO-aziridine, —(CH₂)$_n$SO₂F, —(CH₂)$_n$OSO₂F, —(CH₂)$_n$NHSO₂F, substituted or unsubstituted 2-pyridyl or 3-pyridyl or 4-pyridyl, —(CH₂)$_n$B(OH)₂, epoxide, aziridine, oxaziridine; R₃ represents mono, di- or tri-substitutions with —F, —Cl, —CH₃, —C₂H₅, —OH, —OCH₃, —OCF₃, —SO₂F, —SO₂CH=CH₂, —NHSO₂CH=CH₂, —OSO₂F, —B(OH)₂, —NHSO₂F; X=C or N; R₄ and R₅ can independently be —H, —F, —OH, —OCH₃, —OCF₃, guanidine, —OC₂H₅, —SO₂F, —SO₂CH=CH₂, —NHSO₂CH=CH₂, —OSO₂F, —B(OH)₂, —NHSO₂F; Z=—(CH₂)$_n$—, —(CH₂)$_n$O—, —(CH₂)$_n$NHCO—, —(CH₂)$_n$S—, —(CH₂)$_n$CONH—, —O(CH₂)$_n$—, —(CH₂)$_n$NH—, —(CH₂)$_n$NHCH₂—, —(CH₂)$_n$CO—; R₆=—H, —CH3, —C₂H₅, —CH(CH₃)₂, cyclopropyl-, cyclopropyl-CH₂—, cyclobutyl-, cyclobutyl-CH₂—, cyclopentyl-, cyclopentyl-CH₂—, cyclohexyl-, cyclohexyl-CH₂, n-butyl, isobutyl, sec-butyl, pentyl, hexyl, phenyl, benzyl (substituted or unsubstituted); n=1, 2, 3, 4, 5.

Embodiment 7: according to embodiments of present invention, there are provided compounds having the general structures VII, or pharmaceutically acceptable salts thereof, including pro-drug versions:

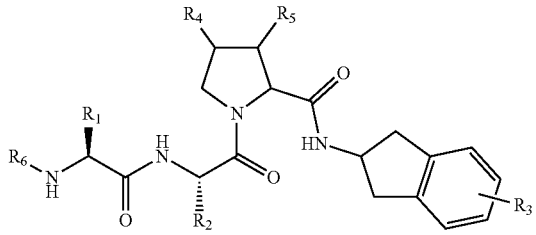

VII wherein R₁ is any of the following: —CH₃, —C₂H₅, —CF₃, —CH₂F, —CHF₂, —CH₂CF₃, CF₂CH₃, —CH₂OH, —CF₂OH, —CHFOH; R₂=—(CH₂)$_n$NH₂, —(CH₂)$_n$COOH, —(CH₂)$_n$CONH₂, —(CH₂)$_n$-tetrazolium, —(CH₂)$_n$SO₂NH₂, —(CH₂)$_n$CONHSO₂CH₃, —(CH₂)$_n$CONHSO₂CF₃, —(CH₂)$_n$NHSO₂CH₃, —(CH₂)$_n$SO₂NH₂, —(CH₂)$_n$NHCOCl; —(CH₂)$_n$CONH-aziridine, —(CH₂)$_n$NHCOCH=CH₂, —(CH₂)$_n$CO-epoxide, —(CH₂)$_n$SO₂F, substituted or unsubstituted 2-pyridyl or 3-pyridyl or 4-pyridyl, —(CH₂)$_n$B(OH)₂; R₃ represents mono, di- or tri-substitutions with —F, —Cl, —CH$_3$, —C$_2$H$_5$, —OH, —OCH$_3$, —OCF$_3$; X=C or N; R$_4$ and R$_5$ can independently be —H, —F, —OH, —OCH$_3$, —OCF$_3$, guanidine, —OC$_2$H$_5$; R$_6$=—H, —CH3, —C$_2$H$_5$, —CH(CH$_3$)$_2$, cyclopropyl-, cyclopropyl-CH$_2$—, cyclobutyl-, cyclobutyl-CH$_2$—, cyclopentyl-, cyclopentyl-CH$_2$—, cyclohexyl-, cyclohexyl-CH$_2$, n-butyl, isobutyl, sec-butyl, pentyl, hexyl, phenyl, benzyl (substituted or unsubstituted); n=1, 2, 3, 4, 5.

Embodiment 7-i: according to embodiments of present invention, there are provided compounds having the general structures VII-i, or pharmaceutically acceptable salts thereof, including pro-drug versions:

VII-i

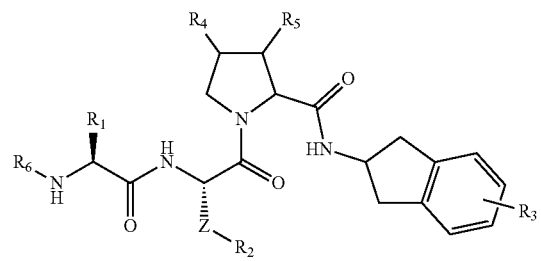

wherein R$_1$ is any of the following: —CH$_3$, —C$_2$H$_5$, —CF$_3$, —CH$_2$F, —CHF$_2$, —CH$_2$CF$_3$, CF$_2$CH$_3$, —CH$_2$OH, —CF$_2$OH, —CHFOH; R$_2$=—(CH$_2$)$_n$NH$_2$, —(CH$_2$)$_n$COOH, —(CH$_2$)$_n$CONH$_2$, —(CH$_2$)$_n$-tetrazolium, —(CH$_2$)$_n$SO$_2$NH$_2$, —(CH$_2$)$_n$CONHSO$_2$CH$_3$, —(CH$_2$)$_n$CONHSO$_2$CF$_3$, —(CH$_2$)$_n$NHSO$_2$CH$_3$, —(CH$_2$)$_n$NHCOCl, —(CH$_2$)$_n$CONH-aziridine, —(CH$_2$)$_n$NHCOCH=CH$_2$, —(CH$_2$)$_n$CO-epoxide, —(CH$_2$)$_n$CO-aziridine, —(CH$_2$)$_n$SO$_2$F, —(CH$_2$)$_n$OSO$_2$F, —(CH$_2$)$_n$NHSO$_2$F, substituted or unsubstituted 2-pyridyl or 3-pyridyl or 4-pyridyl, —(CH$_2$)$_n$B(OH)$_2$, epoxide, aziridine, oxaziridine; R$_3$ represents mono, di- or tri-substitutions with —F, —Cl, —CH$_3$, —C$_2$H$_5$, —OH, —OCH$_3$, —OCF$_3$, —SO$_2$F, —SO$_2$CH=CH$_2$, —NHSO$_2$CH=CH$_2$, —OSO$_2$F, —B(OH)$_2$, —NHSO$_2$F; X=C or N; R$_4$ and R$_5$ can independently be —H, —F, —OH, —OCH$_3$, —OCF$_3$, guanidine, —OC$_2$H$_5$, —SO$_2$F, —SO$_2$CH=CH$_2$, —NHSO$_2$CH=CH$_2$, —OSO$_2$F, —B(OH)$_2$, —NHSO$_2$F; Z=—(CH$_2$)$_n$—, —(CH$_2$)$_n$O—, —(CH$_2$)$_n$NHCO—, —(CH$_2$)$_n$S—, —(CH$_2$)$_n$CONH—, —O(CH$_2$)$_n$—, —(CH$_2$)$_n$NH—, —(CH$_2$)$_n$NHCH$_2$—, —(CH$_2$)$_n$CO—; R$_6$=—H, —CH3, —C$_2$H$_5$, —CH(CH$_3$)$_2$, cyclopropyl-, cyclopropyl-CH$_2$—, cyclobutyl-, cyclobutyl-CH$_2$—, cyclopentyl-, cyclopentyl-CH$_2$—, cyclohexyl-, cyclohexyl-CH$_2$, n-butyl, isobutyl, sec-butyl, pentyl, hexyl, phenyl, benzyl (substituted or unsubstituted); n=1, 2, 3, 4, 5.

Embodiment 8: according to embodiments of present invention, there are provided compounds having the general structures VIII, or pharmaceutically acceptable salts thereof, including pro-drug versions:

VIII

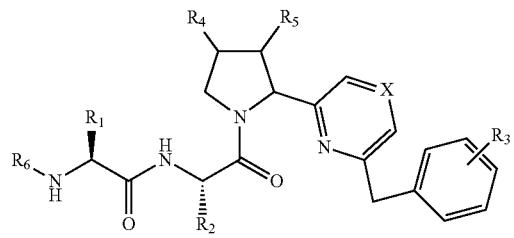

wherein R$_1$ is any of the following: —CH$_3$, —C$_2$H$_5$, —CF$_3$, —CH$_2$F, —CHF$_2$, —CH$_2$CF$_3$, CF$_2$CH$_3$, —CH$_2$OH, —CF$_2$OH, —CHFOH; R$_2$=—(CH$_2$)$_n$NH$_2$, —(CH$_2$)$_n$COOH, —(CH$_2$)$_n$CONH$_2$, —(CH$_2$)$_n$-tetrazolium, —(CH$_2$)$_n$SO$_2$NH$_2$, —(CH$_2$)$_n$CONHSO$_2$CH$_3$, —(CH$_2$)$_n$CONHSO$_2$CF$_3$, —(CH$_2$)$_n$NHSO$_2$CH$_3$, —(CH$_2$)$_n$SO$_2$NH$_2$, —(CH$_2$)$_n$NHCOCl; —(CH$_2$)$_n$CONH-aziridine, —(CH$_2$)$_n$NHCOCH=CH$_2$, —(CH$_2$)$_n$CO-epoxide, —(CH$_2$)$_n$SO$_2$F, substituted or unsubstituted 2-pyridyl or 3-pyridyl or 4-pyridyl, —(CH$_2$)$_n$B(OH)$_2$; R$_3$ represents mono, di- or tri-substitutions with —F, —Cl, —CH$_3$, —C$_2$H$_5$, —OH, —OCH$_3$, —OCF$_3$; X=C or N; R$_4$ and R$_5$ can independently be —H, —F, —OH, —OCH$_3$, —OCF$_3$, guanidine, —OC$_2$H$_5$; R$_6$=—H, —CH3, —C$_2$H$_5$, —CH(CH$_3$)$_2$, cyclopropyl-, cyclopropyl-CH$_2$—, cyclobutyl-, cyclobutyl-CH$_2$—, cyclopentyl-, cyclopentyl-CH$_2$—, cyclohexyl-, cyclohexyl-CH$_2$, n-butyl, isobutyl, sec-butyl, pentyl, hexyl, phenyl, benzyl (substituted or unsubstituted); n=0, 1, 2, 3.

Embodiment 8-i: according to embodiments of present invention, there are provided compounds having the general structures VIII-i, or pharmaceutically acceptable salts thereof, including pro-drug versions:

VIII-i

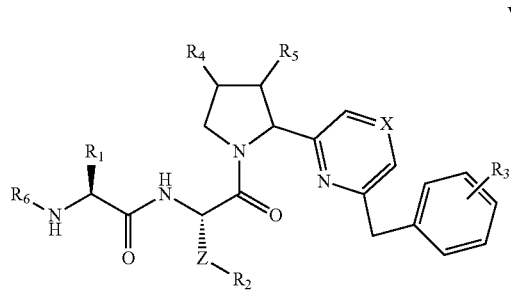

wherein R$_1$ is any of the following: —CH$_3$, —C$_2$H$_5$, —CF$_3$, —CH$_2$F, —CHF$_2$, —CH$_2$CF$_3$, CF$_2$CH$_3$, —CH$_2$OH, —CF$_2$OH, —CHFOH; R$_2$=—(CH$_2$)$_n$NH$_2$, —(CH$_2$)$_n$COOH, —(CH$_2$)$_n$CONH$_2$, —(CH$_2$)$_n$-tetrazolium, —(CH$_2$)$_n$SO$_2$NH$_2$, —(CH$_2$)$_n$CONHSO$_2$CH$_3$, —(CH$_2$)$_n$CONHSO$_2$CF$_3$, —(CH$_2$)$_n$NHSO$_2$CH$_3$, —(CH$_2$)$_n$NHCOCl, —(CH$_2$)$_n$CONH-aziridine, —(CH$_2$)$_n$NHCOCH=CH$_2$, —(CH$_2$)$_n$CO-epoxide, —(CH$_2$)$_n$CO-aziridine, —(CH$_2$)$_n$SO$_2$F, —(CH$_2$)$_n$OSO$_2$F, —(CH$_2$)$_n$NHSO$_2$F, substituted or unsubstituted 2-pyridyl or 3-pyridyl or 4-pyridyl, —(CH$_2$)$_n$B(OH)$_2$, epoxide, aziridine, oxaziridine; R$_3$ represents mono, di- or tri-substitutions with —F, —Cl, —CH$_3$, —C$_2$H$_5$, —OH, —OCH$_3$, —OCF$_3$, —SO$_2$F, —SO$_2$CH=CH$_2$, —NHSO$_2$CH=CH$_2$, —OSO$_2$F, —B(OH)$_2$, —NHSO$_2$F; X=C or N; R$_4$ and R$_5$ can independently be —H, —F, —OH, —OCH$_3$, —OCF$_3$, guanidine, —OC$_2$H$_5$, —SO$_2$F, —SO$_2$CH=CH$_2$, —NHSO$_2$CH=CH$_2$, —OSO$_2$F, —B(OH)$_2$, —NHSO$_2$F;

Z=—(CH$_2$)$_n$—, —(CH$_2$)$_n$O—, —(CH$_2$)$_n$NHCO—, —(CH$_2$)$_n$S—, —(CH$_2$)$_n$CONH—, —O(CH$_2$)$_n$—, —(CH$_2$)$_n$NH—, —(CH$_2$)$_n$NHCH$_2$—, —(CH$_2$)$_n$CO—; R$_6$=—H, —CH3, —C$_2$H$_5$, —CH(CH$_3$)$_2$, cyclopropyl-, cyclopropyl-CH$_2$—, cyclobutyl-, cyclobutyl-CH$_2$—, cyclopentyl-, cyclopentyl-CH$_2$—, cyclohexyl-, cyclohexyl-CH$_2$, n-butyl, isobutyl, sec-butyl, pentyl, hexyl, phenyl, benzyl (substituted or unsubstituted); n=0, 1, 2, 3.

Embodiment 9: according to embodiments of the present invention, there are provided bivalent compounds having the general structure IX, or pharmaceutically acceptable salts thereof, including pro-drug versions: D1-Linker-D2, (IX); wherein D1 and D2 are any of the agents I-VIII and the linker can be any saturated or unsaturated aliphatic, aromatic, or hetero-aromatic, or saturated or unsaturated aliphatic and aromatic, or aliphatic and hetero-aromatic, including ethers, thioethers, amides, amines, esters, carbamates, ureas, sulfonamides, acyl-sulfonamides.

Embodiment 10. A method for inducing apoptosis in cancer cells comprising administering a patient with any suitable formulation or prodrug of any of the compounds from embodiments 1-9, provided as single agent or in combination with any apoptosis induces, including chemotherapy or radiation.

Embodiment 11. The method of embodiment 10 where the chemotherapy is a Bcl-2 family antagonist such as venetoclax or navitoclax.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

VI. ADDITIONAL EMBODIMENTS

Embodiment P1. A compound, or a pharmaceutical salt thereof, or a prodrug thereof, having the formula:

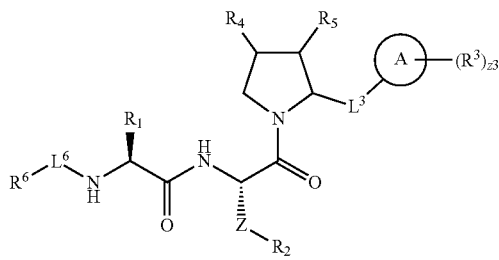

wherein,

R$^1$ is —CX$^1_3$, —CHX$^1_2$, —CH$_2$X$^1$, substituted or unsubstituted C$_1$-C$_4$ alkyl;

L$^2$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^2$ is independently halogen, —CX$^2_3$, —CHX$^2_2$, —CH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^2_3$, —OCHX$^2_2$, —OCH$_2$X$^2$, —SO$_2$CH$_3$, —SO$_2$CX$^2_3$, —SO$_2$CH$_3$, —SO$_2$X$^2$, —B(OH)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^3$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene;

Ring A is a cycloalkyl, heterocycloalkyl, aryl, or heteroaryl;

R$^3$ is independently halogen, —CX$^3_3$, —CHX$^3_2$, —CH$_2$X$^3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^3$ substituents may optionally be joined to form a substituted or unsubstituted cycloalkyl, substituted or unsubstituted heterocycloalkyl, substituted or unsubstituted aryl, or substituted or unsubstituted heteroaryl;

R$^4$ is independently hydrogen, halogen, —CX$^4_3$, —CHX$^4_2$, —CH$_2$X$^4$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^4_3$, —OCHX$^4_2$, —OCH$_2$X$^4$, —NHC(NH)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is independently hydrogen, halogen, —CX$^5_3$, —CHX$^5_2$, —CH$_2$X$^5$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^5_3$, —OCHX$^5_2$, —OCH$_2$X$^5$, —NHC(NH)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^6$ is a bond or unsubstituted methylene;

R$^6$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each X$^1$, X$^2$, X$^3$, X$^4$, and X$^5$ is independently —F, —Cl, —Br, or —I; and z3 is independently an integer from 0 to 3;

wherein the compound is not

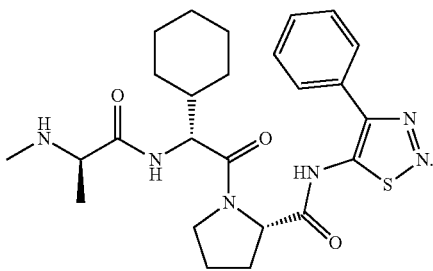 [SMILES: CN[C@H](C)C(=O)N[C@@H](C(=O)N1CCC[C@H]1C(=O)Nc1snnc1-c1ccccc1)C1CCCCC1]

Embodiment P2. The compound, or a pharmaceutical salt thereof, or a prodrug thereof, of embodiment P1, wherein $R^1$ is —CH$_3$, —C$_2$H$_5$, —CF$_3$, —CH$_2$F, —CHF$_2$, —CH$_2$CF$_3$, —CF$_2$CH$_3$, —CH$_2$OH, —CF$_2$OH, or —CHFOH.

Embodiment P3. The compound, or a pharmaceutical salt thereof, or a prodrug thereof, of one of embodiments P1 to P2, wherein $L^2$ is a bond, —NH—, —O—, —S—, —C(O)—, —C(O)NH—, —NHC(O)—, —NHC(O)NH—, —C(O)O—, —OC(O)—, —(CH$_2$)$_{1-5}$—, —(CH$_2$)$_{1-5}$O—, —(CH$_2$)$_{1-5}$NHC(O)—, —(CH$_2$)$_{1-5}$S—, —(CH$_2$)$_{1-5}$C(O)NH—, —O(CH$_2$)$_{1-5}$—, —(CH$_2$)$_{1-5}$NH—, or —(CH$_2$)$_{1-5}$C(O)—.

Embodiment P4. The compound, or a pharmaceutical salt thereof, or a prodrug thereof, of one of embodiments P1 to P2, wherein $L^2$ is a bond, —NH—, —O—, —S—, —C(O)—, —C(O)NH—, —NHC(O)—, —NHC(O)NH—, —C(O)O—, —OC(O)—, —(CH$_2$)$_{1-3}$—, —(CH$_2$)$_{1-3}$O—, —(CH$_2$)$_{1-3}$NHC(O)—, —(CH$_2$)$_{1-3}$S—, —(CH$_2$)$_{1-3}$C(O)NH—, —O(CH$_2$)$_{1-3}$—, —(CH$_2$)$_{1-3}$NH—, or —(CH$_2$)$_{1-3}$C(O)—.

Embodiment P5. The compound, or a pharmaceutical salt thereof, or a prodrug thereof, of one of embodiments P1 to P2, wherein $L^2$ is a bond.

Embodiment P6. The compound, or a pharmaceutical salt thereof, or a prodrug thereof, of one of embodiments P1 to P5, wherein $R^2$ is independently —Cl, —NH$_2$, —COOH, —CONH$_2$, —SO$_2$NH$_2$, —SO$_2$CH$_3$, —SO$_2$CF$_3$, SO$_2$F, —B(OH)$_2$, —CHCH$_2$, unsubstituted tetrazolyl, unsubstituted aziridinyl, unsubstituted oxiranyl, substituted or unsubstituted 2-pyridyl, substituted or unsubstituted 3-pyridyl, substituted or unsubstituted 4-pyridyl,

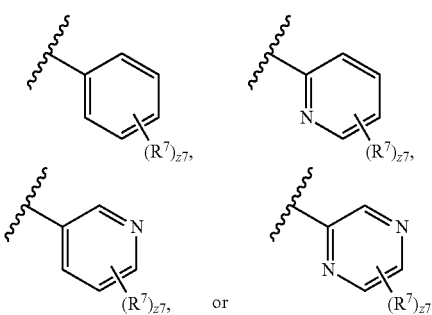

$R^7$ is independently halogen, —CX$^7_3$, —CHX$^7_2$, —CH$_2$X$^7$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^7_3$, —OCHX$^7_2$, —OCH$_2$X$^7$, —NHC(NH)NH$_2$, CH$_2$SO$_3^-$, —PO$_3^{-2}$, —SO$_3^-$, —SO$_2$NH$_2$, —CH$_2$PO$_3^{-2}$, —CH$_2$SO$_2$NH$_2$, —NHC(O)CHCH$_2$, —NHC(O)CH$_2$Cl, —B(OH)$_2$, —SO$_2$F, —SO$_2$CHCH$_2$, —COH, —CO-oxiranyl; —CO-aziridinyl substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $X^7$ is independently —F, —Cl, —Br, or —I; and z7 is an integer from 0 to 3.

Embodiment P7. The compound, or a pharmaceutical salt thereof, or a prodrug thereof, of one of embodiments P1 to P5, wherein $R^2$ is independently —(CH$_2$)$_{1-5}$NH$_2$, —(CH$_2$)$_{1-5}$COOH, —(CH$_2$)$_{1-5}$CONH$_2$, —(CH$_2$)$_{1-5}$-tetrazolium, —(CH$_2$)$_{1-5}$SO$_2$NH$_2$, —(CH$_2$)$_{1-5}$CONHSO$_2$CH$_3$, —(CH$_2$)$_{1-5}$CONHSO$_2$CF$_3$, —(CH$_2$)$_{1-5}$NHSO$_2$CH$_3$, —(CH$_2$)$_{1-5}$SO$_2$NH$_2$, —(CH$_2$)$_{1-5}$NHCOCl, —(CH$_2$)$_{1-5}$CONH-aziridine, —(CH$_2$)$_{1-5}$NHCOCH═CH$_2$, —(CH$_2$)$_{1-5}$CO-epoxide, —(CH$_2$)$_{1-5}$SO$_2$F, substituted or unsubstituted 2-pyridyl, substituted or unsubstituted 3-pyridyl, substituted or unsubstituted 4-pyridyl, or —(CH$_2$)$_{1-5}$B(OH)$_2$.

Embodiment P8. The compound, or a pharmaceutical salt thereof, or a prodrug thereof, of one of embodiments P1 to P5, wherein $R^2$ is independently

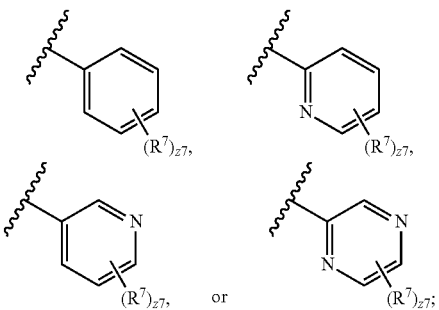

$R^7$ is independently —CH$_2$SO$_3^-$, —PO$_3^{-2}$, —SO$_3^-$, —SO$_2$NH$_2$, —CH$_2$PO$_3^{-2}$, —CH$_2$SO$_2$NH$_2$, —CF$_3$, —Cl, —F, —CH$_3$, —NO$_2$, —C$_2$H$_5$, —OCH$_3$, —OCF$_3$, guanidino, acrylamide, -2-chloroacetamide, —B(OH)$_2$, —SO$_2$F, —SO$_2$CH═CH$_2$, —COH, —CO-epoxide; —CO-aziridine; and
z7 is an integer from 0 to 3.

Embodiment P9. The compound, or a pharmaceutical salt thereof, or a prodrug thereof, of one of embodiments P1 to P8, wherein $L^3$ is a bond, —C(O)NH—, or unsubstituted alkylheteroarylene.

Embodiment P10. The compound, or a pharmaceutical salt thereof, or a prodrug thereof, of one of embodiments P1 to P8, wherein $L^3$ is a bond, —C(O)NH—,

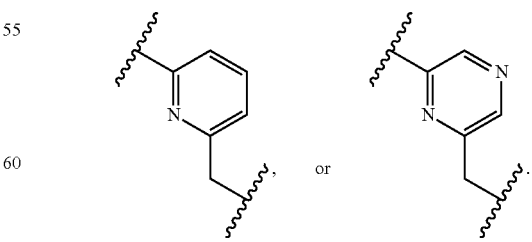

Embodiment P11. The compound, or a pharmaceutical salt thereof, or a prodrug thereof, of one of embodiments P1 to P10, wherein -(Ring A)-(R$^3$)$_{z3}$ is

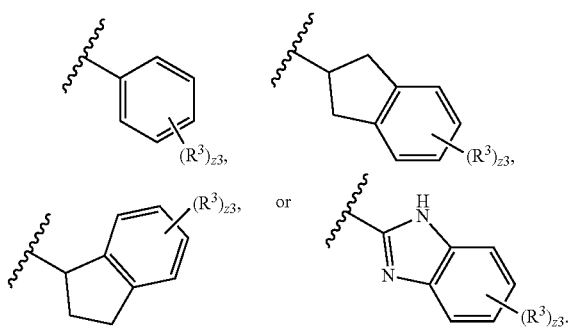

Embodiment P12. The compound, or a pharmaceutical salt thereof, or a prodrug thereof, of one of embodiments P1 to P11, wherein $R^3$ is independently halogen, —$CX^3_3$, —$CHX^3_2$, —$CH_2X^3$, —OH, —$OCX^3_3$, —$OCHX^3_2$, —$OCH_2X^3$, unsubstituted $C_1$-$C_4$ alkyl, or unsubstituted 2 to 3 membered heteroalkyl.

Embodiment P13. The compound, or a pharmaceutical salt thereof, or a prodrug thereof, of one of embodiments P1 to P11, wherein $R^3$ is independently —F, —Cl, —$CH_3$, —$C_2H_5$, —OH, —$OCH_3$, or —$OCF_3$.

Embodiment P14. The compound, or a pharmaceutical salt thereof, or a prodrug thereof, of one of embodiments P1 to P13, wherein $R^4$ is independently hydrogen, —F, —OH, —$OCF_3$, —$OCH_3$, —$OCH_2CH_3$, —$NHC(NH)NH_2$.

Embodiment P15. The compound, or a pharmaceutical salt thereof, or a prodrug thereof, of one of embodiments P1 to P14, wherein $R^5$ is independently hydrogen, —F, —OH, —$OCF_3$, —$OCH_3$, —$OCH_2CH_3$, —$NHC(NH)NH_2$.

Embodiment P16. The compound, or a pharmaceutical salt thereof, or a prodrug thereof, of one of embodiments P1 to P15, wherein $L^6$ is a bond.

Embodiment P17. The compound, or a pharmaceutical salt thereof, or a prodrug thereof, of one of embodiments P1 to P15, wherein $L^6$ is unsubstituted methylene.

Embodiment P18. The compound, or a pharmaceutical salt thereof, or a prodrug thereof, of one of embodiments P1 to P17, wherein $R^6$ is independently hydrogen, substituted or unsubstituted methyl, substituted or unsubstituted ethyl, substituted or unsubstituted isopropyl, substituted or unsubstituted cyclopropyl, substituted or unsubstituted cyclobutyl, substituted or unsubstituted cyclopentyl, substituted or unsubstituted cyclohexyl, substituted or unsubstituted n-butyl, substituted or unsubstituted isobutyl, substituted or unsubstituted sec-butyl, substituted or unsubstituted pentyl, substituted or unsubstituted hexyl, or substituted or unsubstituted phenyl.

Embodiment P19. The compound, or a pharmaceutical salt thereof, or a prodrug thereof, of one of embodiments P1 to P17, wherein $R^6$ is independently hydrogen, unsubstituted methyl, unsubstituted ethyl, unsubstituted isopropyl, unsubstituted cyclopropyl, unsubstituted cyclobutyl, unsubstituted cyclopentyl, unsubstituted cyclohexyl, unsubstituted n-butyl, unsubstituted isobutyl, unsubstituted sec-butyl, unsubstituted pentyl, unsubstituted hexyl, or unsubstituted phenyl.

Embodiment P20. The compound, or a pharmaceutical salt thereof, or a prodrug thereof, of one of embodiments P1 to P17, wherein $R^6$ is independently hydrogen, —$CH_3$, —$C_2H_5$, —$CH(CH_3)_2$, cyclopropyl, cyclopropyl-$CH_2$—, cyclobutyl, cyclobutyl-$CH_2$—, cyclopentyl, cyclopentyl-$CH_2$—, cyclohexyl, cyclohexyl-$CH_2$—, n-butyl, isobutyl, sec-butyl, pentyl, hexyl, phenyl, or substituted or unsubstituted benzyl.

Embodiment P21. The compound, or a pharmaceutical salt thereof, or a prodrug thereof, of one of embodiments P6 to P20, having the formula:

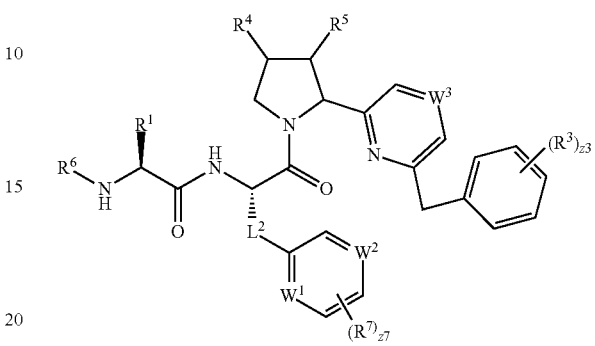

wherein $W^1$, $W^2$, and $W^3$ are independently —CH= or —N=.

Embodiment P22. The compound, or a pharmaceutical salt thereof, or a prodrug thereof, of one of embodiments P6 to P20, having the formula:

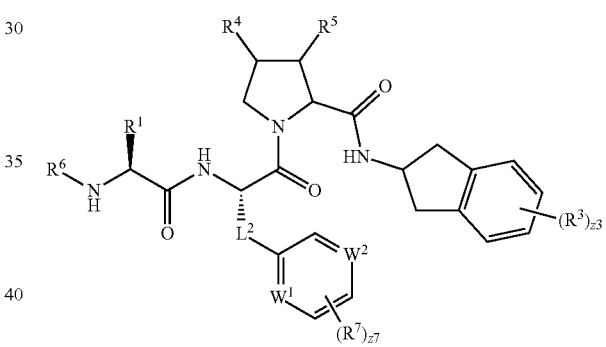

wherein $W^1$, and $W^2$ are independently —CH= or —N=.

Embodiment P23. The compound, or a pharmaceutical salt thereof, or a prodrug thereof, of one of embodiments P6 to P20, having the formula:

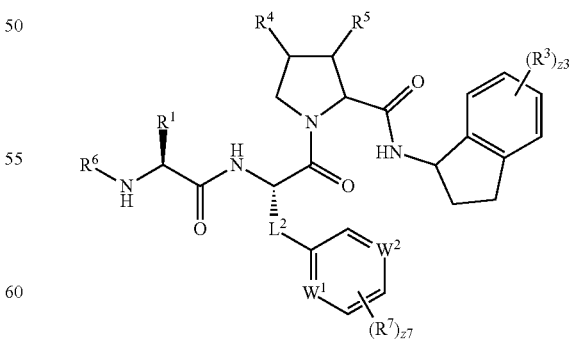

wherein $W^1$, and $W^2$ are independently —CH= or —N=.

Embodiment P24. The compound, or a pharmaceutical salt thereof, or a prodrug thereof, of one of embodiments P6 to P20, having the formula:

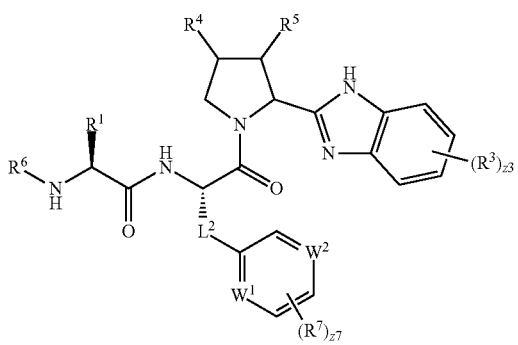

wherein $W^1$, and $W^2$ are independently —CH= or —N=.

Embodiment P25. The compound, or a pharmaceutical salt thereof, or a prodrug thereof, of one of embodiments P1 to P20, having the formula:

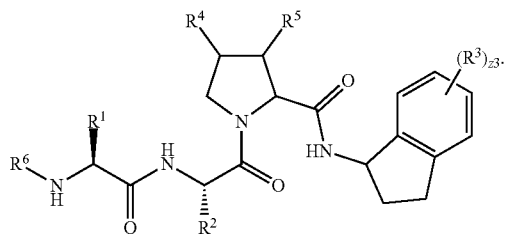

Embodiment P26. The compound, or a pharmaceutical salt thereof, or a prodrug thereof of one of embodiments P1 to P20, having the formula:

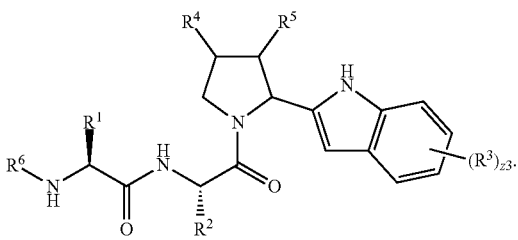

Embodiment P27. The compound, or a pharmaceutical salt thereof, or a prodrug thereof, of one of embodiments P1 to P20, having the formula:

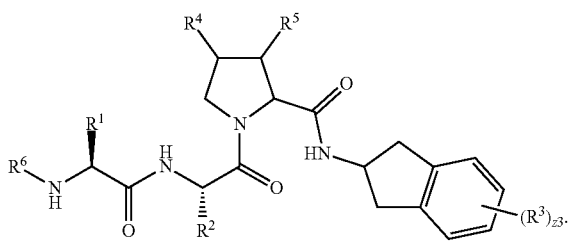

Embodiment P28. The compound, or a pharmaceutical salt thereof, or a prodrug thereof, of one of embodiments P1 to P20, having the formula:

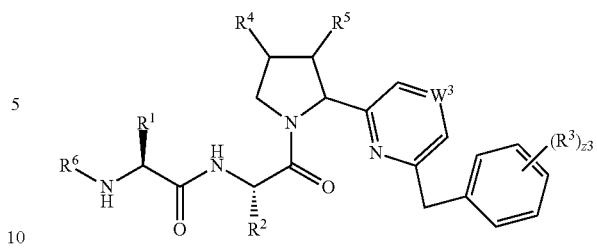

wherein $W^3$ is independently —CH= or —N=.

Embodiment P29. A composition comprising a first moiety of a compound of one of embodiments P1 to P28 and a second moiety of a compound of one of embodiments P1 to P28, wherein said first and second moieties are connected by a divalent linker.

Embodiment P30. The composition of embodiment P29, wherein said linker is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene.

Embodiment P31. The composition of embodiment P29, or pharmaceutical salt thereof or a prodrug thereof, wherein said linker is a bioconjugate linker.

Embodiment P32. The composition of embodiment P29, or pharmaceutical salt thereof or a prodrug thereof, wherein said linker is a divalent saturated or unsaturated aliphatic, aromatic, heteroaromatic, saturated or unsaturated aliphatic and aromatic, saturated or unsaturated aliphatic and heteroaromatic, ether, thioether, amide, amine, ester, carbamate, urea, sulfonamide, or acyl-sulfonamide.

Embodiment P33. A pharmaceutical composition comprising a compound, pharmaceutical salt, or prodrug, of one of embodiments P1 to P32 and a pharmaceutically acceptable excipient.

Embodiment P34. A method of reducing the level of activity of XIAP, cIAP1, and/or cIAP2, said method comprising contacting the XIAP, cIAP1, and/or cIAP2 with a compound, pharmaceutical salt, or prodrug of one of embodiments P1 to P32.

Embodiment P35. A method for treating cancer, said method comprising administering to a subject in need thereof a therapeutically effective amount of a compound, pharmaceutical salt, or prodrug of one of embodiments P1 to P32.

Embodiment P36. A method for increasing apoptosis in a cancer cell, said method comprising administering to a subject in need thereof a therapeutically effective amount of a compound, pharmaceutical salt, or prodrug of a compound of one of embodiments P1 to P28.

Embodiment P37. The method of embodiment P36, further comprising administering to the subject a therapeutically effective amount of a second agent.

Embodiment P38. The method of embodiment P37, wherein said second agent is an apoptosis increasing agent.

Embodiment P39. The method of embodiment P37, wherein said second agent is a Bcl-2 family antagonist.

Embodiment P40. The method of embodiment P39, wherein said Bcl-2 family antagonist is venetoclax or navitoclax.

Embodiment P41. The method of embodiment P36, further comprising administering to the subject a therapeutically effective amount of radiation.

Embodiment P42. A method for inducing apoptosis in a cancer cell, said method comprising administering to a subject in need thereof a therapeutically effective amount of a compound, pharmaceutical salt thereof, or prodrug thereof, of one of embodiments P1 to P28.

Embodiment P43. The method of embodiment P42, further comprising administering to the subject a therapeutically effective amount of a second agent.

Embodiment P44. The method of embodiment P43, wherein said second agent is an apoptosis inducing agent.

Embodiment P45. The method of embodiment P44, wherein second agent is a Bcl-2 family antagonist.

Embodiment P46. The method of embodiment P45, wherein said Bcl-2 family antagonist is venetoclax or navitoclax.

Embodiment P47. The method of embodiment P42, further comprising administering to the subject a therapeutically effective amount of radiation.

Embodiment S1. A compound, or a pharmaceutical salt thereof, or a prodrug thereof, having the formula:

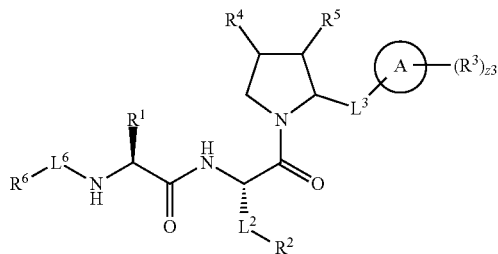

wherein,
$R^1$ is —$CX^1_3$, —$CHX^1_2$, —$CH_2X^1$, substituted or unsubstituted $C_1$-$C_4$ alkyl;
$L^2$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^2$ is independently $R^7$-substituted or unsubstituted aryl, or $R^7$-substituted or unsubstituted heteroaryl;
$L^3$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene;
Ring A is a cycloalkyl, heterocycloalkyl, aryl, or heteroaryl;
$R^3$ is independently halogen, —$CX^3_3$, —$CHX^3_2$, —$CH_2X^3$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^3_3$, —$OCHX^3_2$, —$OCH_2X^3$, —$SO_2X^3$, —$SO_2CH=CH_2$, —$NHSO_2CH=CH_2$, —$OSO_2X^3$, —$NHSO_2X^3$, —B(OH)$_2$, —CO-oxiranyl, —CO-aziridinyl, epoxidinyl, oxaziridinyl, aziridinyl, —$OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl;
$R^4$ is independently hydrogen, halogen, —$CX^4_3$, —$CHX^4_2$, —$CH_2X^4$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^4_3$, —$OCHX^4_2$, —$OCH_2X^4$, —NHC(NH)$NH_2$, —$SO_2X^4$, —$SO_2CH=CH_2$, —$NHSO_2CH=CH_2$, —$OSO_2X^4$, —$NHSO_2X^4$, —B(OH)$_2$, —CO— oxiranyl, —CO-aziridinyl, epoxidinyl, oxaziridinyl, aziridinyl, —$OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is independently hydrogen, halogen, —$CX^5_3$, —$CHX^5_2$, —$CH_2X^5$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^5_3$, —$OCHX^5_2$, —$OCH_2X^5$, —NHC(NH)$NH_2$, —$SO_2X^5$, —$SO_2CH=CH_2$, —$NHSO_2CH=CH_2$, —$OSO_2X^5$, —$NHSO_2X^5$, —B(OH)$_2$, —CO— oxiranyl, —CO-aziridinyl, epoxidinyl, oxaziridinyl, aziridinyl, —$OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^6$ is a bond or unsubstituted methylene;
$R^6$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^7$ is independently halogen, —$CX^7_3$, —$CHX^7_2$, —$CH_2X^7$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^7_3$, —$OCHX^7_2$, —$OCH_2X^7$, —NHC(NH)$NH_2$, —N=C($NH_2$)$_2$, —$CH_2SO_3$, —$PO_3^{-2}$, —$SO_3$, —$SO_2NH_2$, —$CH_2PO_3^{-2}$, —$CH_2SO_2NH_2$, —NHC(O)$CHCH_2$, —NHC(O)$CH_2Cl$, —B(OH)$_2$, —$SO_2X^7$, —$OSO_2X^7$, —$NHSO_2X^7$, —$SO_2CH=CH_2$, —$NHSO_2CH=CH_2$, —CO-oxiranyl, —CO-aziridinyl, epoxidinyl, oxaziridinyl, aziridinyl, —$OCH_2C\equiv CH$, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl;
$R^8$ is independently halogen, —$CX^8_3$, —$CHX^8_2$, —$CH_2X^8$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^8_3$, —$OCHX^8_2$, —$OCH_2X^8$, —NHC(NH)$NH_2$, —N=C($NH_2$)$_2$, —$CH_2SO_3^-$, —$PO_3^{-2}$, —SO—, —$SO_2NH_2$, —$CH_2PO_3^{-2}$, —$CH_2SO_2NH_2$, —NHC(O)$CHCH_2$, —NHC(O)$CH_2Cl$, —B(OH)$_2$, —$SO_2X^8$, —OSO$_2$X$^8$, —NHSO$_2$X$^8$, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, R$^9$-substituted or unsubstituted alkyl, R$^9$-substituted or unsubstituted heteroalkyl, R$^9$-substituted or unsubstituted cycloalkyl, R$^9$-substituted or unsubstituted heterocycloalkyl, R$^9$-substituted or unsubstituted aryl, or R$^9$-substituted or unsubstituted heteroaryl;

R$^9$ is independently halogen, —CX$^9{}_3$, —CHX$^9{}_2$, —CH$_2$X$^9$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^9{}_3$, —OCHX$^9{}_2$, —OCH$_2$X$^9$, —NHC(NH)NH$_2$, —N=C(NH$_2$)$_2$, —CH$_2$SO$_3{}^-$, —PO$_3$-2, —SO—, —SO$_2$NH$_2$, —CH$_2$PO$_3{}^{-2}$, —CH$_2$SO$_2$NH$_2$, —NHC(O)CHCH$_2$, —NHC(O)CH$_2$Cl, —B(OH)$_2$, —SO$_2$X$^9$, —OSO$_2$X$^9$, —NHSO$_2$X$^9$, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, unsubstituted alkyl, unsubstituted heteroalkyl, unsubstituted cycloalkyl, unsubstituted heterocycloalkyl, unsubstituted aryl, or unsubstituted heteroaryl;

each X$^1$, X$^2$, X$^3$, X$^4$, X$^5$, X$^7$, X$^8$, and X$^9$ is independently —F, —Cl, —Br, or —I; and z3 is independently an integer from 0 to 3.

Embodiment S2. The compound, or a pharmaceutical salt thereof, or a prodrug thereof, of embodiment S1, wherein R$^8$ is unsubstituted alkyl, unsubstituted heteroalkyl, unsubstituted cycloalkyl, unsubstituted heterocycloalkyl, unsubstituted aryl, or unsubstituted heteroaryl.

Embodiment S3. The compound, or a pharmaceutical salt thereof, or a prodrug thereof, of one of embodiments S1 to S2, wherein R$^1$ is —CH$_3$, —C$_2$H$_5$, —CF$_3$, —CH$_2$F, —CHF$_2$, —CH$_2$CF$_3$, —CF$_2$CH$_3$, —CH$_2$OH, —CF$_2$OH, or —CHFOH.

Embodiment S4. The compound, or a pharmaceutical salt thereof, or a prodrug thereof, of one of embodiments S1 to S3, wherein L$^2$ is a
bond, —NH—, —O—, —S—, —C(O)—, —C(O)NH—, —NHC(O)—, —NHC(O)NH—, —C(O)O—, —OC(O)—, —(CH$_2$)$_{1-5}$—, —(CH$_2$)$_{1-5}$O—, —(CH$_2$)$_{1-5}$NHC(O)—, —(CH$_2$)$_{1-5}$S—, —(CH$_2$)$_{1-5}$C(O)NH—, —O(CH$_2$)$_{1-5}$—, —(CH$_2$)$_{1-5}$NH—, —(CH$_2$)$_{1-5}$NHCH$_2$—, or —(CH$_2$)$_{1-5}$C(O)—.

Embodiment S5. The compound, or a pharmaceutical salt thereof, or a prodrug thereof, of one of embodiments S1 to S3, wherein L$^2$ is a
bond, —NH—, —O—, —S—, —C(O)—, —C(O)NH—, —NHC(O)—, —NHC(O)NH—, —C(O)O—, —OC(O)—, —(CH$_2$)$_{1-3}$—, —(CH$_2$)$_{1-3}$O—, —(CH$_2$)$_{1-3}$NHC(O)—, —(CH$_2$)$_{1-3}$S—, —(CH$_2$)$_{1-3}$C(O)NH—, —O(CH$_2$)$_{1-3}$—, —(CH$_2$)$_{1-3}$NH—, —(CH$_2$)$_{1-3}$NHCH$_2$—, or —(CH$_2$)$_{1-3}$C(O)—.

Embodiment S6. The compound, or a pharmaceutical salt thereof, or a prodrug thereof, of one of embodiments S1 to S3, wherein L$^2$ is a bond.

Embodiment S7. The compound, or a pharmaceutical salt thereof, or a prodrug thereof, of one of embodiments S1 to S6, wherein R$^2$ is independently unsubstituted tetrazolyl, unsubstituted aziridinyl, unsubstituted oxiranyl, unsubstituted epoxidinyl, R$^7$-substituted or unsubstituted 2-pyridyl, R$^7$-substituted or unsubstituted 3-pyridyl, R$^7$-substituted or unsubstituted 4-pyridyl,

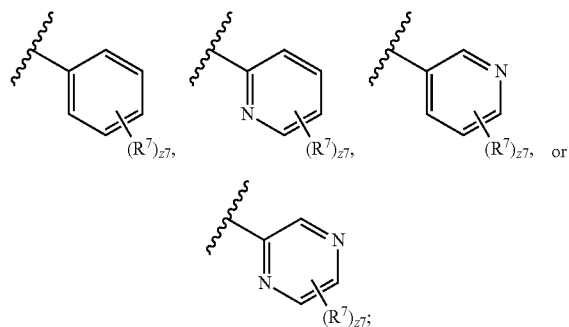

z7 is an integer from 0 to 3

Embodiment S8. The compound, or a pharmaceutical salt thereof, or a prodrug thereof, of one of embodiments S1 to S6, wherein R$^2$ is independently R$^7$-substituted or unsubstituted 2-pyridyl, R$^7$-substituted or unsubstituted 3-pyridyl, or R$^7$-substituted or unsubstituted 4-pyridyl.

Embodiment S9. The compound, or a pharmaceutical salt thereof, or a prodrug thereof, of one of embodiments S1 to S6, wherein R$^2$ is independently

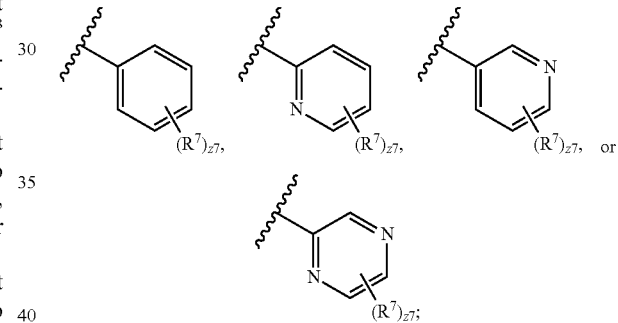

R$^7$ is independently —CH$_2$F, —CH$_2$SO$_3{}^-$, —PO$_3{}^{-2}$, —SO$_3{}^-$, —SO$_2$NH$_2$, —CH$_2$PO$_3{}^{-2}$, —CH$_2$SO$_2$NH$_2$, —CF$_3$, —Cl, —F, —CH$_3$, —NO$_2$, —C$_2$H$_5$, —OCH$_3$, —OCF$_3$, guanidino, acrylamide, -2-chloroacetamide, —B(OH)$_2$, —SO$_2$F, —OSO$_2$F, —NHSO$_2$F, —SO$_2$CH=CH$_2$, —NHSO$_2$CH=CH$_2$, —COH, —CO-epoxide, —CO-aziridine, epoxide, oxaziridine, aziridine, or —OCH$_2$C≡CH; and z7 is an integer from 0 to 3.

Embodiment S10. The compound, or a pharmaceutical salt thereof, or a prodrug thereof, of one of embodiments S1 to S9, wherein L$^3$ is a bond, —C(O)NH—, or unsubstituted alkylheteroarylene.

Embodiment S11. The compound, or a pharmaceutical salt thereof, or a prodrug thereof, of one of embodiments S1 to S9, wherein L$^3$ is a bond, —C(O)NH—, —CH$_2$—

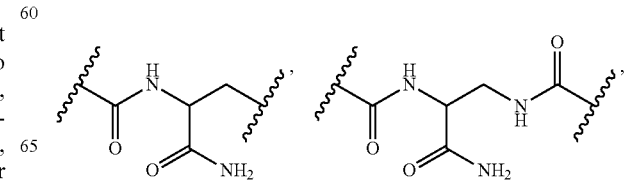

151

-continued

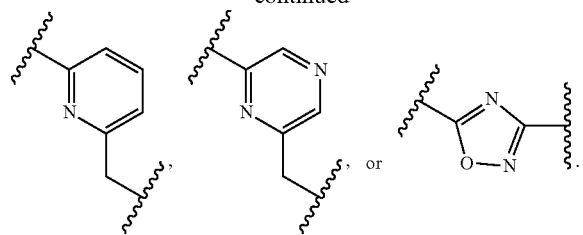

Embodiment S12. The compound, or a pharmaceutical salt thereof, or a prodrug thereof, of one of embodiments S1 to S11, wherein -(Ring A)-$(R^3)_{z3}$ is

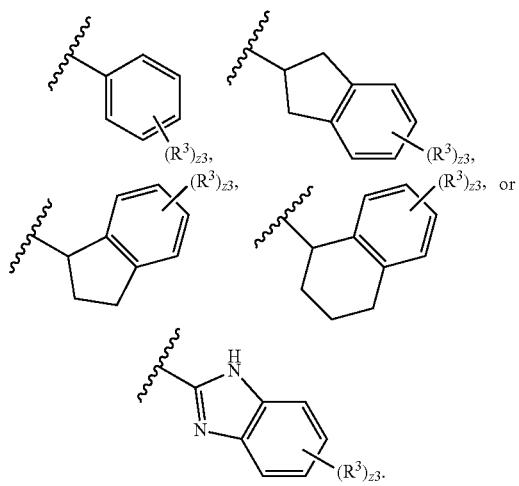

Embodiment S13. The compound, or a pharmaceutical salt thereof, or a prodrug thereof, of one of embodiments S1 to S12, wherein $R^3$ is independently halogen, —$CX^3_3$, —$CHX^3_2$, —$CH_2X^3$, —OH, —$OCX^3_3$, —$OCHX^3_2$, —$OCH_2X^3$, unsubstituted $C_1$-$C_4$ alkyl, or unsubstituted 2 to 3 membered heteroalkyl.

Embodiment S14. The compound, or a pharmaceutical salt thereof, or a prodrug thereof, of one of embodiments S1 to S12, wherein $R^3$ is independently —F, —Cl, —$CH_3$, —$C_2H_5$, —OH, —$OCH_3$, or —$OCF_3$.

Embodiment S15. The compound, or a pharmaceutical salt thereof, or a prodrug thereof, of one of embodiments S1 to S14, wherein $R^4$ is independently hydrogen, —F, —OH, —$OCF_3$, —$OCH_3$, —$OCH_2CH_3$, or —$NHC(NH)NH_2$.

Embodiment S16. The compound, or a pharmaceutical salt thereof, or a prodrug thereof, of one of embodiments S1 to S15, wherein $R^5$ is independently hydrogen, —F, —OH, —$OCF_3$, —$OCH_3$, —$OCH_2CH_3$, or —$NHC(NH)NH_2$.

Embodiment S17. The compound, or a pharmaceutical salt thereof, or a prodrug thereof, of one of embodiments S1 to S16, wherein $L^6$ is a bond.

Embodiment S18. The compound, or a pharmaceutical salt thereof, or a prodrug thereof, of one of embodiments S1 to S16, wherein $L^6$ is unsubstituted methylene.

Embodiment S19. The compound, or a pharmaceutical salt thereof, or a prodrug thereof, of one of embodiments S1 to S18, wherein $R^6$ is independently hydrogen, substituted or unsubstituted methyl, substituted or unsubstituted ethyl, substituted or unsubstituted isopropyl, substituted or unsubstituted cyclopropyl, substituted or unsubstituted cyclobutyl,

152 substituted or unsubstituted cyclopentyl, substituted or unsubstituted cyclohexyl, substituted or unsubstituted n-butyl, substituted or unsubstituted isobutyl, substituted or unsubstituted sec-butyl, substituted or unsubstituted pentyl, substituted or unsubstituted hexyl, or substituted or unsubstituted phenyl.

Embodiment S20. The compound, or a pharmaceutical salt thereof, or a prodrug thereof, of one of embodiments S1 to S18, wherein $R^6$ is independently hydrogen, unsubstituted methyl, unsubstituted ethyl, unsubstituted isopropyl, unsubstituted cyclopropyl, unsubstituted cyclobutyl, unsubstituted cyclopentyl, unsubstituted cyclohexyl, unsubstituted n-butyl, unsubstituted isobutyl, unsubstituted sec-butyl, unsubstituted pentyl, unsubstituted hexyl, or unsubstituted phenyl.

Embodiment S21. The compound, or a pharmaceutical salt thereof, or a prodrug thereof, of one of embodiments S1 to S18, wherein $R^6$ is independently hydrogen, —$CH_3$, —$C_2H_5$, —$CH(CH_3)_2$, cyclopropyl, cyclopropyl-$CH_2$—, cyclobutyl, cyclobutyl-$CH_2$—, cyclopentyl, cyclopentyl-$CH_2$—, cyclohexyl, cyclohexyl-$CH_2$—, n-butyl, isobutyl, sec-butyl, pentyl, hexyl, phenyl, or substituted or unsubstituted benzyl.

Embodiment S22. The compound, or a pharmaceutical salt thereof, or a prodrug thereof, of one of embodiments S1 to S21, having the formula:

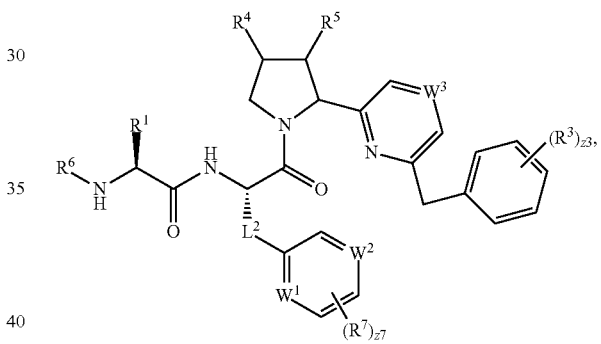

wherein $W^1$, $W^2$, and $W^3$ are independently —CH= or —N=; and z7 is an integer from 0 to 3.

Embodiment S23. The compound, or a pharmaceutical salt thereof, or a prodrug thereof, of one of embodiments S1 to S21, having the formula:

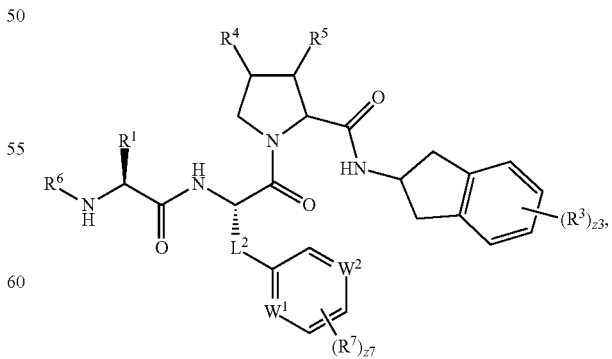

wherein $W^1$ and $W^2$ are independently —CH= or —N=; and z7 is an integer from 0 to 3.

Embodiment S24. The compound, or a pharmaceutical salt thereof, or a prodrug thereof, of one of embodiments S1 to S21, having the formula:

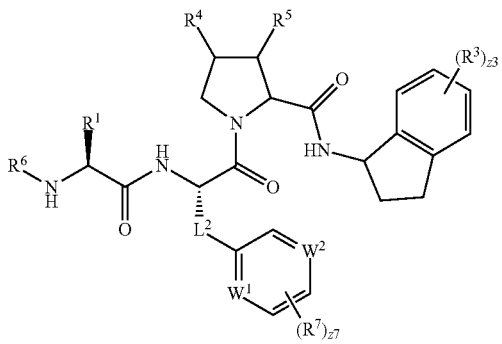

wherein $W^1$ and $W^2$ are independently —CH= or —N=; and
$z7$ is an integer from 0 to 3.

Embodiment S25. The compound, or a pharmaceutical salt thereof, or a prodrug thereof, of one of embodiments S1 to S21, having the formula:

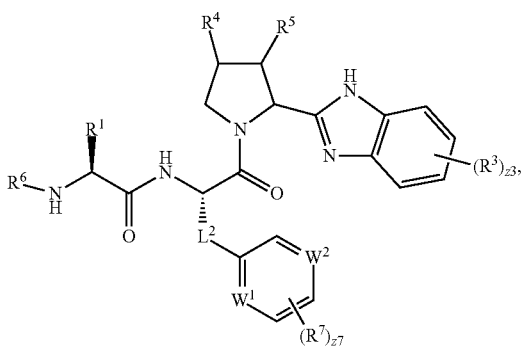

wherein $W^1$ and $W^2$ are independently —CH= or —N=; and
$z7$ is an integer from 0 to 3.

Embodiment S26. The compound, or a pharmaceutical salt thereof, or a prodrug thereof, of one of embodiments S1 to S25, wherein at least one of $R^2$, $R^3$, $R^4$, or $R^5$ comprises a covalent modifier moiety selected from —SO$_2$CH=CH$_2$, —SO$_2$X, —NHSO$_2$CH=CH$_2$, —OSO$_2$X, —B(OH)$_2$, —NHSO$_2$X, or —CH$_2$X; and
X is independently —F, —Cl, —Br, or —I.

Embodiment S27. A compound, or a pharmaceutical salt thereof, or a prodrug thereof, having the formula:

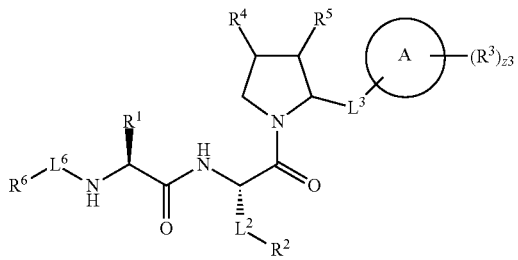

wherein,
$R^1$ is —CX$^1_3$, —CHX$^1_2$, —CH$_2$X$^1$, substituted or unsubstituted C$_1$-C$_4$ alkyl;
$L^2$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^2$ is independently hydrogen, halogen, —CX$^2_3$, —CHX$^2_2$, —CH$_2$X$^2$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^2_3$, —OCHX$^2_2$, —OCH$_2$X$^2$, —SO$_2$CH$_3$, —SO$_2$CX$^2_3$, —SO$_2$CH$_3$, —SO$_2$X$^2$, —SO$_2$CH=CH$_2$, —NHSO$_2$CH=CH$_2$, —OSO$_2$X$^2$, —NHSO$_2$X$^2$, —B(OH)$_2$, —CO-oxiranyl, —CO-aziridinyl, epoxidinyl, oxaziridinyl, aziridinyl, —OCH$_2$C≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^3$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene;
Ring A is a cycloalkyl, heterocycloalkyl, aryl, or heteroaryl;
$R^3$ is independently halogen, —CX$^3_3$, —CHX$^3_2$, —CH$_2$X$^3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^3_3$, —OCHX$^3_2$, —OCH$_2$X$^3$, —SO$_2$CH$_3$, —SO$_2$CX$^3_3$, —SO$_2$CH$_3$, —SO$_2$X$^3$, —SO$_2$CH=CH$_2$, —NHSO$_2$CH=CH$_2$, —OSO$_2$X$^3$, —NHSO$_2$X$^3$, —B(OH)$_2$, —CO-oxiranyl, —CO-aziridinyl, epoxidinyl, oxaziridinyl, aziridinyl, —OCH$_2$C≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl;
$R^4$ is independently hydrogen, halogen, —CX$^4_3$, —CHX$^4_2$, —CH$_2$X$^4$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^4_3$, —OCHX$^4_2$, —OCH$_2$X$^4$, —NHC(NH)NH$_2$, —SO$_2$CH$_3$, —SO$_2$CX$^4_3$, —SO$_2$CH$_3$, —SO$_2$X$^4$, —SO$_2$CH=CH$_2$, —NHSO$_2$CH=CH$_2$, —OSO$_2$X$^4$, —NHSO$_2$X$^4$, —B(OH)$_2$, —CO-oxiranyl, —CO-aziridinyl, epoxidinyl, oxaziridinyl, aziridinyl, —OCH$_2$C≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁵ is independently hydrogen, halogen, —CX⁵₃, —CHX⁵₂, —CH₂X⁵, —CN, —OH, —NH₂, —COH, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCX⁵₃, —OCHX⁵₂, —OCH₂X⁵, —NHC(NH)NH₂, —SO₂CH₃, —SO₂CX⁵₃, —SO₂CH₃, —SO₂X⁵, —SO₂CH=CH₂, —NHSO₂CH=CH₂, —OSO₂X⁵, —NHSO₂X⁵, —B(OH)₂, —CO-oxiranyl, —CO-aziridinyl, epoxidinyl, oxaziridinyl, aziridinyl, —OCH₂C≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; at least one of R², R³, R⁴, or R⁵ comprises a covalent modifier moiety selected from —SO₂CH=CH₂, —SO₂X, —NHSO₂CH=CH₂, —OSO₂X, —B(OH)₂, —NHSO₂X, or CH₂X;

L⁶ is a bond or unsubstituted methylene;

R⁶ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each X¹, X², X³, X⁴, X⁵, and X is independently —F, —Cl, —Br, or —I; and z3 is independently an integer from 0 to 3.

Embodiment S28. A compound, or a pharmaceutical salt thereof, or a prodrug thereof, comprising a first moiety of a compound of one of embodiments S1 to S27 and an optionally different second moiety of a compound of one of embodiments S1 to S27, wherein said first and second moieties are connected by a covalent linker, having the formula:

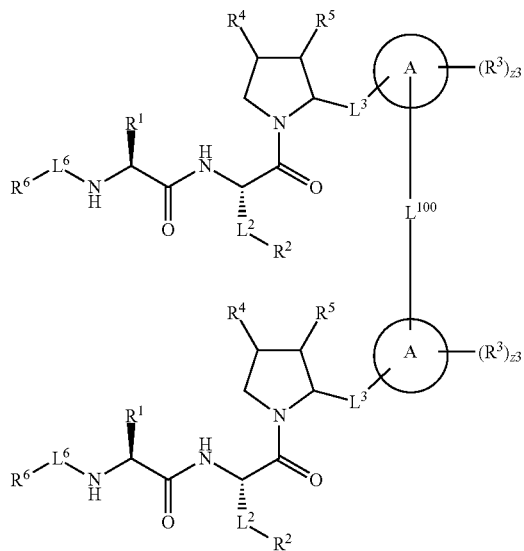

wherein,
L¹⁰⁰ is a covalent linker.

Embodiment S29. The compound of embodiment S28, or a pharmaceutical salt thereof, or a prodrug thereof, wherein L¹⁰⁰ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene.

Embodiment S30. The compound of embodiment S28, or pharmaceutical salt thereof or a prodrug thereof, wherein L¹⁰⁰ is substituted or unsubstituted alkylene, substituted or unsubstituted heteroalkylene.

Embodiment S31. The compound of embodiment S28, or pharmaceutical salt thereof or a prodrug thereof, wherein L¹⁰⁰ is substituted or unsubstituted C₄-C₁₂ alkylene, or substituted or unsubstituted 4 to 12 membered heteroalkylene.

Embodiment S32 A pharmaceutical composition comprising a compound, pharmaceutical salt, or prodrug, of one of embodiments S1 to S31 and a pharmaceutically acceptable excipient.

Embodiment S33. A method of reducing the level of activity of XIAP, cIAP1, and/or cIAP2, said method comprising contacting the XIAP, cIAP1, and/or cIAP2 with a compound, pharmaceutical salt, or prodrug of one of embodiments S1 to S31.

Embodiment S34. A method for treating cancer, said method comprising administering to a subject in need thereof a therapeutically effective amount of a compound, pharmaceutical salt, or prodrug of one of embodiments S1 to S31.

Embodiment S35. The method of embodiment S34, wherein said cancer is pancreatic cancer, Acute lymphoblastic leukemia (ALL), or multiple myeloma.

Embodiment S36. A method for increasing apoptosis in a cancer cell in a subject in need thereof, said method comprising administering to the subject in need thereof a therapeutically effective amount of a compound, pharmaceutical salt, or prodrug of a compound of one of embodiments S1 to S31.

Embodiment S37. The method of one of embodiments S34 to S36, further comprising administering to the subject a therapeutically effective amount of a second agent.

Embodiment S38. The method of embodiment S37, wherein said second agent is an apoptosis increasing agent.

Embodiment S39. The method of embodiment S37, wherein said second agent is a Bcl-2 family antagonist.

Embodiment S40. The method of embodiment S39, wherein said Bcl-2 family antagonist is venetoclax or navitoclax.

Embodiment S41. The method of embodiment S37, wherein said second agent is abraxane or gemcitabine.

Embodiment S42. The method of embodiment S37, wherein said second agent is gemcitabine.

Embodiment S43. The method of one of embodiment S34 to S36, further comprising administering to the subject a therapeutically effective amount of radiation.

Embodiment S44. A method for inducing apoptosis in a cancer cell in a subject in need thereof, said method comprising administering to the subject in need thereof a therapeutically effective amount of a compound, pharmaceutical salt thereof, or prodrug thereof, of one of embodiments S1 to S31.

Embodiment S45. The method of embodiment S44, further comprising administering to the subject a therapeutically effective amount of a second agent.

Embodiment S46. The method of embodiment S45, wherein said second agent is an apoptosis inducing agent.

Embodiment S47. The method of embodiment S46, wherein second agent is a Bcl-2 family antagonist.

Embodiment S48. The method of embodiment S47, wherein said Bcl-2 family antagonist is venetoclax or navitoclax.

Embodiment S49. The method of embodiment S44, further comprising administering to the subject a therapeutically effective amount of radiation.

EXAMPLES

The X-Linked Inhibitor of Apoptosis Protein (XIAP) baculovirus IAP repeat 3 (Bir3) domain inhibit Caspase-9 by directly binding its N-terminal end. This binding results in inhibition of apoptosis or programmed cell death. Other domains of XIAP (Bir2) inhibit other caspases such as caspases 3 and 7, and various XIAP like proteins are present in the cell, such as cIAP1 and cIAP2, Survivin, and ML-IAP, among others. These proteins, while sharing great similarities with XIAP, have additional or distinct functions. A natural antagonist of these anti-apoptotic proteins is the protein SMAC (second mitochondrial activator of caspases), in particular its N-terminal tetrapeptide region (of general sequence AVPI (SEQ ID NO: 4) or AVPF (SEQ ID NO: 5)) is responsible for its activity. Hence, several SMAC-derived peptides as therapeutic compounds have been proposed. Researchers have reported on the discovery of small-molecule XIAP inhibitors by various methods and are summarized in a recent review article, "Small molecule inhibitor of apoptosis proteins antagonists: a patent review" by Hird et al. and have broad spectrum activity, with some exceptions, or are agents that are allegedly selective for the Bir2 of XIAP. No XIAP Bir3 selective agents have been explicitly reported to our knowledge. Disclosed herein are compounds which have different functionalities in various positions of the molecule, and are anticipated to be potent and selective. Hence, described herein are novel compositions and methods of use of these agents for innovative anti-cancer therapies targeting broadly or selectively the Bir3 or Bir2 domains of the proteins XIAP, cIAP1, and/or cIAP2. In some embodiments, potent and selective XIAP Bir3 antagonists can be further obtained by placing an electrophile in the $R^2$ or $R^7$ substituent of molecules as described herein (e.g., of general structures I-VIII) (e.g., $-CH_2SO_3^-$, $-PO_3^{-2}$, $-SO_3$, $-SO_2NH_2$, $-CH_2PO_3^{-2}$, $-CH_2SO_2NH_2$, $-CF_3$, $-Cl$, $-F$, $-CH_3$, $-NO_2$, $-C_2H_5$, $-OCH_3$, $-OCF_3$, guanidino, acrylamide, -2-chloroacetamide, $-B(OH)_2$, $-SO_2F$, $-SO_2CH=CH_2$, $-COH$, $-CO$-epoxide, $-CO$-aziridine), resulting in compounds that covalently could interact with unique residues on the surface of the targets. In some embodiments, potent and dual selective XIAP and cIAP1 Bir3 antagonists can be obtained. In addition, in some embodiments, potent and selective XIAP Bir2 antagonists can be obtained that do not target the Bir3 domains from other proteins of the family including XIAP or cIAP1 and cIAP3. In some other embodiments, novel pan-Bir3 active compounds are obtained. Provided herein are means to obtain potent bi-valent agents that would target Bir3 and Bir2 of XIAP and of other members of the protein families including cIAP1 and cIAP2.

Example 1: XIAP BIR3 Selective Compounds

Described herein are compounds 139H3 and 139H2 which are XIAP Bir3 selective, as shown in FIG. 1. Pan active compound GDG-0152 is showed as reference, obtained from MedChem Express. In a DELFIA displacement assay, the compounds are potent in displacing a biotin-labeled AVPF (SEQ ID NO: 5) reference peptide from the Bir3 domains of XIAP, cIAP1, and cIAP2, with $IC_{50}$ values of approximately 25 nM, 12 nM, and 19 nM, respectively. On the contrary, agents 139H3 and 139H2, while still active against the Bir3 domain of XIAP, with $IC_{50}$ values of 194 and 228 nM, respectively, are much less active against the Bir3 domains of cIAP1 and cIAP2.

Compounds 139H3 and 139H2 bind to the Bir3 domain of XIAP with increased enthalpy compared to other pan XIAP inhibitors. Pan active compounds such as GDG-0152, bind with limited enthalpy of binding, usually around 3-5 kCal/mol only. Selective agents 139H2 and 139H3, were designed to display an increased enthalpy of binding that translates in increased selectivity for this target. In the example, GDG-0152 ΔH~−5.2 kcal/mol, Kd=95 nM; 139H3 (middle panel) ΔH~−8.5 kcal/mol, Kd=780 nM; 139H2 (right panel) ΔH~5.8 kcal/mol, Kd=330 nM.

Compound 139H4 targets the Bir3 domains of XIAP and cIAP1, but are not cIAP2 selective. The chemical structure of compound 139H4 is reported together with DELFIA displacement values for the 3 targets. In addition, ITC data relative to the binding of 139H4 to the Bir3 of XIAP is reported.

Compound 139H9 targets all the Bir3 domains of XIAP, cIAP1 and cIAP2 The chemical structure of compound 139H9 is reported in FIG. 5 together with DELFIA displacement values for the 3 targets. In addition, ITC data relative to the binding of 139H9 to the Bir3 of XIAP is reported (Kd~100 nM).

Figure 2:
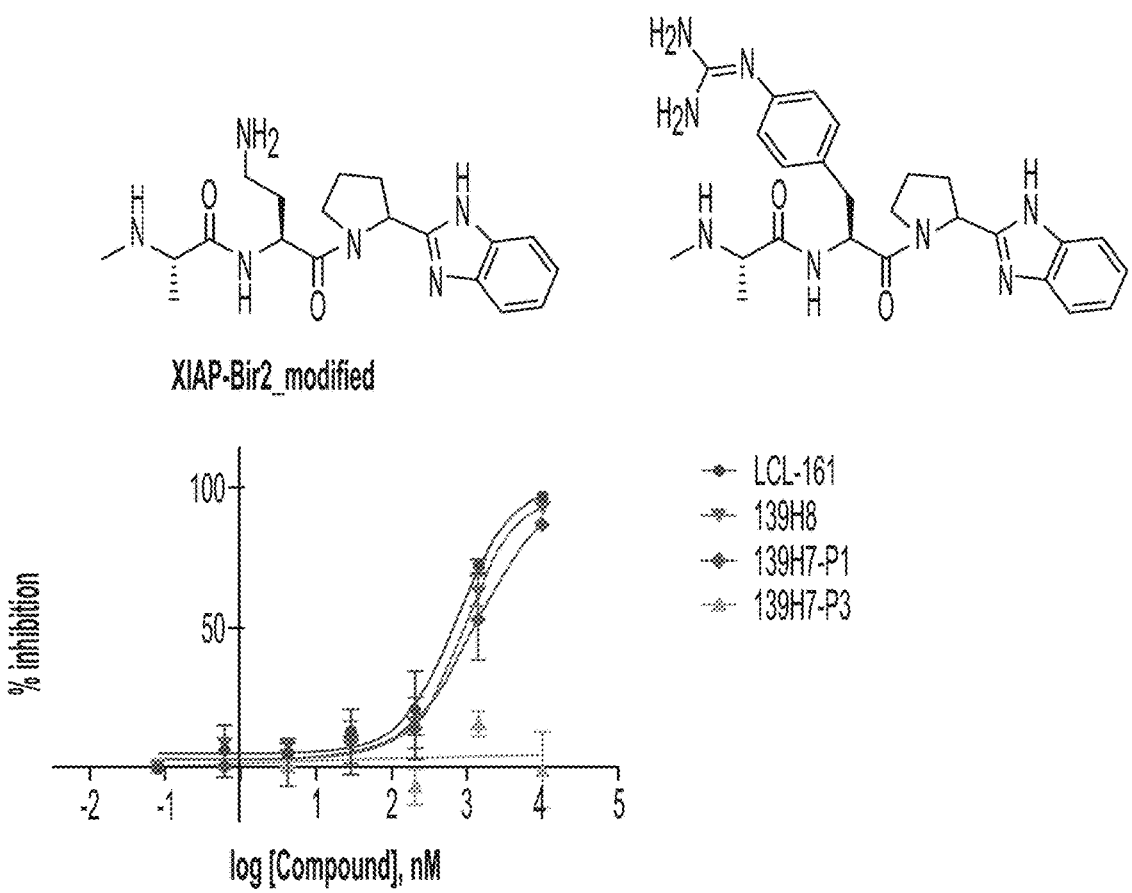
FIG. 2. Compounds 139H8 and 139H7 target the Bir2 domain of XIAP. The chemical structure of compounds 139H7 (top left) and 139H8 (top right) are reported together with DELFIA displacement values against the Bir2 domain of XIAP. As a reference, data relative to the Novartis compound LCL-161 is reported. $IC_{50}$ values for all 3 compounds is about 1 μM. 138H7-P3 is an enantiomer of 139H7 (P1), and it is shown as negative control. However, unlike LCL-161, the agents are not active against the Bir3 domains. LCL-161 $IC_{50}$ values for Bir3 domains of XIAP, cIAP1, and cIAP2 are 53 nM, 10 nM, and 13 nM, respectively. $IC_{50}$ values for these Bir3 domains for 139H8 and 139H8 are generally >5000 nM and >10000 nM, respectively.
Figure 3A:
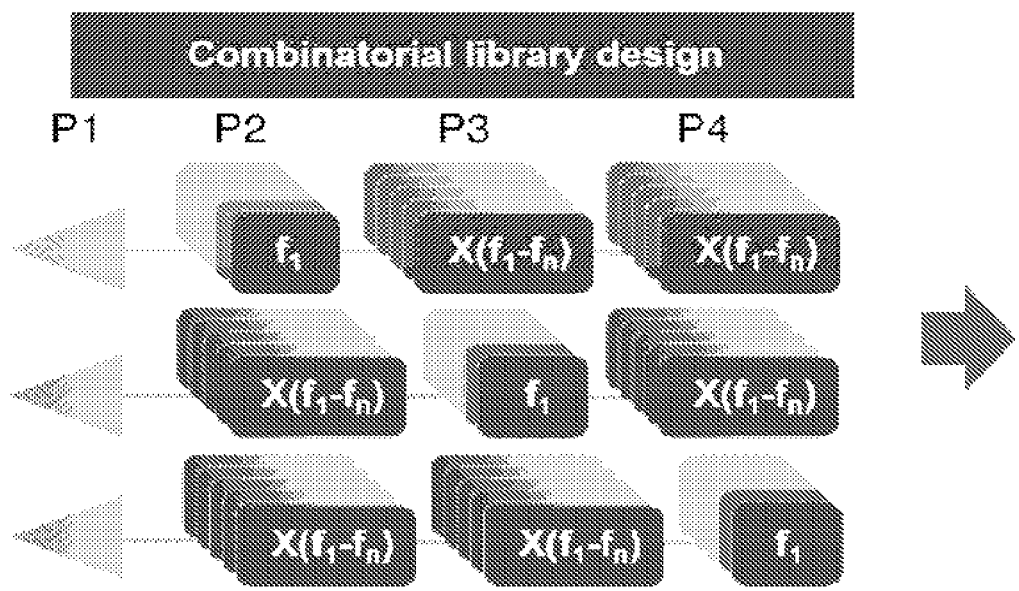
FIGS. 3A-3D. Schematic representation of the HTS by ΔH approach.
Figure 3B:
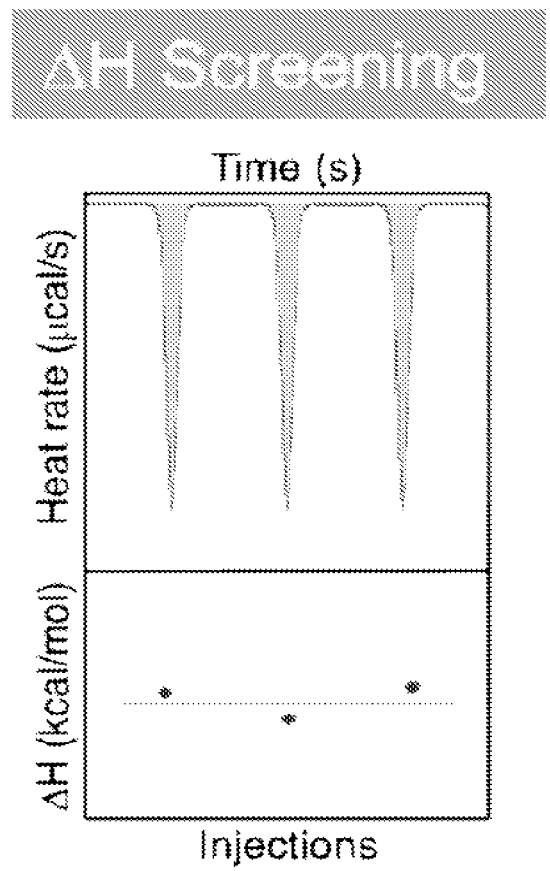
Figure 3C:
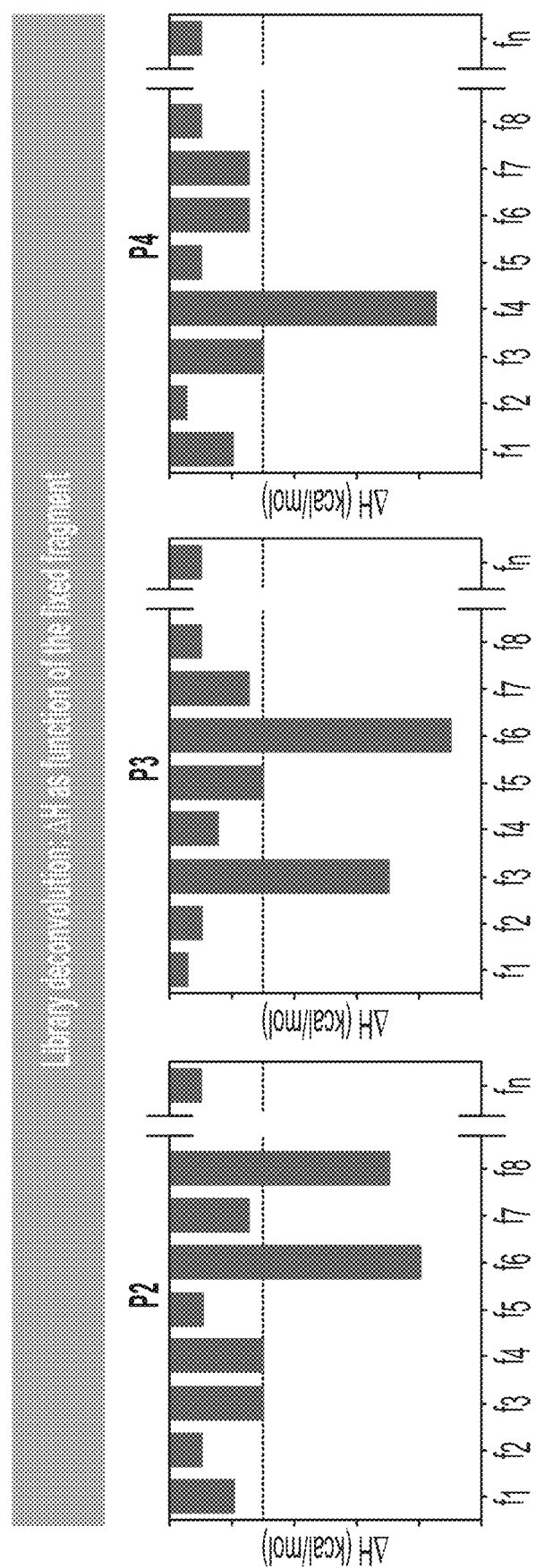
Figure 3D:
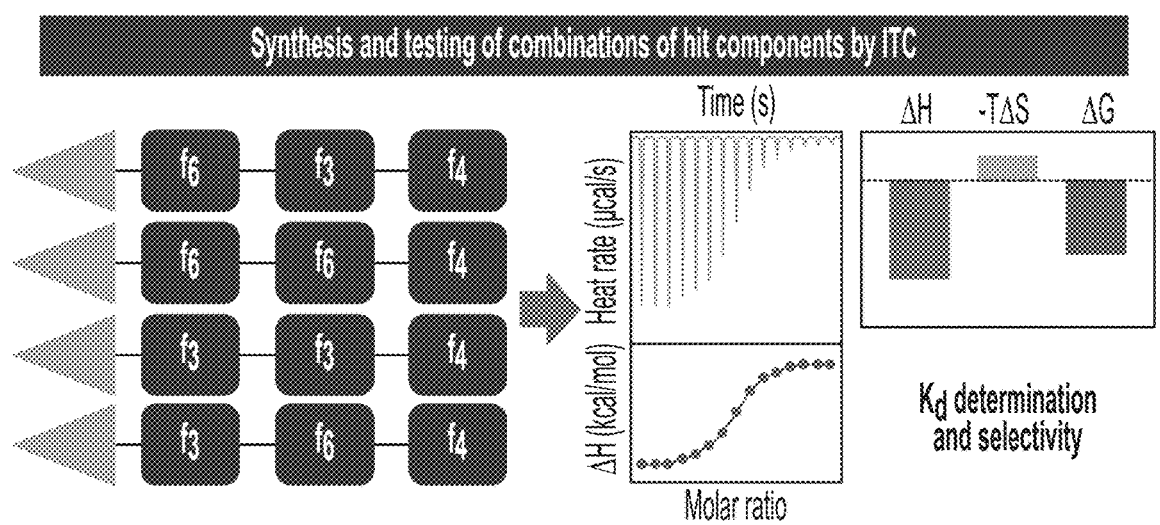
Figure 4A:
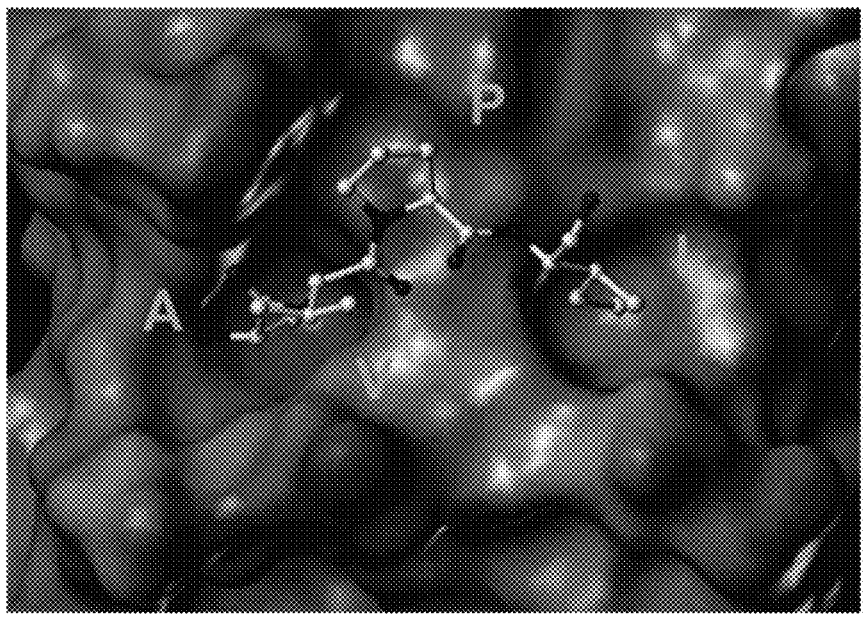
FIGS. 4A-4D. Identification of the BIR3 consensus binding motif using the HTS by ΔH approach.
Figure 4B:
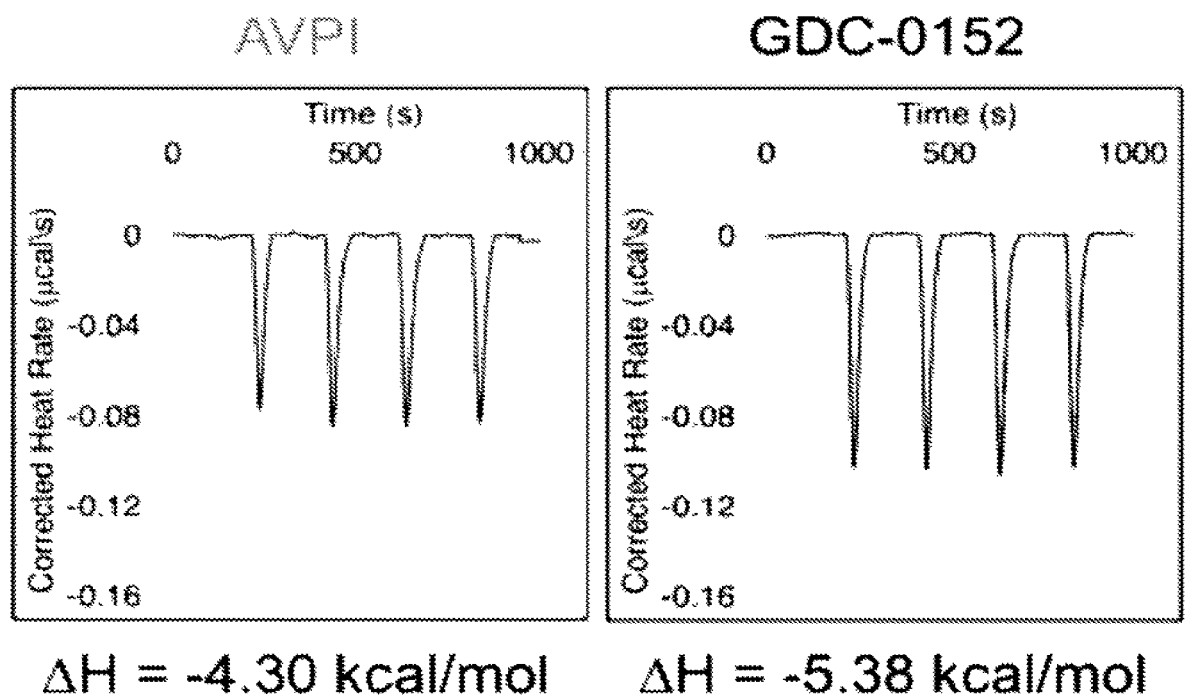
Figure 4C:
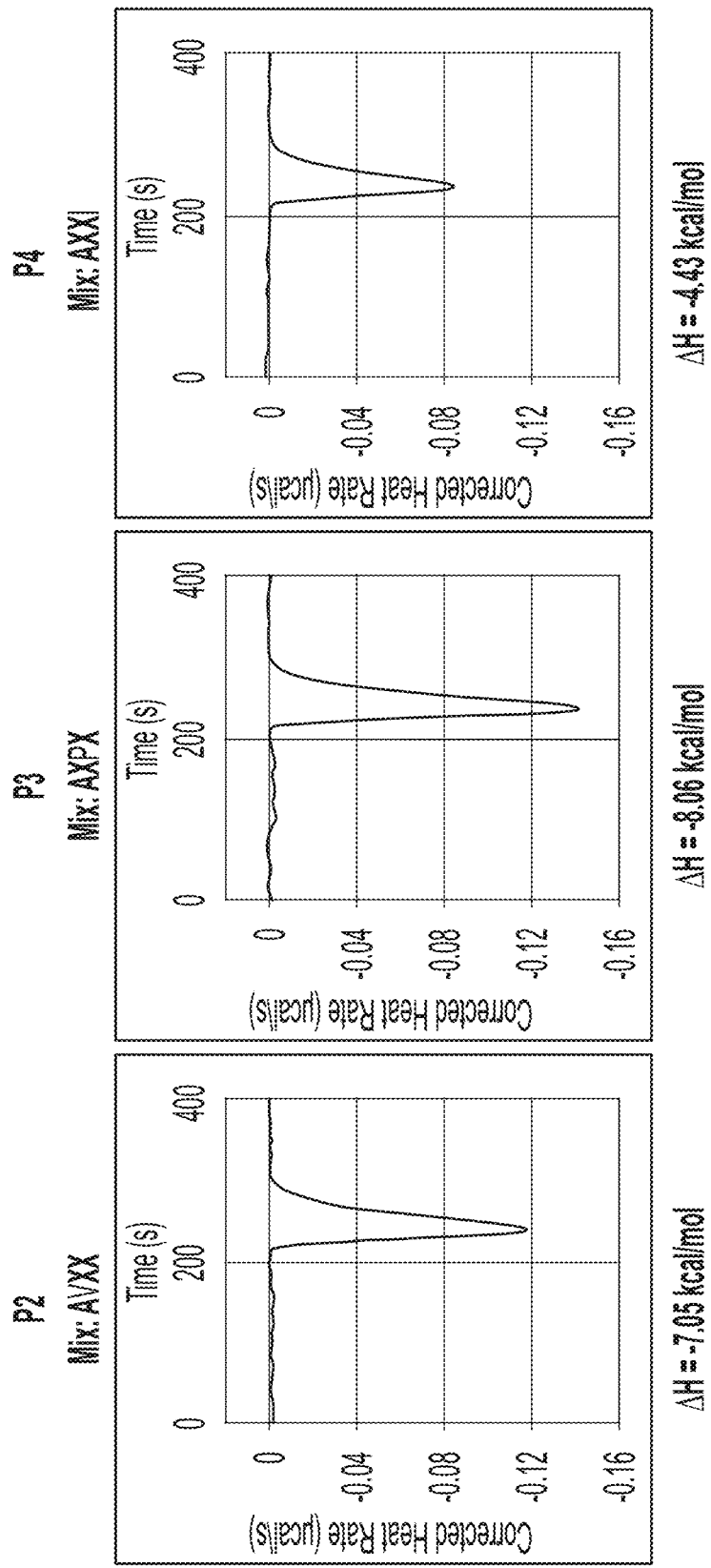
Figure 4D:
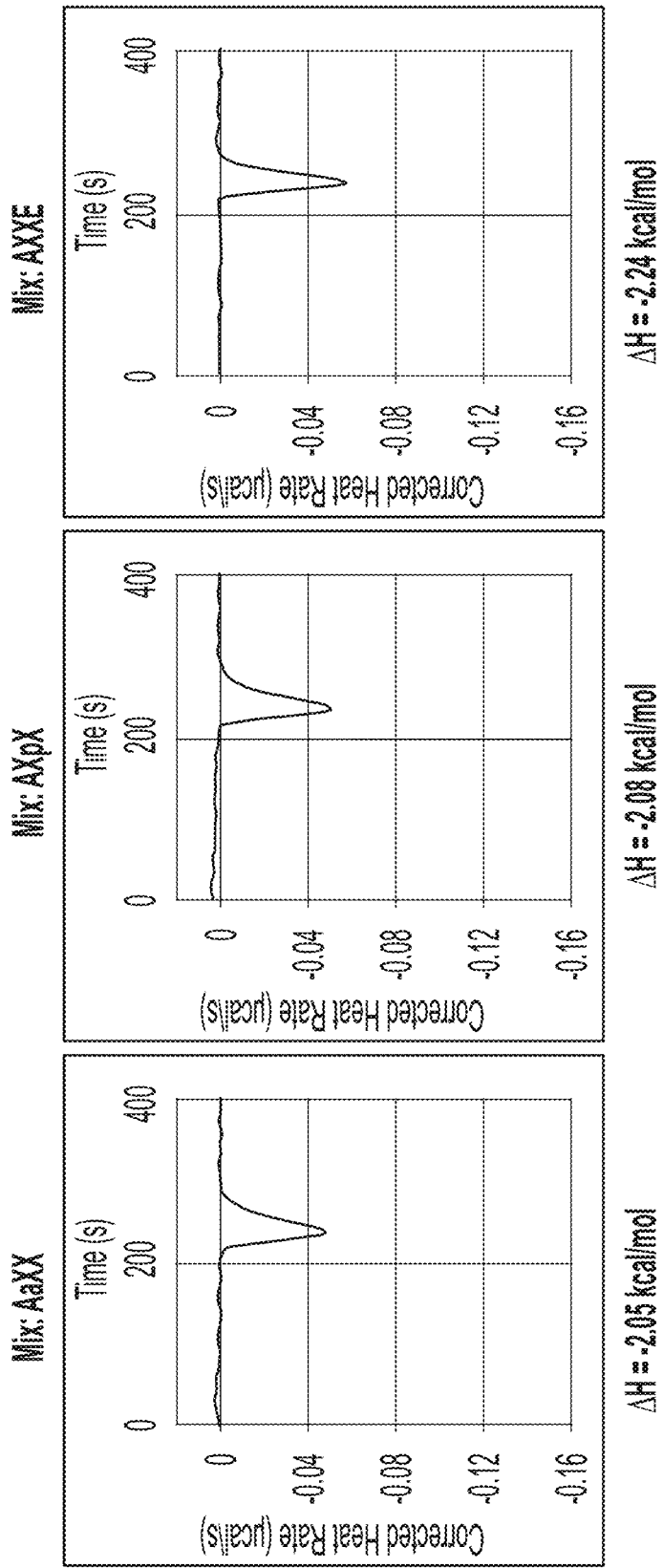
Figure 5A:
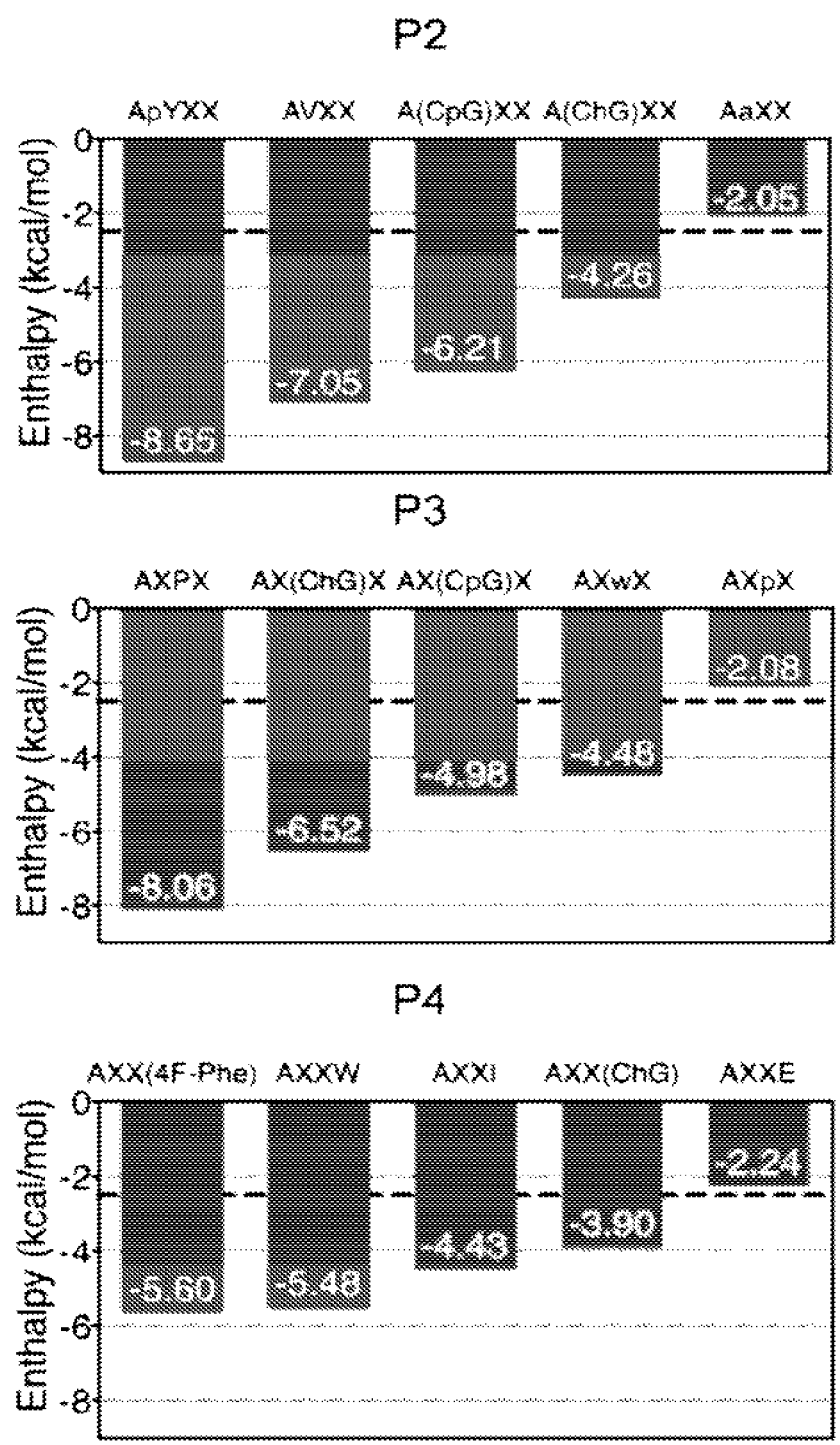
FIGS. 5A-5C. Library deconvolution and identification of the novel XIAP-BIR3-binding agent Ala(pY)Pro(4F-Phe) (SEQ ID NO: 6).
Figure 5B:
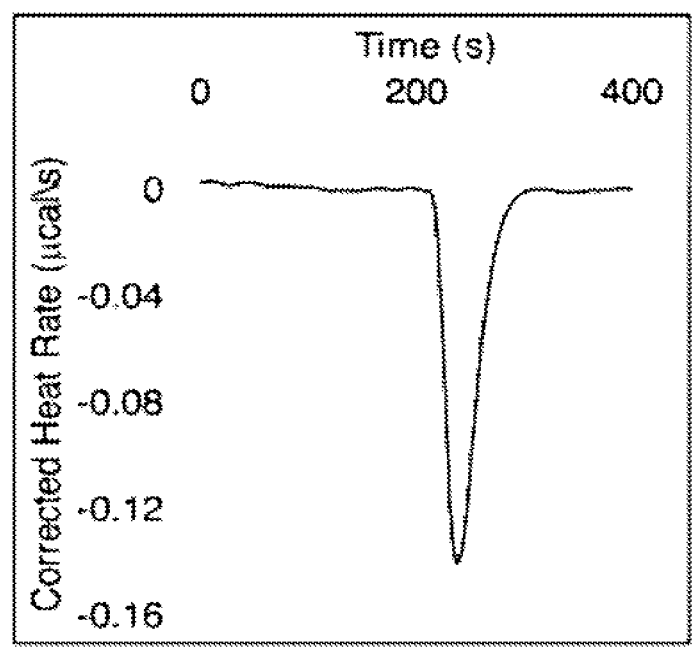
Figure 5B:
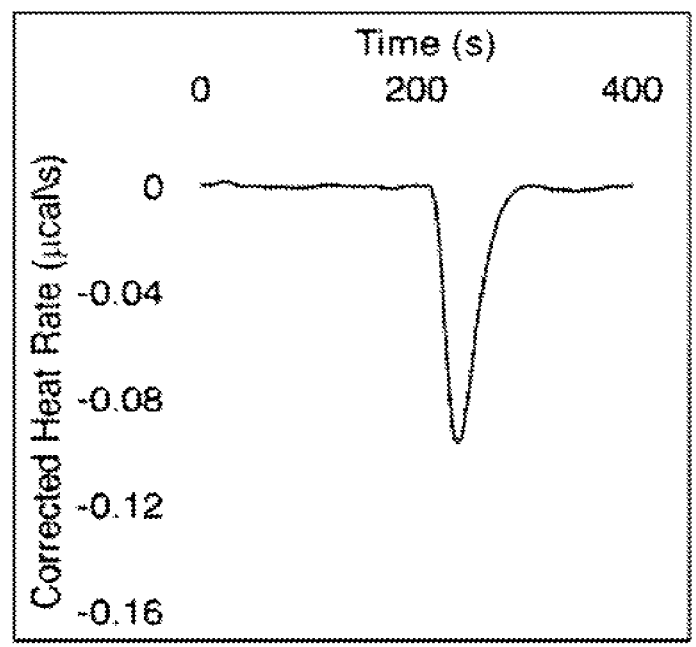
Figure 5C:
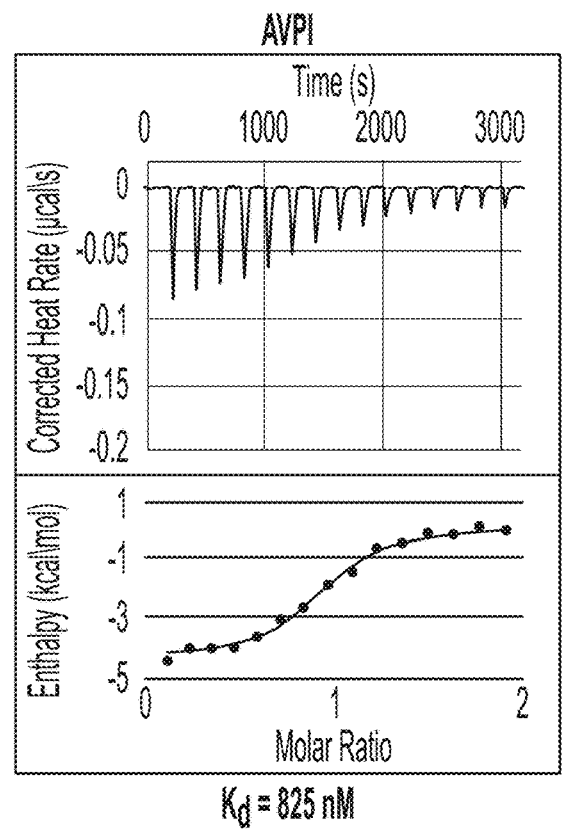
Figure 5C:
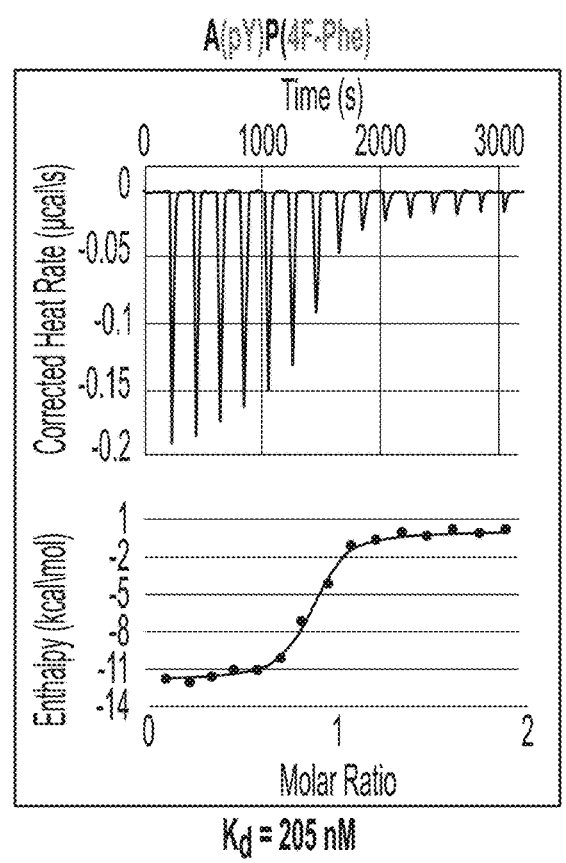

Compounds 139H8 and 139H7 target the Bir2 domain of XIAP. The chemical structure of compounds 139H7 (top left of FIG. 2) and 139H8 (top right of FIG. 2) are reported together with DELFIA displacement values against the Bir2 domain of XIAP. As a reference, data relative to the Novartis compound LCL-161 is reported. $IC_{50}$ values for all 3 compounds is about 1 μM. 138H7-P3 is an enantiomer of 139H7 (P1), and it is shown as negative control. However, unlike LCL-161, the agents are not active against the Bir3 domains. LCL-161 $IC_{50}$ values for Bir3 domains of XIAP, cIAP1, and cIAP2 are 53 nM, 10 nM, and 13 nM, respectively. $IC_{50}$ values for these Bir3 domains for 139H8 and 139H8 are generally >5000 nM and >10000 nM, respectively.

Example 2: Design of Potent Pan-IAP and Lys-Covalent XIAP Selective Inhibitors Using a Thermodynamics Driven Approach Recently we reported that rapid determination of enthalpy of binding can be achieved for a large number of congeneric agents or in combinatorial libraries, fairly efficiently. We show that using a Thermodynamic Craig plot can be very useful in dissecting the enthalpy and entropy contribution of different substituents on a common scaffold, in order to design potent, selective or pan-active compounds. In our implementation, the approach identified a critical Lys residue in the BIR3 domain of XIAP. We report for the first time that it is possible to target such residue covalently to attain potent and selective agents. Preliminary cellular studies in various models of leukemia, multiple myeloma and pancreatic cancers, suggest that the derived agents possess a potentially intriguing pattern of activity, especially for cell lines that are resistant to the pan-IAP antagonist and clinical candidate LCL161.

Apoptosis or programmed cell death is a natural cellular process designed to eliminate unwanted or damaged cells in the body. In healthy tissues, a well-regulated balance exists between pro- and anti-apoptotic proteins that work together to control the occurrence of this natural process. However, an imbalance in the expression of anti-apoptotic proteins can result in defective apoptosis. This phenomenon can in turn can lead to tumorigenesis with concomitant resistance of cancer cells to chemotherapy, radiotherapy, or even immunotherapy, given that these therapeutic strategies are aimed at inducing apoptosis. A common consequence of activating the pro-apoptotic cascade is the final activation of a class of cysteine proteases (caspases) that digest the cellular content. Critical regulators of apoptosis are the Inhibitors of Apoptosis Proteins (IAPs) (1,2). To date, eight members of this protein family have been identified and among these, the X-linked IAP (XIAP) has been shown to prevent apoptosis by directly binding to caspases. Structurally, XIAP contains three baculovirus IAP repeat (BIR) domains, and it has been shown that the third BIR domain (BIR3) potently binds to and inhibits caspase-9, while the second BIR domain (BIR2) and the linker between BIR1 and BIR2, potently inhibit the effector caspases: caspase-3 and caspase-7 (3). In addition to XIAP, two other members of the family, namely cellular IAP1 (cIAP1) and cellular IAP2 (cIAP2), have been shown to interact with tumor necrosis factor receptor-associated factor 2 (TRAF2), and the resulting complex reportedly antagonizes the activation of caspase-8, hence, inhibiting TNF receptor-mediated apoptosis (4-7). Due to their ability to prevent caspase activation and inhibit apoptosis, it is not surprising that XIAP, cIAP1 and cIAP2 are overexpressed in many tumor cell lines and human tumor tissues, conferring a poor prognosis to anticancer treatments (8-12). These observations inspired a fervid drug hunt for possible effective inhibitors of these proteins (13-17). As mentioned above, apoptosis is a tightly regulated process, and in normal cells a natural IAP inhibitor, second mitochondria-derived activator of caspases (SMAC) has been identified. SMAC is a mitochondrial protein that when released into the cytosol following pro-apoptotic signals binds potently to both cIAP1/2 and XIAP, thus counteracting their anti-apoptotic activity (18-20). Proteolytic SMAC activation after mitochondrial release into the cytosol exposes an N-terminal tetrapeptide of sequence Ala-Val-Pro-Ile (AVPI (SEQ ID NO: 4)) that mediates its interactions with XIAP, cIAP1 and cIAP2. In particular, dimeric SMAC binds to both the BIR2 and BIR3 domains of XIAP, hence, antagonizing the binding of XIAP to both caspase-9 and caspase-3/7 (21-23). On the contrary, in cIAP1 and cIAP2, SMAC AVPI (SEQ ID NO: 4) N-terminal peptide binds potently only to their BIR3 domain.[5] On these premises, agents that could mimic SMAC AVPI peptide (SEQ ID NO: 4) could serve as potential new therapeutic agents to restore apoptosis in tumors that are driven by XIAP and/or cIAP1/2 expression (24-45). Most SMAC mimetics reported to date are either pan-IAP antagonists, which means they potently inhibit XIAP, cIAP1 and cIAP2 (23-26,28,30-43), while only few examples exist for compounds that are selective for cIAP1 or cIAP1/2 (30). To date, several pan-IAP inhibitors have been shown to work as single agents in cellular and animal models (6,19,26, 36) and few have advanced (7,20,27,37) into clinical trials (4,24,26, 27, 42). Mechanistically, however, AVPI (SEQ ID NO: 4) mimetics act quite distinctly depending on the cell lines and on the given agent's relative affinity for XIAP versus cIAP1 or cIAP2, and the benefits of antagonizing one versus all members of the family remain to date an unsolved matter (30,46). With the exception of a moderately selective XIAP BIR2 domain antagonist (47), no potent and selective agents have been reported that target XIAP alone. In our recent studies we reported that using a thermodynamic driven screening approach, small variations on the surface of BIR3 domains of XIAP, cIAP1, and cIAP2 could be potentially targeted to achieve such agents (48). Here we report detailed thermodynamic driven structure-activity relationship studies that led to innovative agents that target reversibly or covalently the BIR3 domain of XIAP. First, we demonstrated that careful considerations of enthalpy and entropy of binding can be used to derive potent and either pan-active or selective compounds. In addition, we demonstrated that selective covalent XIAP antagonists can be obtained by carefully targeting a unique Lys residue on its surface. Hence, not only the agents reported should help decipher the relative potential of XIAP versus cIAP1/2 as clinical targets, but open the way to the design of covalent inhibitors targeting binding site Lys residues. Finally, our studies demonstrated that a determination of thermodynamic parameters of binding can be successfully employed to analyze structure-activity relationships and to provide a general avenue to guide the lengthy and often unpredictable hit-to-lead optimization process.

Figure 7B:
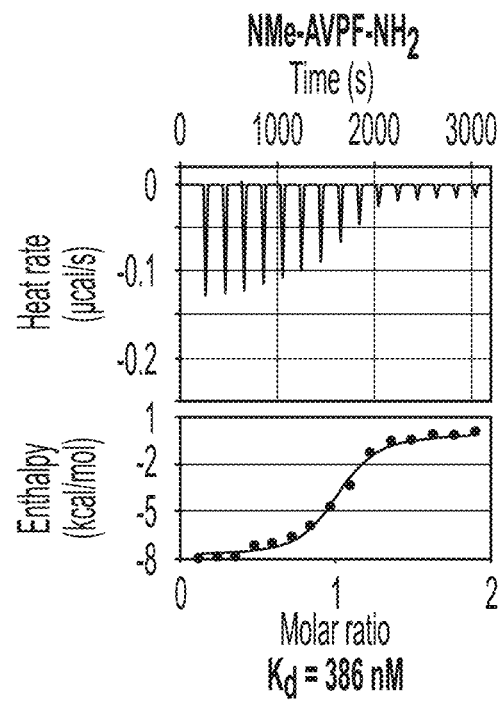
Figure 7C:
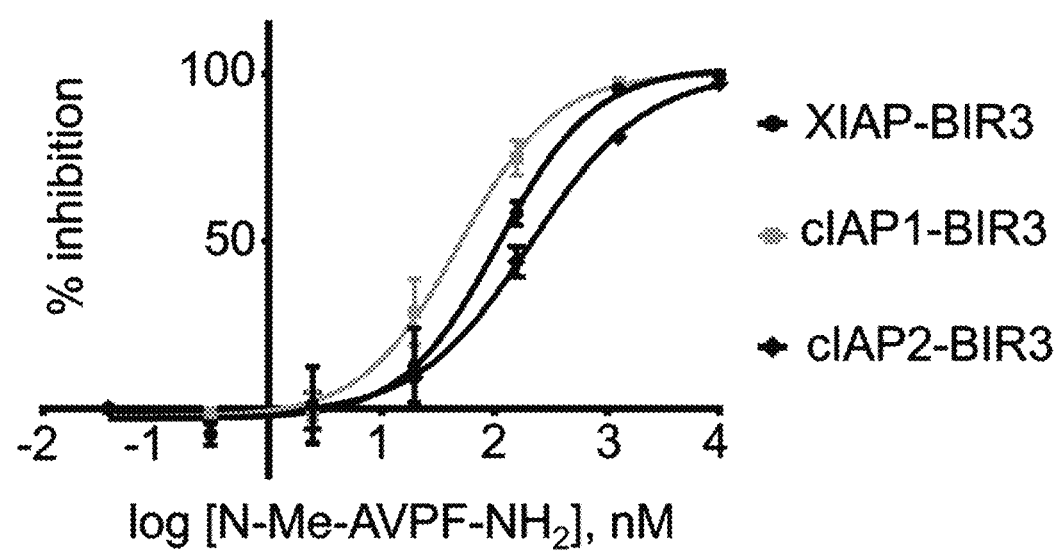
Figure 7D:
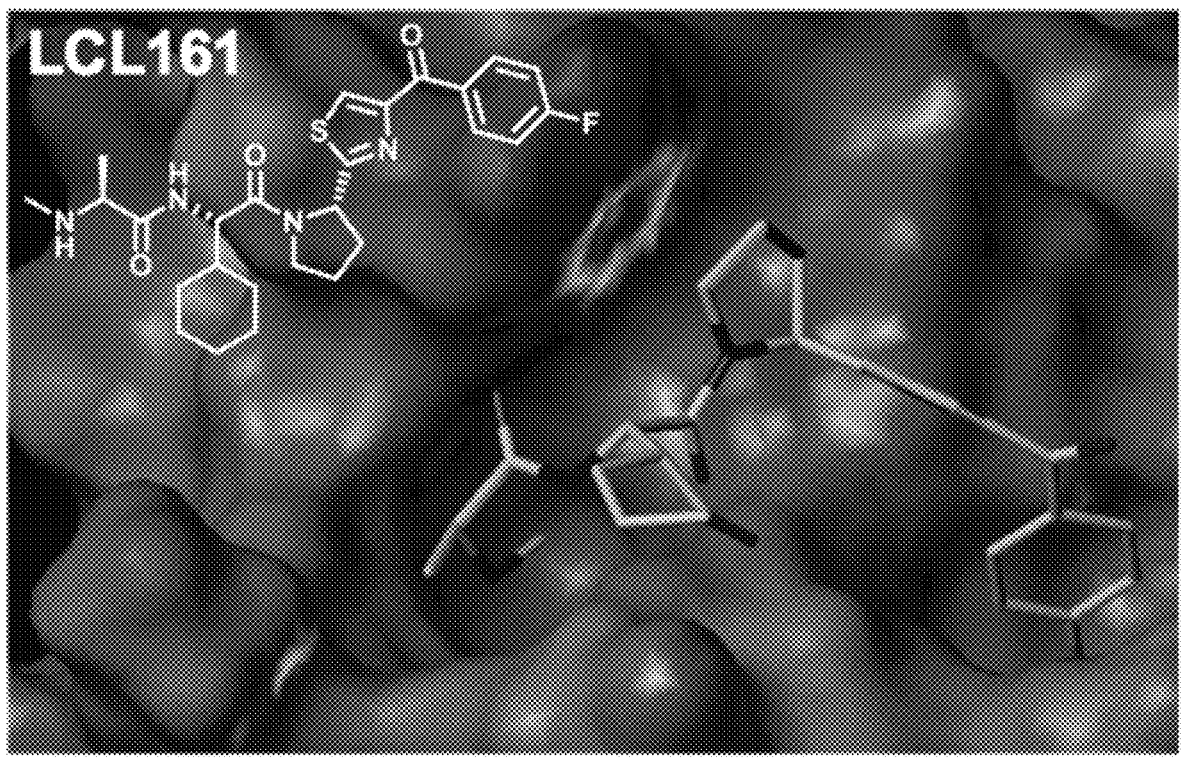
Figure 7E:
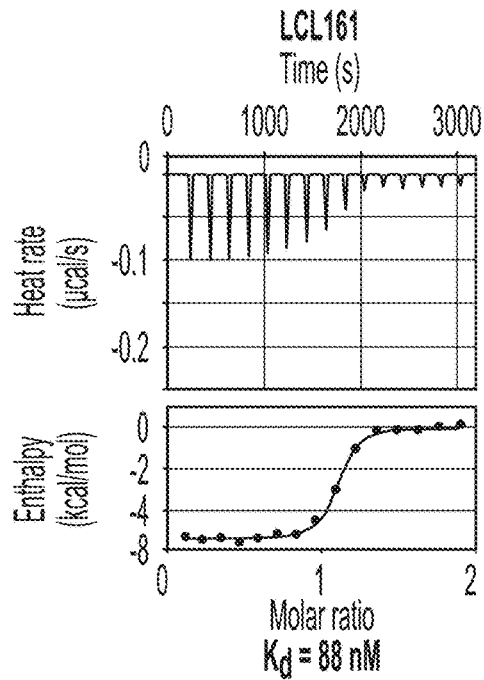
Figure 7F:
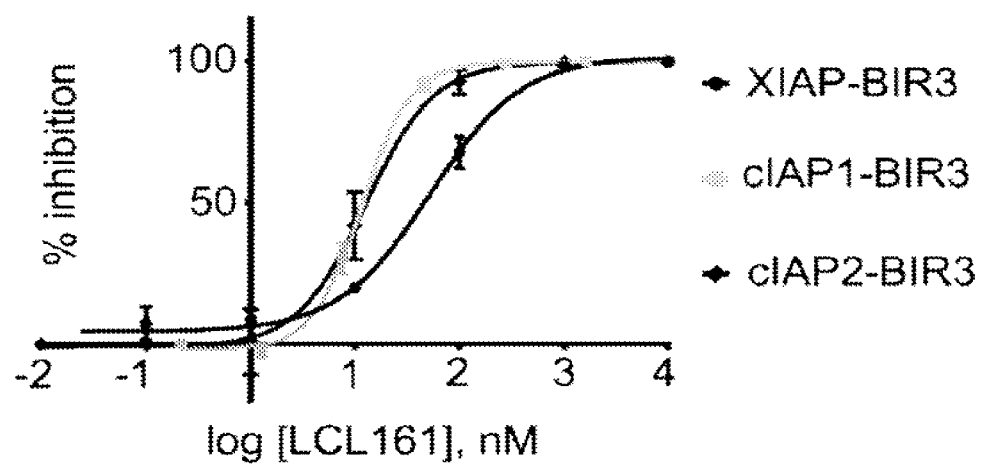
Figure 7G:
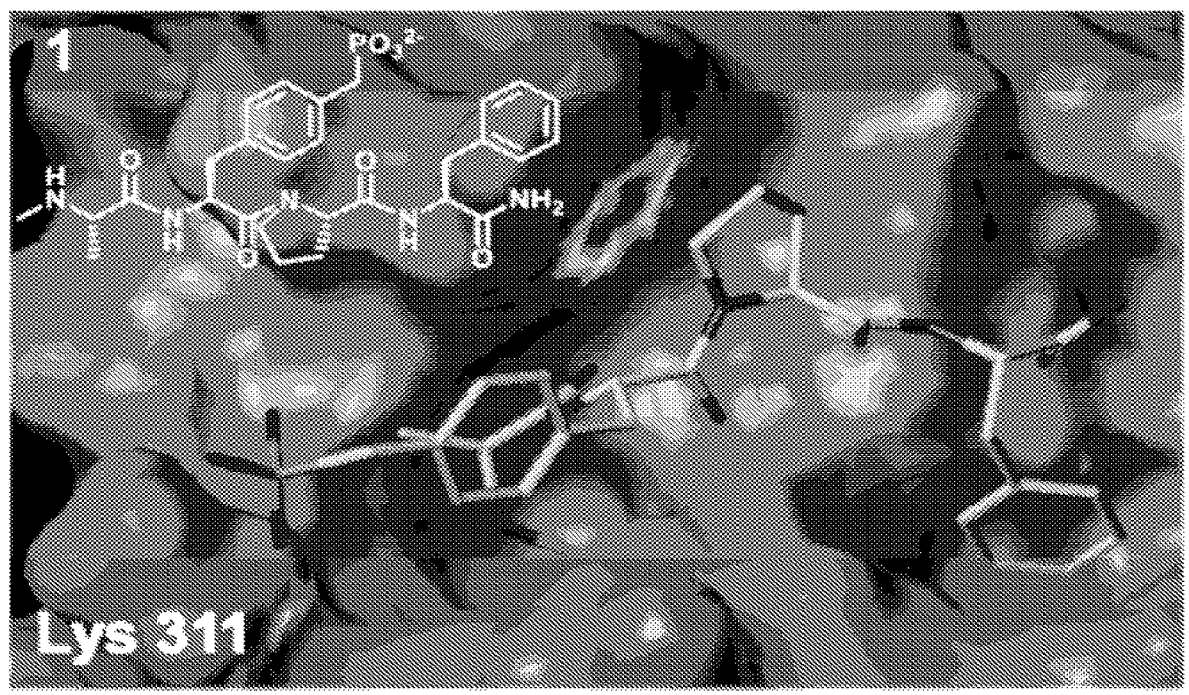
Figure 7H:
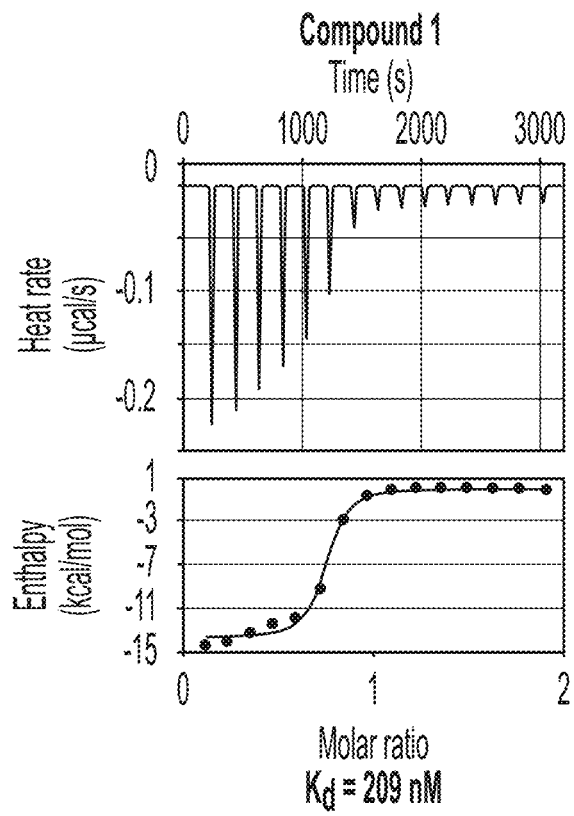
Figure 7I:
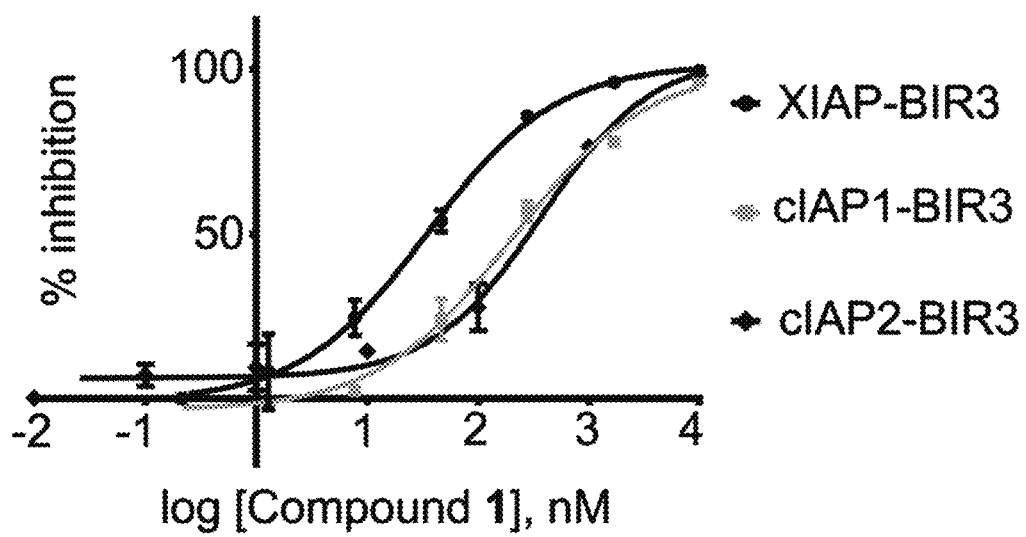
Figure 8A:
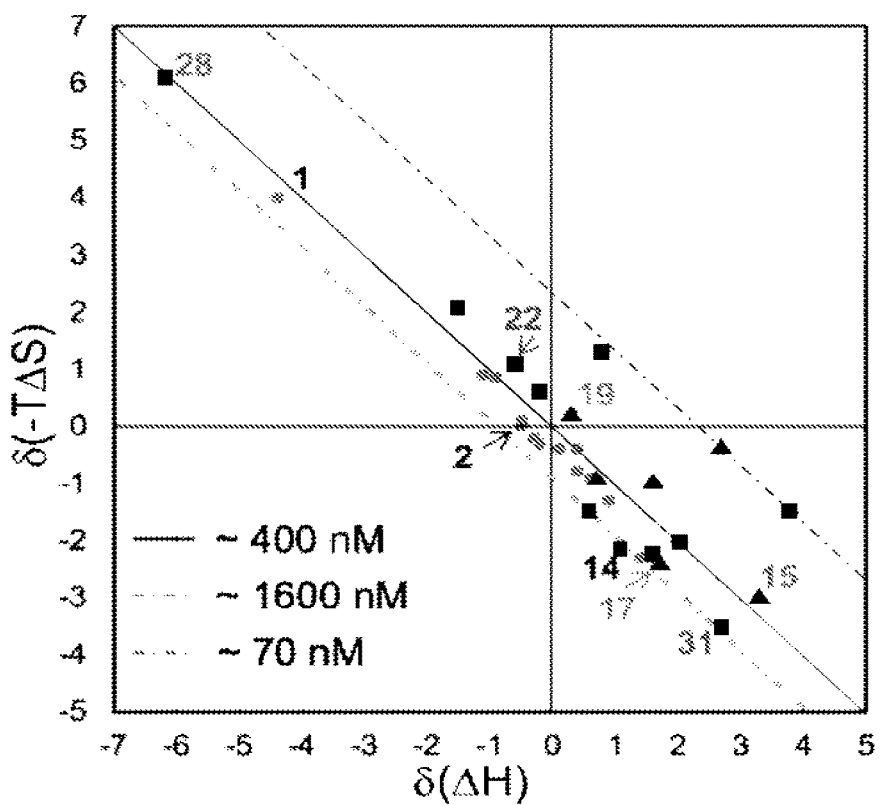
FIGS. 8A-8E. A Craig plot of thermodynamic parameters guided the design of selective and pan-inhibitors, against the BIR3 domains of XIAP, cIAP1, and cIAP2.
Figure 8B:
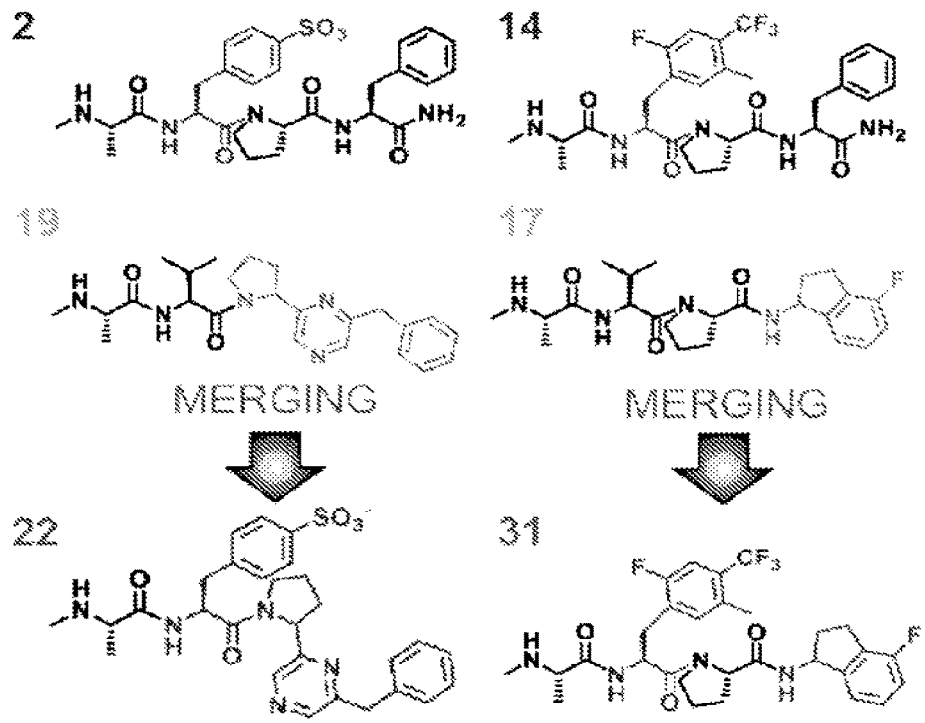
Figure 8C:
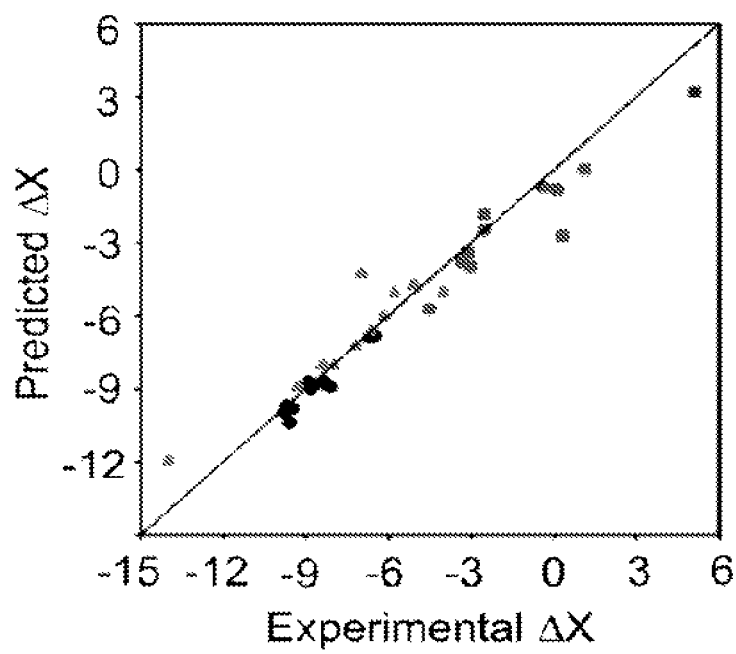
Figure 8D:
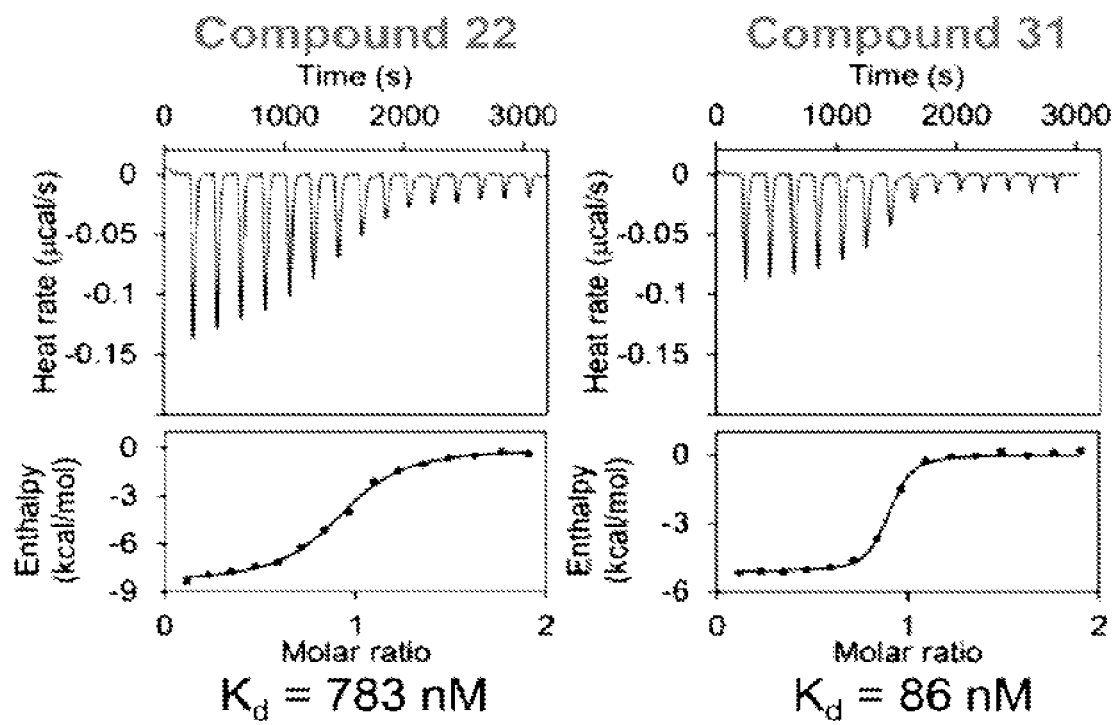
Figure 8E:
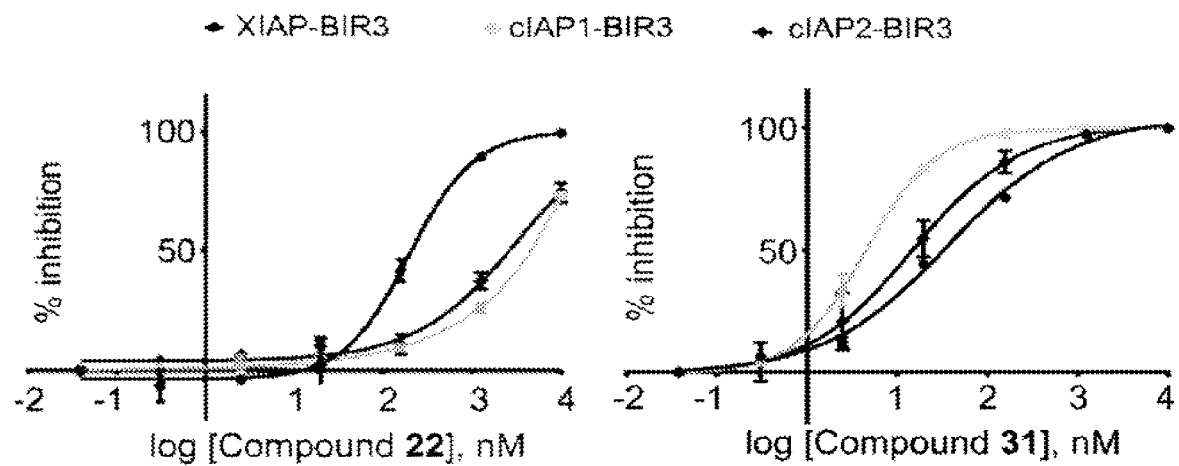
Figure 11A:
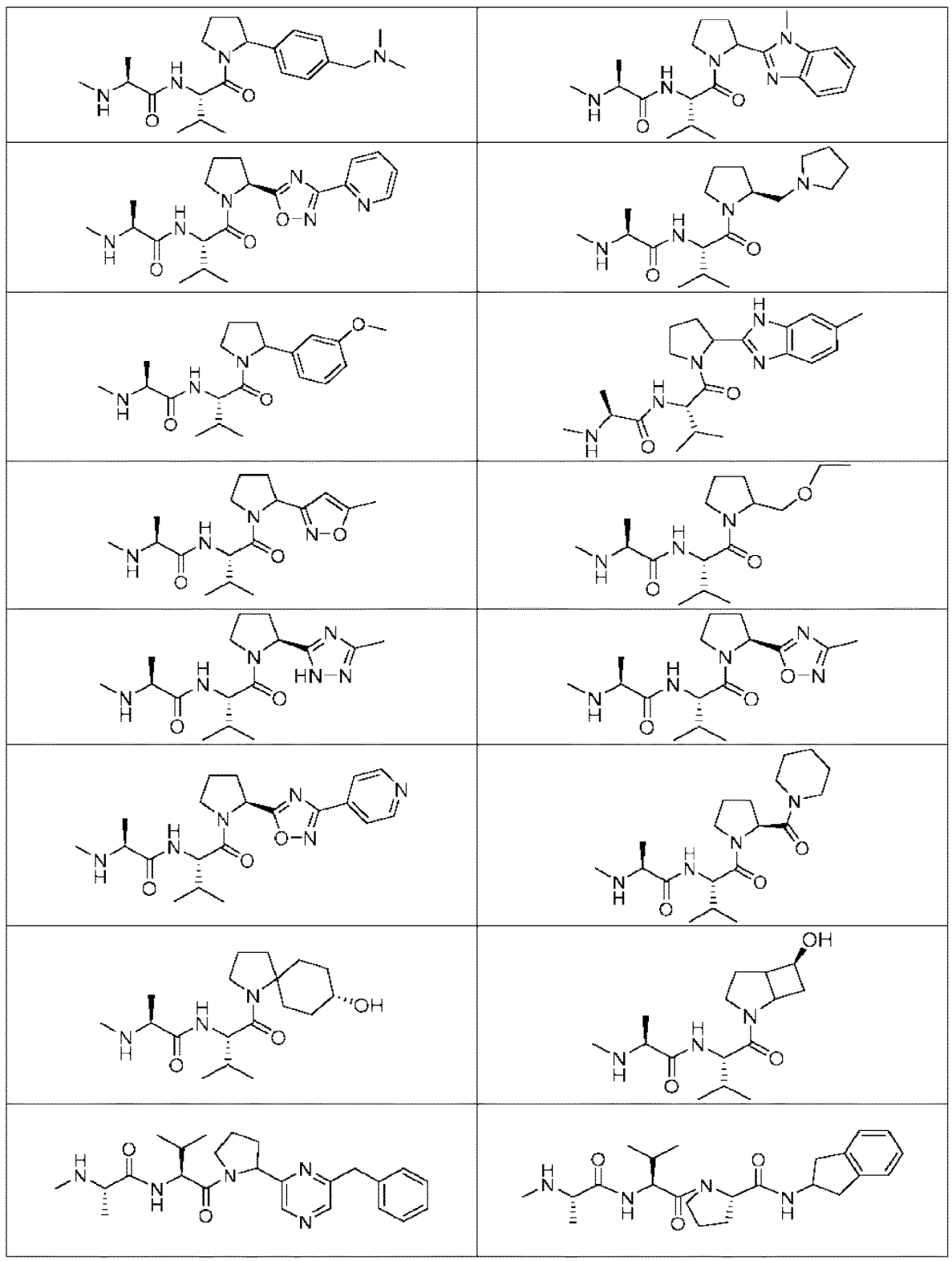
FIGS. 11A-11B. Chemical structures of 32 compounds synthesized to probe for P3/P4 substituents in NMe-Ala-Val-P3/P4. Each compound was synthesized and tested against the BIR3 domain of XIAP using an enthalpy screening approach.
Figure 11B:
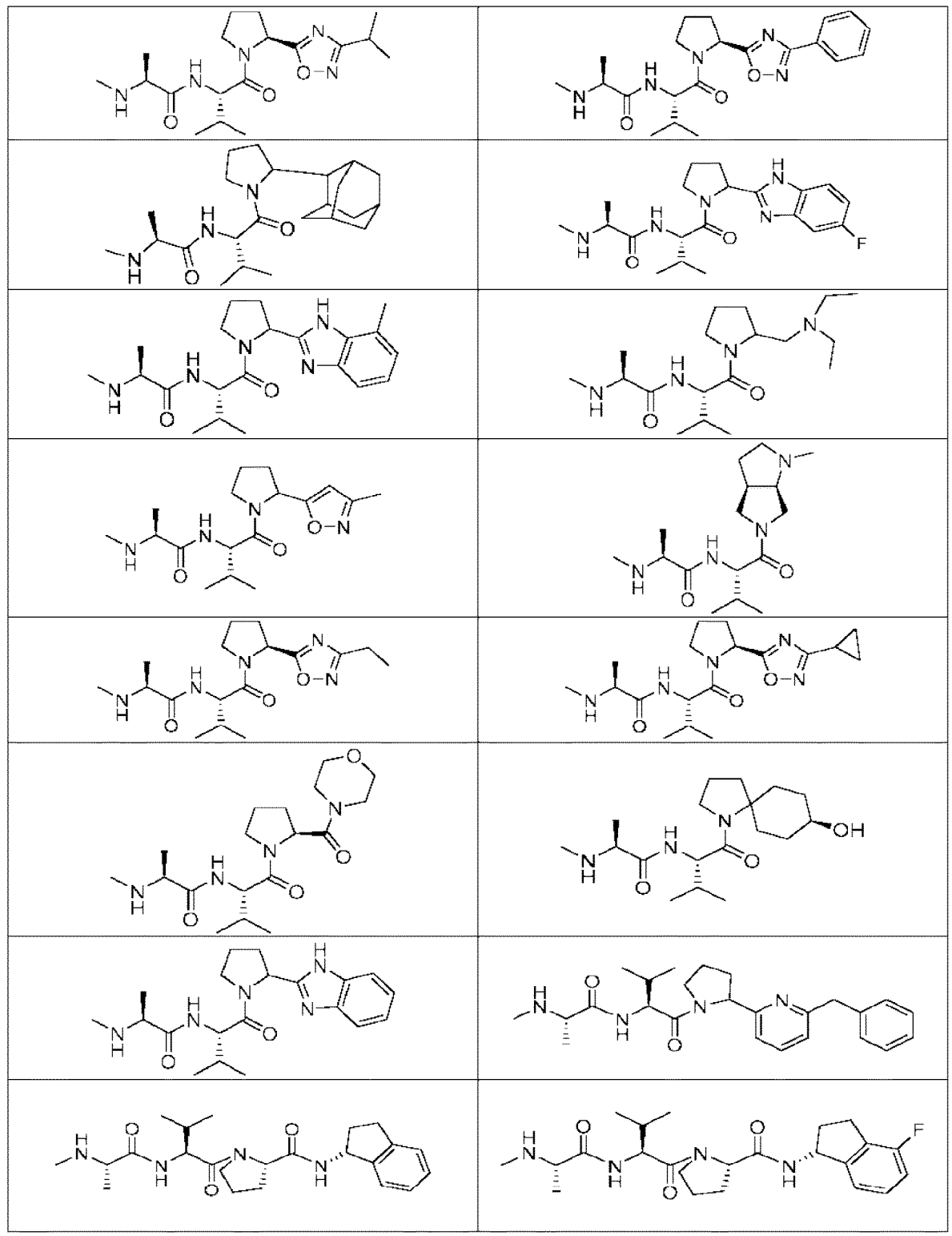
Figure 13:
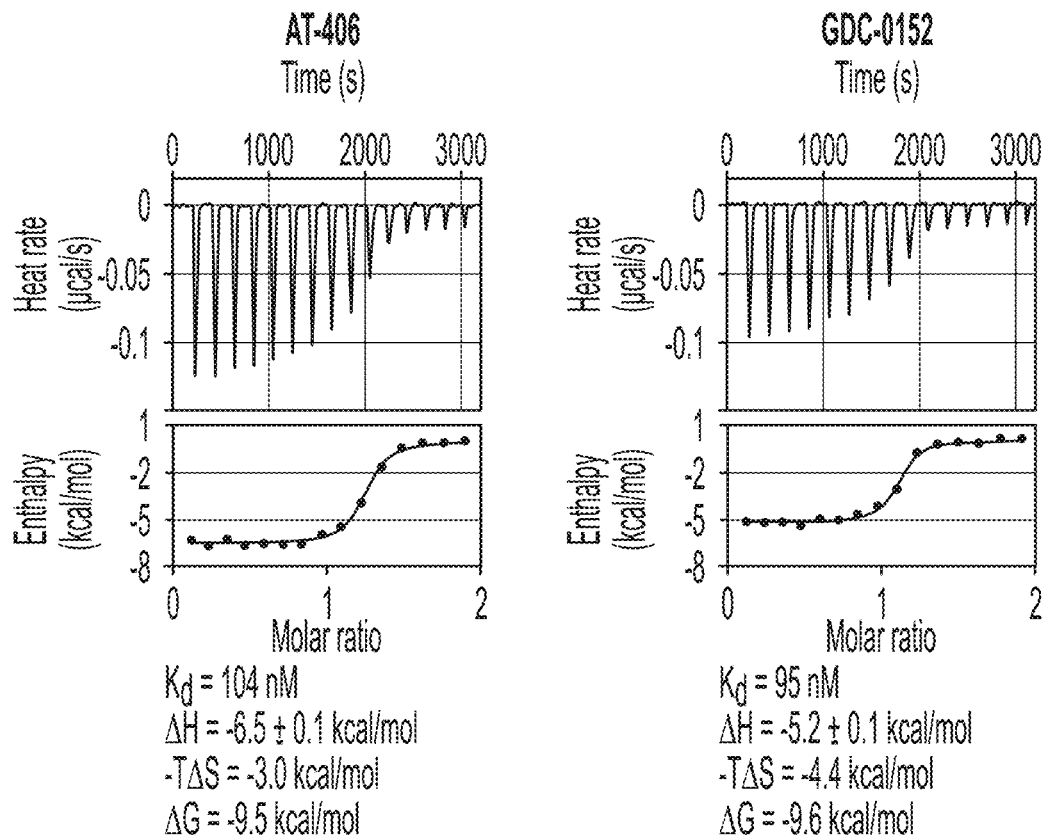
FIG. 13. ITC curves for compounds AT-406 (K is 1.9 nM, 5.1 nM, and 66.4 nM for the BIR3 domains of cIAP1, cIAP2 and XIAP, respectively) and GDC-0152 (K is 17 nM, 43 nM, 28 nM, for the BIR3 domains of cIAP1, cIAP2, and XIAP, respectively).

Thermodynamic driven design of novel IAP antagonists. Very recently we reported on a novel enthalpy-based screening strategy of focused combinatorial libraries aimed at identifying novel binding motifs targeting XIAP, cIAP1 or cIAP2 (48). In that work, a tetrapeptide library of 100,000 compounds of structures Ala-XXX, where X represented 46 natural and non-natural amino acids occupying the P2-P3-P4 positions of the SMAC-binding pocket on BIR3 (FIG. 7A), revealed a novel consensus motif for XIAP BIR3 of sequence Ala-pTyr-Pro-(4F)Phe-NH2 (SEQ ID NO: 8) or N-Me-Ala-(p-phosphonomethyl)Phe-Pro-Phe-NH$_2$ (SEQ ID NO: 9) (compound 1, FIG. 7G). However, while this agent presented a markedly high enthalpy ($\Delta$H) of binding for XIAP BIR3 of −12.2 kcal/mol (FIGS. 7G-7I) compared to that for the reference peptide of −7.8 kcal/mol (FIGS. 7A-7C; Table 1) or other pan-IAP inhibitors such as LCL161 (FIGS. 7D-7F, $\Delta$H=−5.2 kcal/mol), AT-406, or GDC-0156 ($\Delta$H=−6.5 kcal/mol and −5.2 kcal/mol, respectively; FIG. 13) (26), it exhibited only a modest, yet encouraging, selectivity in inhibiting the BIR3 domain of XIAP compared to cIAP1/2 (FIG. 7I) (48). Hence, our working hypothesis was that selecting for ligands that displayed the largest $\Delta$H of binding for the given target would also display the greatest selectivity (49). Therefore, based on the new identified consensus motif we sought to derive novel XIAP BIR3 targeting agents by iteratively synthesizing and testing a variety of phosphonomethyl or phosphate bioisosters at the P2 position of tetrapeptides of general sequence NMe-Ala-P2-Pro-Phe-NH$_2$ (Table 1). Ranking the agents by enthalpy of binding to the BIR3 domain of XIAP revealed that compounds with a formal negative charge in P2, such as 4-sulfone-Phe (compound 2, Table 1) displayed the largest −$\Delta$H for binding to the BIR3 domain of XIAP and, in agreement with our central hypothesis, these agents also displayed the largest selectivity especially for XIAP versus cIAP1, with IC$_{50}$ values for compound 1 of 35 nM, 197.6 nM, for XIAP and cIAP1, respectively (FIG. 7I), and IC$_{50}$ values for compound 2 of 38.3 nM, 143.5 nM, for XIAP and cIAP1, respectively (Table 1). The reported IC$_{50}$ values represented the ability of the agents to displace the binding of the given target from a biotinylated AVPI peptide (SEQ ID NO: 4) in a Dissociation Enhanced Lanthanide Fluorescent Immunoassay (DELFIA) displacement assay platform, as we have recently described (48). To further assess if potency and selectivity could be further achieved also by varying the P4 position, we designed, synthesized and tested against the BIR3 domain of XIAP using an enthalpy screening approach a number of compounds with the general sequence NMe-Ala-Val-P3/P4 where P3/P4 represent Pro-Phe bioisosters (Table 1, FIGS. 11A-11B). Out of 32 compounds synthesized and tested, we selected those compounds that displayed a ΔH of binding >4 kcal/mol. However, when selected agents were subsequently tested in full isothermal titration calorimetry (ITC) measurements and in the DELFIA displacement assays, we found a poor correlation between the ΔH values and dissociation constant ($K_d$), indicating that each agent displayed varying entropic contributions to binding to the BIR3 domain of XIAP. Hence, in an attempt to predict whether given combinations of P2 and P3/P4 elements could result in more potent and/or more selective compounds, we computed the enthalpy and entropy contribution of binding to the BIR3 of XIAP of each element with respect to a reference molecule, namely NMe-Ala-Val-Pro-Phe-NH$_2$ (SEQ ID NO: 7). In essence, given the thermodynamics of binding of NMe-Ala-Val-Pro-Phe-NH$_2$ (SEQ ID NO: 7) (FIG. 7B), differential δΔH and δ(-TΔS) values were calculated from experimental values and assigned to each P2 element in the NMe-Ala-P2-Pro-Phe-NH$_2$ compounds (Table 1) and to each P3/P4 elements in the NMe-Ala-Val-P3/P4 agents (Table 2). We found it useful to report the data using a thermodynamic Craig plot of δΔH versus δ(-TΔS) for each agent (FIG. 8A). In this representation, compounds that are close to the diagonal would possess similar ΔG values (hence, similar dissociation constants) for XIAP BIR3 as the reference molecule NMe-Ala-Val-Pro-Phe-NH$_2$ (SEQ ID NO: 7), while ligands that fall on the dashed lines parallel to this diagonal would have dissociation constants that are approximately either 4 times greater (less potent, upper line) or about 6 times smaller (more potent, lower line) than the reference compound (FIG. 8A). In addition, and based on our previous hypothesis, compounds that possess a greater ΔH of binding could also result more selective for XIAP BIR3, compared to cIAP1 or cIAP2. Hence, to probe the utility of this thermodynamic Craig plot, we selected proper combinations of elements that we predicted being able to confer either the greatest potency or the greatest selectivity towards the BIR3 domain of XIAP (FIG. 8B). Hence, merging compound 2 (δΔH=-0.5 kcal/mol, δ(-TΔS)=0 kcal/mol) with compound 19 (δΔH=0.3 kcal/mol, δ(-TΔS)=0.2 kcal/mol), compounds with the best compromise between largest enthalpy without losing too much in potency, resulted in compound 22 that displayed a ΔH value of -8.4 kcal/mol, and a -TΔS value of 0.1 kcal/mol that are remarkably close to the predicted additive values derived from the two compounds (Table 2, FIGS. 8B-8D). Likewise, merging compounds with the largest free energy of binding ΔG, namely compound 14 (δΔH=1.4 kcal/mol, δ(-TΔS)=-2.3 kcal/mol) and compound 17 (δΔH=1.7 kcal/mol, δ(-TΔS)=-2.4 kcal/mol), resulted in agent compound 31 with a ΔH value of -5.1 kcal/mol, and a -TΔS value of -4.5 kcal/mol that are again remarkably close to the additive values derived from the two compounds (Table 2, FIGS. 8B-8D). A systematic merging of agents reported in Table 1 and Table 2 revealed a remarkable predictive ability of the thermodynamic Craig plot (FIGS. 8B, 8C). From these studies, compound 31 was the most potent, but perhaps not particularly selective by virtue of the smaller ΔH of binding for XIAP, while compound 22 was predicted to be the most selective for XIAP BIR3 by virtue of its largest enthalpy of binding for this target. In agreement with these predictions, compound 31 was very potent in displacing a SMAC peptide in the DELFIA assays against XIAP, cIAP1 and cIAP2 with IC$_{50}$ values of 37.1 nM, 4.5 nM, 15 nM, respectively (FIG. 8E, Table 3). Whereas, as predicted, compound 22, was XIAP selective with IC$_{50}$ values of approximately 190.7 nM, and >1000 nM against XIAP, and cIAP1 and cIAP2, respectively (FIG. 8E, Table 3).

TABLE 1

Binding affinities and thermodynamics parameters for different P2 and P3/P4 substituents of XIAP BIR3 targeting agents. ΔH, -TΔS, and $K_d$ were calculated using ITC measurement against the BIR3 domain of XIAP. ΔH values are reported with a confidence interval level 95%. δ(ΔH) and δ(-TΔS) are the difference in ΔH or -TΔS with respect to the thermodynamics of binding between BIR3 of XIAP and the reference peptide N—Me-AVPF-NH$_2$ (ΔH = -7.8 kcal/mol, and -TΔS = -1 kcal/mol). The differences are calculated as: δ(ΔH) = ΔH - ΔH$_{ref}$ and δ(-TΔS) = -TΔS - (-TΔS$_{ref}$).

| Compd | P2 | ΔH | -TΔS | $K_d$ (nM) | δ(ΔH) | δ(-TΔS) |
|---|---|---|---|---|---|---|
| | N—Me-Ala-P2-Pro-Phe-NH$_2$ | | | | | |
| 1 | 4-(phosphonomethyl)Phe | -12.2 ± 0.5 | 3.0 | 206 | -4.4 | 4 |
| 2 | (4SO$_3^-$)-Phe | -8.3 ± 0.3 | -1.0 | 155 | -0.5 | 0 |
| 3 | (4-NO$_2$)-Phe | -8.9 ± 0.3 | -0.1 | 280 | -1.1 | 0.9 |
| 4 | (4-sulfomethyl)-Phe | -8.7 ± 0.4 | -0.2 | 346 | -0.9 | 0.8 |
| 5 | (3Cl—4CF$_3$)Phe | -8.3 ± 0.2 | -0.9 | 190 | -0.5 | 0.1 |
| 6 | (3F—4CF$_3$)Phe | -8.1 ± 0.2 | -1.2 | 155 | -0.3 | -0.2 |
| 7 | (3Cl—5CF$_3$)Phe | -8.0 ± 0.1 | -1.3 | 133 | -0.2 | -0.3 |
| 8 | Cyclohexyl Glycine | -7.8 ± 0.4 | -1.4 | 354 | 0 | -0.4 |
| 9 | Dab | -7.7 ± 0.3 | -1.4 | 230 | 0.1 | -0.4 |
| 10 | (2F—4CF$_3$)Phe | -7.4 ± 1.0 | -1.8 | 194 | 0.4 | -0.8 |
| 11 | Phe(4-CF$_3$) | -7.2 ± 0.3 | -1.9 | 213 | 0.6 | -0.9 |
| 12 | (4-OCF$_3$)Phe | -7.1 ± 0.3 | -1.9 | 227 | 0.7 | -0.9 |
| 13 | (p-guanidino)Phe | -6.9 ± 0.2 | -2.3 | 182 | 0.9 | -1.3 |
| 14 | (2F—4CF$_3$—5Me)Phe | -6.4 ± 0.2 | -3.3 | 81 | 1.4 | -2.3 |
| | N—Me-Ala-Val-P3/P4 | | | | | |
| 15 | Pro-(2-aminoindan) | -4.5 ± 0.2 | -4.0 | 602 | 3.3 | -3 |
| 16 | Pro-(1-aminoindan) | -7.1 ± 0.4 | -1.9 | 269 | 0.7 | -0.9 |
| 17 | Pro-((R)-4-F-2,3-dihydro-1H-inden-1-amine) | -6.1 ± 0.1 | -3.4 | 122 | 1.7 | -2.4 |

TABLE 1-continued

Binding affinities and thermodynamics parameters for different P2 and P3/P4 substituents of XIAP BIR3 targeting agents. ΔH, −TΔS, and $K_d$ were calculated using ITC measurement against the BIR3 domain of XIAP. ΔH values are reported with a confidence interval level 95%. δ(ΔH) and δ(−TΔS) are the difference in ΔH or −TΔS with respect to the thermodynamics of binding between BIR3 of XIAP and the reference peptide N—Me-AVPF-NH$_2$ (ΔH = −7.8 kcal/mol, and −TΔS = −1 kcal/mol). The differences are calculated as: δ(ΔH) = ΔH − ΔH$_{ref}$ and δ(−TΔS) = −TΔS − (−TΔS$_{ref}$).

| Compd | P2 | ΔH | −TΔS | $K_d$ (nM) | δ(ΔH) | δ(−TΔS) |
|---|---|---|---|---|---|---|
| 18 | 2-{5-[(2S)-2-pyrrolidinyl]-1,2,4-oxadiazol-3-yl}pyridine | −6.2 ± 0.5 | −2.0 | 1000 | 1.6 | −1 |
| 19 | 2-benzyl-6-(pyrrolidine-2-yl)pyrazine | −7.5 ± 0.4 | −0.8 | 719 | 0.3 | 0.2 |
| 20 | 2-(2-pyrrolidinyl)-1H-benzamidazole | −5.1 ± 5.0 | −1.4 | 12000 | 2.7 | −0.4 |

TABLE 2

Comparison of experimental and predicted thermodynamics parameters for XIAP BIR3 agents obtained from combinations of P2 and P3/P4 substituents. ΔH$_{exp}$, -TΔS$_{exp}$, and ΔG$_{exp}$ were calculated using ITC measurement against the BIR3 domain of XIAP. ΔH$_{exp}$ values are reported with a confidence interval level 95%. ΔH$_{pred}$, -TΔS$_{pred}$, and ΔG$_{pred}$ were calculated as: ΔX$_{pred}$ = ΔX$_{ref}$ + δ(ΔX)$_{P2}$ + δ(ΔX)$_{P3/P4}$, where ΔX$_{ref}$ are the thermodynamics parameters of the reference agent N-Me-AVPF-NH$_2$ (ΔH = −7.8 kcal/mol, and -TΔS = −1 kcal/mol), and δ(ΔX) values are calculated as in Table 1.

| Structure | ΔH$_{exp}$ | -TΔS$_{exp}$ | ΔG$_{exp}$ | ΔH$_{pred}$ | -TΔS$_{pred}$ | ΔG$_{pred}$ |
|---|---|---|---|---|---|---|
| 21 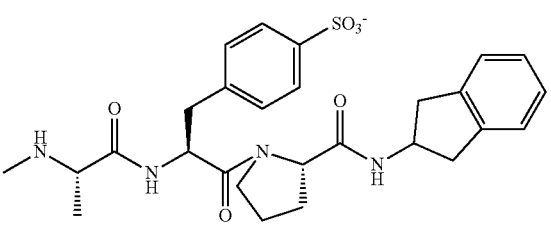 | −5.8 ± 0.4 | −3 | −8.8 | −5 | −4 | −9 |
| 22 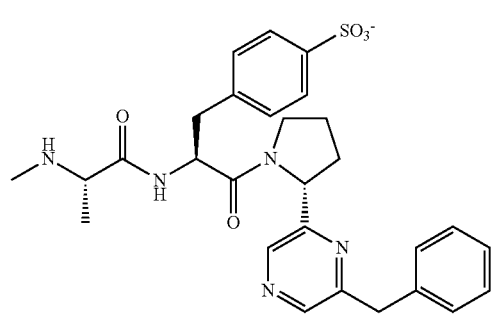 | −8.4 ± 0.2 | 0.1 | −8.3 | −8 | −0.8 | −8.8 |

TABLE 2-continued

Comparison of experimental and predicted thermodynamics parameters for XIAP BIR3 agents obtained from combinations of P2 and P3/P4 substituents. $\Delta H_{exp}$, $-T\Delta S_{exp}$, and $\Delta G_{exp}$ were calculated using ITC measurement against the BIR3 domain of XIAP. $\Delta H_{exp}$ values are reported with a confidence interval level 95%. $\Delta H_{pred}$, $-T\Delta S_{pred}$, and $\Delta G_{pred}$ were calculated as: $\Delta X_{pred} = \Delta X_{ref} + \delta(\Delta X)_{P2} + \delta(\Delta X)_{P3/P4}$, where $\Delta X_{ref}$ are the thermodynamics parameters of the reference agent N-Me-AVPF-NH$_2$ ($\Delta H = -7.8$ kcal/mol, and $-T\Delta S = -1$ kcal/mol), and $\delta(\Delta X)$ values are calculated as in Table 1.

| Structure | Predicted versus experimental parameters (kcal/mol) | | | | | |
|---|---|---|---|---|---|---|
| | $\Delta H_{exp}$ | $-T\Delta S_{exp}$ | $\Delta G_{exp}$ | $\Delta H_{pred}$ | $-T\Delta S_{pred}$ | $\Delta G_{pred}$ |
| 23 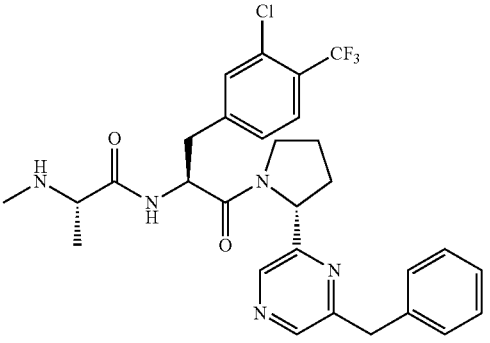 | $-8.0 \pm 0.3$ | $-0.4$ | $-8.4$ | $-8$ | $-0.7$ | $-8.7$ |
| 24 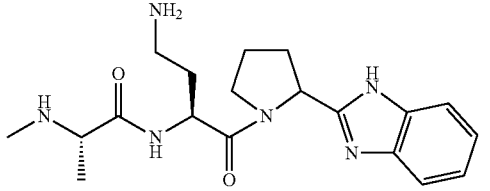 | $-4 \pm 2$ | $-2.5$ | $-6.5$ | $-5$ | $-1.8$ | $-6.8$ |
| 25 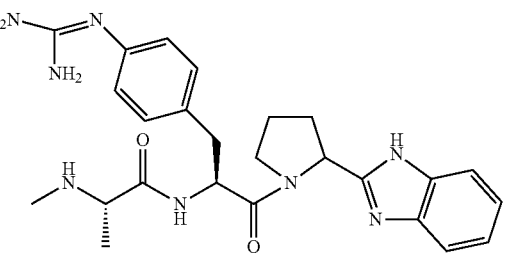 | $-7 \pm 2$ | $0.3$ | $-6.7$ | $-4.2$ | $-2.7$ | $-6.9$ |
| 26 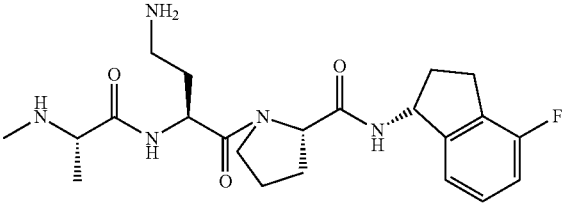 | $-6.2 \pm 0.2$ | $-3.3$ | $-9.5$ | $-6$ | $-3.8$ | $-9.8$ |

TABLE 2-continued

Comparison of experimental and predicted thermodynamics parameters for XIAP BIR3 agents obtained from combinations of P2 and P3/P4 substituents. $\Delta H_{exp}$, $-T\Delta S_{exp}$, and $\Delta G_{exp}$ were calculated using ITC measurement against the BIR3 domain of XIAP. $\Delta H_{exp}$ values are reported with a confidence interval level 95%. $\Delta H_{pred}$, $-T\Delta S_{pred}$, and $\Delta G_{pred}$ were calculated as: $\Delta X_{pred} = \Delta X_{ref} + \delta(\Delta X)_{P2} + \delta(\Delta X)_{P3/P4}$, where $\Delta X_{ref}$ are the thermodynamics parameters of the reference agent N-Me-AVPF-NH$_2$ ($\Delta H = -7.8$ kcal/mol, and $-T\Delta S = -1$ kcal/mol), and $\delta(\Delta X)$ values are calculated as in Table 1.

| Structure | Predicted versus experimental parameters (kcal/mol) | | | | | |
|---|---|---|---|---|---|---|
| | $\Delta H_{exp}$ | $-T\Delta S_{exp}$ | $\Delta G_{exp}$ | $\Delta H_{pred}$ | $-T\Delta S_{pred}$ | $\Delta G_{pred}$ |
| 27 | −9.3 ± 0.6 | 1.1 | −8.1 | −8.9 | 0 | −8.9 |
| 28 | −14.0 ± 0.6 | 5.1 | −8.9 | −11.9 | 3.2 | −8.7 |
| 29 | −7.2 ± 0.2 | −2.5 | −9.7 | −7.2 | −2.5 | −9.7 |
| 30 | −6.7 ± 0.2 | −3.1 | −9.8 | −6.6 | −3.4 | −10 |

TABLE 2-continued

Comparison of experimental and predicted thermodynamics parameters for XIAP
BIR3 agents obtained from combinations of P2 and P3/P4 substituents. $\Delta H_{exp}$, $-T\Delta S_{exp}$, and $\Delta G_{exp}$
were calculated using ITC measurement against the BIR3 domain of XIAP. $\Delta H_{exp}$ values are
reported with a confidence interval level 95%. $\Delta H_{pred}$, $-T\Delta S_{pred}$, and $\Delta G_{pred}$ were calculated as:
$\Delta X_{pred} = \Delta X_{ref} + \delta(\Delta X)_{P2} + \delta(\Delta X)_{P3/P4}$, where $\Delta X_{ref}$ are the thermodynamics parameters of the
reference agent N-Me-AVPF-NH$_2$ ($\Delta H = -7.8$ kcal/mol, and $-T\Delta S = -1$ kcal/mol), and $\delta(\Delta X)$ values
are calculated as in Table 1.

| | Predicted versus experimental parameters (kcal/mol) | | | | | |
|---|---|---|---|---|---|---|
| Structure | $\Delta H_{exp}$ | $-T\Delta S_{exp}$ | $\Delta G_{exp}$ | $\Delta H_{pred}$ | $-T\Delta S_{pred}$ | $\Delta G_{pred}$ |
| 31 | $-5.1 \pm 0.1$ | $-4.5$ | $-9.6$ | $-4.7$ | $-5.7$ | $-10.4$ |

TABLE 3

Relative binding affinities and selectivity for XIAP BIR3 targeting agents
designed from combinations of various P2 and P3/P4 substituents. IC$_{50}$
values with respective standard errors for the BIR3 domains of XIAP, cIAP1,
and cIAP2 were obtained with a DELFIA displacement assay. Selectivity was
calculated as a ratio of cIAP1 or cIAP2 IC$_{50}$ values versus IC$_{50}$ values for XIAP.

| | XIAP | | cIAP1 | | cIAP2 | |
|---|---|---|---|---|---|---|
| Compd | $K_d$ (ITC, nM) | IC$_{50}$ (DELFIA, nM) | IC$_{50}$ (DELFIA, nM) | Selectivity cIAP1/XIAP | IC$_{50}$ (DELFIA, nM) | Selectivity cIAP2/XIAP |
| 21 | 337 | 229.4 ± 35.9 | >1000 | >4.4 | >1000 | >4.4 |
| 22 | 783 | 190.7 ± 25.6 | >1000 | >5.2 | >1000 | >5.2 |
| 23 | 753 | 175.9 ± 0.4 | 352.6 ± 36.4 | 2.0 | >9000 | >51.1 |
| 24 | 17000 | >10000 | >16000 | >1.6 | >10000 | 1.0 |
| 25 | 13000 | 5944 ± 816 | >5000 | >0.8 | >10000 | >1.7 |
| 26 | 110 | 76.9 ± 3.9 | 17.2 ± 3.8 | 0.2 | 56.6 ± 3.0 | 0.7 |
| 27 | 1100 | 215.3 ± 12.1 | 1203 ± 55 | 5.6 | 1103 ± 126 | 5.1 |
| 28 | 321 | 275.7 ± 12.7 | >2000 | >7.2 | >1500 | >5.5 |
| 29 | 81 | 86.8 ± 14.9 | 23.9 ± 0.1 | 0.3 | 53.5 ± 4.7 | 0.6 |
| 30 | 70 | 23.2 ± 2.2 | 21.7 ± 0.9 | 0.9 | 30.6 ± 0.4 | 1.3 |
| 31 | 86 | 37.1 ± 1.1 | 4.5 ± 0.7 | 0.1 | 15.0 ± 5.1 | 0.4 |

Potent and selective, covalent XIAP antagonists targeting the BTR3 domain residue Lys311. While using the thermodynamic Craig plot was instrumental in deriving novel pan-IAP (compound 31) and moderately selective XIAP BTR3 agents (compound 22), we further investigated the basis for this selectivity using single point mutation analysis as corroborated by our docking studies (FIGS. 7A-7I) and sequence alignment between XIAP, cIAP1 and cIAP2, that had identified residue Lys311 of XIAP as possibly a discriminating feature between these proteins. In cIAP1 and cIAP2 this position is occupied by a glutamic acid (48), while most of other SMAC binding site residues are conserved among the three proteins. The possible involvement of Lys311 in the selectivity of our agents for XIAP is also suggested by the nature of the compounds, with agents presenting a formal negative charge displaying the largest enthalpy of binding and greater selectivity over neutral compounds, indicating a possible salt bridge formation.

Figure 9A:
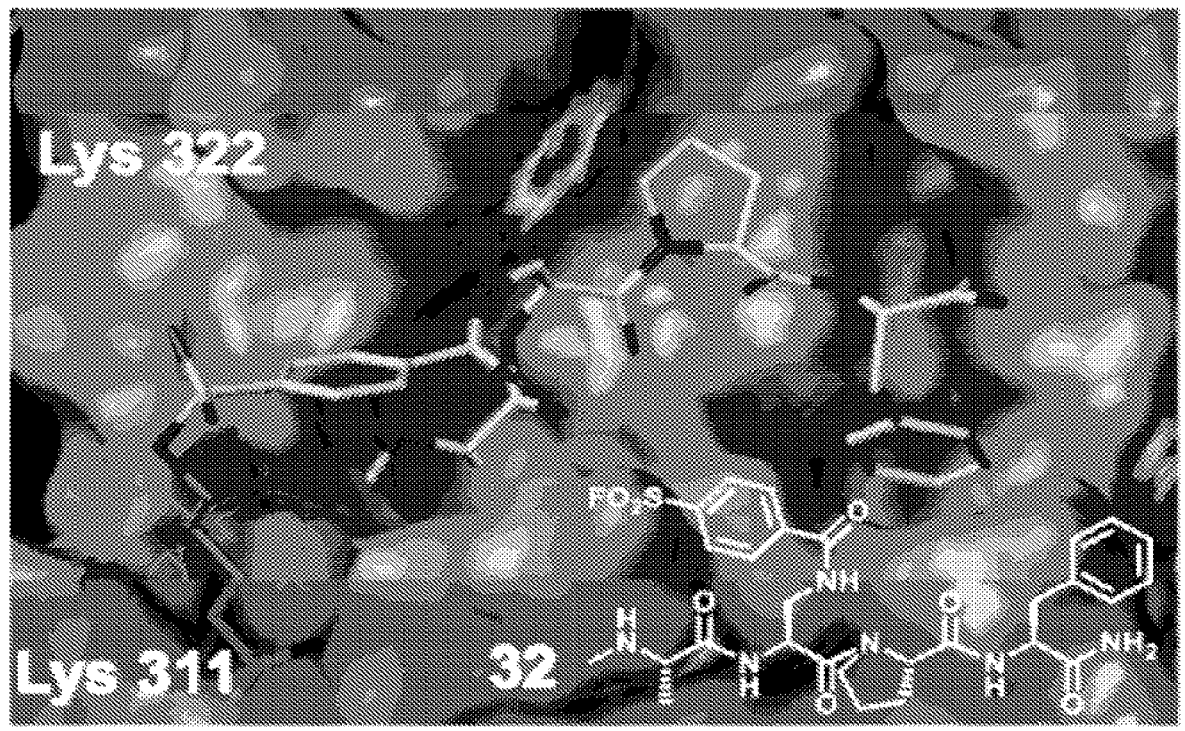
FIGS. 9A-9K. Design and characterization of covalent XIAP BIR inhibitors.
Figure 9B:
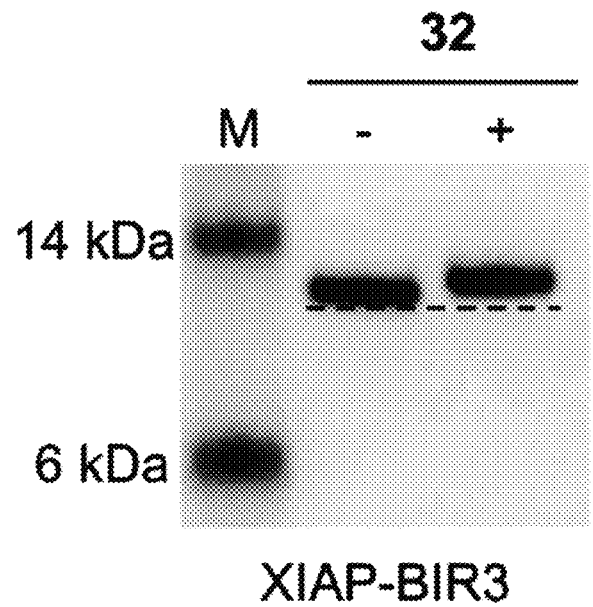
Figure 9C:
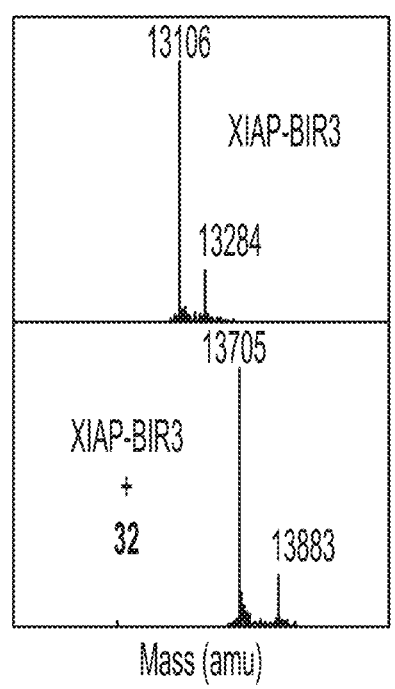
Figure 9D:
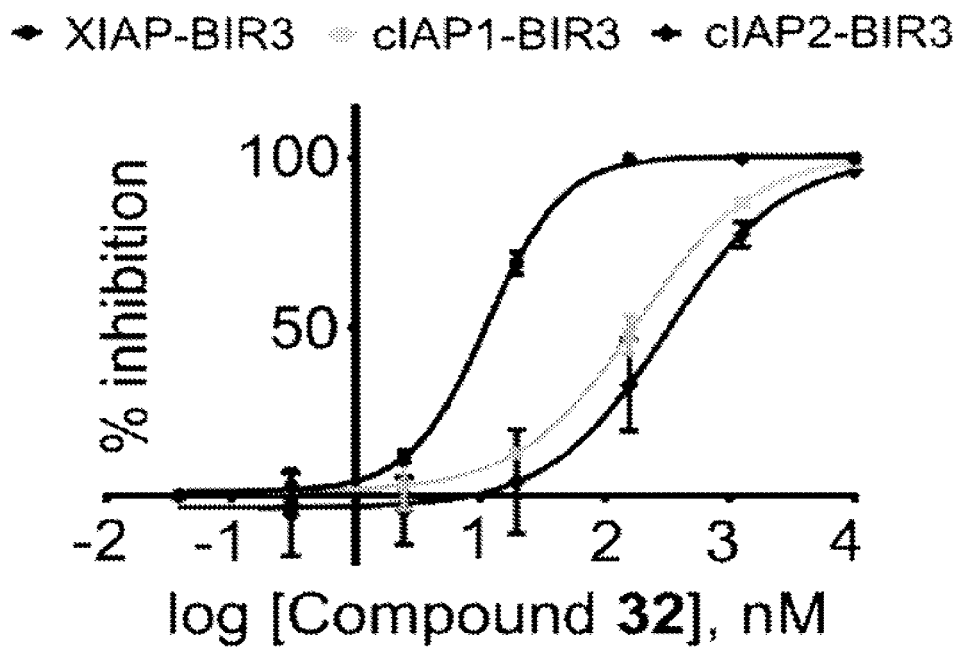
Figure 9E:
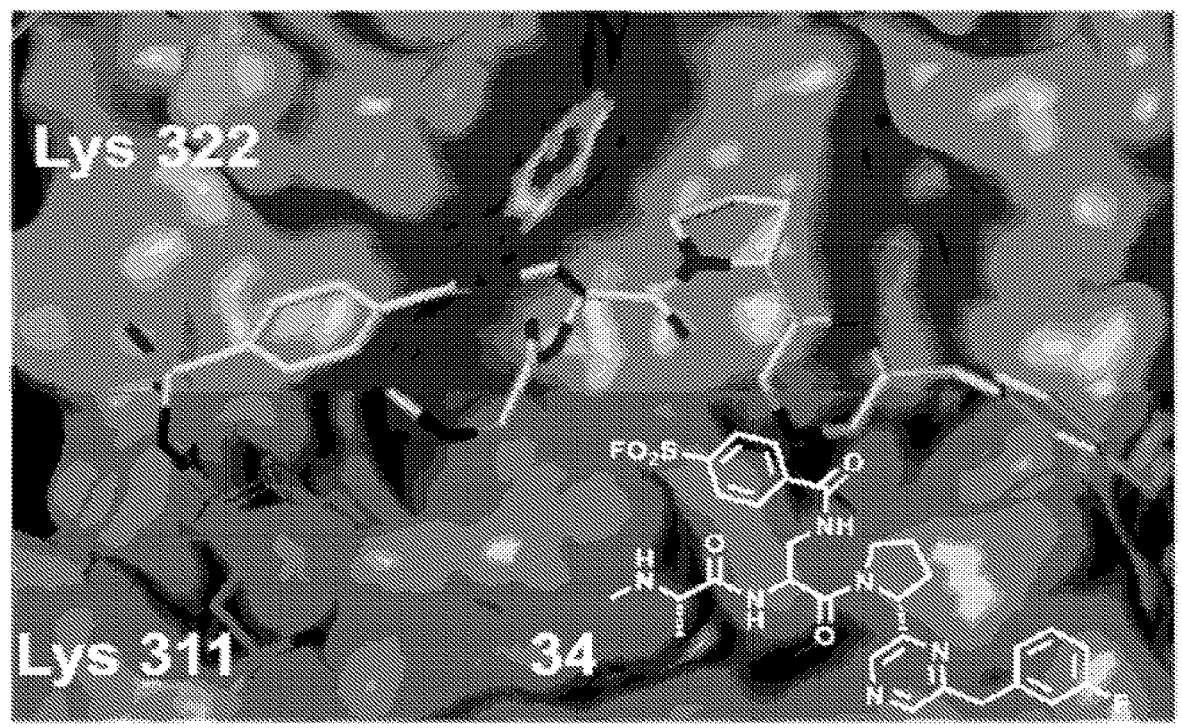
Figure 9F:
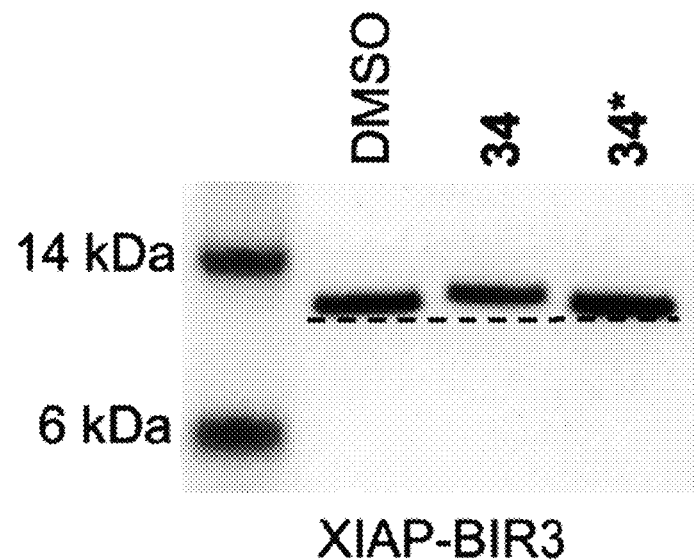
Figure 9G:
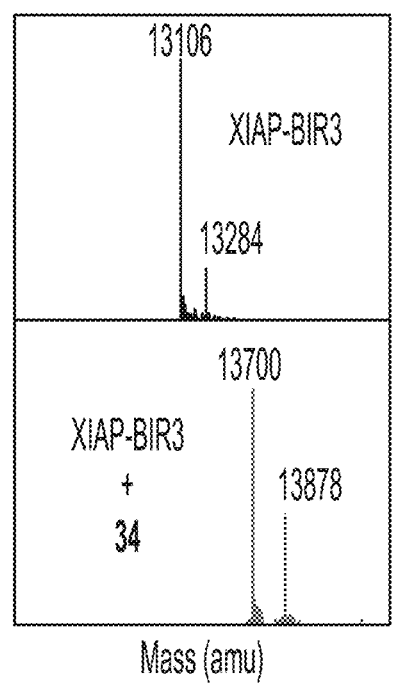
Figure 9H:
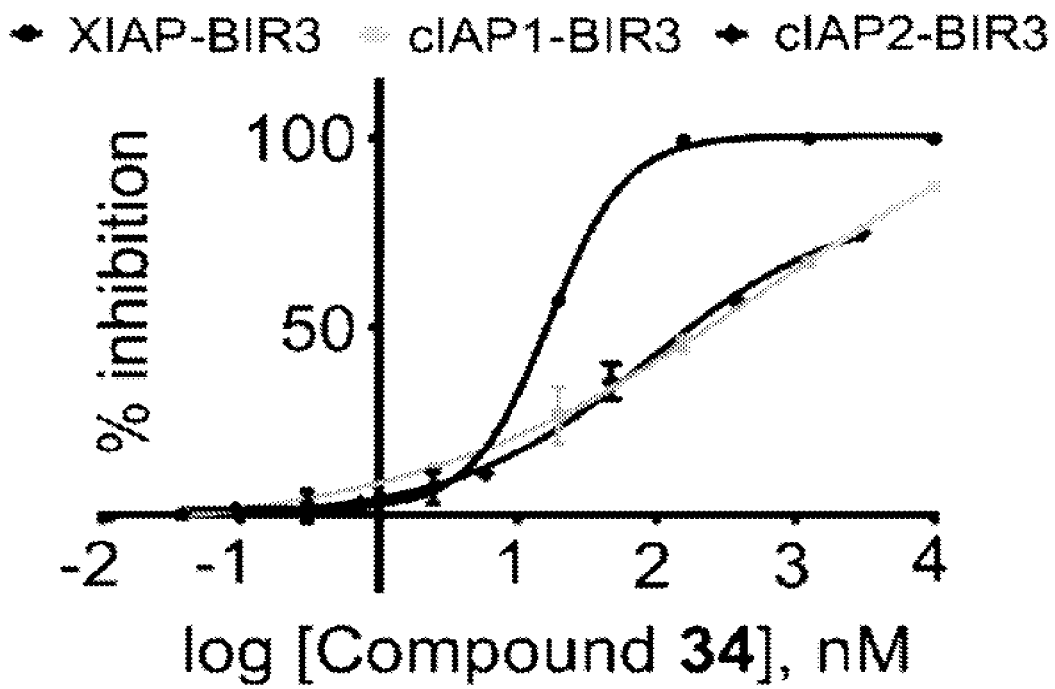
Figure 9I:
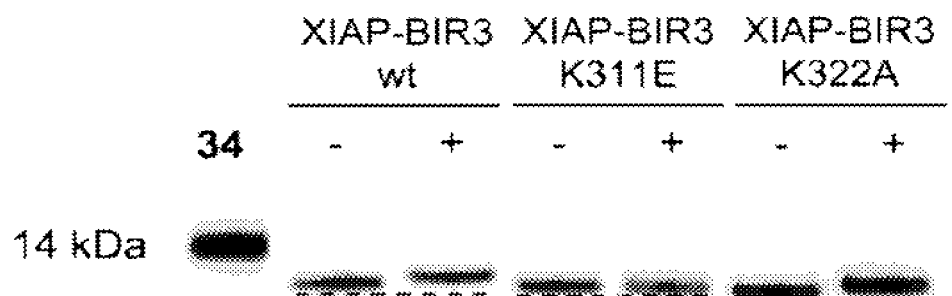
Figure 9J:
Figure 9K:
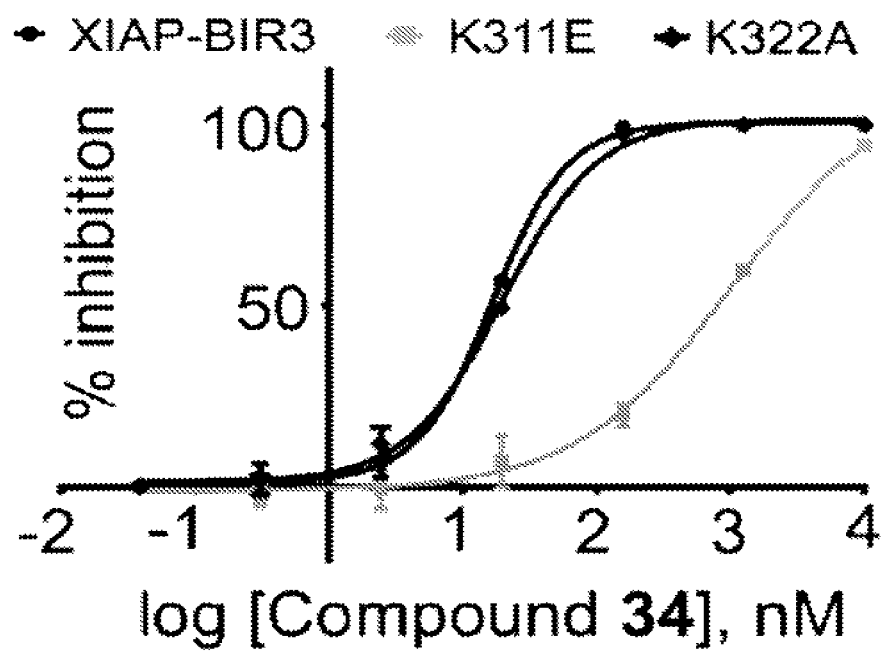

Hence, given that our most selective ligands are likely juxtaposed across from Lys311, we sought to derive novel P2 derivatives containing an electrophile that could react covalently and specifically with this residue. Among the various possible electrophiles (Table 4), introduction of sulfonyl fluoride placed on the side chain of L-diaminopropionic acid in P2 (L-Dap; FIG. 9A) placed the electrophile at proper distance and juxtaposition for reaction with Lys311, without altering the pose of the other substructures. Indeed, we found that this agent efficiently formed a covalent adduct with the BIR3 of XIAP, as clearly appreciable using both SDS gel electrophoresis and mass spectrometry (FIGS. 9B, 9C) of the complex between BIR3 of XIAP and the agent NMe-Ala-pSFB-Dap-Pro-Phe-NH$_2$(SEQ ID NO: 23) (compound 32) where pSFB-Dap represent a p-Sulfonyl fluoride benzoic acid coupled via amide bond to the side chain amino group of an L-Dap (L-diaminopropionic acid) in P2. The IC$_{50}$ value for this compound against XIAP BIR3 was 11.3 nM, in contrary to the $IC_{50}$ values for cIAP1 and cIAP2 of 181 nM, and 304 nM, respectively (FIG. 9D, Table 4). These results confirmed our hypothesis that we can design a compound that can selectively targets the Lys311 is present just in XIAP BIR3. Hence, proper combination of this covalent P2 substituent with the above identified P3/P4 (or in principle any previously identified P3/P4 substituents such as those present in clinical candidates GDC-0152 or LCL161, for example) could lead to potent and selective XIAP antagonists. Several agents were therefore prepared as listed in Table 4. Among these agents, compound 34 (with a 2-(3-fluorobenzyl)-6-(pyrrolidine-2-yl)pyrazine in P3/P4; FIG. 9E) displayed a remarkable $IC_{50}$ value for XIAP BIR3 of 16.6 nM, and very modest inhibition of cIAP1 and cIAP2 with $IC_{50}$ values >200 nM for both proteins (FIG. 9H). SDS gel electrophoresis and mass spectrometry data confirmed the covalent interaction of this agent with XIAP BIR3 (FIGS. 9F, 9G) but not with cIAP1 or cIAP2 (FIG. 9J). We mutated XIAP BIR3 not only at the Lys311 with a Glu (XIAP BIR3 K311E), but also the nearby Lys322 with an Ala (XIAP BIR3 K322A) to further confirm if the covalent interaction is specific to the Lys311. SDS gel electrophoresis data confirmed that the covalent interaction is present just when the target protein has the Lys311 (FIG. 9I). Furthermore, mutating Lys311 with a glutamic acid in BTR3 of XIAP resulted in a drop in affinity also in the DELFIA displacement assays for compound 34 ($IC_{50}$ values dropped from 16.6 nM with wt-BIR3 to >1 µM when the agent was tested against the Lys311Glu mutant, while the inhibition is not affected by the mutation of Lys322 with an Ala, $IC_{50}$=19.7 nM; FIG. 9K) further clearly substantiating our SDS gel data implicating XIAP BTR3 Lys311 as the target for the covalent compound.

TABLE 4

Relative binding affinities and selectivity for XIAP BIR3 targeting covalent agents. $IC_{50}$ values with respective standard errors for the ability of test agents to displace a reference AVPI peptide from the BIR3 domains of XIAP, cIAP1, and cIAP2, were obtained with a DELFIA assay. Selectivity was calculated as the ratio of cIAP1 or cIAP2 $IC_{50}$ values versus $IC_{50}$ values for XIAP.

N-Me-Ala-P2-P3/P4

| | | | cIAP1 | | cIAP2 | |
|---|---|---|---|---|---|---|
| Structure | $IC_{50}$ (nM) | XIAP $IC_{50}$ (nM) | Selectivity cIAP1/ XIAP | $IC_{50}$ (nM) | Selectivity cIAP2/ XIAP |
| 32 | 11.3 ± 0.8 | 181.0 ± 20.1 | 16.0 | 304.0 ± 60.2 | 27.0 |
| 33 | 47.3 ± 3.3 | 264.1 ± 35.5 | 5.6 | 212.1 ± 8.9 | 4.5 |

TABLE 4-continued

Relative binding affinities and selectivity for XIAP BIR3 targeting covalent agents. IC$_{50}$ values with respective standard errors for the ability of test agents to displace a reference AVPI peptide from the BIR3 domains of XIAP, cIAP1, and cIAP2, were obtained with a DELFIA assay. Selectivity was calculated as the ratio of cIAP1 or cIAP2 IC$_{50}$ values versus IC$_{50}$ values for XIAP.

N-Me-Ala-P2-P3/P4

| | | | cIAP1 | cIAP2 | |
| --- | --- | --- | --- | --- | --- |
| Structure | IC$_{50}$ (nM) | XIAP IC$_{50}$ (nM) | Selectivity cIAP1/ XIAP | IC$_{50}$ (nM) | Selectivity cIAP2/ XIAP |
| 34 | 16.6 ± 2.1 | >200 | >12.0 | 353.3 ± 118.2 | 17.6 |
| 34* | 189.4 ± 1.3 | >1000 | >5.3 | >1000 | >5.3 |

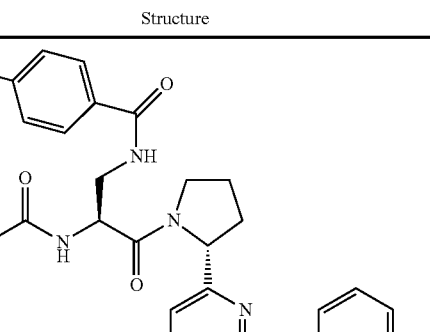

34

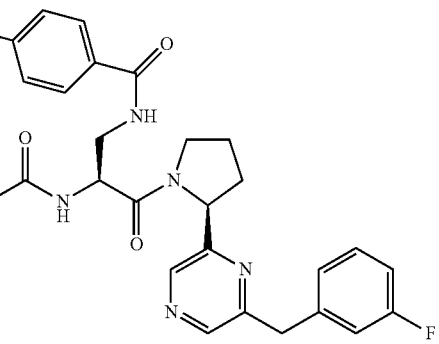

34*

Figure 10A:
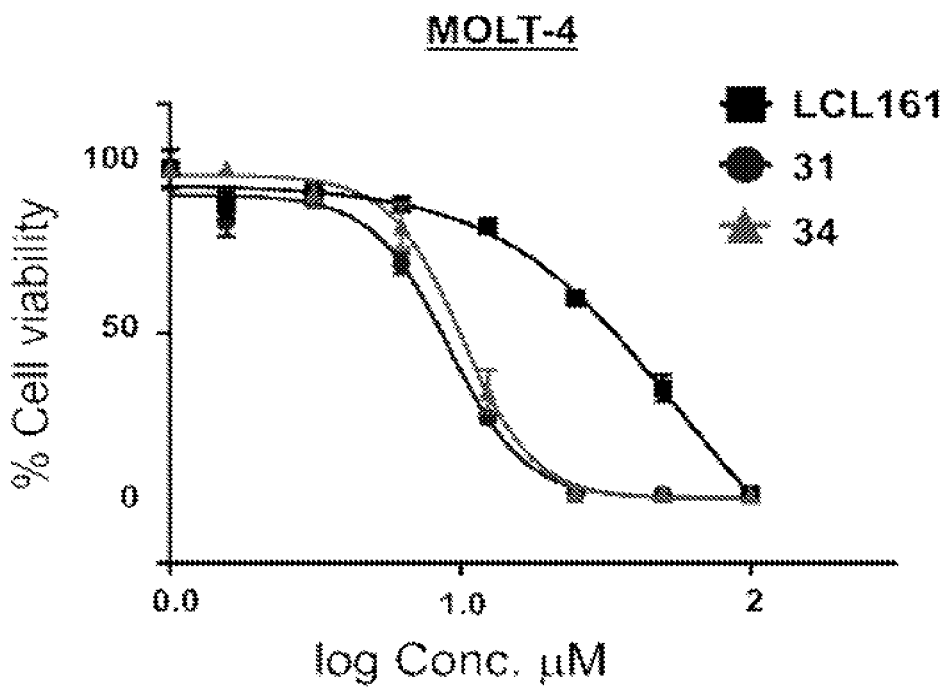
FIGS. 10A-10E. Comparative cellular activity of LCL161, compound 31, and compound 34 in ALL, MM, and pancreatic cancer cell lines.
Figure 10B:
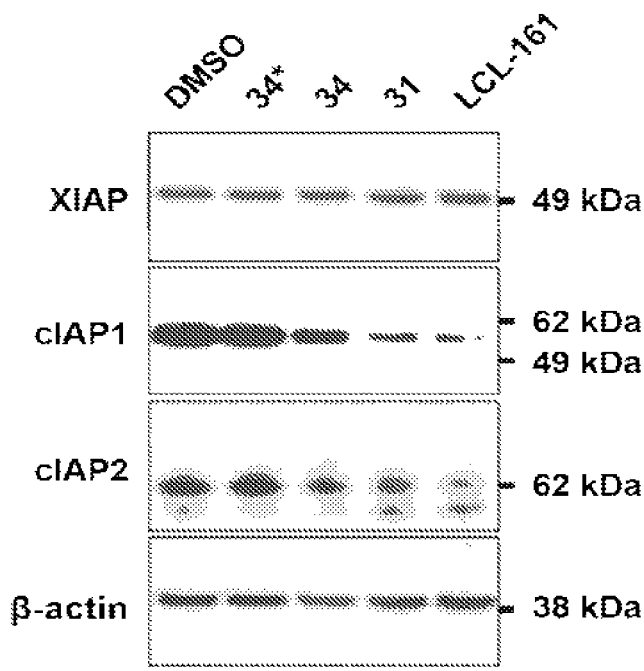
Figure 10C:
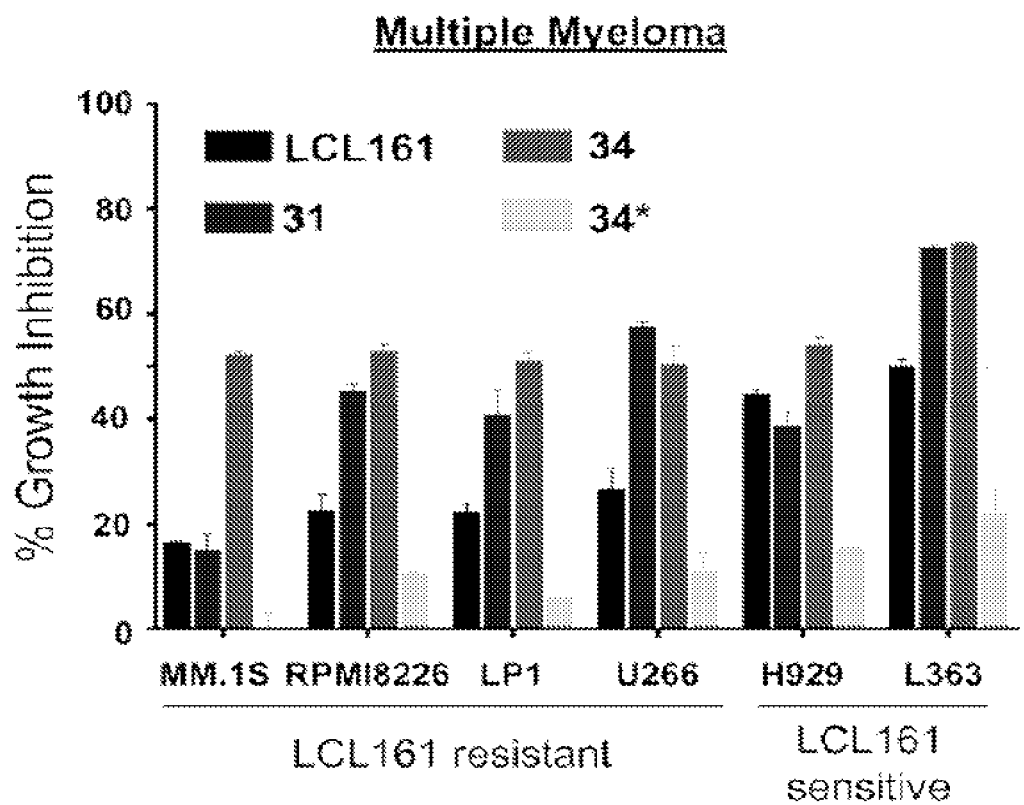
Figure 10D:
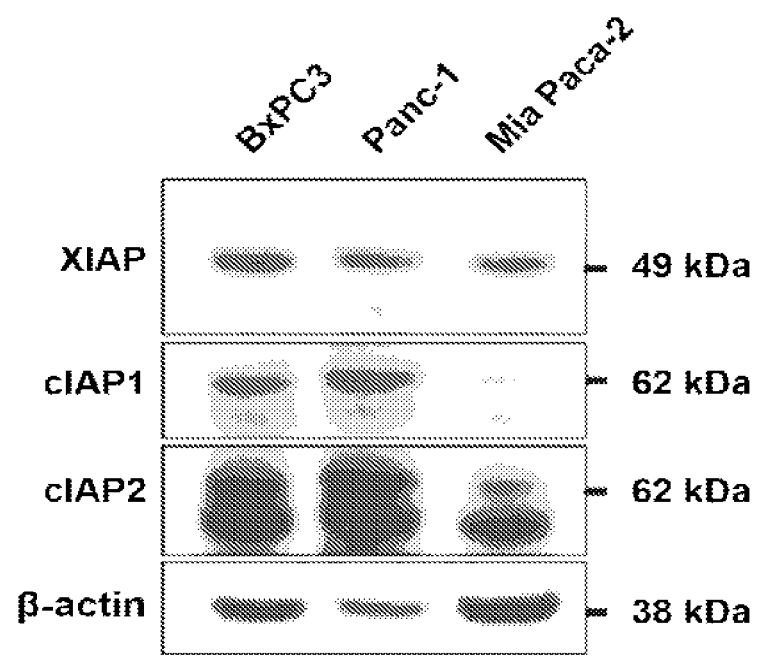
Figure 10E:
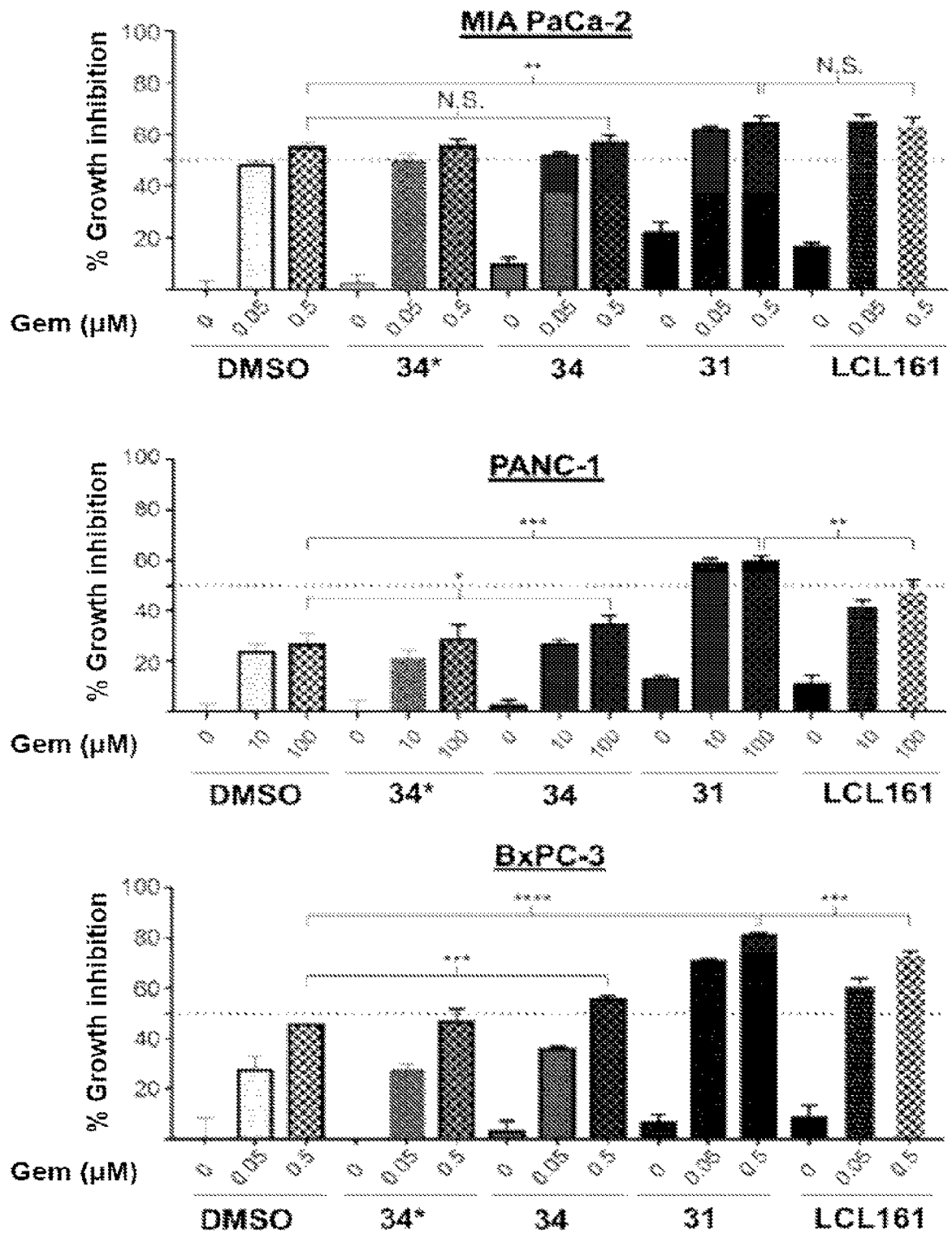

The novel pan-IAP agent and the XIAP-BIR3 covalent agent are both effective against LCL161 resistant cell lines and sensitize cell lines to chemotherapy. To further characterize the cellular activity of the identified compounds, we tested them against the LCL161-resistant Acute Lymphoblastic Leukemia (ALL) cell line MOLT-4. Cell viability assay confirmed that LCL161 is not particularly active against this cell line, despite it causes significant degradation of both cIAP1 and cIAP2. On the contrary, both the pan-IAP compound 31 and the XIAP BIR3 covalent compound 34 (FIG. 10A) were equally effective with IC$_{50}$ values in the single digit micromolar range. Interestingly, in this cell line compound 31 was able to induce cIAP1 and cIAP2 degradation, like LCL161 and as expected by its pan-IAP inhibitory activity, while compound 34 (and its inactive diastereoisomer compound 34*) was less effective in inducing degradation of these proteins in agreement with its increased activity against XIAP BIR3 compared to these other two IAPs (FIG. 10B). To further corroborate these data, we compared the activity of our agents side by side with LCL161 against a panel of multiple myeloma (MM) cell lines, given the clinical application of LCL161 for this indication in clinical trials. Of the 6 MM cell lines tested, two are known to be LCL161 sensitive (namely, H929 and L363) while 4 others are known to be LCL161 resistant (namely, MM1S, RPMI 8226, LP1, and U266). In agreement, we found that LCL161 was particularly active in the two sensitive cell lines; likewise, both compound 31 and compound 34 were approximately equipotent in these LCL161-sensitive MM cell lines (FIG. 10C). However, and in agreement with the data with MOLT-4, compound 31 and 34 (but not its less active enantiomer, 34*) were equally effective against the LCL161-resistant MM cell lines RPMI 8226, LP1 and U266, while only compound 34 was effective against the cell line MM1 S (FIG. 10C). Finally, to assess whether our agent can restore cancer cell sensitivity in chemoresistant cell lines, we tested LCL161, compound 31, and compound 34 in combination with gemcitabine in various pancreatic cancer cell lines (FIG. 10E). In the most gemcitabine-sensitive cell line (MIA PaCa-2 that expresses only XIAP; FIG. 10D), the effect of the SMAC mimetics is at best additive, given the efficacy of gemcitabine as a single agent (FIG. 10E). However, for less sensitive cell lines such as BxPC3, and to the largest extent the gemcitabine-resistant cell line PANC-1 (both expressing XIAP, cIAP1, and cIAP2; FIG. 10D), both LCL161 and to a greater extent compound 31, were able to significantly restore growth inhibition by gemcitabine (FIG. 10E). To rule out that the activity of our agents compared to LCL161 could be due to inhibition of the BIR2 domain of XIAP, the BIR2 domain was expressed and a DELFIA assay was further developed, and the compounds tested. The data, reported in supplementary Table 5, indicated that like LCL161, our agents displayed only modest affinity for this domain (in the micromolar range).

TABLE 5

$IC_{50}$ values with respective standard errors for the BIR2 domain of XIAP were obtained with a DELFIA displacement assay.

| Compound | XIAP-BIR2 $IC_{50}$ (DELFIA, nM) |
|---|---|
| LCL161 | 659 ± 67 |
| 24 | 1396 ± 221 |
| 25 | 1163 ± 185 |
| 26 | 782 ± 151 |
| 31 | 981 ± 90 |
| 32 | 2219 ± 870 |
| 34 | 1450 ± 248 |

Figure 6A:
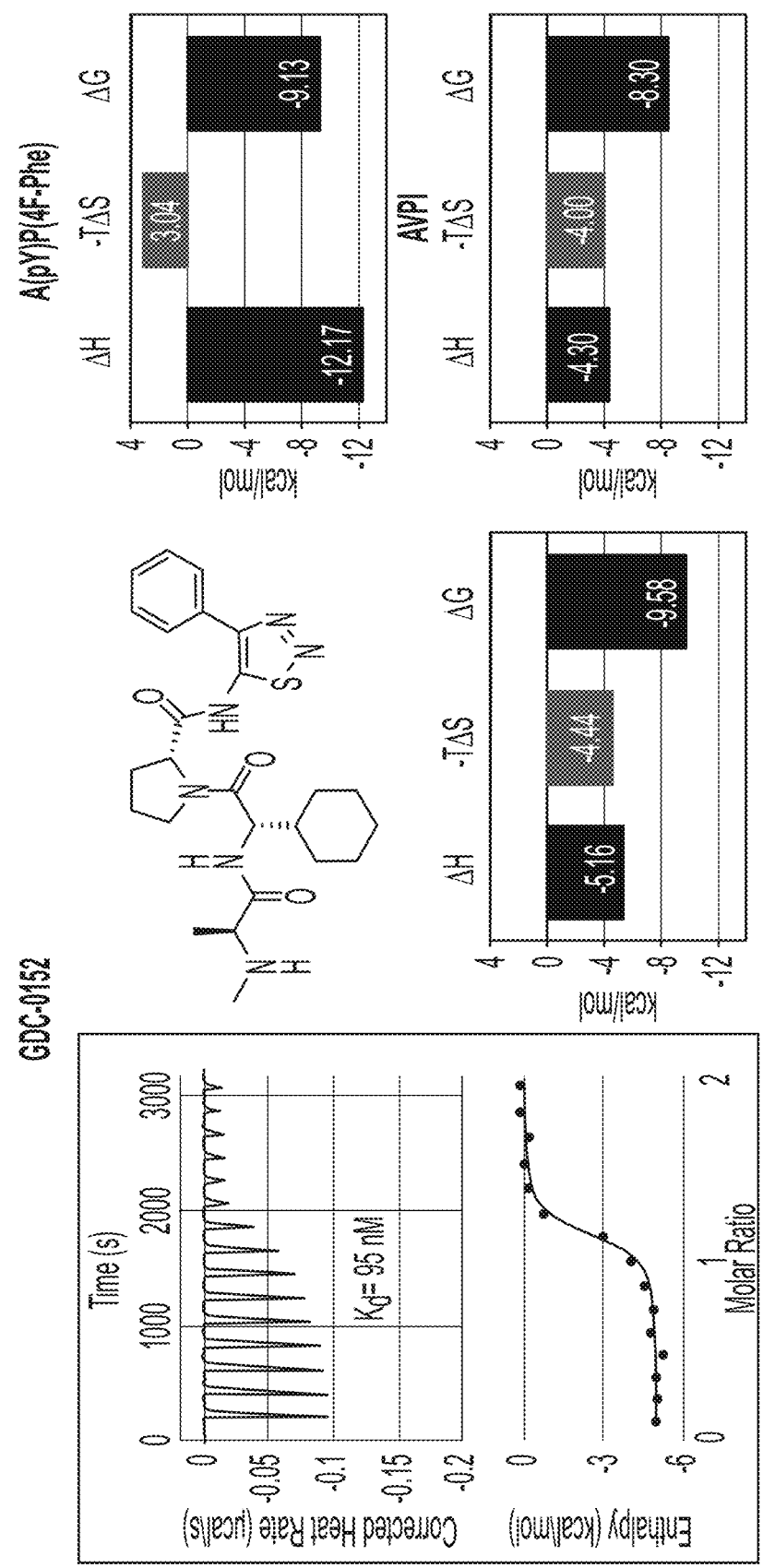
FIGS. 6A-6D. Thermodynamic analysis of A(pY)P(4F-Phe) (SEQ ID NO: 6), GDC-0152, and AVPI (SEQ ID NO: 4) followed by selectivity studies against the BIR3 domains of XIAP, cIAP1, and cIAP2.
Figure 6B:
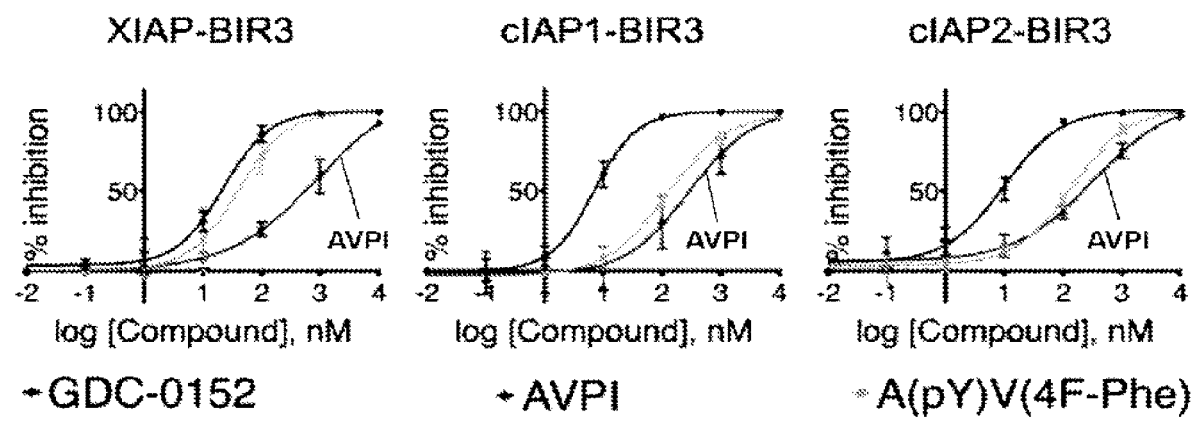
Figure 6C:
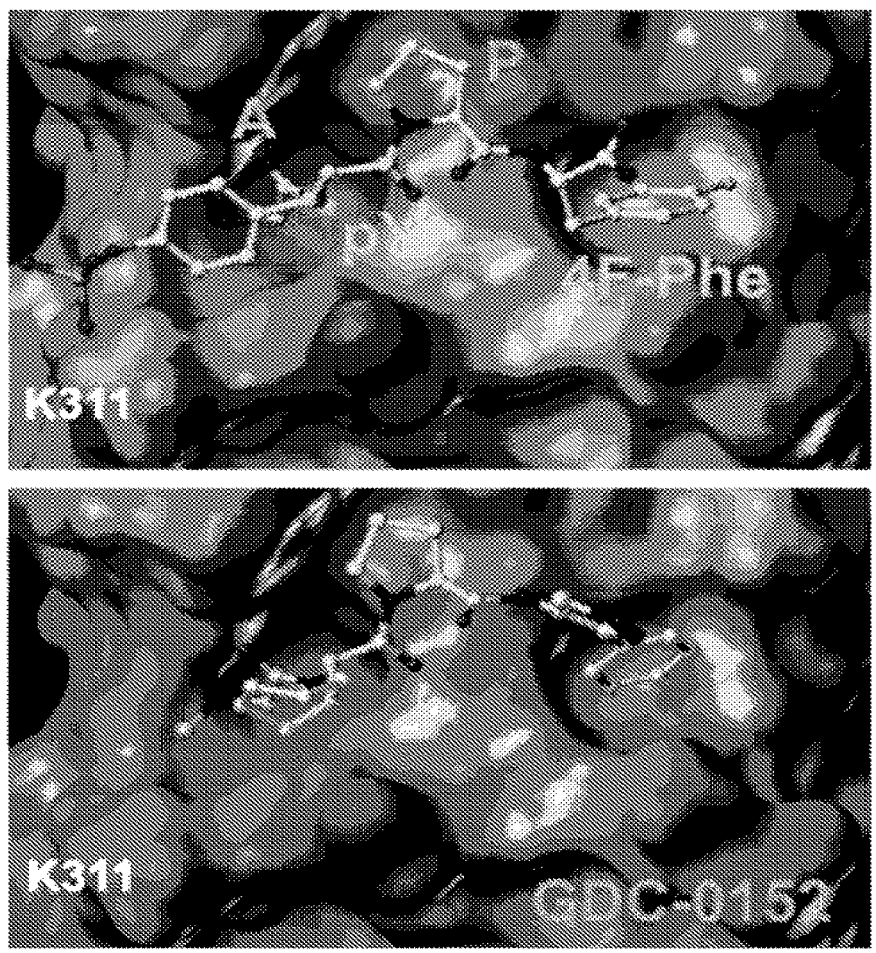
Figures 6D, 7A:
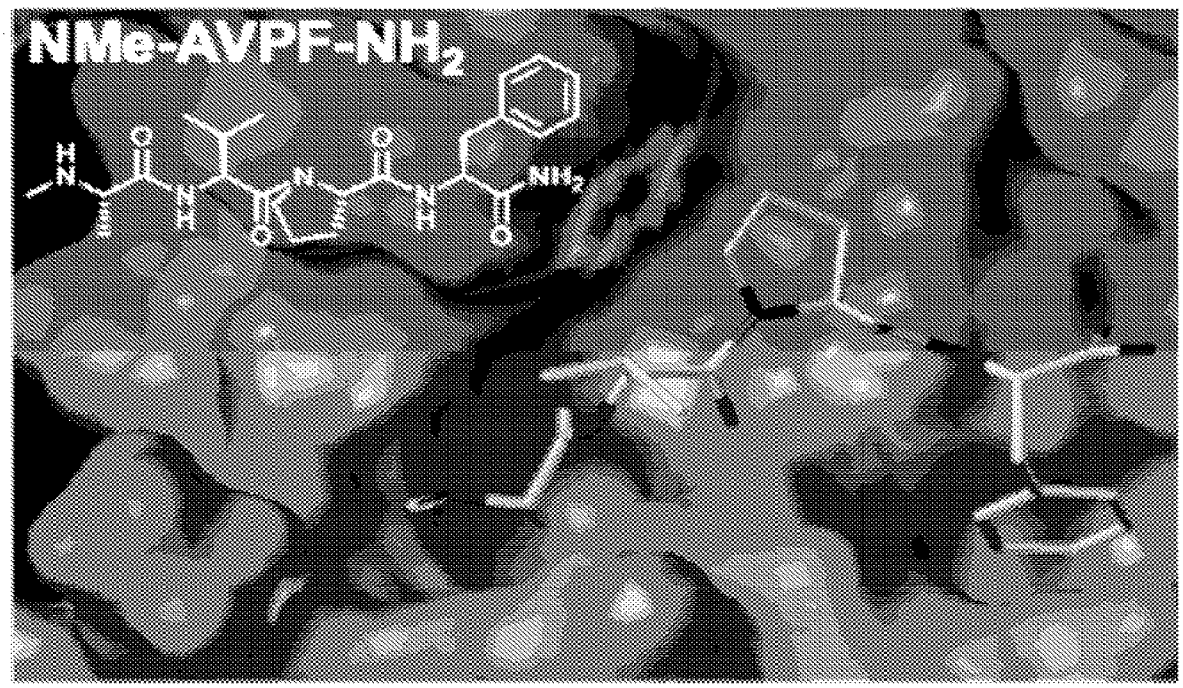
FIGS. 7A-7I. Molecular docking and thermodynamic analysis of N-Me-AVPF-NH$_2$ (SEQ ID NO: 7), LCL161, and compound 1 followed by selectivity studies against the BIR3 domains of XIAP, cIAP1, and cIAP2.

In the realm of drug discovery, the design of effective therapeutics often relies on a lengthy and elaborate iterative process known as the hit-to-lead optimization process. In such process, the chemical structure of a hit compound is iteratively modified in an attempt to increase potency and in most cases also selectivity against the given target. In some circumstances, pan-active compounds (i.e., agents that inhibit simultaneously several members of a given class of proteins) are desirable or needed to achieve maximal efficacy. In targeting protein-protein interaction (PPIs), these studies usually rely primarily on assessments of potency of test agents using biochemical assays that can measure the ability of the new molecules to displace a reference compound. Hence, one can usually follow the iterative optimizations of potency by measuring $IC_{50}$ values of test agents, and the data are interpreted and used to guide next iteration of synthesis and testing. This approach is best suited when supported by structural data of the complex between the test agents and the target(s) that can be used to formulate hypotheses. Recently, the use of biophysical approaches has been introduced at both ends of the hit-to-lead optimization process particularly for the design of PPIs antagonists, first as screening tools to discover initial fragment hits in fragment-based drug discovery, and finally to validate a handful of optimized agents. Traditionally, during the optimization process, biochemical $IC_{50}$ measurements are usually preferred as these offer a more rapid and cost effective means to rank order agents. However, we and others have recently reported that rapid determination of enthalpy of binding can be achieved for a large number of congeneric agents (49) or in combinatorial libraries (48) fairly efficiently. Our working hypothesis was that ligands displaying the largest enthalpy of binding would result not only as more potent but also as more selective for a given target (48). We found however that this hypothesis is only partially correct, especially with respect to potency, as unpredictable enthalpy/entropy compensation mechanisms play a major role in determining the binding affinity of a given molecule (50). In this study we targeted the BIR3 domain of XIAP given that most known inhibitors discovered to date are usually more potent for two other members of this protein family, namely cIAP1 and cIAP2 (51). The binding properties of these tetrapeptide mimetics have been well established, requiring invariably an Ala and a Pro residue (or mimetics) in positions P1 and P3, respectively, while aliphatic and aromatic residues are preferred in P2 and P4, respectively (FIG. 7A). Recently, we surprisingly discovered using an enthalpy screening campaign against the BIR3 domain of XIAP that the position P2 can be occupied by a phosphotyrosine residue, resulting in molecules with a large enthalpy of binding for XIAP BIR3 (48). Likewise, replacing the P2 valine residue in AVPF (SEQ ID NO: 5) with a non-hydrolysable 4-phosphonomethyl-Phe resulted in an agent (compound 1) with an increased $-\Delta H$ of binding (FIGS. 7G, 7H), resulting relatively more selective for XIAP BIR3 versus cIAP1/2 in the biochemical displacement assay ($IC_{50}$ values 35 nM, 198 nM and 364 nM against the BIR3 domains of XIAP, cIAP1, and cIAP2, respectively; Table 1). To assess whether thermodynamic based structure-activity relationship (SAR) studies can be used to optimize these initial agents into more potent and selective, and/or more potent and pan-active compounds, we systematically explored various substitutions in the P2 position with bioisoters of a 4-phosphonomethyl-Phe, and in P3/P4 with bioisosters of pyrrolidine-aromatic moieties (Table 1, FIGS. 11A-11B). In particular, in an attempt to predict whether given combinations of P2 and P3/P4 elements could result in more potent and/or more selective compounds, we decided to tabulate the enthalpy and entropy contribution of binding to the BIR3 domain of XIAP of each P2 and P3/P4 elements with respect to a reference molecule, namely NMe-Ala-Val-Pro-Phe-NH$_2$ (SEQ ID NO: 7). Therefore, differential $\delta\Delta H$ and $\delta(-T\Delta S)$ values were tabulated from experimental ITC curves and assigned to each P2 element in the NMe-Ala-P2-Pro-Phe-NH$_2$ compounds and to each P3/P4 elements in the NMe-Ala-Val-P3/P4 agents (Table 1). Reporting these values using a thermodynamic Craig plot of $\delta\Delta H$ versus $\delta(-T\Delta S)$ for each agent (FIG. 8A) provided a visualization of the entropy-enthalpy compensation phenomenon for each element. Indeed, in this representation, compounds that fall near or on the diagonal would have a similar $\Delta G$ of binding (hence, a similar dissociation constant) as the reference molecule, regardless of $\Delta H$ and -TAS values. For example, the 4-Phosphonomethyl-Phe residue in P2 (compound 1, Table 1, FIG. 7G) is approximately equipotent with NMe-AVPF-NH2 (SEQ ID NO: 7) despite the larger $\Delta H$ of binding that was entirely compensated by a concomitant loss in entropy (Table 1, FIG. 8A). However, while it is very challenging to alter the entropy/enthalpy compensation of individual substituents (50), we sought to verify if it is possible to predict the thermodynamic profile of combined P2 and P3/P4 elements based on their individual entropy and enthalpy contributions to binding. We found that simple additivity of the thermodynamic parameters resulted in a remarkably close agreement between predicted ($\Delta H_{pred}$ and $-T\Delta S_{pred}$) and experimental thermodynamic values in agents containing various combinations of P2 and P3/P4 elements (FIG. 8C, Table 2). Practically, we could predict $\Delta H_{pred}$, $-T\Delta S_{pred}$, and $\Delta G_{pred}$ using the simple relation: $\Delta X_{pred} = \Delta X_{ref} + \delta(\Delta X)_{P2} + \delta(\Delta X)_{P3/P4}$, where $\Delta X_{ref}$ are the thermodynamics parameters of the reference agent N-Me-AVPF-NH$_2$ (SEQ ID NO: 7) ($\Delta H = -7.8$ kcal/mol, and $-T\Delta S = -1$ kcal/mol), and $\delta(\Delta X)$ values are calculated as in Table 1 for each P2 and P3/P4 element. For example, merging the P2 element of compound 2 with the P3/P4 of compound 19 resulted in compound 22 ($\Delta H_{pred} - 8 =$ kcal/ mol, $\Delta H_{exp}=-8.8$; $-T\Delta S_{pred}=-0.8$, $-T\Delta S_{exp}=0.1$ kcal/mol), while merging compound 14 P2 with compound 17 P3/P4 resulted in compound 31 ($\Delta H_{pred}=-4.7$=kcal/mol, $\Delta H_{exp}=-5.1$; $-T\Delta S_{pred}=-5.7$, $-T\Delta S_{exp}=-4.5$ kcal/mol) (FIG. 8B). A complete list of combined molecules and their respective predicted and experimental thermodynamic values is reported in Table 2, while a plot illustrating the correlation is reported in FIG. 8C. We also found a very good correlation between the thermodynamic Kd values and $IC_{50}$ values determined using a DELFIA displacement assay (Table 3). Furthermore, to assess the selectivity of these agents, $IC_{50}$ values were determined also against the BIR3 domains of cIAP1, and cIAP2 (Table 3). From these studies we concluded that nearly additive behavior can be observed in the thermodynamic parameters of various substituents, and that a thermodynamic Craig plot can be useful in selecting suitable combinations of substituents with the predicted desired thermodynamics of binding. For example, selecting for agents that could confer the greatest enthalpy of binding also correlated with largest selectivity as exemplified by compound 28, the agent with the largest $\Delta H$ of binding to XIAP BIR3 ($\Delta H=-14$ kcal/mol; FIG. 8A, Table 2) that also resulted in the most selective albeit not the most potent agent (Table 3). Likewise, compound 31 was among the most potent agents, while because it displayed a relatively smaller enthalpy of binding ($\Delta H=-5.1$ kcal/mol; FIG. 8A, Table 2) it was also anticipated to be less selective, as indeed experimentally observed (Table 3). These studies clearly suggested that thermodynamic measurements aimed at dissecting entropy and enthalpy contributions in various substituents in a hit molecule can be very effective in selecting compounds with the most desired binding profiles during the hit-to-lead optimization process. While the approach was very successful in identifying potent pan-active compounds such as compound 31, attaining even relatively modest selectivity often came at the expense of potency mostly because of the well-known issue of enthalpy/entropy compensation.

Figure 12:
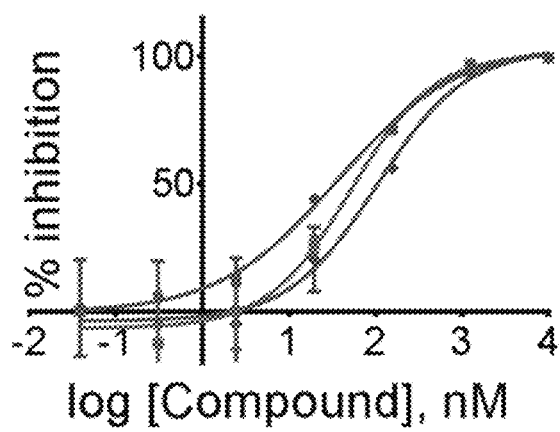
FIG. 12. Dose-response curves in DELFIA displacement assays for compound 31 against XIAP BIR3, XIAP BIR3 K311E, and XIAP BIR3 K322A, respectively.
Figure 14:
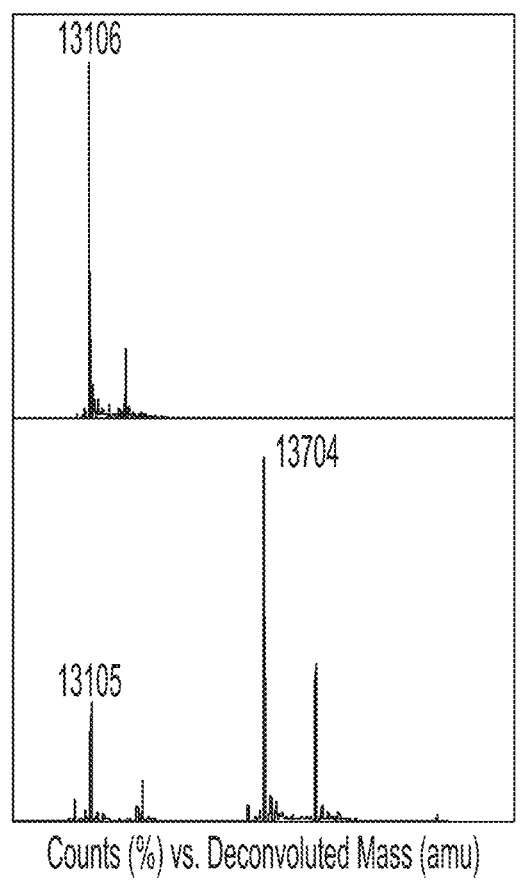
FIG. 14. LC-MS spectra of the BIR3 domain of XIAP in the absence (top) and presence (bottom) of compound 33 at a protein-ligand ratio 1:2.

Therefore, we next conducted molecular modeling studies to try to rationalize the observed partial selectivity and to design more potent and selective agents. As we recognized in our most recent work, a reasonable responsible residue for the selectivity of the P2 pTyr derivatives was Lys311, which is indeed a Glu residue in both cIAP1 and cIAP2. Recently, a few reports have emerged that successfully demonstrated covalent targeting of Lys residues in active sites of proteins by introduction of appropriately placed electrophiles on an existing ligand (52). These examples include not only targeting active site catalytic and non-catalytic Lys residues (53,54) but, and perhaps most excitingly, also targeting surface exposed Lys residues at protein-protein interfaces, such as in the recent examples of a covalent Mcl-1 inhibitor (55), and a covalent inhibitor of MDM2/P53 interactions (56). Accordingly, and based on our observations that our agents may target Lys311, we introduced a sulfonyl fluoride at various P2 positions (Table 4), and assessed the ability of these resulting agents to form a stable covalent bond with XIAP BIR3 by various means. Using molecular modeling we could anticipate that coupling a p-Sulfonyl fluoride-benzoic acid to the side chain of a P2 diaminopropionic acid (Dap), would juxtapose the electrophile with Lys311, and could form a covalent bond (FIG. 9A). Excitingly, agents 32 (P2 p-sulfonyl-benzoic acid Dap; P3/P4, Pro-Phe-NH$_2$) formed a stable covalent bond with XIAP BIR3 as detected by SDS gel electrophoresis and mass spectrometry (FIGS. 9B, 9C). In the DELFIA displacement assay panel, compound 32 was significantly more potent against XIAP BIR3 compared to cIAP1 and cIAP2 (Table 4, FIG. 9D). The covalent binding was fairly selective as changing the sulfonyl-fluoride from the para to the meta position resulted in an incomplete reaction and diminished activity (Table 4, FIG. 14). Next we introduced the P3/P4 element of compound 22 into compound 32 to obtain compound 34 (FIG. 9E), hence preserving selectivity (Table 4) and reducing the tPSA of the molecule (tPSA values 197 Å and 140 Å for compound 32 and compound 34, respectively). We were able to separate the two diasteroisomers of this agent differing for chirality at the pyrrolidinyl moiety. Testing these two agents, compound 34 and 34*, against XIAP BIR3 using SDS gel clearly revealed that only one agent, compound 34, but not its diasteroisomer compound 34*, formed a covalent adduct with the protein (FIG. 9F). Moreover, to further establish Lys311 as the residue targeted by these covalent agents we produced single mutant proteins in which either Lys311 or the nearby Lys322 (FIGS. 9A-9K) are mutated to Glu and Ala, respectively. SDS gel electrophoresis with these proteins in the absence and presence of compound 34 revealed indeed a covalent adduct only with wt BIR3 and for the Lys322Ala mutant, that preserved Lys311, whereas no covalent adduct was observed with the Lys311Glu mutant (FIG. 9I). Finally, in similar SDS gel electrophoresis experiments, we also noted that covalent adduct formation occurs only between compound 34 and XIAP BIR3, but not with the BIR3 domains of cIAP1 or cIAP2 (FIG. 9J). $IC_{50}$ values for compound 34 against the panel of BIR3 domains revealed indeed that this molecule is very potent and selective against BIR3 XIAP and compared to cIAP1 and cIAP2 (FIG. 9H, Table 4). Accordingly, mutating Lys311 with a glutamic acid in BIR3 of XIAP resulted in a drop in affinity for compound 34, while the activity is unaffected by the mutation of Lys322 (FIG. 9K). Hence, the thermodynamic driven approach has identified two classes of possible novel antagonists: compound 31, a novel pan-IAP inhibitor, and compound 34, a covalent XIAP BIR3 inhibitor. Of note and as expected, the activity of compound 31 was not affected by mutating Lys311 or Lys322 (FIG. 12). Perhaps another advantage of the covalent agents is that unlike the charged reversible agents such as compound 1 that possess a relatively large tPSA (197 Å$^2$), replacing the charged moiety with an electrophile reduced the polar surface area, as for example in compound 34 (tPSA=140 Å$^2$), presumably increasing cell permeability (57). Finally, compound 31 and LCL161 have both a similar tPSA value of 91 Å$^2$.

Currently the most advanced agent for these targets is the Novartis clinical candidate LCL161 that in our DELFIA assay presents $IC_{50}$ values in displacing a reference AVPI peptide (SEQ ID NO: 4) of 52.7, 10.4, and 12.9 nM against the BIR3 domains of XIAP, cIAP1, and cIAP2, respectively. The agent is currently in clinical trials for various indications including multiple myeloma and pancreatic cancer. The activity of this agent in multiple myeloma is not fully understood, but it is suspected to be mainly due to its ability to activate an immune response as a consequence to cIAP1/2 inhibition, rather than sensitizing cancer cells to apoptosis via the XIAP inhibition (10,58). LCL161 is not active against several cell lines and for example it showed limited in vitro and in vivo activity as a single agent against childhood cancer preclinical models (59). Accordingly, the acute lymphoblastic leukemia (ALL; the most common type of childhood cancer) cell line MOLT-4 was reported to be insensitive to the agent (60). Likewise, several MM cell lines were tested in various laboratories, and many of these were resistant to LCL161 (61). Because of the different binding and selectivity profiles of our agents, we sought to test them side by side with LCL161 in these cell lines. When testing agents 31 and 34 side by side with and LCL161 against MOLT-4 we noticed that while the LCL161 is very effective in inducing cIAP1 and cIAP2 degradation (FIG. 10B), the agent is less potent than both compound 34 and compound 31 in suppressing cell viability (FIG. 10A). This may be perhaps attributable to an increased affinity of our agents for the XIAP BIR3, although our data are still speculative in this regards and further investigations will be needed. Likewise, when profiling the agents against a panel of MM cell lines, both LCL161-sensitive (H929 and L363; FIG. 10C), and LCL161-resistant (RMPI, LP1, and U266; FIG. 10C), we observed again that our compound 31 and compound 34 inhibited cell proliferation in these cell lines equally well (FIG. 10C), while only compound 34 was effective against the MMS1 cell line. In all experiments, the less active enantiomer of compound 34 (namely compound 34*) was not effective, possibly ruling out non-specific cell killing effects due to the electrophile.

LCL161 is currently in clinical trials against advanced pancreatic cancers in combination with Abraxane and gemcitabine (https://clinicaltrials.gov/ct2/show/NCT01-934634). To assess if our agents could enhance gemcitabine (GEM) activity in both GEM-sensitive BxPC3 and MIA PaCa-2 cell lines (FIG. 10E), and the GEM-resistant PANC-1 cell line (FIG. 10E), we tested our agents in combination. For the GEM-sensitive MIA-PaCa-2 cell line, we found at best a modest significant additive effect for only compound 31 (FIG. 10E). However, when compound 34 or compound 31 were used in combination with cell lines PANC-1 and BxPC3, both expressing all 3 IAPs (FIG. 10D), we observed a significant synergism, with compound 31 producing the most remarkable effect against the GEM-resistant PANC-1 cell line (FIG. 10E).

Obviously the complex interplay between expression and regulation of the three oncogenes and the different activity of LCL161 compared to our agents can result in one or the other molecule to perform better against certain cell lines or situations (single agent versus combinations). Hence, the full potential of our agents in oncology and for other indications such as pulmonary fibrosis (62), has yet to be fully determined and it will require additional cellular mechanistic studies followed by detailed in vivo pharmacology and efficacy studies, and likely involving further optimizations including evaluating various war-heads for compound 34, exploring further P3/P4 substituents both compound 34 and compound 31, or obtaining homo- or hetero-dimeric versions of these agents (33,35,51,63). Nonetheless, we feel that our work presents several novel insights not only into the inhibition of this important class of targets, but also into the use of thermodynamic parameters to guide the hit-to-lead optimization process, and in targeting Lys residues with covalent agents. Our discoveries and considerations are likely of general applicability to other targets, and in particular those involving protein-protein interactions (PPIs) where ligands of peptide or peptide mimetic nature can be designed in a modular fashion. Given that PPIs represent a largely untapped target space, we believe that our studies provide novel insights into possible effective strategies to guide the identification and the optimization of potent and selective agents against this challenging class of drug targets.

Example 3: Materials and Methods

General chemistry. Solvent and reagents were commercially obtained and used without further purification. NMR spectra used to check concentration were recorded on Bruker Avance III 700 MHz. High-resolution mass spectral data were acquired on an Agilent LC-TOF instrument. RP-HPLC purifications were performed on a JASCO preparative system equipped with a PDA detector and a fraction collector controlled by a ChromNAV system (JASCO) on a Luna C18 10µ 10×250 mm (Phenomenex) to >95% purity. RP-chromatography purification for intermediates was performed using a CombiFlash Rf (Teledyne ISCO). LCL161 was obtained from MedChem Express.

Fmoc Protection of Unnatural AA

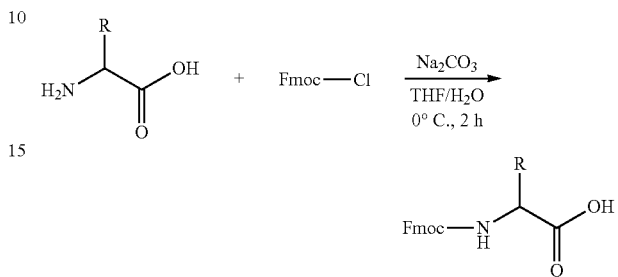

The unprotected amino acid (1 eq.) and $Na_2CO_3$ (3.75 eq.) were dissolved in THF/water (1:1) and cooled to 0° C. Fmoc chloride (1.1 eq.) was dissolved in THF and added dropwise to the mixture over 10 min. The reaction was stirred for 2 h at 0° C., after which the organic solvent was evaporated under reduced pressure and the pH lowered to 0 using 3 M HCl. The aqueous phase was extracted with AcOEt (3×) and the collected organic phases were dried with $Na_2SO_4$, filtered and evaporated. The resulting crude was purified using preparative RP-chromatography using a water/acetonitrile (10% to 100%). The protected amino acid was characterized by HRMS.

| Amino Acid | Calculated Mass | Found Mass | Yield |
|---|---|---|---|
| DL-2, Fluoro-4, Trifluoromethyl-5, methyl-Phenylalanine | 487.1407 | 488.1479 $[M+H]^+$ | 94.9% |
| DL-2, Fluoro-4, Trifluoromethyl-Phenylalanine | 473.1250 | 473.1245 $[M+H]^+$ | 50.8% |
| DL-3, Chloro-4, Trifluoromethyl-Phenylalanine | 512.0852 | 512.0681 $[M+Na+H]^+$ | 96.9% |
| DL-3, Chloro-5, Trifluoromethyl-Phenylalanine | 512.0852 | 512.0687 $[M+Na+H]^+$ | 72.6% |

General Peptide Synthesis. Peptides were synthesized by using standard solid-phase synthesis protocols either by Innopep, or in our laboratory except using standard microwave-assisted Fmoc peptide synthesis protocols on Rink amide resin on a Liberty Blue Peptide Synthesizer (CEM). For each coupling reaction, 6 eq. of Fmoc-AA, 3 eq. of DIC and 1 eq. of OximaPure in 4.5 mL of DMF were used. The coupling reaction was allowed to proceed for 5 min at 90° C. Fmoc deprotection was performed by treating the resin-bound peptide with 20% piperidine in DMF (2×3 mL) for 3 min at 90° C.

Peptides were cleaved from Rink amide resin with a cleavage cocktail containing TFA/TIS/water/phenol (94:2:2:2) for 3 h. The cleaving solution was filtered from the resin, evaporated under reduced pressure and the peptides precipitated in $Et_2O$, centrifuged and dried in high vacuum. The crude peptide was purified by preparative RP-HPLC using a Luna C18 column (Phenomenex) and water/acetonitrile gradient (5% to 70%) containing 0.1% TFA. The final compound was characterized by HRMS.

General Synthesis of Covalent Compounds (32, 33, 34)

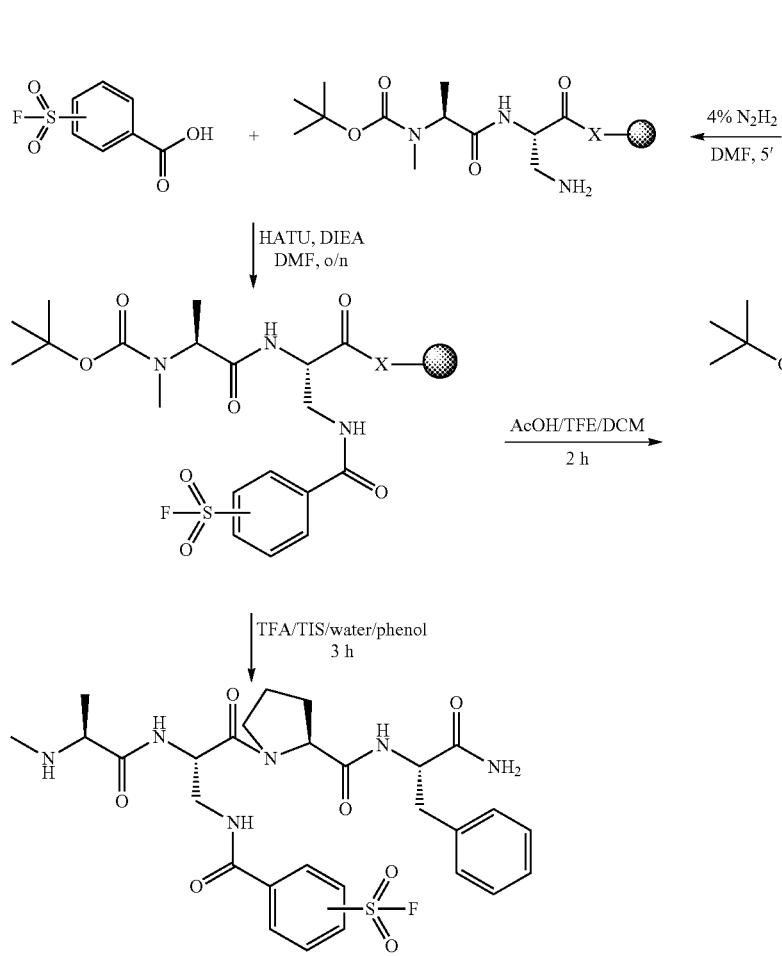
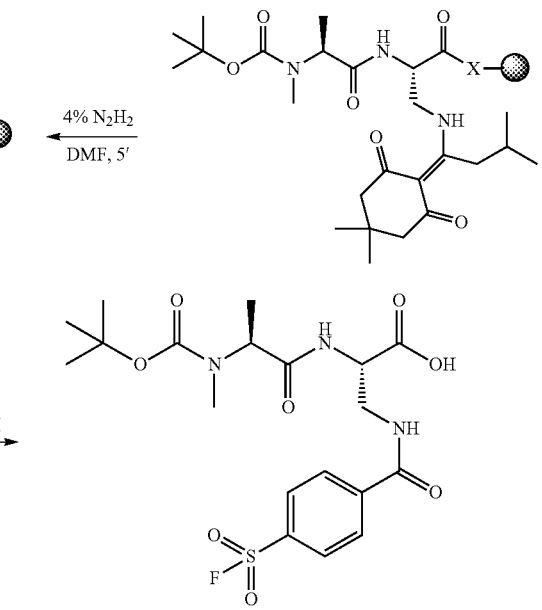

Compounds 33 and 34 were synthesized using standard microwave-assisted Fmoc peptide synthesis protocols on Rink amide resin on a Liberty Blue Peptide Synthesizer (CEM). For each coupling reaction, 6 eq. of Fmoc-AA, 3 eq. of DIC and 1 eq. of OximaPure in 4.5 mL of DMF were used. The coupling reaction was allowed to proceed for 5 min at 90° C. Fmoc deprotection was performed by treating the resin-bound peptide with 20% piperidine in DMF (2×3 mL) for 3 min at 90° C.

Compound 34 was synthesized using standard Fmoc peptide synthesis protocols on 2-Chlorotrityl Chloride resin (2CTC). For each coupling reaction, 3 eq. of Fmoc-AA, 3 eq. of HATU and 5 eq. of DIEA in 1.5 mL of DMF were used. The coupling reaction was allowed to proceed for 45 min at rt. Fmoc deprotection was performed by treating the resin-bound peptide with 20% piperidine in DMF (2×3 mL) for 15 min.

The introduction of the covalent warhead was accomplished on-resin using the orthogonally protected sidechain of Dap(ivDde), which was removed using 4% $N_2H_2$ in DMF (3×5 mL) for 5 min. A solution of 3- or 4-fluorosulfonyl benzoic acid (1.2 eq.), HATU (2 eq.) and DIEA (5 eq.) in DMF was then added to the resin for an overnight coupling.

The cleavage conditions were chosen according to the resin used in the synthesis:

1. Peptides were cleaved from Rink amide resin with a cleavage cocktail containing TFA/TIS/water/phenol (94:2:2:2) for 3 h. The cleaving solution was filtered from the resin, evaporated under reduced pressure and the peptides precipitated in $Et_2O$, centrifuged and dried in high vacuum.

2. A cleavage cocktail containing AcOH/TFE/DCM (1:2:7) was used in order to obtain the fully protected sequence from 2CTC resin.

In both cases, the crude peptide was purified by preparative RP-HPLC using a Luna C18 column (Phenomenex) and water/acetonitrile gradient (5% to 70%) containing 0.1% TFA. The final compound was characterized by HRMS.

Synthesis of Compound 34

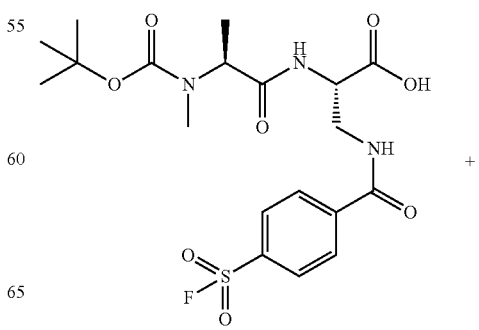 +

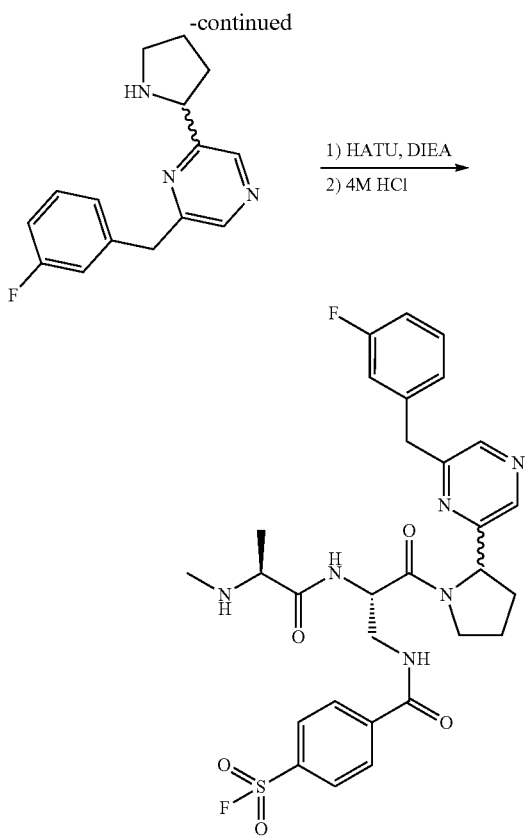

The fully protected dipeptide (1 eq.) and the desired amine (1.2 eq.) were dissolved in THF. This solution was then added HATU (1.5 eq.) and DIEA (2 eq.) and the reaction stirred overnight at rt. The organic solvent was evaporated, the crude dissolved in DCM and then washed with 1 M HCl (2×), NaHCO$_3$ sat. (2×), water and brine. The organic phase was dried over Na$_2$SO$_4$ and evaporated. The crude was then suspended in 1 mL of 4 M HCl in dioxane and stirred for 1 h, then evaporated. The resulting crude was purified using RP-HPLC, and the final compound characterized by HRMS.

| Compound | Calcd Mass | Found Mass | Yield |
|---|---|---|---|
| 31 | 581.2546 | 581.2455 [M+H]$^+$ | 36% |
| 32 | 619.2345 | 619.2384 [M+H]$^+$ | 23% |
| 33 | 619.2345 | 619.2460 [M+H]$^+$ | 27% |
| 34 | 615.2196 | 615.2309 [M+H]$^+$ | 18% |
| 34* | 615.2458 | 615.2402 [M+H]$^+$ | 7% |

Protein expression and purification. For the expression of XIAP BIR3, a pET15b vector encoding for the human BIR3 domain of XIAP fragment (residues 253-347) and an N-terminal His tag was transformed into *E. coli* BL21(DE3) Gold cells. The transformed cells were transferred to LB medium at 37° C. with 100 μg/L of ampicillin until reaching an OD$_{600}$ of 0.6-0.7, followed by induction with 1 mM IPTG overnight at 25° C. Bacteria were collected and lysed by sonication at 4° C. The overexpressed protein was purified using Ni$^{2+}$ affinity chromatography. The buffer of the eluted protein was exchanged with a desalting column into an aqueous buffer composed of 50 mM MES pH=6.0, 100 mM NaCl, 50 μM Zn(Ac)$_2$, and 1 mM DTT. The BIR3 domain of XIAP where the Lys 311 was mutated to Glu (K311E), was expressed in the same way described previously; while the BIR3 domain of XIAP where the Lys 322 was mutated to Ala (K322A), was expressed as previously described but after Ni$^{2+}$ affinity chromatography the buffer of the protein was exchange with a desalting column in 25 mM TRIS pH=7.5, 300 mM NaCl, 50 μM Zn(Ac)$_2$, and 1 mM DTT. The recombinant BIR3 domains of cIAP1 and cIAP2 with N-terminal 6×His tag (SEQ ID NO: 10) were obtained from Reaction Biology Corp. (Malvern, Pa.).

ITC measurements. Isothermal titration calorimetry measurements were performed using the Affinity ITC Autosampler from TA Instruments (New Castle, Del.). The titrations were performed in a reverse fashion by titrating the protein into the ligand solution. All the measurements were performed at 25° C. dissolving the agents in buffer 50 mM MES, pH=6.0, 100 mM NaCl, 50 μM Zn(Ac)$_2$, and 1 mM DTT, and a final DMSO concentration of 1%. The syringe was filled with a 200 μM solution of XIAP BIR3 domain and 15 injections of 2.5 μL each were performed into the cell containing a 25 μM solution of the compounds. The injections were made at a 200-second interval with a stirring speed of 75 rpm. All the solutions were kept in the autosampler at 4° C. in two different 96-well plates for the reaction cell solutions and syringe solutions, respectively. The volume of the reaction cell is 180 μL, but 630 μL were loaded as an excess volume is needed for the cell conditioning and to avoid the introduction of air. The analysis of the thermodynamics signatures and for dissociation constant determination was performed by the NanoAnalyze software (TA Instruments, New Castle, Del.), and subsequently exported into Microsoft Excel.

Gel electrophoresis. 10 μM of each protein were incubated for 10 min with 20 μM of each compound in a buffer composed of 25 mM TRIS at pH 8, 150 mM NaCL, 50 μM zinc acetate, and 1 mM DTT. Samples were subjected to gel electrophoresis with SDS-PAGE gel using the NuPAGE 12% bis-tris mini gels (Life Technologies), MES as running buffer, and were stained with SimplyBlue SafeStain (Life Technologies) according to the manufacture's protocol.

Cell lines and antibodies. Human Acute lymphoblastic leukemia, pancreatic cancer cell lines, and multiple myeloma cell lines were obtained from the American Type Culture Collection (ATCC; www.atcc.org): MOLT-4 (ATCC® CRL-1582™), BxPC-3 (ATCC® CRL-1687™) PANC-1 (ATCC® CRL-1469™), MIA PaCa-2 (ATCC® CRL-1420™), MM.1S (ATCC® CRL-2974™), RPMI 8226 (ATCC® CCL-155™), U266B1 [U266] (ATCC® TIB-196™), NCI-H929 [H929] (ATCC® CRL-9068™), and from the Leibniz Institute DSMZ-German Collection of Microorganisms and Cell Cultures (DSMZ; www.dsmz.de): LP-1 (ACC 41), L363 (ACC 49). Cells were cultured according to standard mammalian tissue culture protocols, and sterile technique in RPMI medium 1640 with or DMEM L-glutamine supplemented with 10% fetal bovine serum, 100 units/mL penicillin/100 μg/mL streptomycin. Primary antibody XIAP (Cat. No. 2045), cIAP1 (Cat. No. 7065), and cIAP2 (Cat. No3130) were purchased from Cell Signaling Technology and diluted at 1:1000 concentration. β-actin antibody (Santa Cruz Biotechnologies) was used as a loading control.

MTS assay. MM.1S, U266, L363, H929, LP1, RPMI cells were seeded on 96-well plates in three replicates at 100 μL/well (2.5×10$^5$cells/ml) in growing medium and exposed to 20 μM) of different chemical compounds. The effects of the drugs on growth inhibition were measured at 48 h. At the above indicated time points, 20 μl of MTS, (Promega Corporation, Madison, Wis. CellTiter 96® AQueous Non- Radioactive Cell Proliferation Assay), was added to each well, and the plates were incubated for 1-4 h at 37° C. in a humidified, 5% $CO_2$ atmosphere. The absorbance was measured in a microtiter plate reader at 492 nm. The ratio of detection reagents to cell culture was selected according to recommendations of a commercially available test kit.

Cell proliferation assay. On day one, MOLT-4 cells were collected and resuspended in serum-free OPTI-MEM supplemented with 1% Penicillin-Streptomycin, and they were seeded at 20×10^3 cells per well in 96-well plates. Compounds or DMSO were added to treated or control wells, respectively and every well had 1% of DMSO. Cells were further incubated for 48 h in a cell culture incubator.

Pancreatic cancer cells co-treatment with gemcitabine (GEM) and IAP inhibitors. Pancreatic cancer cells were plated at 30×10^3 cells per well in 96-well plates. The next day, cells were treated with different concentrations of GEM. After 24-h incubation, media was removed and replenished with the same GEM concentration alone or with 15 µM of IAP inhibitors in serum-free media and cells were further incubated for 24 h.

Cell proliferation assay was determined using ATPlite 1Step Luminescence Assay System (PerkinElmer) according to the manufacturer's instructions, and luminescence was measured by VICTOR X5 microplate reader (PerkinElmer). Finally, data was plotted, and $IC_{50}$ values were calculated using Prism GraphPad version 7. $IC_{50}$ is the concentration of compound that inhibits 50% growth of the treated cells compared to control wells. This experiment was repeated three times, and each concentration was tested in triplicate.

Immunoblot study. Cells were collected and lysed with lysis buffer (20 mM Tris, pH 7.4, 120 mM NaCl, 1% Triton X-100, 0.5% sodium deoxycholate, 0.1% SDS, 1% IGEPAL, 5 mM EDTA) supplemented with EDTA-free Protease Inhibitor Cocktail and PhosStop (Sigma-Aldrich) for 10 min on cold ice. Lysates were centrifuged and supernatants were collected. Protein content was quantified and samples were prepared using NuPAGE antioxidant and LDS sample buffer (ThermoFisher) and heated for 10 min at 70° C. Each sample containing 16 µg of proteins were loaded into 4-12% NuPAGE Bis-Tris precast gels and transferred to PVDF membranes. The membranes were blocked with 5% milk in TBS and 0.1% Tween (TBST) and incubated with primary antibodies overnight at 4° C. Next day, the membrane was washed with TBST and incubated with goat anti-mouse HRP secondary antibodies. The antigen-antibody complexes were visualized using a Clarity Western ECL kit (BIO-RAD).

Molecular modeling. Compounds N-Me-AVPF-$NH_2$ (SEQ ID NO: 7), compound 1, compound 32, LCL161, and compound 34 were docked using Gold [Cambridge Crystallographic Data Center (www.ccdc.cam.ac.uk)] and Protein Data Bank entry 2OPZ. The docking preparation for both protein and ligands were performed using SYBYL-X 2.1.1 (Certara, Princeton, N.J.). The surface figures were prepared using MOLCAD as implemented in SYBYL-X 2.1.1.

DELFIA (Dissociation-Enhanced Lanthanide Fluorescent Immunoassay). A solution containing 100 µL of 100 nM AVPI-Biotin (AVPIAQKSEK-Biotin (SEQ ID NO: 11)) was added to each well of the 96-well streptavidin-coated plates (PerkinElmer) and incubated for 1 h, followed by three washing steps to remove the unbound AVPI-Biotin. Subsequently, 89 µL of 1.56 nM (for XIAP BIR3 and cIAP1 BIR3) or 2.08 nM (for cIAP2 BIR3) solutions of Eu-N1-labeled anti-6×His ("6×His" disclosed as SEQ ID NO: 10) antibody (PerkinElmer) and a mixture containing 11 µL of the protein and a serial dilution of the test compounds were added to each well. Following 1 h of incubation, the unbound protein-Eu antibody complexes, which were displaced by a test compound, were eliminated through the second washing step and 200 µL of the DELFIA enhancement solution (PerkinElmer) was then added to each well and incubated for 10 min. The fluorescence was measured using the VICTOR X5 microplate reader (PerkinElmer) with excitation and emission wavelengths of 340 and 615 nm, respectively. The final protein concentrations were 30 nM for XIAP BIR3 and cIAP1 BIR3, and 15 nM for cIAP2 BIR3. The final antibody concentrations used for XIAP BIR3 and cIAP1 BIR3 was 22.2 ng/well and 29.7 ng/well for cIAP2 BIR3. DELFIA assay buffer (PerkinElmer) was used to prepare the protein, peptide and antibody solutions and the incubations were done at room temperature. All of the samples were normalized to 1% DMSO and reported as % inhibition. The $IC_{50}$ values were calculated by GraphPad Prism version 7.

Example 4: Additional Compounds and Data

TABLE 6

BIR3-binding agents and relative binding affinities, selectivity and thermodynamics

| Agents | $\Delta H^a$ (kcal/mol) | $K_d$ (nM) by ITC | $IC_{50}$ (nM) by DELFIA assay | | | Selectivity[b] | LLE[c] |
|---|---|---|---|---|---|---|---|
| | XIAP | | XIAP | cIAP1 | cIAP2 | cIAP/XIAP | XIAP |
| GDC-0152 | −5.16 | 94.7 | 22.1 | 7.0 | 9.9 | 0.4 | 4.18 |
| AVPI (SEQ ID NO: 4) | −4.30 | 824.6 | 957.0 | 289.1 | 320.0 | 0.3 | 5.34 |
| AVPF (SEQ ID NO: 5) | −7.64 | 174.6 | 60.0 | 50.9 | 168.2 | 1.8 | 6.06 |
| A(pY)P(4F-Phe) (SEQ ID NO: 6) | −12.17 | 204.6 | 40.1 | 124.1 | 142.7 | 3.3 | 7.35 |

[a]Measured from a full curve titration.
[b]Ratio of the average $IC_{50}$ values for cIAP1-BIR3 versus $IC_{50}$ values for XIAP-BIR3.
[c]LLE was defined as $pK_d$(XIAP-BIR3) − cLogP.

TABLE 7

| ID | Structure & Sequence | DELFIA IC$_{50}$ (nM) for 2-h incubation | | |
| --- | --- | --- | --- | --- |
| | | XIAP-BIR3 | cIAP1-BIR3 | cIAP2-BIR3 |
| GDC-0152 | | 21.4 ± 1.7, n = 10 | 14.5 ± 1.3, n = 11 | 23.2 ± 2.1, n = 11 |
| 142A3 | MeHN-A-Dap(4-FSB)-P-F-NH$_2$ (SEQ ID NO: 15) | 11.3 | 180.4 | 306.7 |
| 142A10 | MeHN-A-Dap(3-FSB)-P-F-NH$_2$ (SEQ ID NO: 16) | 47.2 | 266.1 | 207 |
| 142B6 | MeNH-A-Dap(4-VSB)P-F-CONH$_2$ (SEQ ID NO: 17) | 31 | 4.3 | 1.3 |
| 142B9 | MeHN-A-F(OSO$_2$F)-P-F-CONH$_2$ (SEQ ID NO: 18) | 118 | 112.7 | 342.7 |
| 142B10 | MeHN-A-Dap(p-OSO$_2$F-Benzamide)-P-F-CONH$_2$ (SEQ ID NO: 19) | 579.2 | 335.4 | >1000 |
| 142B11 | MeNH-A-hF(OSO$_2$F)-P-F-CONH$_2$ (SEQ ID NO: 20) | 197 | 26 | 187.6 |

Dap = L-2,3-diaminopropionic acid

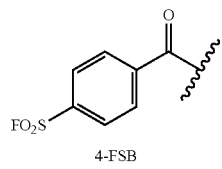

4-FSB

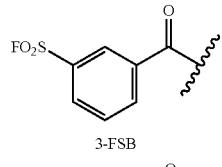

3-FSB

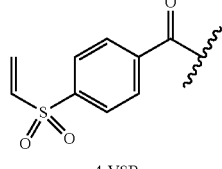

4-VSB

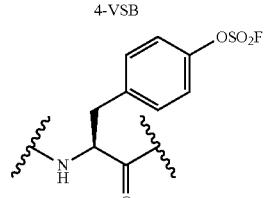

F(OSO$_2$F)

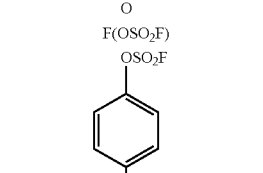

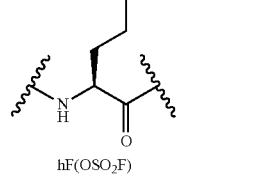

hF(OSO$_2$F)

TABLE 8

| ID | Sequence | DELFIA IC$_{50}$ (nM) for 2-h incubation | | |
| --- | --- | --- | --- | --- |
| | | XIAP-BIR3 | cIAP1-BIR3 | cIAP2-BIR3 |
| GDC-0152 | | 21.4 ± 1.7, n = 10 | 14.5 ± 1.3, n = 11 | 23.2 ± 2.1, n = 11 |
| 142A3 | MeHN-A-Dap(4-FSB)-P-F-NH$_2$ (SEQ ID NO: 15) | 11.3 | 180.4 | 306.7 |
| 142A8-P2 | MeHN-A-Dap(4-FSB)-BBD-NH$_2$ | 20.6 ± 4.0, n = 2 | 324.6 ± 55.5, n = 2 | 353.2 ± 162.7, n = 2 |
| 142A9-P2 | MeHN-A-Dap(4-FSB)-(LAS)-NH$_2$ | 18.4 ± 1.1, n = 2 | 69.3 ± 3.6, n = 2 | 195.2 ± 61.5, n = 2 |
| 142B1 | MeHN-A-Dap(4-FSB)-P-(1-aminoindan) | 6.9 | 29.8 | 59.3 |
| 142B2 | MeHN-A-Dap(4-FSB)-P-(2-aminoindan) | 18.8 | ~1,000 | ~1,300 |
| 142B3 | MeHN-A-Dap(4-FSB)-P-4F,1-aminoindan | 8.9 | 43.2 | 87.8 |

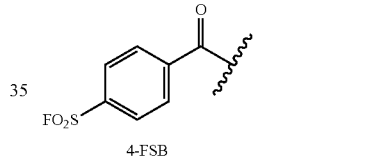

4-FSB

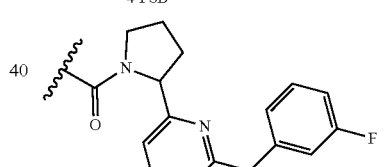

BBD

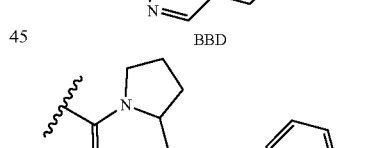

LAS

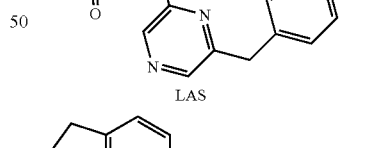

1-aminoindane

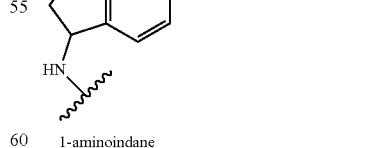

2-aminoindane

TABLE 9

| ID | Sequence | DELFIA IC$_{50}$ (nM) for 2-h incubation | | |
|---|---|---|---|---|
| | | XIAP-BIR3 | cIAP1-BIR3 | cIAP2-BIR3 |
| GDC-0152 | | 21.4 ± 1.7, n = 10 | 14.5 ± 1.3, n = 11 | 23.2 ± 2.1, n = 11 |
| 142B6 | MeHN-A-Dap(4-VSB)-P-F-CONH$_2$ (SEQ ID NO: 17) | 31 | 4.3 | 1.3 |
| 142B4 | MeHN-A-Dap(4-VSB)-P-(2-aminoindan) | 49.8 | 5.1 | 1.2 |
| 142B8 | MeHN-A-Dap(4-VSB)-P-(4F,1-aminoindan)-CONH$_2$ | 44.4 | 4 | 2.9 |
| 142B5 | MeHN-A-Dap(4-FSBz)-P-4F,1-aminoindan | 24.2 | 29.7 | 58.5 |
| 142B7 | MeHN-A-Dap(4-FSBz)-P-F-CONH$_2$ (SEQ ID NO: 21) | 17.1 | 18.6 | 85.7 |
| 142B9 | MeHN-A-F(OSO$_2$F)-P-F-CONH$_2$ (SEQ ID NO: 18) | 64.4 | 112.7 | 342.7 |
| 142B12 | MeHN-A-F(OSO$_2$F)-P-4,F-1-aminoindan | 68.2 ± 2.6, n = 2 | 23.1 ± 0.5, n = 2 | 36.7 ± 2.0, n = 2 |
| 142C1 | MeHN-A-F(OSO$_2$F)-P-2-aminoindan | 266.0 ± 1.5, n = 2 | 316.2 ± 6.4, n = 2 | 864.1 ± 8.3, n = 2 |

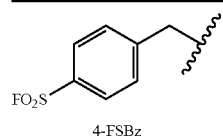

4-FSBz

TABLE 10

| ID | Sequence | DELFIA IC$_{50}$ (nM) | | | | | |
|---|---|---|---|---|---|---|---|
| | | XI4P-BIR3 | | cI4P1-BIR3 | | cIAP2-BIR3 | |
| | | 2-h | 6-h pre, 2-h | 2-h | 6-h pre, 2-h | 2-h | 6-h pre, 2-h |
| GDC-0152 | | 21.4 ± 1.7, n = 10 | 17.9 | 14.5 ± 1.3, n = 11 | 12.2 | 23.2 ± 2.1, n = 11 | 33.4 |
| 142C2-P1 | MeHN-A-F(OSO$_2$F)-BBD | 1318 | 504.2 | 963.2 | 1560 | 1303 | 3602 |
| 142C3 | MeHN-A-F(OSO$_2$F)-1-P-aminoindan | 86.7 | 51.8 | 127.6 | 56.9 | 96 | 144.5 |

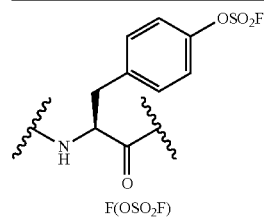

F(OSO$_2$F)

REFERENCES

1. Deveraux, Q. L.; Reed, J. C. (1999). IAP family proteins—suppressors of apoptosis. Genes Dev., 13, 239-252. 2. Salvesen, G. S.; Duckett, C. S. (2002). IAP proteins: blocking the road to death's door. Nat. Rev. Mol. Cell Biol., 3, 401-410. 3. Holcik, M.; Gibson, H.; Korneluk, R. G. (2001). XIAP: apoptotic brake and promising therapeutic target. Apoptosis, 6, 253-261. 4. Gyrd-Hansen, M.; Meier, P. (2010). IAPs: from caspase inhibitors to modulators of NF-kappaB, inflammation and cancer. Nat. Rev. Cancer, 10, 561-574. 5. Samuel, T.; Welsh, K.; Lober, T.; Togo, S. H.; Zapata, J. M.; Reed, J. C. (2006). Distinct BIR domains of cIAP1 mediate binding to and ubiquitination of tumor necrosis factor receptor-associated factor 2 and second mitochondrial activator of caspases. J. Biol. Chem., 281, 1080-1090. 6. Varfolomeev, E.; Blankenship, J. W.; Wayson, S. M.; Fedorova, A. V.; Kayagaki, N.; Garg, P.; Zobel, K.; Dynek, J. N.; Elliott, L. O.; Wallweber, H. J.; Flygare, J. A.; Fairbrother, W. J.; Deshayes, K.; Dixit, V. M.; Vucic, D. (2007). IAP antagonists induce autoubiquitination of c-IAPs, NF-kappaB activation, and TNFalpha-dependent apoptosis. Cell, 131, 669-681. 7. Vince, J. E.; Wong, W. W.; Khan, N.; Feltham, R.; Chau, D.; Ahmed, A. U.; Benetatos, C. A.; Chunduru, S. K.; Condon, S. M.; McKinlay, M.; Brink, R.; Leverkus, M.; Tergaonkar, V.; Schneider, P.; Callus, B. A.; Koentgen, F.; Vaux, D. L.; Silke, J. (2007). IAP antagonists target cIAP1 to induce TNFalpha-dependent apoptosis. Cell, 131, 682-693. 8. Lopes, R. B.; Gangeswaran, R.; McNeish, I. A.; Wang, Y.; Lemoine, N. R. (2007) Expression of the IAP protein family is dysregulated in pancreatic cancer cells and is important for resistance to chemotherapy. Int. J. Cancer, 120, 2344-2352. 9. Mizutani, Y.; Nakanishi, H.; Li, Y. N.; Matsubara, H.; Yamamoto, K.; Sato, N.; Shiraishi, T.; Nakamura, T.; Mikami, K.; Okihara, K.; Takaha, N.; Ukimura, O.; Kawauchi, A.; Nonomura, N.; Bonavida, B.; Miki, T. (2007). Overexpression of XIAP expression in renal cell carcinoma predicts a worse prognosis. Int. J. Oncol., 30, 919-925. 10. Nakagawa, Y.; Abe, S.; Kurata, M.; Hasegawa, M.; Yamamoto, K.; Inoue, M.; Takemura, T.; Suzuki, K.; Kitagawa, M. (2006). IAP family protein expression correlates with poor outcome of multiple myeloma patients in association with chemotherapy-induced overexpression of multidrug resistance genes. Am. J. Hematol., 81, 824-831. 11. Tamm, I.; Kornblau, S. M.; Segall, H.; Krajewski, S.; Welsh, K.; Kitada, S.; Scudiero, D. A.; Tudor, G.; Qui, Y. H.; Monks, A.; Andreeff, M.; Reed, J. C. (2000). Expression and prognostic significance of IAP-family genes in human cancers and myeloid leukemias. Clin. Cancer Res., 6, 1796-1803. 12. Mannhold, R.; Fulda, S.; Carosati, E. (2010). IAP antagonists: promising candidates for cancer therapy. Drug Discov. Today, 15, 210-219. 13. Fulda, S. (2007). Inhibitor of apoptosis proteins as targets for anticancer therapy. Expert Rev. Anticancer Ther., 7, 1255-1264. 14. Fulda, S.; Vucic, D. (2012). Targeting IAP proteins for therapeutic intervention in cancer. Nat. Rev. Drug Discov., 11, 109-124. 15. LaCasse, E. C.; Mahoney, D. J.; Cheung, H. H.; Plenchette, S.; Baird, S.; Korneluk, R. G. (2008). IAP-targeted therapies for cancer. Oncogene, 27, 6252-6275. 16. Vucic, D.; Fairbrother, W. J. (2007). The inhibitor of apoptosis proteins as therapeutic targets in cancer. Clin. Cancer Res., 13, 5995-6000. 17. Huang, J. W.; Zhang, Z.; Wu, B.; Cellitti, J. F.; Zhang, X.; Dahl, R.; Shiau, C. W.; Welsh, K.; Emdadi, A.; Stebbins, J. L.; Reed, J. C.; Pellecchia, M. (2008). Fragment-based design of small molecule X-linked inhibitor of apoptosis protein inhibitors. J. Med. Chem., 51, 7111-7118. 18. Du, C.; Fang, M.; Li, Y.; Li, L.; Wang, X. (2000). Smac, a mitochondrial protein that promotes cytochrome c-dependent caspase activation by eliminating IAP inhibition. Cell, 102, 33-42. 19. Shiozaki, E. N.; Shi, Y. (2004). Caspases, IAPs and Smac/DIABLO: mechanisms from structural biology. Trends Biochem. Sci., 29, 486-494. 20. Verhagen, A. M.; Ekert, P. G.; Pakusch, M.; Silke, J.; Connolly, L. M.; Reid, G. E.; Moritz, R. L.; Simpson, R. J.; Vaux, D. L. (2000). Identification of DIABLO, a mammalian protein that promotes apoptosis by binding to and antagonizing IAP proteins. Cell, 102, 43-53. 21. Huang, Y.; Rich, R. L.; Myszka, D. G.; Wu, H. (2003). Requirement of both the second and third BIR domains for the relief of X-linked inhibitor of apoptosis protein (XIAP)-mediated caspase inhibition by Smac. J. Biol. Chem., 278, 49517-49522. 22. Liu, Z.; Sun, C.; Olejniczak, E. T.; Meadows, R. P.; Betz, S. F.; Oost, T.; Herrmann, J.; Wu, J. C.; Fesik, S. W. (2000). Structural basis for binding of Smac/DIABLO to the XIAP BIR3 domain. Nature, 408, 1004-1008. 23. Wu, G.; Chai, J.; Suber, T. L.; Wu, J. W.; Du, C.; Wang, X.; Shi, Y. (2000). Structural basis of IAP recognition by Smac/DIABLO. Nature, 408, 1008-1012. 24. Cai, Q.; Sun, H.; Peng, Y.; Lu, J.; Nikolovska-Coleska, Z.; McEachern, D.; Liu, L.; Qiu, S.; Yang, C. Y.; Miller, R.; Yi, H.; Zhang, T.; Sun, D.; Kang, S.; Guo, M.; Leopold, L.; Yang, D.; Wang, S. (2011). A potent and orally active antagonist (SM-406/AT-406) of multiple inhibitor of apoptosis proteins (IAPs) in clinical development for cancer treatment. J. Med. Chem., 54, 2714-2726. 25. Cohen, F.; Alicke, B.; Elliott, L. O.; Flygare, J. A.; Goncharov, T.; Keteltas, S. F.; Franklin, M. C.; Frankovitz, S.; Stephan, J. P.; Tsui, V.; Vucic, D.; Wong, H.; Fairbrother, W. J. (2009). Orally bioavailable antagonists of inhibitor of apoptosis proteins based on an azabicyclooctane scaffold. J. Med. Chem., 52, 1723-1730. 26. Flygare, J. A.; Beresini, M.; Budha, N.; Chan, H.; Chan, I. T.; Cheeti, S.; Cohen, F.; Deshayes, K.; Doerner, K.; Eckhardt, S. G.; Elliott, L. O.; Feng, B.; Franklin, M. C.; Reisner, S. F.; Gazzard, L.; Halladay, J.; Hymowitz, S. G.; La, H.; LoRusso, P.; Maurer, B.; Murray, L.; Plise, E.; Quan, C.; Stephan, J. P.; Young, S. G.; Tom, J.; Tsui, V.; Um, J.; Varfolomeev, E.; Vucic, D.; Wagner, A. J.; Wallweber, H. J.; Wang, L.; Ware, J.; Wen, Z.; Wong, H.; Wong, J. M.; Wong, M.; Wong, S.; Yu, R.; Zobel, K.; Fairbrother, W. J. (2012). Discovery of a potent small-molecule antagonist of inhibitor of apoptosis (IAP) proteins and clinical candidate for the treatment of cancer (GDC-0152). J. Med. Chem., 55, 4101-4113. 27. Gaither, A.; Porter, D.; Yao, Y.; Borawski, J.; Yang, G.; Donovan, J.; Sage, D.; Slisz, J.; Tran, M.; Straub, C.; Ramsey, T.; Iourgenko, V.; Huang, A.; Chen, Y.; Schlegel, R.; Labow, M.; Fawell, S.; Sellers, W. R.; Zawel, L. (2007). A Smac mimetic rescue screen reveals roles for inhibitor of apoptosis proteins in tumor necrosis factor-alpha signaling. Cancer Res., 67, 11493-11498. 28. Hashimoto, K.; Saito, B.; Miyamoto, N.; Oguro, Y.; Tomita, D.; Shiokawa, Z.; Asano, M.; Kakei, H.; Taya, N.; Kawasaki, M.; Sumi, H.; Yabuki, M.; Iwai, K.; Yoshida, S.; Yoshimatsu, M.; Aoyama, K.; Kosugi, Y.; Kojima, T.; Morishita, N.; Dougan, D. R.; Snell, G. P.; Imamura, S.; Ishikawa, T. (2013). Design and synthesis of potent inhibitor of apoptosis (IAP) proteins antagonists bearing an octahydropyrrolo [1,2-a]pyrazine scaffold as a novel proline mimetic. J. Med. Chem., 56, 1228-1246. 29. Li, L.; Thomas, R. M.; Suzuki, H.; De Brabander, J. K.; Wang, X.; Harran, P. G. (2004). A small molecule Smac mimic potentiates TRAIL- and TNFalpha-mediated cell death. Science, 305, 1471-1474. 30. Ndubaku, C.; Varfolomeev, E.; Wang, L.; Zobel, K.; Lau, K.; Elliott, L. O.; Maurer, B.; Fedorova, A. V.; Dynek, J. N.; Koehler, M.; Hymowitz, S. G.; Tsui, V.; Deshayes, K.; Fairbrother, W. J.; Flygare, J. A.; Vucic, D. (2009). Antagonism of c-IAP and XIAP proteins is required for efficient induction of cell death by small-molecule IAP antagonists. ACS Chem. Biol., 4, 557-566. 31. Oost, T. K.; Sun, C.; Armstrong, R. C.; Al-Assaad, A. S.; Betz, S. F.; Deckwerth, T. L.; Ding, H.; Elmore, S. W.; Meadows, R. P.; Olejniczak, E. T.; Oleksijew, A.; Oltersdorf, T.; Rosenberg, S. H.; Shoemaker, A. R.; Tomaselli, K. J.; Zou, H.; Fesik, S. W. (2004). Discovery of potent antagonists of the antiapoptotic protein XIAP for the treatment of cancer. J. Med. Chem., 47, 4417-4426. 32. Peng, Y.; Sun, H.; Nikolovska-Coleska, Z.; Qiu, S.; Yang, C. Y.; Lu, J.; Cai, Q.; Yi, H.; Kang, S.; Yang, D.; Wang, S. (2008). Potent, orally bioavailable diazabicyclic small-molecule mimetics of second mitochondria-derived activator of caspases. J. Med. Chem., 51, 8158-8162. 33. Sheng, R.; Sun, H.; Liu, L.; Lu, J.; McEachern, D.; Wang, G.; Wen, J.; Min, P.; Du, Z.; Lu, H.; Kang, S.; Guo, M.; Yang, D.; Wang, S. (2013). A potent bivalent Smac mimetic (SM-1200) achieving rapid, complete, and durable tumor regression in mice. J. Med. Chem., 56, 3969-3979. 34. Sun, H.; Lu, J.; Liu, L.; Yi, H.; Qiu, S.; Yang, C. Y.; Deschamps, J. R.; Wang, S. (2010). Nonpeptidic and potent small-molecule inhibitors of cIAP-1/2 and XIAP proteins. J. Med. Chem., 53, 6361-6367. 35. Sun, H.; Nikolovska-Coleska, Z.; Lu, J.; Meagher, J. L.; Yang, C. Y.; Qiu, S.; Tomita, Y.; Ueda, Y.; Jiang, S.; Krajewski, K.; Roller, P. P.; Stuckey, J. A.; Wang, S. (2007). Design, synthesis, and characterization of a potent, nonpeptide, cell-permeable, bivalent Smac mimetic that concurrently targets both the BIR2 and BIR3 domains in XIAP. J. Am. Chem. Soc., 129, 15279-15294. 36. Sun, H.; Nikolovska-Coleska, Z.; Lu, J.; Qiu, S.; Yang, C. Y.; Gao, W.; Meagher, J.; Stuckey, J.; Wang, S. (2006). Design, synthesis, and evaluation of a potent, cell-permeable, conformationally constrained second mitochondria derived activator of caspase (Smac) mimetic. J. Med. Chem., 49, 7916-7920. 37. Sun, H.; Nikolovska-Coleska, Z.; Yang, C. Y.; Qian, D.; Lu, J.; Qiu, S.; Bai, L.; Peng, Y.; Cai, Q.; Wang, S. (2008). Design of small-molecule peptidic and nonpeptidic Smac mimetics. Acc. Chem. Res., 41, 1264-1277. 38. Sun, H.; Nikolovska-Coleska, Z.; Yang, C. Y.; Xu, L.; Liu, M.; Tomita, Y.; Pan, H.; Yoshioka, Y.; Krajewski, K.; Roller, P. P.; Wang, S. (2004). Structure-based design of potent, conformationally constrained Smac mimetics. J. Am. Chem. Soc., 126, 16686-16687. 39. Sun, H.; Nikolovska-Coleska, Z.; Yang, C. Y.; Xu, L.; Tomita, Y.; Krajewski, K.; Roller, P. P.; Wang, S. (2004). Structure-based design, synthesis, and evaluation of conformationally constrained mimetics of the second mitochondria-derived activator of caspase that target the X-linked inhibitor of apoptosis protein/caspase-9 interaction site. J. Med. Chem., 47, 4147-4150. 40. Sun, H.; Stuckey, J. A.; Nikolovska-Coleska, Z.; Qin, D.; Meagher, J. L.; Qiu, S.; Lu, J.; Yang, C. Y.; Saito, N. G.; Wang, S. (2008). Structure-based design, synthesis, evaluation, and crystallographic studies of conformationally constrained Smac mimetics as inhibitors of the X-linked inhibitor of apoptosis protein (XIAP). J. Med. Chem., 51, 7169-7180. 41. Sun, W.; Nikolovska-Coleska, Z.; Qin, D.; Sun, H.; Yang, C. Y.; Bai, L.; Qiu, S.; Wang, Y.; Ma, D.; Wang, S. (2009). Design, synthesis, and evaluation of potent, nonpeptidic mimetics of second mitochondria-derived activator of caspases. J. Med. Chem., 52, 593-596. 42. Wang, S. (2011). Design of small-molecule Smac mimetics as IAP antagonists. Curr. Top. Microbiol. Immunol., 348, 89-113. 43. Zhang, B.; Nikolovska-Coleska, Z.; Zhang, Y.; Bai, L.; Qiu, S.; Yang, C. Y.; Sun, H.; Wang, S.; Wu, Y. (2008). Design, synthesis, and evaluation of tricyclic, conformationally constrained small-molecule mimetics of second mitochondria-derived activator of caspases. J. Med. Chem., 51, 7352-7355. 44. Zobel, K.; Wang, L.; Varfolomeev, E.; Franklin, M. C.; Elliott, L. O.; Wallweber, H. J.; Okawa, D. C.; Flygare, J. A.; Vucic, D.; Fairbrother, W. J.; Deshayes, K. (2006). Design, synthesis, and biological activity of a potent Smac mimetic that sensitizes cancer cells to apoptosis by antagonizing IAPs. ACS Chem. Biol., 1, 525-533. 45. Hennessy, E. J.; Saeh, J. C.; Sha, L.; MacIntyre, T.; Wang, H.; Larsen, N. A.; Aquila, B. M.; Ferguson, A. D.; Laing, N. M.; Omer, C. A. (2012). Discovery of aminopiperidine-based Smac mimetics as IAP antagonists. Bioorg. Med. Chem. Lett., 22, 1690-1694. 46. Sun, H.; Lu, J.; Liu, L.; Yang, C. Y.; Wang, S. (2014). Potent and selective small-molecule inhibitors of cIAP1/2 proteins reveal that the binding of Smac mimetics to XIAP BIR3 is not required for their effective induction of cell death in tumor cells. ACS Chem. Biol., 9, 994-1002. 47. Donnell, A. F.; Michoud, C.; Rupert, K. C.; Han, X.; Aguilar, D.; Frank, K. B.; Fretland, A. J.; Gao, L.; Goggin, B.; Hogg, J. H.; Hong, K.; Janson, C. A.; Kester, R. F.; Kong, N.; Le, K.; Li, S.; Liang, W.; Lombardo, L. J.; Lou, Y.; Lukacs, C. M.; Mischke, S.; Moliterni, J. A.; Polonskaia, A.; Schutt, A. D.; Solis, D. S.; Specian, A.; Taylor, R. T.; Weisel, M.; Remiszewski, S. W. (2013). Benzazepinones and benzoxazepinones as antagonists of inhibitor of apoptosis proteins (IAPs) selective for the second baculovirus IAP repeat (BIR2) domain. J. Med. Chem., 56, 7772-7787. 48. Baggio, C.; Udompholkul, P.; Barile, E.; Pellecchia, M. (2017). Enthalpy-based screening of focused combinatorial libraries for the identification of potent and selective ligands. ACS Chem. Biol., 12, 2981-2989. 49. Schon, A.; Freire, E. (2016). Enthalpy screen of drug candidates. Anal. Biochem., 513, 1-6. 50. Fox, J. M.; Zhao, M.; Fink, M. J.; Kang, K.; Whitesides, G. M. (2018). The molecular origin of enthalpy/entropy compensation in biomolecular recognition. Annu. Rev. Biophys., 47, 223-250. 51. Flygare, J. A.; Fairbrother, W. J. (2010). Small-molecule pan-IAP antagonists: a patent review. Expert Opin. Ther. Pat., 20, 251-267. 52. Pettinger, J.; Jones, K.; Cheeseman, M. D. (2017). Lysine-targeting covalent inhibitors. Angew. Chem. Int. Ed. Engl., 56, 15200-15209. 53. Zhao, Q.; Ouyang, X.; Wan, X.; Gajiwala, K. S.; Kath, J. C.; Jones, L. H.; Burlingame, A. L.; Taunton, J. (2017). Broad-spectrum kinase profiling in live cells with lysine-targeted sulfonyl fluoride probes. J. Am. Chem. Soc., 139, 680-685. 54. Anscombe, E.; Meschini, E.; Mora-Vidal, R.; Martin, M. P.; Staunton, D.; Geitmann, M.; Danielson, U. H.; Stanley, W. A.; Wang, L. Z.; Reuillon, T.; Golding, B. T.; Cano, C.; Newell, D. R.; Noble, M. E.; Wedge, S. R.; Endicott, J. A.; Griffin, R. J. (2015). Identification and characterization of an irreversible inhibitor of CDK2. Chem. Biol., 22, 1159-1164. 55. Akcay, G.; Belmonte, M. A.; Aquila, B.; Chuaqui, C.; Hird, A. W.; Lamb, M. L.; Rawlins, P. B.; Su, N.; Tentarelli, S.; Grimster, N. P.; Su, Q. (2016). Inhibition of Mcl-1 through covalent modification of a noncatalytic lysine side chain. Nat. Chem. Biol., 12, 931-936. 56. Hoppmann, C.; Wang, L. (2016). Proximity-enabled bioreactivity to generate covalent peptide inhibitors of p53-Mdm4. Chem. Commun. (Camb.), 52, 5140-5143. 57. Clark, D. E. (1999). Rapid calculation of polar molecular surface area and its application to the prediction of transport phenomena. 1. Prediction of intestinal absorption. J. Pharm. Sci., 88, 807-814. 58. Chesi, M.; Mirza, N. N.; Garbitt, V. M.; Sharik, M. E.; Dueck, A. C.; Asmann, Y. W.; Akhmetzyanova, I.; Kosiorek, H. E.; Calcinotto, A.; Riggs, D. L.; Keane, N.; Ahmann, G. J.; Morrison, K. M.; Fonseca, R.; Lacy, M. Q.; Dingli, D.; Kumar, S. K.; Ailawadhi, S.; Dispenzieri, A.; Buadi, F.; Gertz, M. A.; Reeder, C. B.; Lin, Y.; Chanan-Khan, A. A.; Stewart, A. K.; Fooksman, D.; Bergsagel, P. L. (2016). IAP antagonists induce anti-tumor immunity in multiple myeloma. Nat. Med., 22, 1411-1420. 59. Houghton, P. J.; Kang, M. H.; Reynolds, C. P.; Morton, C. L.; Kolb, E. A.; Gorlick, R.; Keir, S. T.; Carol, H.; Lock, R.; Maris, J. M.; Billups, C. A.; Smith, M. A. (2012). Initial testing (stage 1) of LCL161, a SMAC mimetic, by the pediatric preclinical testing program. Pediatr. Blood Cancer, 58, 636-639. 60. Hass, C.; Belz, K.; Schoeneberger, H.; Fulda, S. (2016). Sensitization of acute lymphoblastic leukemia cells for LCL161-induced cell death by targeting redox homeostasis. Biochem. Pharmacol., 105, 14-22. 61. Ramakrishnan, V.; Painuly, U.; Kimlinger, T.; Haug, J.; Rajkumar, S. V.; Kumar, S. (2014). Inhibitor of apoptosis proteins as therapeutic targets in multiple myeloma. Leukemia, 28, 1519-1528. 62. Ashley, S. L.; Sisson, T. H.; Wheaton, A. K.; Kim, K. K.; Wilke, C. A.; Ajayi, I. O.; Subbotina, N.; Wang, S.; Duckett, C. S.; Moore, B. B.; Horowitz, J. C. (2016). Targeting inhibitor of apoptosis proteins protects from bleomycin-induced lung fibrosis. Am. J. Respir. Cell Mol. Biol., 54, 482-492. 63. Lu, J.; Bai, L.; Sun, H.; Nikolovska-Coleska, Z.; McEachern, D.; Qiu, S.; Miller, R. S.; Yi, H.; Shangary, S.; Sun, Y.; Meagher, J. L.; Stuckey, J. A.; Wang, S. (2008). SM-164: a novel, bivalent Smac mimetic that induces apoptosis and tumor regression by concurrent removal of the blockade of cIAP-1/2 and XIAP. Cancer Res., 68, 9384-9393.

What is claimed is:

1. A compound, or a pharmaceutical salt thereof, or a prodrug thereof, having the formula:

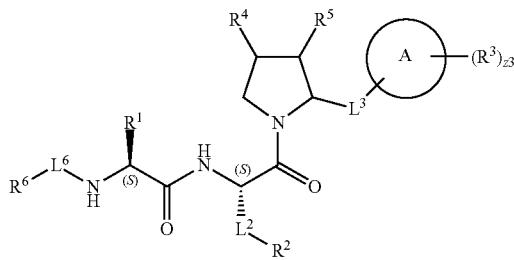

wherein, $R^1$ is —$CX^1_3$, —$CFHX^1_2$, —$CH_2X^1$, substituted or unsubstituted $C_1$-$C_4$ alkyl;

$L^2$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^2$ is independently cycloalkyl, aryl, or heteroaryl, wherein any cycloalkyl, aryl, or heteroaryl of $R^2$ is optionally substituted with one or more $R^7$ groups;

$L^3$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, substituted or unsubstituted alkylarylene, substituted or unsubstituted alkylheteroarylene;

Ring A is a cycloalkyl, heterocycloalkyl, aryl, or heteroaryl;

$R^3$ is independently halogen, —$CX^3_3$, —$CHX^3_2$, —$CH_2X^3$, —CN, —OH, —$NH_2$, —COH, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHHSO_2H$, —NHC(O)H, —NHC(O)OH, —NHOH, —$OCX^3_3$, —$OCX^3_2$, —$OCH_2X^3$, —$SO_2X^3$, —$SO_2C=CH_2$, —$NHSO_2CH=CH_2$, —$OSO_2X^3$, —$NHSO_2X^3$, —$B(OH)_2$, —CO-oxiranyl, —CO-aziridinyl, epoxidinyl, oxaziridinyl, aziridinyl, —$OCH_2C\equiv CH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl;
wherein -(Ring A)-(R$^3$)$_{z3}$ is

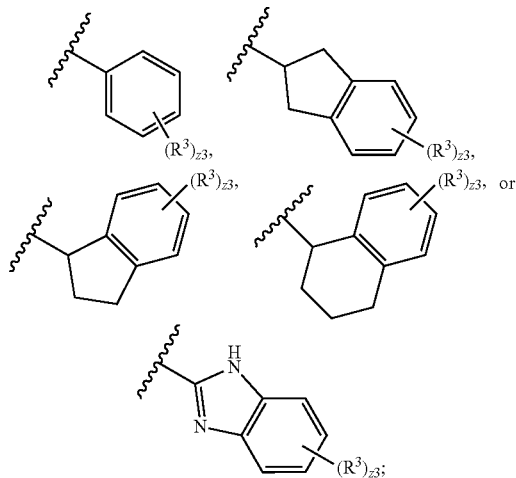

R$^4$ is independently hydrogen, halogen, —CX$^4$$_3$, —CHX$^4$$_2$, —CH$_2$X$^4$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^4$$_3$, —OCHX$^4$$_2$, —OCH$_2$X$^4$, —NHC(NH)NH$_2$, —SO$_2$X$^4$, —SO$_2$CH=CH$_2$, —NHSO$_2$CH=CH$_2$, —OSO$_2$X$^4$, —NHSO$_2$X$^4$, —B(OH)$_2$, —CO-oxiranyl, —CO-aziridinyl, epoxidinyl, oxaziridinyl, aziridinyl, —OCH$_2$C≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is independently hydrogen, halogen, —CX$^5$$_3$, —CHX$^5$$_2$, —CH$_2$X$^5$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^5$$_3$, —OCHX$^5$$_2$, —OCH$_2$X$^5$, —NHC(NH)NH$_2$, —SO$_2$X$^5$, —SO$_2$CH=CH$_2$, —NHSO$_2$CH=CH, —OSO$_2$X$^5$, —NHSO$_2$X$^5$, —B(OH)$_2$, —CO-oxiranyl, —CO-aziridinyl, epoxidinyl, oxaziridinyl, aziridinyl, —OCH$_2$C≡CH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^6$ is a bond or unsubstituted methylene;

R$^6$ is independently hydrogen, substituted or unsubstituted alkyl, substituted or unsubstituted heteroalkyl, substituted or unsubstituted cycloalkyl, substituted or un substituted heterocycloalkyl, substituted or unsubstituted aryl, or substituted or unsubstituted heteroaryl;

R$^7$ is independently halogen, —CX$^7$$_3$, —CHX$^7$$_2$, —CH$_2$X$^7$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^7$$_3$, —OCHX$^7$$_2$, —OCH$_2$X$^7$, —NHC(NH)NH$_2$, —N=C(NH$_2$)$_2$, —CH$_2$SO$_3$$^-$, —PO$_3$$^{-2}$, —SO$_3$$^-$, —SO$_2$NH$_2$, —CH$_2$PO$_3$$^{-2}$, —CH$_2$SO$_2$NH$_2$, —NHC(O)CHCH$_2$, —NHC(O)CH$_2$Cl, —B(OH)$_2$, —SO$_2$X$^7$, —OSO$_2$X$^7$, —NHSO$_2$X$^7$, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, alkyl, heteroalkyl, cycloalkyl, heterocycloalkyl, aryl, or heteroaryl, wherein any alkyl, heteroalkyl, cycloalkyl, heterocyloalkyl, aryl, or heteroaryl of R$^7$ is optionally substituted with one or more R$^8$ groups;

R$^8$ is independently halogen, —CX$^8$$_3$, —CHX$^8$$_2$, —CH$_2$X$^8$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^8$$_3$, —OCHX$^8$$_2$, —OCH$_2$X$^8$, —NHC(NH)NH$_2$, —N=C(NH$_2$)$_2$, —CH$_2$SO$_3$$^-$, —PO$_3$$^{-2}$, —SO$_3$$^-$, —SO$_2$NH$_2$, —CH$_2$PO$_3$$^{-2}$, —CH$_2$SO$_2$NH$_2$, —NHC(O)CHCH$_2$, —NHC(O)CH$_2$Cl, —B(OH)$_2$, —SO$_2$X$^8$, —OSO$_2$X$^8$, —NHSO$_2$X$^8$, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, alkyl, heteroalkyl, cycloalkyl, heterocycloalkyl, aryl, or heteroaryl, wherein any alkyl, heteroalkyl, cycloalkyl, heterocycloalkyl, aryl, or heteroaryl of R$^8$ is optionally substituted with one or more R$^8$ groups;

R$^9$ is independently halogen, —CX$^9$$_3$, —CHX$^9$$_2$, —CH$_2$X$^9$, —CN, —OH, —NH$_2$, —COH, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^9$$_3$, —OCHX$^9$$_2$, —OCH$_2$X$^9$, —NHC(NH)NH$_2$, —N=C(NH$_2$)$_2$, —CH$_2$SO$_3$$^-$, —PO$_3$$^{-2}$, —SO$_3$$^-$, —SO$_2$NH$_2$, —CH$_2$PO$_3$$^{-2}$, —CH$_2$SO$_2$NH$_2$, —NHC(O)CHCH$_2$, —NHC(O)CH$_2$Cl, —B(OH)$_2$, —SO$_2$X$^9$, —OSO$_2$X$^9$, —NHSO$_2$X$^9$, —SO$_2$CH=CH$_2$, —NHSO$_2$CH=CH$_2$, —CO-oxiranyl, —CO-aziridinyl, epoxidinyl, oxaziridinyl, aziridinyl, —OCH$_2$C≡CH, unsubstituted alkyl, unsubstituted heteroalkyl, unsubstituted cycloalkyl, unsubstituted heterocycloalkyl, unsubstituted aryl, or unsubstituted heteroaryl;

each X$^1$, X$^2$, X$^3$, X$^4$, X$^5$, X$^7$, X$^8$, and X$^9$ is independently —F, —Cl, —Br, or —I; and z3 is independently an integer from 0 to 3.

2. The compound, or a pharmaceutical salt thereof, or a prodrug thereof, of claim 1, wherein R$^8$ is unsubstituted alkyl, unsubstituted heteroalkyl, unsubstituted cycloalkyl, unsubstituted heterocycloalkyl, unsubstituted aryl, or unsubstituted heteroaryl.

3. The compound, or a pharmaceutical salt thereof, or a prodrug thereof, of claim 1, wherein R is —CH$_3$, —C$_2$H$_5$, —CF$_3$, —CH$_2$F, —CHF$_2$, —CH$_2$CF$_3$, —CF$_2$CH$_3$, —CH$_2$OH, —CF$_2$OH, or —CHFOH.

4. The compound, or a pharmaceutical salt thereof, or a prodrug thereof, of claim 1, wherein L$^2$ is a bond, —NH—, —O—, —S—, —C(O)—, —C(O)NH—, —NHC(O)—, —NHC(O)NH—, —C(O)O—, —OC(O)—, —(CH$_2$)$_{1-5}$—, —(CH$_2$)$_{1-5}$O—, —(CH$_2$)$_{1-5}$NHC(O)—, —(CH$_2$)$_{1-5}$S—, —(CH$_2$)$_{1-5}$C(O)NH—, —O(CH$_2$)$_{1-5}$—, —(CH$_2$)$_{1-5}$NH—, —(CH$_2$)$_{1-5}$NHCH$_2$—, or —(CH$_2$)$_{1-5}$C(O)—.

5. The compound, or a pharmaceutical salt thereof, or a prodrug thereof, of claim 1, wherein R$^2$ is independently unsubstituted tetrazolyl, unsubstituted aziridinyl, unsubstituted oxiranyl, unsubstituted epoxidinyl, 4-pyridyl that is optionally substituted with one or more $R^7$ group,

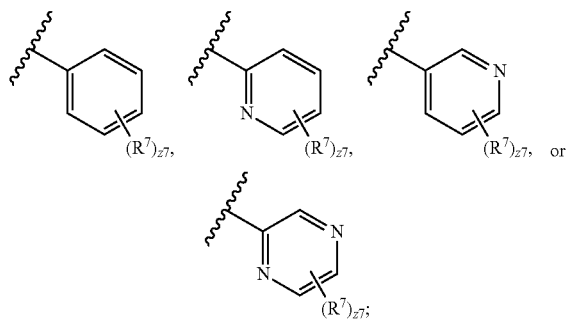

wherein $R^7$ is independently —$CH_2F$, —$CH_2SO_3^-$, —$PO_3^{-2}$, —$SO_3^-$, —$SO_2NH_2$, —$CH_2PO_3^{-2}$, —$CH_2SO_2NH_2$, —$CF_3$, —Cl, —F, —$CH_3$, —$NO_2$, —$C_2H_5$, —$OCH_3$, —$OCF_3$, guanidino, acrylamide, -2-chloroacetamide, —$B(OH)_2$, —$SO_2F$, —$OSO_2F$, —$NHSO_2F$, —$SO_2$, $CH=CH_2$, —$NHSO_2CH=CH_2$, —COH, —CO-epoxide, —CO-aziridine, epoxide, oxaziridine, aziridine, or —$OCH_2C\equiv CH$; and z7 is an integer from 0 to 3.

6. The compound, or a pharmaceutical salt thereof, or a prodrug thereof, of claim 1, wherein $L^3$ is a bond, —C(O)NH—, unsubstituted alkylheteroarylene,

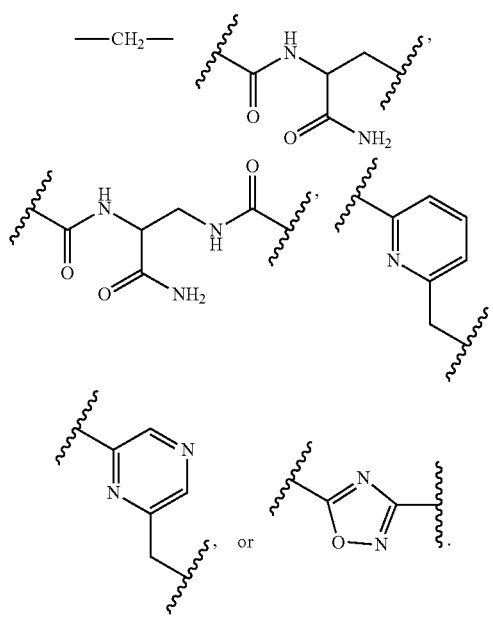

7. The compound, or a pharmaceutical salt thereof, or a prodrug thereof, of claim 1, wherein $R^3$ is independently halogen, —$CX^3_3$, —$CHX^3_2$, —$CH_2X^3$, —OH, —$OCX^3_3$, —$OCHX^3_2$, —$OCH_2X^3$, —$OSO_2X^3$, unsubstituted $C_1$-$C_4$ alkyl, or unsubstituted 2 to 3 membered heteroalkyl.

8. The compound, or a pharmaceutical salt thereof, or a prodrug thereof, of claim 1, wherein each $R^4$ and $R^5$ is independently hydrogen, —F, —OH, —$OCF_3$, —$OCH_3$, —$OCH_2CH_3$, or —$NHC(NH)NH_2$.

9. The compound, or a pharmaceutical salt thereof, or a prodrug thereof of claim 1, wherein $L^6$ is a bond or unsubstituted methylene.

10. The compound, or a pharmaceutical salt thereof, or a prodrug thereof, of claim 1, wherein $R^6$ is independently hydrogen, substituted or unsubstituted methyl, substituted or unsubstituted ethyl, substituted or unsubstituted isopropyl, substituted or unsubstituted cyclopropyl, substituted or unsubstituted cyclobutyl, substituted or unsubstituted cyclopentyl, substituted or unsubstituted cyclohexyl, substituted or unsubstituted n-butyl, substituted or unsubstituted isobutyl, substituted or unsubstituted sec-butyl, substituted or unsubstituted pentyl, substituted or unsubstituted hexyl, substituted or unsubstituted phenyl, or substituted or unsubstituted benzyl.

11. The compound, or a pharmaceutical salt thereof, or a prodrug thereof, of claim 1, having the formula:

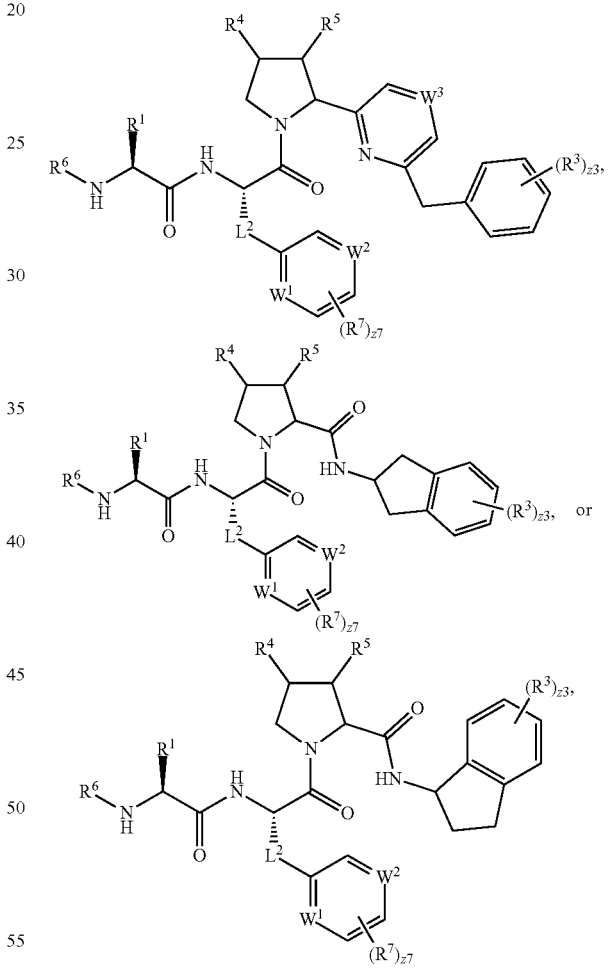

wherein $W^1$, $W^2$, and $W^3$ are independently —CH= or —N=; and z7 is an integer from 0 to 3.

12. The compound, or a pharmaceutical salt thereof, or a prodrug thereof, of claim 1, wherein at least one of $R^2$, $R^3$, $R^4$, or $R^5$ comprises a covalent modifier moiety selected from the group consisting of —$SO_2CH=CH_2$, —$SO_2X$, —$NHSO_2CH=CH_2$, —$OSO_2X$, —$B(OH)_2$, —$NHSO_2X$, and $CH_2X$; and X is independently —F, —Cl, —Br, or —I.

13. A pharmaceutical composition comprising a compound, pharmaceutical salt, or prodrug, of claim 1 and a pharmaceutically acceptable excipient.

14. A compound having the structure

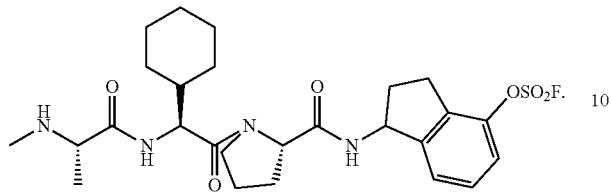

15. A method for increasing apoptosis in a cancer cell in a subject in need thereof, said method comprising administering to the subject in need thereof a therapeutically effective amount of a compound, pharmaceutical salt, or prodrug of a compound of claim 1.

16. A method for inducing apoptosis in a cancer cell in a subject in need thereof, said method comprising administering to the subject in need thereof a therapeutically effective amount of a compound, pharmaceutical salt thereof, or prodrug thereof, of claim 1.

17. The method of claim 16, further comprising administering to the subject a therapeutically effective amount of a second agent selected from the group consisting of an apoptosis increasing agent, a Bcl-2 family antagonist, abraxane, and gemcitabine, and/or a therapeutically effective amount of radiation.

* * * * *

SEQUENCE LISTING

<160> NUMBER OF SEQ ID NOS: 23

<210> SEQ ID NO 1

-continued

```
<211> LENGTH: 497
<212> TYPE: PRT
<213> ORGANISM: Homo sapiens

<400> SEQUENCE: 1

Met Thr Phe Asn Ser Phe Glu Gly Ser Lys Thr Cys Val Pro Ala Asp
1               5                   10                  15

Ile Asn Lys Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
        50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
        195                 200                 205

Asn Trp Glu Pro Cys Asp Arg Ala Trp Ser Glu His Arg Arg His Phe
210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
        355                 360                 365

Thr Ile Phe Gln Asn Pro Met Val Gln Glu Ala Ile Arg Met Gly Phe
370                 375                 380

Ser Phe Lys Asp Ile Lys Lys Ile Met Glu Glu Lys Ile Gln Ile Ser
```

```
                385                 390                 395                 400
            Gly Ser Asn Tyr Lys Ser Leu Glu Val Leu Val Ala Asp Leu Val Asn
                            405                 410                 415

Ala Gln Lys Asp Ser Met Gln Asp Glu Ser Ser Gln Thr Ser Leu Gln
                            420                 425                 430

Lys Glu Ile Ser Thr Glu Gln Leu Arg Arg Leu Gln Glu Glu Lys
                            435                 440                 445

Leu Cys Lys Ile Cys Met Asp Arg Asn Ile Ala Ile Val Phe Val Pro
                            450                 455                 460

Cys Gly His Leu Val Thr Cys Lys Gln Cys Ala Glu Ala Val Asp Lys
            465                 470                 475                 480

Cys Pro Met Cys Tyr Thr Val Ile Thr Phe Lys Gln Lys Ile Phe Met
                            485                 490                 495

Ser

<210> SEQ ID NO 2
<211> LENGTH: 618
<212> TYPE: PRT
<213> ORGANISM: Homo sapiens

<400> SEQUENCE: 2

Met His Lys Thr Ala Ser Gln Arg Leu Phe Pro Gly Pro Ser Tyr Gln
1               5                   10                  15

Asn Ile Lys Ser Ile Met Glu Asp Ser Thr Ile Leu Ser Asp Trp Thr
                20                  25                  30

Asn Ser Asn Lys Gln Lys Met Lys Tyr Asp Phe Ser Cys Glu Leu Tyr
            35                  40                  45

Arg Met Ser Thr Tyr Ser Thr Phe Pro Ala Gly Val Pro Val Ser Glu
        50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
                100                 105                 110

Ile Gln Asn Leu Val Ser Ala Ser Leu Gly Ser Thr Ser Lys Asn Thr
            115                 120                 125

Ser Pro Met Arg Asn Ser Phe Ala His Ser Leu Ser Pro Thr Leu Glu
        130                 135                 140

His Ser Ser Leu Phe Ser Gly Ser Tyr Ser Ser Leu Ser Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
                180                 185                 190

Met Trp Pro Leu Thr Phe Leu Ser Pro Ser Glu Leu Ala Arg Ala Gly
            195                 200                 205

Phe Tyr Tyr Ile Gly Pro Gly Asp Arg Val Ala Cys Phe Ala Cys Gly
        210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
```

```
            260                 265                 270
Met Arg Thr Phe Met Tyr Trp Pro Ser Ser Val Pro Val Gln Pro Glu
        275                 280                 285

Gln Leu Ala Ser Ala Gly Phe Tyr Tyr Val Gly Arg Asn Asp Asp Val
        290                 295                 300

Lys Cys Phe Cys Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
                340                 345                 350

Pro His Leu Leu Glu Gln Leu Leu Ser Thr Ser Asp Thr Thr Gly Glu
                355                 360                 365

Glu Asn Ala Asp Pro Pro Ile Ile His Phe Gly Pro Gly Glu Ser Ser
        370                 375                 380

Ser Glu Asp Ala Val Met Met Asn Thr Pro Val Val Lys Ser Ala Leu
385                 390                 395                 400

Glu Met Gly Phe Asn Arg Asp Leu Val Lys Gln Thr Val Gln Ser Lys
                405                 410                 415

Ile Leu Thr Thr Gly Glu Asn Tyr Lys Thr Val Asn Asp Ile Val Ser
                420                 425                 430

Ala Leu Leu Asn Ala Glu Asp Glu Lys Arg Glu Glu Lys Glu Lys
                435                 440                 445

Gln Ala Glu Glu Met Ala Ser Asp Asp Leu Ser Leu Ile Arg Lys Asn
        450                 455                 460

Arg Met Ala Leu Phe Gln Gln Leu Thr Cys Val Leu Pro Ile Leu Asp
465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
                500                 505                 510

Ile Leu Val Lys Gly Asn Ala Ala Ala Asn Ile Phe Lys Asn Cys Leu
                515                 520                 525

Lys Glu Ile Asp Ser Thr Leu Tyr Lys Asn Leu Phe Val Asp Lys Asn
                530                 535                 540

Met Lys Tyr Ile Pro Thr Glu Asp Val Ser Gly Leu Ser Leu Glu Glu
545                 550                 555                 560

Gln Leu Arg Arg Leu Gln Glu Glu Arg Thr Cys Lys Val Cys Met Asp
                565                 570                 575

Lys Glu Val Ser Val Val Phe Ile Pro Cys Gly His Leu Val Val Cys
                580                 585                 590

Gln Glu Cys Ala Pro Ser Leu Arg Lys Cys Pro Ile Cys Arg Gly Ile
                595                 600                 605

Ile Lys Gly Thr Val Arg Thr Phe Leu Ser
        610                 615

<210> SEQ ID NO 3
<211> LENGTH: 604
<212> TYPE: PRT
<213> ORGANISM: Homo sapiens

<400> SEQUENCE: 3

Met Asn Ile Val Glu Asn Ser Ile Phe Leu Ser Asn Leu Met Lys Ser
1               5                   10                  15
```

-continued

```
Ala Asn Thr Phe Glu Leu Lys Tyr Asp Leu Ser Cys Glu Leu Tyr Arg
             20                  25                  30

Met Ser Thr Tyr Ser Thr Phe Pro Ala Gly Val Pro Val Ser Glu Arg
             35                  40                  45

Ser Leu Ala Arg Ala Gly Phe Tyr Tyr Thr Gly Val Asn Asp Lys Val
             50                  55                  60

Lys Cys Phe Cys Cys Gly Leu Met Leu Asp Asn Trp Lys Arg Gly Asp
 65                  70                  75                  80

Ser Pro Thr Glu Lys His Lys Lys Leu Tyr Pro Ser Cys Arg Phe Val
                 85                  90                  95

Gln Ser Leu Asn Ser Val Asn Asn Leu Glu Ala Thr Ser Gln Pro Thr
            100                 105                 110

Phe Pro Ser Ser Val Thr Asn Ser Thr His Ser Leu Leu Pro Gly Thr
            115                 120                 125

Glu Asn Ser Gly Tyr Phe Arg Gly Ser Tyr Ser Asn Ser Pro Ser Asn
            130                 135                 140

Pro Val Asn Ser Arg Ala Asn Gln Asp Phe Ser Ala Leu Met Arg Ser
145                 150                 155                 160

Ser Tyr His Cys Ala Met Asn Asn Glu Asn Ala Arg Leu Leu Thr Phe
                165                 170                 175

Gln Thr Trp Pro Leu Thr Phe Leu Ser Pro Thr Asp Leu Ala Lys Ala
            180                 185                 190

Gly Phe Tyr Tyr Ile Gly Pro Gly Asp Arg Val Ala Cys Phe Ala Cys
            195                 200                 205

Gly Gly Lys Leu Ser Asn Trp Glu Pro Lys Asp Asn Ala Met Ser Glu
210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
            260                 265                 270

Pro Glu Gln Leu Ala Ser Ala Gly Phe Tyr Tyr Val Gly Asn Ser Asp
            275                 280                 285

Asp Val Lys Cys Phe Cys Cys Asp Gly Gly Leu Arg Cys Trp Glu Ser
290                 295                 300

Gly Asp Asp Pro Trp Val Gln His Ala Lys Trp Phe Pro Arg Cys Glu
305                 310                 315                 320

Tyr Leu Ile Arg Ile Lys Gly Gln Glu Phe Ile Arg Gln Val Gln Ala
                325                 330                 335

Ser Tyr Pro His Leu Leu Glu Gln Leu Leu Ser Thr Ser Asp Ser Pro
            340                 345                 350

Gly Asp Glu Asn Ala Glu Ser Ser Ile Ile His Phe Glu Pro Gly Glu
            355                 360                 365

Asp His Ser Glu Asp Ala Ile Met Met Asn Thr Pro Val Ile Asn Ala
            370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Asn Asp Leu Leu Leu Ile Arg
```

```
                  435                 440                 445
Lys Asn Arg Met Ala Leu Phe Gln His Leu Thr Cys Val Ile Pro Ile
            450                 455                 460

Leu Asp Ser Leu Leu Thr Ala Gly Ile Ile Asn Glu Gln Glu His Asp
465                 470                 475                 480

Val Ile Lys Gln Lys Thr Gln Thr Ser Leu Gln Ala Arg Glu Leu Ile
                485                 490                 495

Asp Thr Ile Leu Val Lys Gly Asn Ile Ala Ala Thr Val Phe Arg Asn
            500                 505                 510

Ser Leu Gln Glu Ala Glu Ala Val Leu Tyr Glu His Leu Phe Val Gln
                515                 520                 525

Gln Asp Ile Lys Tyr Ile Pro Thr Glu Asp Val Ser Asp Leu Pro Val
            530                 535                 540

Glu Glu Gln Leu Arg Arg Leu Gln Glu Glu Arg Thr Cys Lys Val Cys
545                 550                 555                 560

Met Asp Lys Glu Val Ser Ile Val Phe Ile Pro Cys Gly His Leu Val
                565                 570                 575

Val Cys Lys Asp Cys Ala Pro Ser Leu Arg Lys Cys Pro Ile Cys Arg
            580                 585                 590

Ser Thr Ile Lys Gly Thr Val Arg Thr Phe Leu Ser
            595                 600

<210> SEQ ID NO 4
<211> LENGTH: 4
<212> TYPE: PRT
<213> ORGANISM: Homo sapiens

<400> SEQUENCE: 4

Ala Val Pro Ile
1

<210> SEQ ID NO 5
<211> LENGTH: 4
<212> TYPE: PRT
<213> ORGANISM: Homo sapiens

<400> SEQUENCE: 5

Ala Val Pro Phe
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: phospho-Tyr
<220> FEATURE:
<221> NAME/KEY: MOD_RES
<222> LOCATION: (4)..(4)
<223> OTHER INFORMATION: 4F-Phe

<400> SEQUENCE: 6

Ala Tyr Pro Phe
1

<210> SEQ ID NO 7
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Val Pro Phe
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: phospho-Tyr
<220> FEATURE:
<221> NAME/KEY: MOD_RES
<222> LOCATION: (4)..(4)
<223> OTHER INFORMATION: 4F-Phe

<400> SEQUENCE: 8

Ala Tyr Pro Phe
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (p-phosphonomethyl)Phe

<400> SEQUENCE: 9

Ala Phe Pro Phe
1

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Val Pro Ile Ala Gln Lys Ser Glu Lys
1               5                   10
```

```
<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: phospho-Tyr
<220> FEATURE:
<221> NAME/KEY: MOD_RES
<222> LOCATION: (4)..(4)
<223> OTHER INFORMATION: 4F-Phe

<400> SEQUENCE: 12

Ala Tyr Val Phe
1

<210> SEQ ID NO 13
<211> LENGTH: 9
<212> TYPE: PRT
<213> ORGANISM: Homo sapiens

<400> SEQUENCE: 13

Leu Arg Cys Trp Glu Ser Gly Asp Asp
1               5

<210> SEQ ID NO 14
<211> LENGTH: 9
<212> TYPE: PRT
<213> ORGANISM: Homo sapiens

<400> SEQUENCE: 14

Leu Thr Asp Trp Lys Pro Ser Glu Asp
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dap(4-FSB)

<400> SEQUENCE: 15

Ala Xaa Pro Phe
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dap(3-FSB)

<400> SEQUENCE: 16

Ala Xaa Pro Phe
1
```

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dap(4-VSB)

<400> SEQUENCE: 17

Ala Xaa Pro Phe
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe(OSO2F)

<400> SEQUENCE: 18

Ala Phe Pro Phe
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dap(p-OSO2F-Benzamide)

<400> SEQUENCE: 19

Ala Xaa Pro Phe
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hPhe(OSO2F)

<400> SEQUENCE: 20

Ala Phe Pro Phe
1

<210> SEQ ID NO 21
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dap(4-FSBz)

<400> SEQUENCE: 21

Ala Xaa Pro Phe
1

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Arg Cys Trp Glu Ser Gly Asp Asp
1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (p-Sulfonyl fluoride benzoic acid)Dap

<400> SEQUENCE: 23

Ala Xaa Pro Phe
1
```

UNITED STATES PATENT AND TRADEMARK OFFICE
CERTIFICATE OF CORRECTION

PATENT NO. : 11,590,197 B2
APPLICATION NO. : 16/760646
DATED : February 28, 2023
INVENTOR(S) : Maurizio Pellecchia et al.

It is certified that error appears in the above-identified patent and that said Letters Patent is hereby corrected as shown below:

In the Claims

Column 213, Line 50, Claim 1, please delete "-NHSO$_2$CH=CH," and insert -- -NHSO$_2$CH=CH$_2$, --;

Column 214, Line 1, Claim 1, please delete "-NH C(O)NH$_2$," and insert -- -NHC(O)NH$_2$, --;

Column 214, Line 30, Claim 1, please delete "more R$^8$ groups;" and insert -- more R$^9$ groups; --;

Column 214, Line 56, Claim 3, please delete "wherein R is" and insert -- wherein R$^1$ is --; and Column 215, Line 24, Claim 5, please delete "-NHSO$_2$F, -SO$_2$, CH=CH$_2$," and insert -- -NHSO$_2$F, -SO$_2$CH=CH$_2$, -- therefor.

Signed and Sealed this
Twenty-sixth Day of December, 2023

Katherine Kelly Vidal
*Director of the United States Patent and Trademark Office*